(12) United States Patent
Shi et al.

(10) Patent No.: US 12,319,693 B2
(45) Date of Patent: Jun. 3, 2025

(54) CRYSTALLINE FORMS OF CFTR MODULATORS

(71) Applicant: Vertex Pharmaceuticals Incorporated, Boston, MA (US)

(72) Inventors: Yi Shi, Natick, MA (US); Kevin J. Gagnon, Acton, MA (US); Jicong Li, Cambridge, MA (US); Jennifer Lu, San Diego, CA (US); Ales Medek, Winchester, MA (US); Muna Shrestha, Belmont, MA (US); Michael Waldo, Grafton, MA (US); Beili Zhang, San Diego, CA (US); Carl L Zwicker, Wakefield, MA (US); Corey Don Anderson, Brighton, MA (US); Jeremy J. Clemens, San Diego, CA (US); Thomas Cleveland, San Marcos, CA (US); Timothy Richard Coon, Carlsbard, CA (US); Bryan Frieman, La Jolla, CA (US); Peter Grootenhuis, Del Mar, CA (US); Sara Sabina Hadida Ruah, La Jolla, CA (US); Jason McCartney, Cardiff by the Sea, CA (US); Mark Thomas Miller, Rancho Santa Fe, CA (US); Prasuna Paraselli, San Diego, CA (US); Fabrice Pierre, La Jolla, CA (US); Sara E. Swift, San Diego, CA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 18/493,667

(22) Filed: Oct. 24, 2023

(65) Prior Publication Data
US 2025/0051326 A1    Feb. 13, 2025

Related U.S. Application Data

(63) Continuation of application No. 16/992,441, filed on Aug. 13, 2020, now Pat. No. 11,873,300.

(60) Provisional application No. 63/015,903, filed on Apr. 27, 2020, provisional application No. 62/886,565, filed on Aug. 14, 2019.

(51) Int. Cl.
| C07D 401/14 | (2006.01) |
| A61K 31/4439 | (2006.01) |
| C07D 471/08 | (2006.01) |

(52) U.S. Cl.
CPC ........ C07D 471/08 (2013.01); *C07B 2200/13* (2013.01)

(58) Field of Classification Search
CPC ... C07D 401/14; A61K 31/4439; A61P 11/00; A61P 43/00

USPC ........................................ 546/256; 514/333
See application file for complete search history.

(56) References Cited

U.S. PATENT DOCUMENTS

| 2,677,682 | A  | 5/1954  | Fahrenbach et al. |
| 7,332,612 | B2 | 2/2008  | Dolitzky et al. |
| 8,865,902 | B2 | 10/2014 | Morgan |
| 9,663,508 | B2 | 5/2017  | Bregman et al. |
| 9,782,408 | B2 | 10/2017 | Miller et al. |
| 9,981,910 | B2 | 5/2018  | Altenbach et al. |
| 10,118,916 | B2 | 11/2018 | Altenbach et al. |
| 10,131,670 | B2 | 11/2018 | Strohbach et al. |
| 10,138,227 | B2 | 11/2018 | Altenbach et al. |
| 10,208,053 | B2 | 2/2019  | Strohbach et al. |
| 10,258,624 | B2 | 4/2019  | Miller et al. |
| 10,570,115 | B2 | 2/2020  | Alcacio et al. |
| 10,654,829 | B2 | 5/2020  | Dhamankar et al. |
| 10,738,030 | B2 | 8/2020  | Bear et al. |
| 10,758,534 | B2 | 9/2020  | Miller et al. |

(Continued)

FOREIGN PATENT DOCUMENTS

| CL | 2017000824 A1 | 1/2018 |
| CL | 2019002734 A1 | 1/2020 |

(Continued)

OTHER PUBLICATIONS

Alberti, C. and Tironi, C. (1964), "Sulfanilammidi Pirazoliche," VI. 1-(Tolil)-sulfanilamidopirazoli derivati dal 3-aminopirazolo, dal 4-aminopirazolo e dal 3-metil-5-aminopirazolo, Il Farmaco—Ed. Sc. 29(7), 618-637.

(Continued)

*Primary Examiner* — Charanjit Aulakh
(74) *Attorney, Agent, or Firm* — Finnegan, Henderson, Farabow, Garrett & Dunner, LLP

(57) ABSTRACT

Crystalline forms of Compound I:

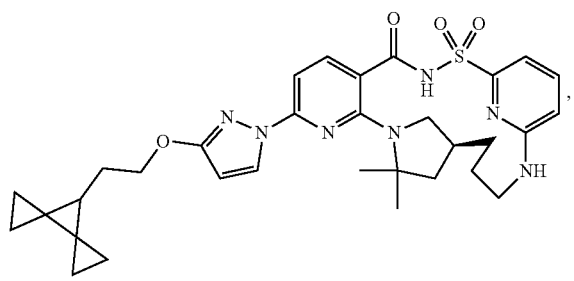

pharmaceutically acceptable salts thereof, and solvates and hydrates thereof are disclosed. Pharmaceutical compositions comprising the same, methods of treating cystic fibrosis using the same, and methods for making the same are also disclosed.

20 Claims, 53 Drawing Sheets

(56) References Cited

U.S. PATENT DOCUMENTS

| | | |
|---|---|---|
| 10,793,547 B2 | 10/2020 | Abela et al. |
| 11,066,417 B2 | 7/2021 | Clemens et al. |
| 11,179,367 B2 | 11/2021 | Chu et al. |
| 11,584,761 B2 | 2/2023 | Angell et al. |
| 11,591,350 B2 | 2/2023 | Anderson et al. |
| 11,873,300 B2 | 1/2024 | Shi et al. |
| 2011/0098311 A1 | 4/2011 | Van Goor et al. |
| 2013/0317000 A1 | 11/2013 | Chowdhury et al. |
| 2013/0317001 A1 | 11/2013 | Andrez et al. |
| 2018/0099932 A1 | 4/2018 | Altenbach et al. |
| 2018/0141954 A1 | 5/2018 | Strohbach et al. |
| 2018/0170938 A1 | 6/2018 | Strohbach et al. |
| 2018/0244640 A1 | 8/2018 | Altenbach et al. |
| 2019/0077784 A1 | 3/2019 | Altenbach et al. |
| 2019/0153000 A1 | 5/2019 | Munoz et al. |
| 2021/0047323 A1 | 2/2021 | Shi et al. |
| 2022/0041621 A1 | 2/2022 | Clemens et al. |
| 2022/0047564 A1 | 2/2022 | Altshuler et al. |
| 2022/0106331 A1 | 4/2022 | Clemens et al. |
| 2022/0127247 A1 | 4/2022 | Azimioara et al. |
| 2022/0184049 A1 | 6/2022 | Borek et al. |
| 2022/0313698 A1 | 10/2022 | Abela et al. |
| 2022/0372047 A1 | 11/2022 | Abela et al. |

FOREIGN PATENT DOCUMENTS

| | | |
|---|---|---|
| CL | 2019001553 A1 | 4/2020 |
| CL | 2020000122 A1 | 7/2020 |
| CL | 2020000856 A1 | 8/2020 |
| CN | 102227424 A | 10/2011 |
| CN | 106432213 A | 2/2017 |
| CO | 12038470 | 3/2012 |
| EA | 202091930 | 3/2021 |
| EC | SP19028690 A | 4/2019 |
| EC | SP19048759 A | 7/2019 |
| EC | SP20003147 A | 2/2020 |
| EC | SP20053845 A | 9/2020 |
| EP | 0 846 687 A1 | 6/1998 |
| JP | 2014-526500 A | 10/2014 |
| JP | 2021-512117 A | 5/2021 |
| JP | 6896619 B2 | 6/2021 |
| JP | 6916285 B2 | 7/2021 |
| JP | 7061115 B2 | 4/2022 |
| NC | 2017/0004538 | 5/2017 |
| NC | 2018/0000413 | 1/2018 |
| NC | 2018/0012171 | 11/2018 |
| TW | 201713617 A | 4/2017 |
| TW | 201811766 A | 1/2018 |
| WO | WO 2001/090092 A1 | 11/2001 |
| WO | WO 2005/049018 A1 | 6/2005 |
| WO | WO 2005/075435 A1 | 8/2005 |
| WO | WO 2006/002421 A2 | 1/2006 |
| WO | WO 2007/021982 A2 | 2/2007 |
| WO | WO 2007/053641 A2 | 5/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/117715 A2 | 10/2007 |
| WO | WO 2007/134279 A2 | 11/2007 |
| WO | WO 2008/127399 A2 | 10/2008 |
| WO | WO 2008/154241 A1 | 12/2008 |
| WO | WO 2009/006315 A1 | 1/2009 |
| WO | WO 2009/038683 A2 | 3/2009 |
| WO | WO 2009/073757 A1 | 6/2009 |
| WO | WO 2009/076142 A2 | 6/2009 |
| WO | WO 2009/108657 A2 | 9/2009 |
| WO | WO 2010/019239 A2 | 2/2010 |
| WO | WO 2010/048526 A2 | 4/2010 |
| WO | WO 2010/053471 A1 | 5/2010 |
| WO | WO 2010/054138 A2 | 5/2010 |
| WO | WO 2010/108162 A1 | 9/2010 |
| WO | WO 2011/019413 A1 | 2/2011 |
| WO | WO 2011/029059 A1 | 3/2011 |
| WO | WO 2011/072241 A1 | 6/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/127290 A2 | 10/2011 |
| WO | WO 2011/133751 A2 | 10/2011 |
| WO | WO 2011/133951 A1 | 10/2011 |
| WO | WO 2012/027247 A2 | 3/2012 |
| WO | WO 2012/027731 A2 | 3/2012 |
| WO | WO 2012/158885 A1 | 11/2012 |
| WO | WO 2012/170061 A1 | 12/2012 |
| WO | WO 2013/038386 A1 | 3/2013 |
| WO | WO 2013/064984 A1 | 5/2013 |
| WO | WO 2013/070961 A1 | 5/2013 |
| WO | WO 2013/112804 A1 | 8/2013 |
| WO | WO 2013/130669 A1 | 9/2013 |
| WO | WO 2013/158121 A1 | 10/2013 |
| WO | WO 2013/160419 A1 | 10/2013 |
| WO | WO 2013/185112 A1 | 12/2013 |
| WO | WO 2014/014841 A1 | 1/2014 |
| WO | WO 2014/071122 A1 | 5/2014 |
| WO | WO 2014/078842 A1 | 5/2014 |
| WO | WO 2015/073231 A1 | 7/2015 |
| WO | WO 2015/160787 A1 | 10/2015 |
| WO | WO 2016/057572 A1 | 4/2016 |
| WO | WO 2016/057730 A1 | 4/2016 |
| WO | WO 2016/081556 A1 | 5/2016 |
| WO | WO 2016/160945 A1 | 10/2016 |
| WO | WO 2017/009804 A1 | 1/2017 |
| WO | WO 2017/053455 A1 | 3/2017 |
| WO | WO 2017/053711 A2 | 3/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/208115 A1 | 12/2017 |
| WO | WO 2017/223188 A1 | 12/2017 |
| WO | WO 2018/064632 A1 | 4/2018 |
| WO | WO 2018/080591 A1 | 5/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 |
| WO | WO 2018/116185 A1 | 6/2018 |
| WO | WO 2018/127130 A1 | 7/2018 |
| WO | WO 2018/183367 A1 | 10/2018 |
| WO | WO 2018/183964 A1 | 10/2018 |
| WO | WO 2018/201126 A1 | 11/2018 |
| WO | WO 2018/227049 A1 | 12/2018 |
| WO | WO 2019/010092 A1 | 1/2019 |
| WO | WO 2019/014352 A1 | 1/2019 |
| WO | WO 2019/018353 A1 | 1/2019 |
| WO | WO 2019/018395 A1 | 1/2019 |
| WO | WO 2019/028228 A1 | 2/2019 |
| WO | WO 2019/071078 A1 | 4/2019 |
| WO | WO 2019/079760 A1 | 4/2019 |
| WO | WO 2019/109021 A1 | 6/2019 |
| WO | WO 2019/113089 A1 | 6/2019 |
| WO | WO 2019/113476 A2 | 6/2019 |
| WO | WO 2019/152940 A1 | 8/2019 |
| WO | WO 2019/161078 A1 | 8/2019 |
| WO | WO 2019/191620 A1 | 10/2019 |
| WO | WO 2019/195739 A1 | 10/2019 |
| WO | WO 2019/200246 A1 | 10/2019 |
| WO | WO 2020/102346 A1 | 5/2020 |
| WO | WO 2020/128925 A1 | 6/2020 |
| WO | WO 2020/191227 A1 | 9/2020 |
| WO | WO 2020/206080 A1 | 10/2020 |
| WO | WO 2020/214921 A1 | 10/2020 |
| WO | WO 2020/242935 A1 | 12/2020 |
| WO | WO 2021/030552 A1 | 2/2021 |
| WO | WO 2021/030554 A1 | 2/2021 |
| WO | WO 2021/030555 A1 | 2/2021 |
| WO | WO 2021/030556 A1 | 2/2021 |
| WO | WO 2021/097054 A1 | 5/2021 |
| WO | WO 2021/097057 A1 | 5/2021 |
| WO | WO 2022/032068 A1 | 2/2022 |
| WO | WO 2022/036060 A1 | 2/2022 |
| WO | WO 2022/076620 A2 | 4/2022 |
| WO | WO 2022/076621 A2 | 4/2022 |
| WO | WO 2022/076622 A2 | 4/2022 |

(56) References Cited

FOREIGN PATENT DOCUMENTS

| WO | WO 2022/076624 A2 | 4/2022 |
|----|-------------------|--------|
| WO | WO 2022/076625 A2 | 4/2022 |
| WO | WO 2022/076626 A2 | 4/2022 |

OTHER PUBLICATIONS

Alberti, C. and Tironi, C. (1971), "Sulfanilammidi Pirazoliche," II Farmaco—Ed. Sc. 26(1), 66-88.
Bastin, Richard J., et al., "Salt selection and optimization procedures for pharmaceutical new chemical entities," Org. Pro. Res. Dev. 2000, 4(5), 427-435.
Borhade, Sanjay R., et al., 'Synthesis of novel Aryl and heteroaryl Acyl sulfonimidamides Borhade, Sanjay R., et al., "Synthesis of Novel Aryl and Heteroaryl Acyl Sulfonimidamides via Pd-Catalyzed Carbonylation Using a Nongaseous Precursor," Organic Letters, 2013, vol. 15, No. 5, pp. 1056-1059, rXP055374206A, © 2013 American Chemical Society, ISSN: 1523-7060, DOI:10.1021/ol4/00049m, published on web Feb. 13, 2013.via Pd-catalyzed carbonylation using a nongaseous precursor' Organic Letters 14(23), 6012-6015 Coden: ORLEF7; ISSN: 1523-7052, vol. 15, No. 5, Mar. 1, 2013(Mar. 1, 2013), pp. 1056-1059, XP055374206, ISSN:1523-7060, DOI:10.1021/01400049m p. 1059, table 3, compound 10.
Braker, William, et al. (1947), "Substituted Sulfanilamidopyrimidines," J. Am. Chem. Society, 69, 3072-3078.
Chen, Liangzhu, et al. (2014), "Synthesis and Antimicrobial Activity of the Hybrid Molecules between Sulfonamides and Active Antimicrobial Pleuromutilin Derivative," Chemical Biology and Drug Design, 86(2), 239-245.
Cherepakha, Artem Yu., et al. (2018), "Hetaryl Bromides Bearing the SO2F Group—Versatile Substrates for Palladium-Catalyzed C—C Coupling Reactions," Eur J Org Chem, 47: 6682-6692.
Chio, Li-Chun, et al. (1996), "Identification of a Class of Sulfonamides Highly Active Against Dihydropteroate Synthase from Toxoplasma Gondii, Pneumocystis Carinii, and Mycobacterium Avium," Antimicrobial Agents and Chemotherapy, American Society for Microbiology, 40(3), 727-733.
Donaldson, S.H. et al. (2017) "Tezacaftor/Ivacaftor in Subjects with Cystic Fibrosis and F508del/F508del-CFTR or F508del/G551D-CFTR", Am. J. Respir. Crit. Care Med., 197(2): 214-224.
Gage, J. C., et al. (1947), "2-P-Aminobenzenesulphonamido-4 : 6-Dimethoxypyrimidine: Experimental Evaluation," British Journal of Pharmacology and Chemotherapy, 2(3), 149-162.
Ghorab, Mostafa M. et al., (2017), "Aromatase inhibitors and apoptotic inducers: Design, synthesis, anticancer activity and molecular modeling studies of novel phenothiazine derivatives carrying sulfonamide moiety as hybrid molecules," Eur. J. Med. Chem., 134, 304-315.
Gomes, Paula, et al. (2003), "Amino acids as selective sulfonamide acylating agents," Tetrahedron, 59(38), 7473-7480.
Hassan, Hammed H. A. and Soliman, R. (2000), "Synthesis and GC-EIMS Analyses of Optically Pure 3-Hydroxy-2-azetidinones Having N-sulfonamide Drugs Side Chain," Synthetic Communications, 30(14), 2465-2478.
International Patent Application No. PCT/US2019/018042: International Search Report and Written Opinion, mailed Apr. 17, 2019 (10 pages).
International Patent Application No. PCT/US2019/061171: International Search Report and Written Opinion, mailed Feb. 12, 2020 (14 pages).
International Patent Application No. PCT/U2020/026331: International Search Report and Written Opinion, mailed May 29, 2020 (14 pages).
International Patent Application No. PCT/US2021/053853: International Search Report and Written Opinion, mailed Dec. 21, 2021 (12 pages).
International Patent Application No. PCT/US2021/053855: International Search Report and Written Opinion, mailed Jan. 3, 2022 (12 pages).
International Patent Application No. PCT/US2021/053856: International Search Report and Written Opinion, mailed Dec. 22, 2021 (12 pages).
International Patent Application No. PCT/US2021/053858: International Search Report and Written Opinion, mailed Mar. 17, 2022 (14 pages).
International Patent Application No. PCT/US2021/053860: International Search Report and Written Opinion, mailed Dec. 23, 2021 (12 pages).
International Patent Application No. PCT/US2021/053861: International Search Report and Written Opinion, mailed Dec. 22, 2021 (12 pages).
International Patent Application No. PCT/US2021/053862: International Search Report and Written Opinion, mailed Dec. 22, 2021 (12 pages).
International Patent Application No. PCT/US2021/053863: International Search Report and Written Opinion, mailed Feb. 4, 2022 (16 pages).
International Patent Application No. PCT/US2021/053864: International Search Report and Written Opinion, mailed Mar. 15, 2022 (17 pages).
International Patent Application No. PCT/US2021/053865: International Search Report and Written Opinion, mailed Jan. 26, 2022 (16 pages).
International Patent Application No. PCT/US2021/062687: International Search Report and Written Opinion, mailed Apr. 4, 2022 (16 pages).
Kim, Taehoon, et al. (2018), "Sulfonamidation of Aryl and Heteroaryl Halides through Photosensitized Nickel Catalysis," Agewandte Chemie, 57, 3488-3492.
Newkome, George R., et al. (1979), "Nicotinic Acid Crown Ethers. Synthesis, Reactions, and Complexation of Nicotinonitrile Macrocycles," J Org Chem, 44(15): 2639-2697.
Nishida, Haruyuki, et al. (2017), "Exploration of pyrrole derivatives to find an effective potassium competitive acid blocker with moderately long-lasting suppression of gastric acid secretion," Bioorg Med Chem, 25(13): 3447-3460.
"A phase 1/2 study of VX-121 in healthy subjects and in subjects with cystic fibrosis", EU Clinical Trials Register, May 3, 2019 (2019-0"A Phase 1/2 Study of VX-121 in Healthy Subjects and in Subjects with Cystic Fibrosis," EU Clinical Trials Register, May 3, 2019 (May 3, 2019), XP055903414, Retrieved from the Internet: URL:https://www.clinicaltrialsregister.eu/ctr-search/trial/2018-000126-55/NL [retrieved on Mar. 21, 2022].5-03), XP055903414, Retrieved from the Internet: URL:https://www.clinicaltrialsregister.eu/ctr-search/trial/2018-000126-55/NL [retrieved on Mar. 21, 2022].
"A Phase 2 Study to Evaluate Efficacy and Safety of VX-561 in Subjects Aged 18 Years and Older With Cystic Fibrosis," ClinicatTials. gov, Apr. 11, 2019 (Apr. 11, 2019), XP055903562, Retrieved from the Internet: URL:https://clinicaltrials.gov/ct2/show/NCT03911713 [retrieved on Mar. 21, 2022].
Prashantha, Gunaga, et al. (2017), "Selective IKur Inhibitors for the Potential Treatment of Atrial Fibrillation: Optimization of the Phenyl Quinazoline Series Leading to Clinical Candidate 5 [5-Phenyl-4-(pyridin-2-ylmethylamino)quinazolin-2-yl]pyridine-3-sulfonamide," J Med Chem, 60(9): 3795-3803.
Rewcastle, Gordon W., et al. (1996), "Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor," J Med Chem, 39(9): 1823-1835.
Raiziss, George W., et al. (1942), "N1-Sulfanilylaminoalkylpyrimidines," J. Am. Chem. Soc. 64, 2340-2342.
Rose, F. L., et al. (1946), "P-Aminobenzenesulphonamide Derivatives of Pyrimidines as Antibacterial Agents," J. Am. Chem. Soc., 81-85.
Sprague, James M., et al. (1941), "Sulfonamido derivatives of thiazoles," J. Am. Chem. Soc. 63, 578-580.
Sprague, James M., et al. (1941), "Sulfonamido derivatives of pyrimidines," J. Am. Chem. Soc. 63, 3028-3030.
"A Study to Evaluate the Safety and Efficacy of VX-121 Combination Therapy in Subjects with Cystic Fibrosis," ClinicalTrials.

(56) References Cited

OTHER PUBLICATIONS gov, Apr. 30, 2019 (Apr. 30, 2019), XP55903330, Retrieved from the Internet: URL:https://clinicaltrials.gov/ct2/show/NCT03912233 [retrieved on Mar. 21, 2022].
Sugasawa, Shigehiko, et al. (1949), "Reaction between sulfaguanidine and 1,3-keto aldehydes. I. Synthesis of 2-sulfanilamido-4-methylpyrimidine," 69, 82-85.
"Symdeko in Cystic Fibrosis Patients", ClinicalTrials.gov, Jul. 23, 2018 (Apr. 23, 2018), XP055661778, Retrieved from the Internet: URL:https://clinicaltrials.gov/ct2/show/record/NCT03506061 [retrieved on Jan. 24, 2020].
Tani, Chiaki, et al. (1950), "Syntheses of sulfanilamide derivatives containing diphenylene oxide," Journal of the Pharmaceutical Society of Japan, 70, 126-127.
International Patent Application No. PCT/US2021/045691: International Search Report and Written Opinion, mailed Dec. 13, 2021 (16 pages).
Notice of Allowance and Fee(s) Due for U.S. Appl. No. 16/992,441, mailed Aug. 25, 2023.

degrees 2-theta degrees 2-theta

CRYSTALLINE FORMS OF CFTR MODULATORS

This application claims the benefit of U.S. Provisional Application No. 62/886,565, filed on Aug. 14, 2019, and U.S. Provisional Application No. 63/015,903, filed on Apr. 27, 2020, the disclosures of which are incorporated by reference in its entirety.

Disclosed herein are modulators of Cystic Fibrosis Transmembrane Conductance Regulator (CFTR), pharmaceutical compositions containing those modulators, methods of treating cystic fibrosis with those modulators and compositions, and processes for making the modulators.

Cystic fibrosis (CF) is a recessive genetic disease that affects approximately 70,000 children and adults worldwide. Despite progress in the treatment of CF, there is no cure.

In patients with CF, mutations in CFTR endogenously expressed in respiratory epithelia lead to reduced apical anion secretion, causing an imbalance in ion and fluid transport. The resulting decrease in anion transport contributes to excess mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease causing mutations (Cutting, G. R. et al. (1990) Nature 346:366-369; Dean, M. et al. (1990) Cell 61:863:870; and Kerem, B—S. et al. (1989) Science 245: 1073-1080; Kerem, B—S et al. (1990) Proc. Natl. Acad. Sci. USA 87:8447-8451). To date, greater than 2000 mutations in the CF gene have been identified; currently, the CFTR2 database contains information on only 412 of these identified mutations, with sufficient evidence to define 346 mutations as disease-causing. The most prevalent disease-causing mutation is a deletion of phenylalanine at position 508 of the CFTR amino acid sequence, and is commonly referred to as the F508del mutation. This mutation occurs in approximately many of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the F508del mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease-causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC (epithelial sodium channel) and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

A number of CFTR-modulating compounds have recently been identified. However, compounds that can treat or reduce the severity of the cystic fibrosis and other CFTR-mediated diseases, and particularly the more severe forms of these diseases, are still needed.

Thus, one aspect of the disclosure provides a CFTR-modulating compound (14S)-8-[3-(2-{Dispiro[2.0.2.1]heptan-7-yl}ethoxy)-1H-pyrazol-1-yl]-12,12-dimethyl-2λ6-thia-3,9,11,18,23-pentaazatetracyclo[17.3.1.111,14.05,10] tetracosa-1(22),5,7,9,19(23),20-hexaene-2,2,4-trione (Compound I) and pharmaceutically acceptable salts thereof. Compound I can be depicted as having the following structure:

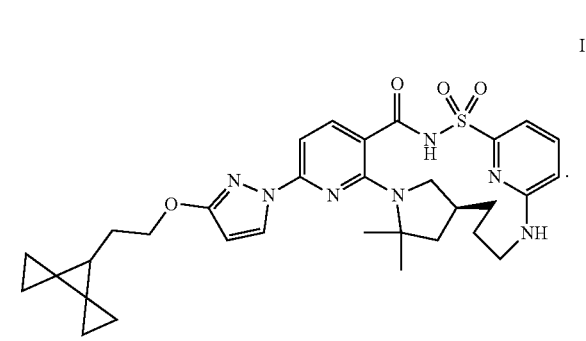 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]

I

Compound I was first described in PCT Publication No. WO 2019/161078 (incorporated herein by reference) as an amorphous (free form) solid, and as amorphous calcium, sodium, and potassium salts.

Crystalline forms are of interest in the pharmaceutical industry, where the control of the crystalline form(s) of the active ingredient may be desirable or even required. Reproducible processes for producing a compound with a particular crystalline form in high purity may be desirable for compounds intended to be used in pharmaceuticals, as different crystalline forms may possess different properties. For example, different crystalline forms may possess different chemical, physical, and/or pharmaceutical properties. In some embodiments, one or more crystalline forms disclosed herein may exhibit a higher level of purity, chemical stability, and/or physical stability compared to the forms produced in WO 2019/161078. Certain crystalline forms (e.g., crystalline free form, crystalline salt, crystalline salt solvate, and crystalline salt hydrate forms of Compound I (collectively referred to as "crystalline forms")) may exhibit lower hygroscopicity than the forms produced in WO 2019/161078. Thus, the crystalline forms of this disclosure may provide advantages during drug substance manufacturing, storage, and handling over the amorphous forms produced in WO 2019/161078. Thus, pharmaceutically acceptable crystalline forms of Compound I may be particularly useful for the production of drugs for the treatment of CFTR-mediated diseases.

In some embodiments, the crystalline form of Compound I is a free form. In some embodiments, the crystalline form of Compound I is Compound I (free form) Form A. In some embodiments, the crystalline form of Compound I is Compound I (free form) Form B. In some embodiments, the crystalline form of Compound I is Compound I (free form) Form C. In some embodiments, the crystalline form of Compound I is Compound I (free form) Form D.

In some embodiments, the crystalline form of Compound I is a solvate. In some embodiments, the crystalline form of Compound I is a calcium salt solvate. In some embodiments, the crystalline form of Compound I is calcium salt EtOH solvate Form A. In some embodiments, the crystalline form of Compound I is calcium salt EtOH solvate Form B. In some embodiments, the crystalline form of Compound I is calcium salt EtOH solvate Form C.

In some embodiments, the crystalline form of Compound I is a hydrate. In some embodiments, the crystalline form of Compound I is a calcium salt hydrate. In some embodiments, the crystalline form of Compound I is calcium salt hydrate Form A. In some embodiments, the crystalline form of Compound I is calcium salt hydrate Form B. In some embodiments, the crystalline form of Compound I is calcium salt hydrate/solvate Form B with MeOH. In some embodiments, the crystalline form of Compound I is calcium salt hydrate Form C. In some embodiments, the crystalline form of Compound I is calcium salt hydrate Form D. In some embodiments, the crystalline form of Compound I is calcium salt hydrate Form E. In some embodiments, the crystalline form of Compound I is Form F. In some embodiments, the crystalline form of Compound I is calcium salt hydrate Form G. In some embodiments, the crystalline form of Compound I is calcium salt hydrate Form H.

In some embodiments, the crystalline form of Compound I is a sodium salt hydrate. In some embodiments, the crystalline form of Compound I is sodium salt hydrate Form A. In some embodiments, the crystalline form of Compound I is sodium salt hydrate Form C. In some embodiments, the crystalline form of Compound I is sodium salt hydrate Form D.

In some embodiments, the crystalline form of Compound I is sodium salt (neat) Form B.

In some embodiments, the crystalline form of Compound I is a potassium salt hydrate. In some embodiments, the crystalline form of Compound I is potassium salt hydrate Form A. In some embodiments, the crystalline form of Compound I is potassium salt hydrate Form B. In some embodiments, the crystalline form of Compound I is potassium salt hydrate Form C. In some embodiments, the crystalline form of Compound I is potassium salt hydrate Form D.

In some embodiments the crystalline form of Compound I is ammonia salt hydrate Form A.

Other aspects of the disclosure provide pharmaceutical compositions comprising Compound I in any of the pharmaceutically acceptable crystalline forms disclosed herein, which compositions may further include at least one additional active pharmaceutical ingredient and/or at least one carrier. Yet other aspects of the disclosure are methods of treating the CFTR-mediated disease cystic fibrosis comprising administering Compound I in any of the pharmaceutically acceptable crystalline forms disclosed herein, optionally as part of a pharmaceutical composition comprising at least one additional component (such as a carrier or additional active agent), to a subject in need thereof. A further aspect of the disclosure provides processes of making the crystalline forms of Compound I disclosed herein.

One embodiment provides a method of treating the CFTR-mediated disease cystic fibrosis comprising administering (14S)-8-[3-(2-{Dispiro[2.0.2.1]heptan-7-yl}ethoxy)-1H-pyrazol-1-yl]-12,12-dimethyl-2$\lambda$6-thia-3,9,11,18,23-pentaazatetracyclo [17.3.1.111,14.05,10]tetracosa-1(22),5,7,9,19(23),20-hexaene-2,2,4-trione (Compound I) as one of the pharmaceutically acceptable crystalline forms disclosed herein, alone or in combination with (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide (Compound II), and/or N-[2,4-bis(1,1-dimethylethyl)-5-hydroxyphenyl]-1,4-dihydro-4-oxoquinoline-3-carboxamide (Compound III) or N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (Compound III-d).

In certain embodiments, the method of treating the CFTR-mediated disease cystic fibrosis comprises administering Compound I in one of the pharmaceutically acceptable crystalline forms disclosed herein, in combination with Compound III or III-d and 3-(6-(1-(2,2-difluorobenzo[d][1,3]dioxol-5-yl)cyclopropanecarboxamido)-3-methylpyridin-2-yl)benzoic acid (Compound IV).

In some embodiments, Compound I in one of the pharmaceutically acceptable crystalline forms disclosed herein, is administered in the same composition with Compound II and Compound III. In some embodiments, Compound I in one of the pharmaceutically acceptable crystalline forms disclosed herein, is administered in the same composition with Compound II and Compound III-d. In some embodiments, Compound I in one of the pharmaceutically acceptable crystalline forms disclosed herein, is administered in the same composition with Compound III and Compound IV. In some embodiments, Compound I in one of the pharmaceutically acceptable crystalline forms disclosed herein, is administered in the same composition with Compound III-d and Compound IV.

In some embodiments, a composition comprising Compound I in one of the pharmaceutically acceptable crystalline forms disclosed herein is co-administered with a separate composition comprising Compound II and/or Compound III. In some embodiments, a composition comprising Compound I in one of the pharmaceutically acceptable crystalline forms disclosed herein is co-administered with a separate composition comprising Compound II and/or Compound III-d. In some embodiments, a composition comprising Compound I in one of the pharmaceutically acceptable crystalline forms disclosed herein is co-administered with a separate composition comprising Compound III and Compound IV. In some embodiments, a composition comprising Compound I in one of the pharmaceutically acceptable crystalline forms disclosed herein is co-administered with a separate composition comprising Compound III-d and Compound IV.

BRIEF DESCRIPTION OF THE FIGURES

FIG. 21A represents a wet sample of Compound I calcium salt IPA solvate Form A. FIG. 21B represents an air-dried sample of Compound I calcium salt IPA solvate Form B.

FIG. 22A represents a wet sample of Compound I calcium salt NPA solvate Form A. FIG. 22B represents an air-dried sample of Compound I calcium salt NPA solvate Form B.

FIG. 23A represents a wet sample of Compound I calcium salt 2-BuOH solvate Form A. FIG. 23B represents an air-dried sample of Compound I calcium salt 2-BuOH solvate Form B.

DEFINITION

Figure 1:
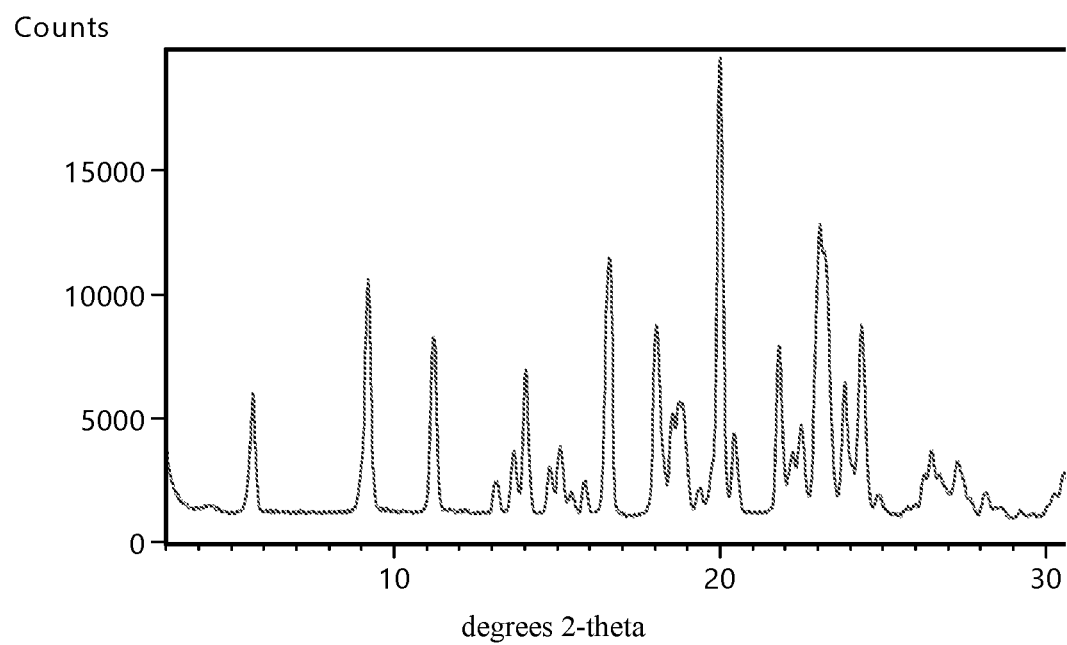
FIG. 1 provides an XRPD pattern of crystalline Compound I (free form) Form A.

"Compound I" as used throughout this disclosure refers to (14S)-8-[3-(2-{Dispiro[2.0.2.1]heptan-7-yl}ethoxy)-1H-pyrazol-1-yl]-12,12-dimethyl-2λ6-thia-3,9,11,18,23-pentaazatetracyclo[17.3.1.111,14.05,10]tetracosa-1(22),5,7,9,19(23),20-hexaene-2,2,4-trione, which can be depicted as having the following structure:

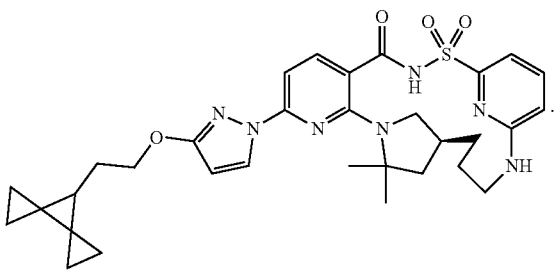

I

Compound I may be a racemic mixture or an enantioenriched (e.g., >90% ee, >95% ee, >98% ee) mixture of isomers. Compound I may be in the form of a pharmaceutically acceptable salt, solvate, and/or hydrate. Compound I and methods for making and using Compound I are disclosed in WO 2019/161078, incorporated herein by reference.

"Compound II" as used throughout this disclosure refers to (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, which can be depicted as having the following structure:

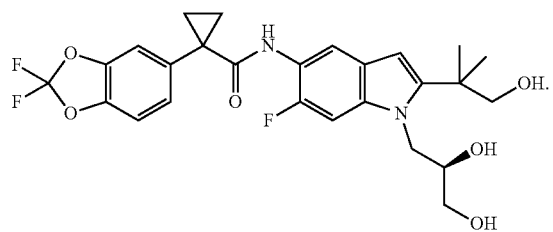

II

Compound II may be in the form of a pharmaceutically acceptable salt. Compound II and methods of making and using Compound II are disclosed in WO 2010/053471, WO 2011/119984, and WO 2015/160787, each incorporated herein by reference.

"Compound III" as used throughout this disclosure refers to N-[2,4-bis(1,1-dimethylethyl)-5-hydroxyphenyl]-1,4-dihydro-4-oxoquinoline-3-carboxamide (also known as N-(5-hydroxy-2,4-di-tert-butyl-phenyl)-4-oxo-1H-quinoline-3-carboxamide) which can be depicted as having the following structure:

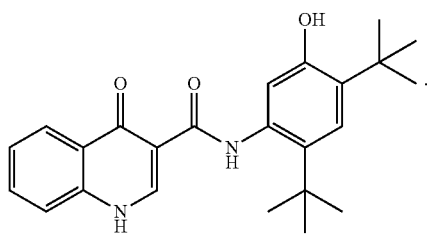

III

Compound III may also be in the form of a pharmaceutically acceptable salt. Compound III and methods of making and using Compound III are disclosed in WO 2006/002421, WO 2007/079139, and WO 2010/019239, each incorporated herein by reference.

In some embodiments, a deuterated derivative of Compound III (Compound III-d) is employed in the compositions and methods disclosed herein. A chemical name for Compound III-d is N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide, which can be depicted as having the following structure:

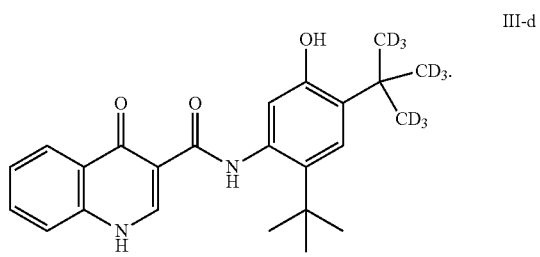 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

III-d

Compound III-d may be in the form of a pharmaceutically acceptable salt. Compound III-d and methods of making and using Compound III-d are disclosed in WO 2012/158885 and WO 2014/078842, incorporated herein by reference.

"Compound IV" as used herein, refers to 3-(6-(1-(2,2-difluorobenzol[d][1,3]dioxol-5-yl)cyclopropanecarboxamido)-3-methylpyridin-2-yl)benzoic acid, which can be depicted as having the following structure:

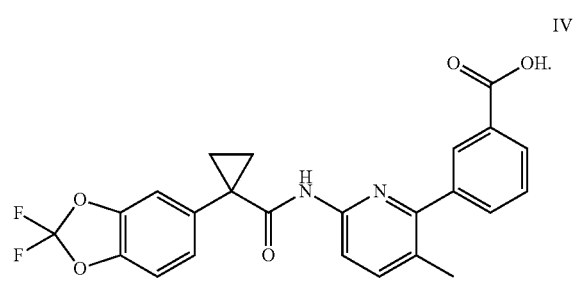 [SMILES: Cc1ccc(NC(=O)C2(c3ccc4c(c3)OC(F)(F)O4)CC2)nc1-c1cccc(C(=O)O)c1]

IV

Compound IV may be in the form of a pharmaceutically acceptable salt. Compound IV and methods of making and using Compound IV are disclosed in WO 2007/056341, WO 2009/073757, and WO 2009/076142, incorporated herein by reference.

As used herein, "CFTR" means cystic fibrosis transmembrane conductance regulator.

As used herein, the terms "CFTR modulator" and "CFTR modulating compound" interchangeably refer to a compound that increases the activity of CFTR. The increase in activity resulting from a CFTR modulator includes but is not limited to compounds that correct, potentiate, stabilize, and/or amplify CFTR.

As used herein, the term "CFTR corrector" refers to a compound that facilitates the processing and trafficking of CFTR to increase the amount of CFTR at the cell surface. Compounds I and II disclosed herein are CFTR correctors.

As used herein, the term "CFTR potentiator" refers to a compound that increases the channel activity of CFTR protein located at the cell surface, resulting in enhanced ion transport. Compound III and III-d disclosed herein are CFTR potentiators. It will be appreciated that when a description of a combination of Compound I and other specified CFTR modulating agents is provided herein, reference to "Compound III or III-d" in connection with the combination means that either Compound III or Compound III-d, but not both, is included in the combination.

As used herein, the term "active pharmaceutical ingredient" or "therapeutic agent" ("API") refers to a biologically active compound.

As used herein, the term "pharmaceutically acceptable crystalline form" refers to a crystalline form of Compound I of this disclosure wherein the crystalline form (e.g., crystalline free form, crystalline salt, crystalline salt solvate, and crystalline salt hydrate) of Compound I is nontoxic and suitable for use in pharmaceutical compositions.

The terms "patient" and "subject" are used interchangeably and refer to an animal including humans.

As used herein, the terms "treatment," "treating," and the like generally mean the improvement of CF or one or more of its symptoms or lessening the severity of CF or one or more of its symptoms in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrently with, or subsequent to each other.

The terms "about" and "approximately," when used in connection with doses, amounts, or weight percents of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. The terms "about" and "approximately" may refer to an acceptable error for a particular value as determined by one of skill in the art, which depends in part on how the values is measured or determined. In some embodiments, the terms "about" and "approximately" mean within 15%, 10%, 5%, 4%, 3%, 2%, 1%, or 0.5% of a given value or range.

As used herein, the term "amorphous" refers to a solid material having no long-range order in the position of its molecules. Amorphous solids are generally supercooled liquids in which the molecules are arranged in a random manner so that there is no well-defined arrangement, e.g., molecular packing, and no long-range order. Amorphous solids are generally isotropic, i.e., exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See, US 2004/0006237 for a comparison of XRPDs of an amorphous material and crystalline material. In some embodiments, a solid material may comprise an amorphous compound, and the material may, for example, be characterized by a lack of sharp characteristic crystalline peak(s) in its XRPD spectrum (i.e., the material is not crystalline, but is amorphous, as determined by XRPD). Instead, one or several broad peaks (e.g., halos) may appear in the XRPD pattern of the material. See US 2004/0006237 for a comparison of XRPDs of an amorphous material and crystalline material. A solid material, comprising an amorphous compound, may be characterized by, for example, a wider temperature range for the melting of the solid material, as compared to the range for the melting of a pure crystalline solid. Other techniques, such as, for example, solid state NMR may also be used to characterize crystalline or amorphous forms.

As used herein, the terms "crystal form," "crystalline form," and "Form" interchangeably refer to a crystal structure (or polymorph) having a particular molecular packing arrangement in the crystal lattice. Crystalline forms can be identified and distinguished from each other by one or more characterization techniques including, for example, X-ray powder diffraction (XRPD), single crystal X-ray diffraction, and $^{13}C$ solid state nuclear magnetic resonance ($^{13}C$ ssNMR). Accordingly, as used herein, the terms "crystalline Form [X] of Compound (I)" and "crystalline Form [C] potassium salt of Compound (I)" refer to unique crystalline forms that can be identified and distinguished from each other by one or more characterization techniques including, for example, XRPD, single crystal X-ray diffraction, and $^{13}C$ ssNMR. In some embodiments, the novel crystalline forms are characterized by an X-ray powder diffractogram having one or more signals at one or more specified two-theta values (°2θ).

As used herein, the term "free form" refers to a non-ionized version of the compound in the solid state. Examples of free forms include free bases and free acids.

As used herein, the term "solvate" refers to a crystal form comprising one or more molecules of a compound of the present disclosure and, incorporated into the crystal lattice, one or more molecules of a solvent or solvents in stoichiometric or nonstoichiometric amounts. When the solvent is water, the solvate is referred to as a "hydrate."

In some embodiments, a solid material may comprise a mixture of crystalline solids and amorphous solids. A solid material comprising an amorphous compound may also, for example, contain up to 30% of a crystalline solid. In some embodiments, a solid material prepared to comprise an amorphous compound may also, for example, contain up to 25%, 20%, 15%, 10%, 5%, or 2% of a crystalline solid. In embodiments wherein the solid material contains a mixture of crystalline solids and amorphous solids, the characterizing data, such as XRPD, may contain indicators of both crystalline and amorphous solids. In some embodiments, a crystalline form of this disclosure may contain up to 30% amorphous compound. In some embodiments, a crystalline preparation of Compound I may contain up to 25%, 20%, 15%, 10%, 5%, or 2% of an amorphous solid.

As used herein, the term "substantially amorphous" refers to a solid material having little or no long-range order in the position of its molecules. For example, substantially amorphous materials have less than 15% crystallinity (e.g., less than 10% crystallinity, less than 5% crystallinity, or less than 2% crystallinity). It is also noted that the term "substantially amorphous" includes the descriptor, "amorphous," which refers to materials having no (0%) crystallinity.

As used herein, the term "substantially crystalline" refers to a solid material having little or no amorphous molecules. For example, substantially crystalline materials have less than 15% amorphous molecules (e.g., less than 10% amorphous molecules, less than 5% amorphous molecules, or less than 2% amorphous molecules). It is also noted that the term "substantially crystalline" includes the descriptor "crystalline," which refers to materials that are 100% crystalline form.

As used herein, a crystalline form is "substantially pure" when it accounts for an amount by weight equal to or greater than 90% of the sum of all solid form(s) in a sample as determined by a method in accordance with the art, such as quantitative XRPD. In some embodiments, the solid form is "substantially pure" when it accounts for an amount by weight equal to or greater than 95% of the sum of all solid form(s) in a sample. In some embodiments, the solid form is "substantially pure" when it accounts for an amount by weight equal to or greater than 99% of the sum of all solid form(s) in a sample.

As used herein, the term "XRPD" refers to the analytical characterization method of X-ray powder diffraction. XRPD patterns disclosed herein were recorded at ambient conditions in transmission or reflection geometry using a diffractometer.

As used herein, the term "ambient conditions" means room temperature, open air condition and uncontrolled humidity condition. The terms "room temperature" and "ambient temperature" mean 15° C. to 30° C.

As used herein, the terms "X-ray powder diffractogram," "X-ray powder diffraction pattern," "XRPD pattern," "XRPD spectrum" interchangeably refer to an experimentally obtained pattern plotting signal positions (on the abscissa) versus signal intensities (on the ordinate). For an amorphous material, an X-ray powder diffractogram may include one or more broad signals; and for a crystalline material, an X-ray powder diffractogram may include one or more signals, each identified by its angular value as measured in degrees $2\theta(° 2\theta)$, depicted on the abscissa of an X-ray powder diffractogram, which may be expressed as "a signal at . . . degrees two-theta," "a signal at [a] two-theta value(s) of . . . " and/or "a signal at at least . . . two-theta value(s) selected from . . . "

A "signal" or "peak" as used herein refers to a point in the XRPD pattern where the intensity as measured in counts is at a local maximum. One of ordinary skill in the art would recognize that one or more signals (or peaks) in an XRPD pattern may overlap and may, for example, not be apparent to the naked eye. Indeed, one of ordinary skill in the art would recognize that some art-recognized methods are capable of and suitable for determining whether a signal exists in a pattern, such as Rietveld refinement.

As used herein, "a signal at . . . degrees two-theta" refer to X-ray reflection positions as measured and observed in X-ray powder diffraction experiments (° $2\theta$).

The repeatability of the measured angular values is in the range of $\pm 0.2°2\theta$, i.e., the angular value can be at the recited angular value +0.2 degrees two-theta, the angular value −0.2 degrees two-theta, or any value between those two end points (angular value +0.2 degrees two-theta and angular value −0.2 degrees two-theta).

The terms "signal intensities" and "peak intensities" interchangeably refer to relative signal intensities within a given X-ray powder diffractogram. Factors that can affect the relative signal or peak intensities include sample thickness and preferred orientation (e.g., the crystalline particles are not distributed randomly).

As used herein, an X-ray powder diffractogram is "substantially similar to that in [a particular] Figure" when at least 90%, such as at least 95%, at least 98%, or at least 99%, of the signals in the two diffractograms overlap. In determining "substantial similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta) generally mean that value is identified as ±0.2 degrees two-theta of the reported value, an art-recognized variance.

As used herein, a $^{13}C$ solid state nuclear magnetic resonance (ssNMR) spectrum is "substantially similar to that in [a particular] Figure" when at least 90%, such as at least 95%, at least 98%, or at least 99%, of the signals in the two spectra overlap. In determining "substantial similarity," one of ordinary skill in the art will understand that there may be variation in the intensities and/or signal positions in ssNMR spectra even for the same crystalline form. Thus, those of ordinary skill in the art will understand that the chemical shifts in ssNMR spectra (in parts per million (ppm) referred to herein) generally mean that value is identified as ±0.2 ppm of the reported value, an art-recognized variance.

The term "X-ray powder diffractogram having a signal at . . . two-theta values" as used herein refers to an XRPD pattern that contains X-ray reflection positions as measured and observed in X-ray powder diffraction experiments (° two-theta).

As used herein, the term "DSC" refers to the analytical method of Differential Scanning Calorimetry.

As used herein, the term "solvent" refers to any liquid in which the product is at least partially soluble (solubility of product >1 g/l).

As used herein, the term "dispersion" refers to a disperse system in which one substance, the dispersed phase, is distributed, in discrete units, throughout a second substance (the continuous phase or vehicle). The size of the dispersed phase can vary considerably (e.g., colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase); or alternatively, an amorphous drug (dispersed phase) in an amorphous polymer (continuous phase). In some embodiments, a solid dispersion includes the polymer constituting the dispersed phase, and the drug constitute the continuous phase. Or, a solid dispersion includes the drug constituting the dispersed phase, and the polymer constituting the continuous phase.

It is noted that the disclosed amounts of the Compound I is based upon its Ca salt. One of ordinary skill in the art would recognize that, when an amount of a Compound I is disclosed, it also refers to the amount of a crystalline form Compound I that is equivalent or bioequivalent to the concentration of the Ca salt of Compound I. For example, "100 mg of Compound I" should be interpreted as also referring not only to 100 mg of Compound I (free form), but also to an amount of any one of the pharmaceutically acceptable crystalline forms disclosed herein that is equivalent or bioequivalent to 100 mg of Compound I Ca salt.

Compound I (Free Form) Crystalline Form A

In some embodiments, the invention provides crystalline Compound I (free form) Form A. FIG. 1 provides an X-ray powder diffractogram of crystalline Compound I (free form) Form A at room temperature.

In some embodiments, Compound I (free form) is substantially pure crystalline Form A. In some embodiments, Compound I (free form) is substantially crystalline Form A. In some embodiments, crystalline Compound I (free form) Form A is characterized by an X-ray powder diffractogram generated by an X-ray powder diffraction analysis with an incident beam of Cu Kα radiation.

In some embodiments, crystalline Compound I (free form) Form A is characterized by an X-ray powder diffractogram having a signal at 9.2±0.2 degrees two-theta. In some embodiments, crystalline Compound I (free form) Form A is characterized by an X-ray powder diffractogram having a signal at 11.3±0.2 degrees two-theta. In some embodiments, crystalline Compound I (free form) Form A is characterized by an X-ray powder diffractogram having a signal at 14.0±0.2 degrees two-theta. In some embodiments, crystalline Compound I (free form) Form A is characterized by an X-ray powder diffractogram having a signal at 22.9±0.2 degrees two-theta. In some embodiments crystalline Compound I (free form) Form A is characterized by an X-ray powder diffractogram having at least one signal selected from 9.2±0.2 degrees two-theta, 11.3±0.2 degrees two-theta, 14.0±0.2 degrees two-theta, and 22.9±0.2 degrees two-theta. In some embodiments crystalline Compound I (free form) Form A is characterized by an X-ray powder diffractogram having at least two signals selected from 9.2±0.2 degrees two-theta, 11.3±0.2 degrees two-theta, 14.0±0.2 degrees two-theta, and 22.9±0.2 degrees two-theta. In some embodiments crystalline Compound I (free form) Form A is characterized by an X-ray powder diffractogram having at least three signals selected from 9.2±0.2 degrees two-theta, 11.3±0.2 degrees two-theta, 14.0±0.2 degrees two-theta, and 22.9±0.2 degrees two-theta. In some embodiments crystalline Compound I (free form) Form A is characterized by an X-ray powder diffractogram having signals at 9.2±0.2 degrees two-theta, 11.3±0.2 degrees two-theta, 14.0±0.2 degrees two-theta, and 22.9±0.2 degrees two-theta.

In some embodiments crystalline Compound I (free form) Form A is characterized by an X-ray powder diffractogram having (a) a signal at 9.2±0.2 degrees two-theta, 11.3±0.2 degrees two-theta, 14.0±0.2 degrees two-theta, and/or 22.9±0.2 degrees two-theta (i.e., one or more signals from this group); and (b) one, two, three, or four signals selected from 20.0±0.2 degrees two-theta, 23.1±0.2 degrees two-theta, 16.6±0.2 degrees two-theta, and 23.3±0.2 degrees two-theta.

In some embodiments crystalline Compound I (free form) Form A is characterized by an X-ray powder diffractogram having (a) a signal at 9.2±0.2 degrees two-theta; (b) a signal at 16.6±0.2 degrees two-theta; and (c) a signal at 20.0±0.2 degrees two-theta. In some embodiments crystalline Compound I (free form) Form A is characterized by an X-ray powder diffractogram having (a) signals at 9.2±0.2 degrees two-theta, 16.6±0.2 degrees two-theta, and 20.0±0.2 degrees two-theta; and (b) signals at 11.3±0.2 degrees two-theta, 14.0±0.2 degrees two-theta, and/or 22.9±0.2 degrees two-theta.

In some embodiments crystalline Compound I (free form) Form A is characterized by an X-ray powder diffractogram having (a) signals at 9.2±0.2 degrees two-theta, 16.6±0.2 degrees two-theta, and 20.0±0.2 degrees two-theta; and (b) one, two, three, four, five, or more signals selected from 11.3±0.2 degrees two-theta, 14.0±0.2 degrees two-theta, 18.1±0.2 degrees two-theta, 22.9±0.2 degrees two-theta, 23.1±0.2 degrees two-theta, and 23.3±0.2 degrees two-theta. In some embodiments crystalline Compound I (free form) Form A is characterized by an X-ray powder diffractogram having signals at 9.2±0.2 degrees two-theta, 16.6±0.2 degrees two-theta, 20.0±0.2 degrees two-theta, 11.3±0.2 degrees two-theta, 14.0±0.2 degrees two-theta, 18.1±0.2 degrees two-theta, 22.9±0.2 degrees two-theta, 23.1±0.2 degrees two-theta, and 23.3±0.2 degrees two-theta.

In some embodiments, crystalline Compound I (free form) Form A is characterized by an X-ray powder diffractogram substantially similar to FIG. 1.

In some embodiments, crystalline Compound I (free form) Form A is characterized as having a $^{13}C$ solid state nuclear magnetic resonance ($^{13}C$ ssNMR) spectrum with one, two, three, four, five, six, seven, or more peaks selected from 163.2±0.2 ppm, 130.2±0.2 ppm, 104.6±0.2 ppm, 103.9±0.2 ppm, 58.3±0.2 ppm, 49.7±0.2 ppm, 43.3±0.2 ppm, and 37.0±0.2 ppm. In some embodiments, crystalline Compound I (free form) Form A is characterized as having a $^{13}C$ ssNMR spectrum with peaks at 163.2±0.2 ppm, 130.2±0.2 ppm, 104.6±0.2 ppm, 103.9±0.2 ppm, 58.3±0.2 ppm, 49.7±0.2 ppm, 43.3±0.2 ppm, and 37.0±0.2 ppm.

Figure 2:
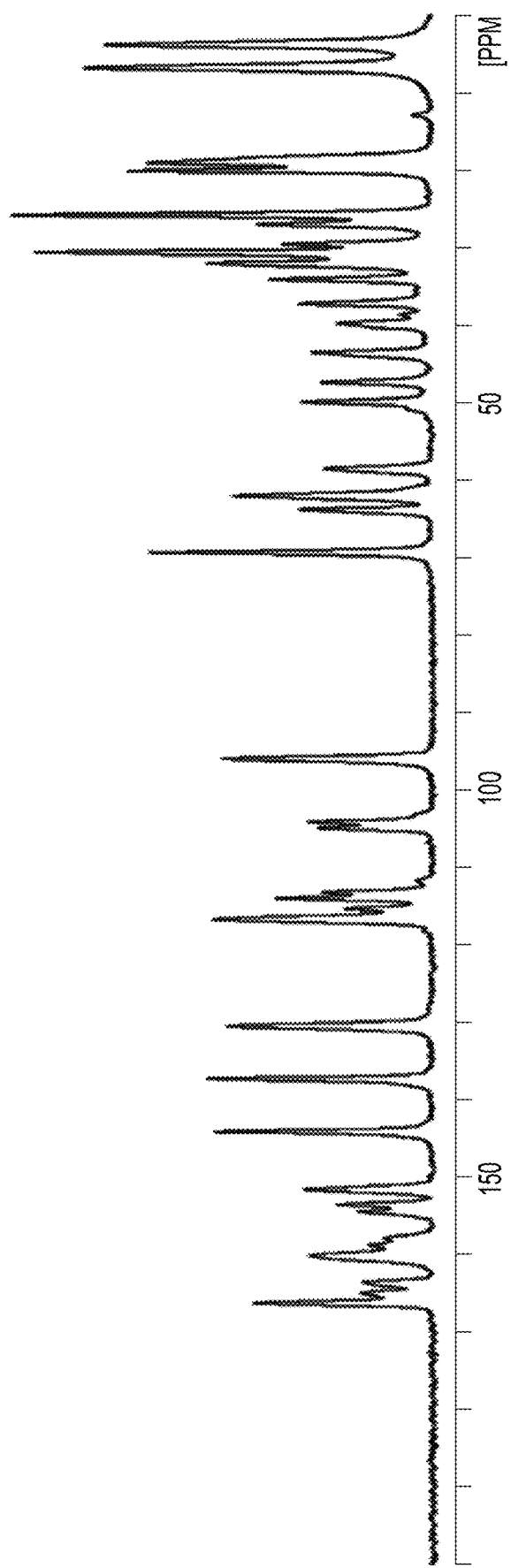
FIG. 2 shows a $^{13}$C solid state NMR spectrum of crystalline Compound I (free form) Form A.

In some embodiments, crystalline Compound I (free form) Form A is characterized by a $^{13}C$ ssNMR spectrum substantially similar to FIG. 2.

In some embodiments, crystalline Compound I (free form) Form A is characterized by a monoclinic crystal system, a $P2_1$ space group, and the following unit cell dimensions measured at 298 K on a Bruker diffractometer equipped with Mo $K_\alpha$ radiation ($\lambda=0.71073$ Å) and a (charge coupled device) CCD detector:

| | | | |
|---|---|---|---|
| a | 15.48 ± .01 Å | α | 90° |
| b | 12.74 ± .01 Å | β | 99.35 ± .01° |
| c | 16.37 ± .01 Å | γ | 90° |

Other aspects of the invention provide methods of making crystalline Compound I (free form) Form A comprising crystallizing amorphous Compound I in toluene and drying under vacuum to provide Compound I (free form) crystalline Form A.

Compound I (Free Form) Crystalline Form B

Figure 3:
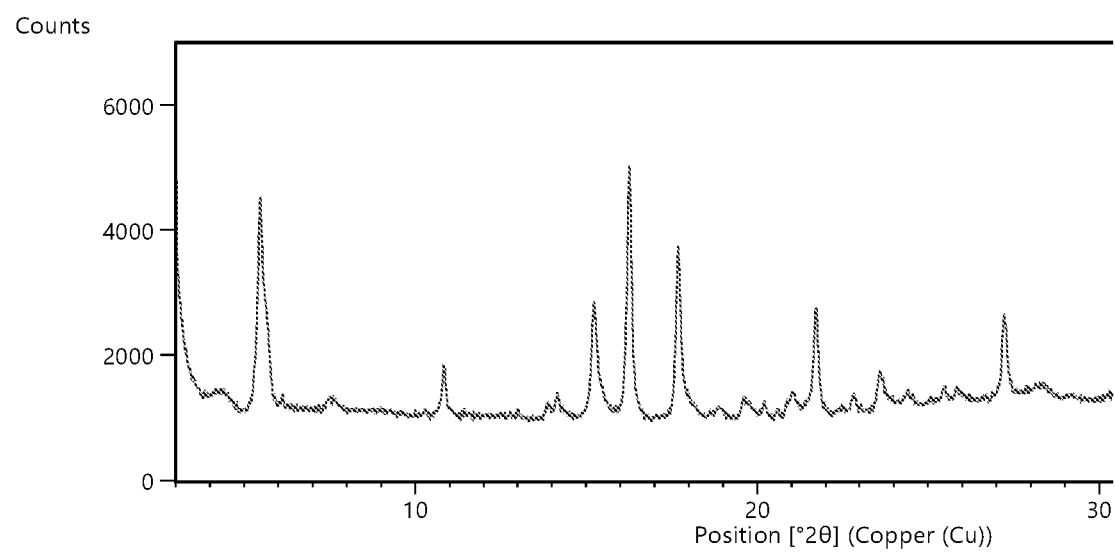
FIG. 3 provides an XRPD pattern of crystalline Compound I (free form) Form B.

In some embodiments, the invention provides crystalline Compound I (free form) Form B. FIG. 3 provides an X-ray powder diffractogram of crystalline Compound I (free form) Form B at room temperature.

In some embodiments, Compound I (free form) is substantially pure crystalline Form B. In some embodiments, Compound I (free form) is substantially crystalline Form B. In some embodiments, crystalline Compound I (free form) Form B is characterized by an X-ray powder diffractogram generated by an X-ray powder diffraction analysis with an incident beam of Cu Kα radiation.

In some embodiments, crystalline Compound I (free form) Form B is characterized by an X-ray powder diffractogram having a signal at 16.3±0.2 degrees two-theta. In some embodiments, crystalline Compound I (free form) Form B is characterized by an X-ray powder diffractogram having a signal at 17.7±0.2 degrees two-theta. In some embodiments, crystalline Compound I (free form) Form B is characterized by an X-ray powder diffractogram having signals at 16.3±0.2 degrees two-theta and 17.7±0.2 degrees two-theta. In some embodiments, crystalline Compound I (free form) Form B is characterized by an X-ray powder diffractogram having signals at 5.5±0.2 degrees two-theta, 16.3±0.2 degrees two-theta, and 17.7±0.2 degrees two-theta.

In some embodiments, crystalline Compound I (free form) Form B is characterized by an X-ray powder diffractogram having (a) a signal at 5.5±0.2 degrees two-theta, 16.3±0.2 degrees two-theta, and 17.7±0.2 degrees two-theta; and (b) one or more peaks selected from 10.8±0.2 degrees two-theta, 28.3±0.2 degrees two-theta, and 25.9±0.2 degrees two-theta. In some embodiments, crystalline Compound I (free form) Form B is characterized by an X-ray powder diffractogram having (a) a signal at 5.5±0.2 degrees two-theta, a signal at 16.3±0.2 degrees two-theta, and a signal at 17.7±0.2 degrees two-theta; and (b) two or more peaks selected from 10.8±0.2 degrees two-theta, 28.3±0.2 degrees two-theta, and 25.9±0.2 degrees two-theta. In some embodiments, crystalline Compound I (free form) Form B is characterized by an X-ray powder diffractogram having signals at 5.5±0.2 degrees two-theta, 16.3±0.2 degrees two-theta, 17.7±0.2 degrees two-theta, 10.8±0.2 degrees two-theta, 28.3±0.2 degrees two-theta, and 25.9±0.2 degrees two-theta.

In some embodiments crystalline Compound I (free form) Form B is characterized by an X-ray powder diffractogram substantially similar to FIG. 3.

In some embodiments, crystalline Compound I (free form) Form B is characterized as having a $^{13}$C ssNMR spectrum with one or more peaks selected from: 142.8±0.2 ppm, 97.8±0.2 ppm, 18.1±0.2 ppm, and 2.3±0.2 ppm. In some embodiments, crystalline Compound I (free form) Form B is characterized as having a 13 C ssNMR spectrum with (a) two or more peaks selected from: 142.8±0.2 ppm, 97.8±0.2 ppm, 18.1±0.2 ppm, and 2.3±0.2 ppm; and (b) one, two, three, four, five or six peaks selected from 166.3±0.2 ppm, 137.2±0.2 ppm, 108.1±0.2 ppm, 37.6±0.2 ppm, 25.3±0.2 ppm, and 20.1±0.2 ppm. In some embodiments, crystalline Compound I (free form) Form B is characterized as having a $^{13}$C ssNMR spectrum with peaks selected from: 166.3±0.2 ppm, 142.8±0.2 ppm, 137.2±0.2 ppm, 108.1±0.2 ppm, 97.8±0.2 ppm, 37.6±0.2 ppm, 25.3±0.2 ppm, 20.1±0.2 ppm, 18.1±0.2 ppm, and 2.3±0.2 ppm.

Figure 4:
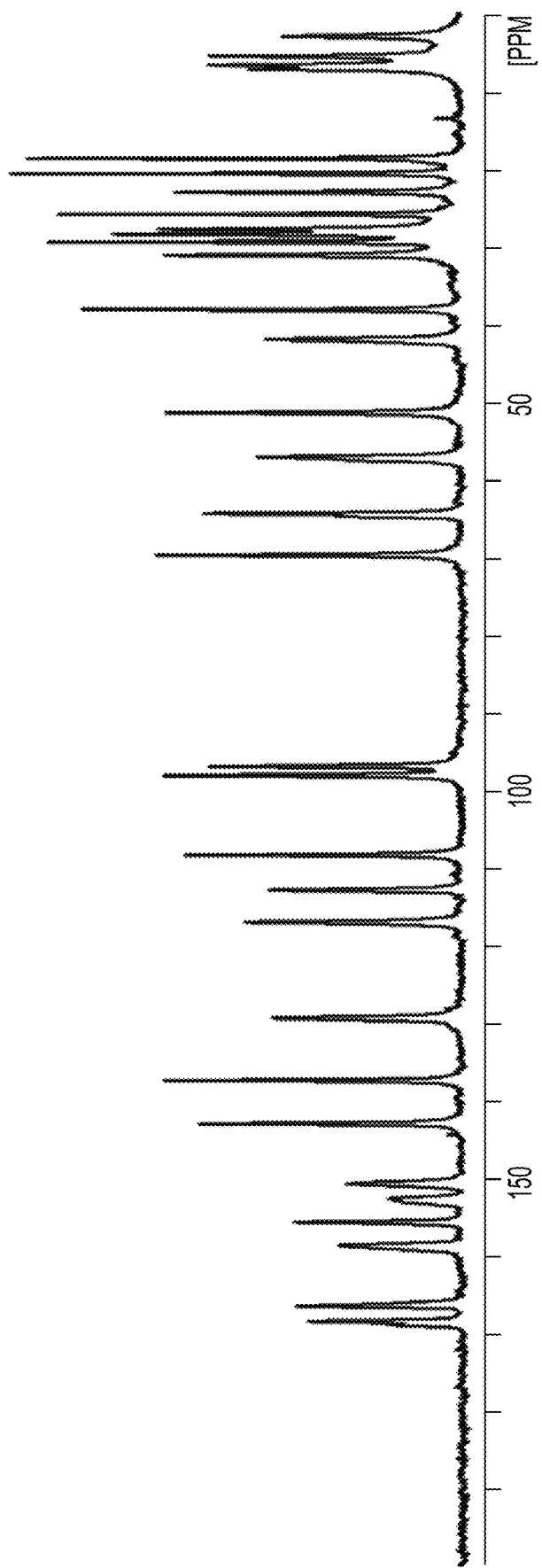
FIG. 4 shows a $^{13}$C solid state NMR spectrum of crystalline Compound I (free form) Form B.

In some embodiments, crystalline Compound I (free form) Form B is characterized by a $^{13}$C ssNMR spectrum substantially similar to FIG. 4.

Another aspect of the invention provides a method of making crystalline Compound I (free form) Form B comprising stirring Compound I calcium salt hydrate Form D in fed-state simulated intestinal fluid, centrifuging the resulting slurry, removing the liquid, and air-drying the solid to provide Compound I (free form) crystalline Form B.

Compound I (Free Form) Crystalline Form C

Figure 5:
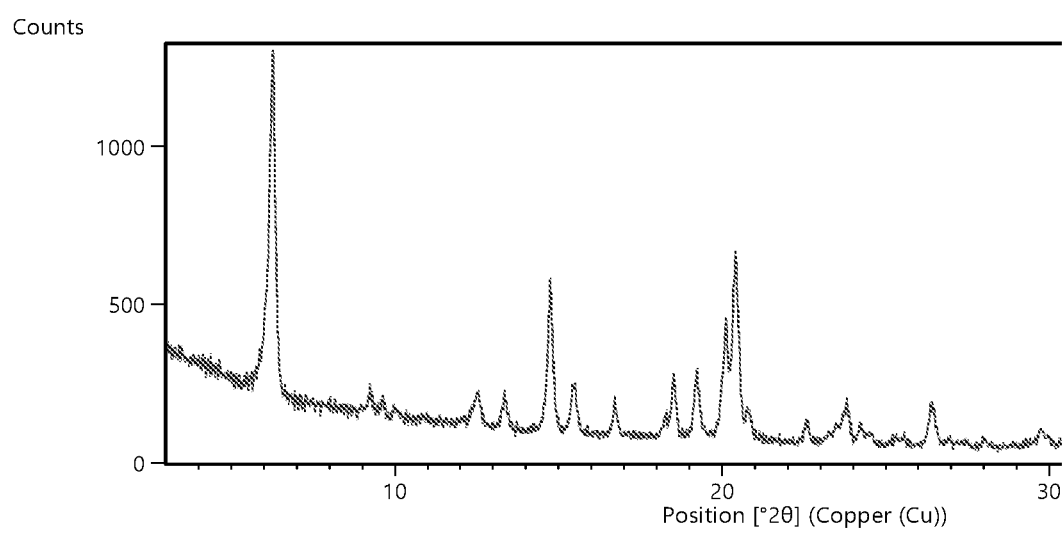
FIG. 5 provides an XRPD pattern of crystalline Compound I (free form) Form C.

In some embodiments, the invention provides crystalline Compound I (free form) Form C. FIG. 5 provides an X-ray powder diffractogram of crystalline Compound I (free form) Form C at room temperature.

In some embodiments, Compound I (free form) is substantially pure crystalline Form C. In some embodiments, Compound I (free form) is substantially crystalline Form C. In some embodiments, crystalline Compound I (free form) Form C is characterized by an X-ray powder diffractogram generated by an X-ray powder diffraction analysis with an incident beam of Cu Kα radiation.

In some embodiments, crystalline Compound I (free form) Form C is characterized by an X-ray powder diffractogram having a signal at 6.3±0.2 degrees two-theta. In some embodiments, crystalline Compound I (free form) Form C is characterized by an X-ray powder diffractogram having signals at 6.3±0.2 degrees two-theta, 14.8±0.2 degrees two-theta, and 20.4±0.2 degrees two-theta.

In some embodiments, crystalline Compound I (free form) Form C is characterized by an X-ray powder diffractogram having (a) signals at 6.3±0.2 degrees two-theta, 14.8±0.2 degrees two-theta, and 20.4±0.2 degrees two-theta; and (b) one or more signals selected from 15.5±0.2 degrees two-theta, 18.5±0.2 degrees two-theta, 19.2±0.2 degrees two-theta, 20.1±0.2 degrees two-theta, 23.8±0.2 degrees two-theta, and 26.4±0.2 degrees two-theta. In some embodiments, crystalline Compound I (free form) Form C is characterized by an X-ray powder diffractogram having (a) a signal at 6.3±0.2 degrees two-theta, 14.8±0.2 degrees two-theta, and 20.4±0.2 degrees two-theta; and (b) two, three, four, five, or six signals selected from 15.5±0.2 degrees two-theta, 18.5±0.2 degrees two-theta, 19.2±0.2 degrees two-theta, 20.1±0.2 degrees two-theta, 23.8±0.2 degrees two-theta, and 26.4±0.2 degrees two-theta. In some embodiments, crystalline Compound I (free form) Form C is characterized by an X-ray powder diffractogram having signals at 6.3±0.2 degrees two-theta, 14.8±0.2 degrees two-theta, 15.5±0.2 degrees two-theta, 18.5±0.2 degrees two-theta, 19.2±0.2 degrees two-theta, 20.1±0.2 degrees two-theta, 20.4±0.2 degrees two-theta, 23.8±0.2 degrees two-theta, and 26.4±0.2 degrees two-theta.

In some embodiments crystalline Compound I (free form) Form C is characterized by an X-ray powder diffractogram substantially similar to FIG. 5.

Another aspect of the invention provides a method of making Compound I (free form) crystalline Form C comprising stirring Compound I (free form) Form A in isopropyl alcohol (IPA)/H$_2$O at 25° C. to provide Compound I (free form) crystalline Form C.

Compound I (Free Form) Crystalline Form D

Figure 47:
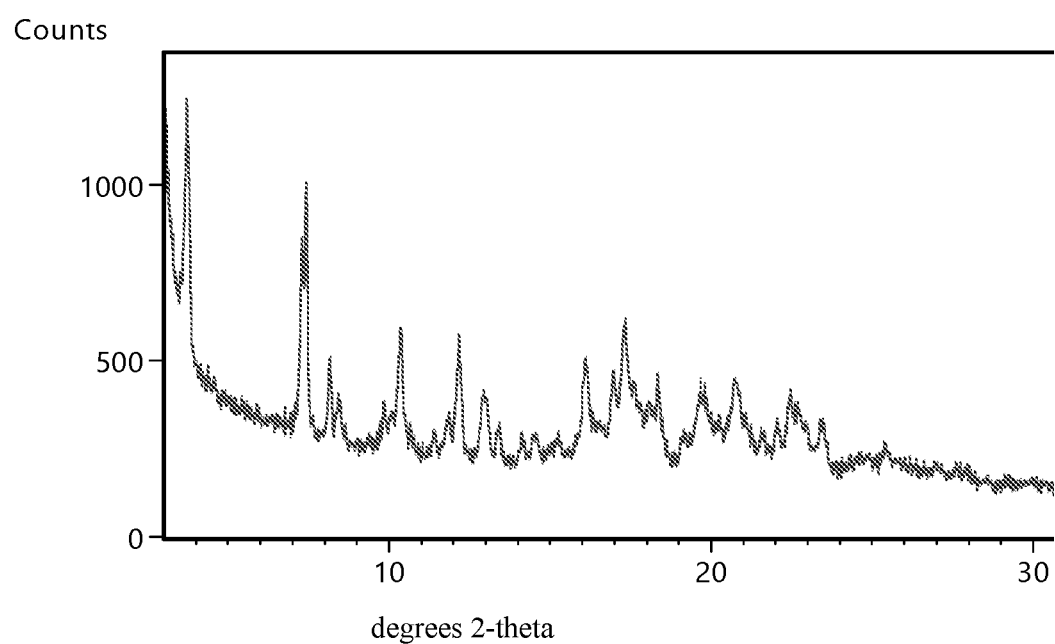
FIG. 47 provides an XRPD pattern of crystalline Compound I (free form) Form D.

In some embodiments, the invention provides crystalline Compound I (free form) Form D. FIG. 47 provides an X-ray powder diffractogram of crystalline Compound I (free form) Form D at room temperature.

In some embodiments, Compound I (free form) is substantially pure crystalline Form D. In some embodiments, Compound I (free form) is substantially crystalline Form D. In some embodiments, crystalline Compound I (free form) Form D is characterized by an X-ray powder diffractogram generated by an X-ray powder diffraction analysis with an incident beam of Cu Kα radiation.

In some embodiments, crystalline Compound I (free form) Form D is characterized by an X-ray powder diffractogram having a signal at 3.7±0.2 degrees two-theta. In some embodiments, crystalline Compound I (free form) Form D is characterized by an X-ray powder diffractogram having a signal at 7.4±0.2 degrees two-theta. In some embodiments, crystalline Compound I (free form) Form D is characterized by an X-ray powder diffractogram having a signal at 12.2±0.2 degrees two-theta. In some embodiments, crystalline Compound I (free form) Form D is characterized by an X-ray powder diffractogram having signals at 3.7±0.2 degrees two-theta, 7.4±0.2 degrees two-theta, and 12.2±0.2 degrees two-theta. In some embodiments, crystalline Compound I (free form) Form D is characterized by an X-ray powder diffractogram having signals at 3.7±0.2 degrees two-theta, 7.4±0.2 degrees two-theta, and 17.3±0.2 degrees two-theta. In some embodiments, crystalline Compound I (free form) Form D is characterized by an X-ray powder diffractogram having signals at 3.7±0.2 degrees two-theta, 7.4±0.2 degrees two-theta, 12.2±0.2 degrees two-theta, and 17.3±0.2 degrees two-theta.

In some embodiments, crystalline Compound I (free form) Form D is characterized by an X-ray powder diffractogram having (a) a signal at 3.7±0.2 degrees two-theta, 7.4±0.2 degrees two-theta, and/or 12.2±0.2 degrees two-theta (i.e., any one, any two, or all three from this group) and (b) a signal at 7.3±0.2 degrees two-theta, 17.3±0.2 degrees two-theta, and/or 10.4±0.2 degrees two-theta. In some embodiments, crystalline Compound I (free form) Form D is characterized by an X-ray powder diffractogram having (a) a signal at 3.7±0.2 degrees two-theta, 7.4±0.2 degrees two-theta, and/or 12.2±0.2 degrees two-theta and (b) a signal at 17.3±0.2 degrees two-theta and/or 10.4±0.2 degrees two-theta. In some embodiments crystalline Compound I (free form) Form D is characterized by an X-ray powder diffractogram having signala at 3.7±0.2 degrees two-theta, 7.4±0.2 degrees two-theta, 12.2±0.2 degrees two-theta, 17.3±0.2 degrees two-theta, and 10.4±0.2 degrees two-theta.

In some embodiments crystalline Compound I (free form) Form D is characterized by an X-ray powder diffractogram substantially similar to FIG. 47.

In some embodiments, crystalline Compound I (free form) Form D is characterized as having a $^{13}$C ssNMR spectrum with two or more peaks selected from: 164.6±0.2 ppm, 149.6±0.2 ppm, 135.7±0.2 ppm, 38.9±0.2 ppm, 27.6±0.2 ppm, and 15.7±0.2 ppm. In some embodiments, crystalline Compound I (free form) Form D is characterized as having a $^{13}$C ssNMR spectrum with three or more peaks selected from: 164.6±0.2 ppm, 149.6±0.2 ppm, 135.7±0.2 ppm, 113.6±0.2 ppm, 38.9±0.2 ppm, 27.6±0.2 ppm, and 15.7±0.2 ppm. In some embodiments, crystalline Compound I (free form) Form D is characterized as having a $^{13}$C ssNMR spectrum with four or more peaks selected from: 164.6±0.2 ppm, 149.6±0.2 ppm, 135.7±0.2 ppm, 113.6±0.2 ppm, 38.9±0.2 ppm, 27.6±0.2 ppm, and 15.7±0.2 ppm. In some embodiments, crystalline Compound I (free form) Form D is characterized as having a $^{13}$C ssNMR spectrum with five, six, seven, or eight peaks selected from: 164.6±0.2 ppm, 149.6±0.2 ppm, 135.7±0.2 ppm, 113.6±0.2 ppm, 38.9±0.2 ppm, 27.6±0.2 ppm, and 15.7±0.2 ppm.

Figure 48:
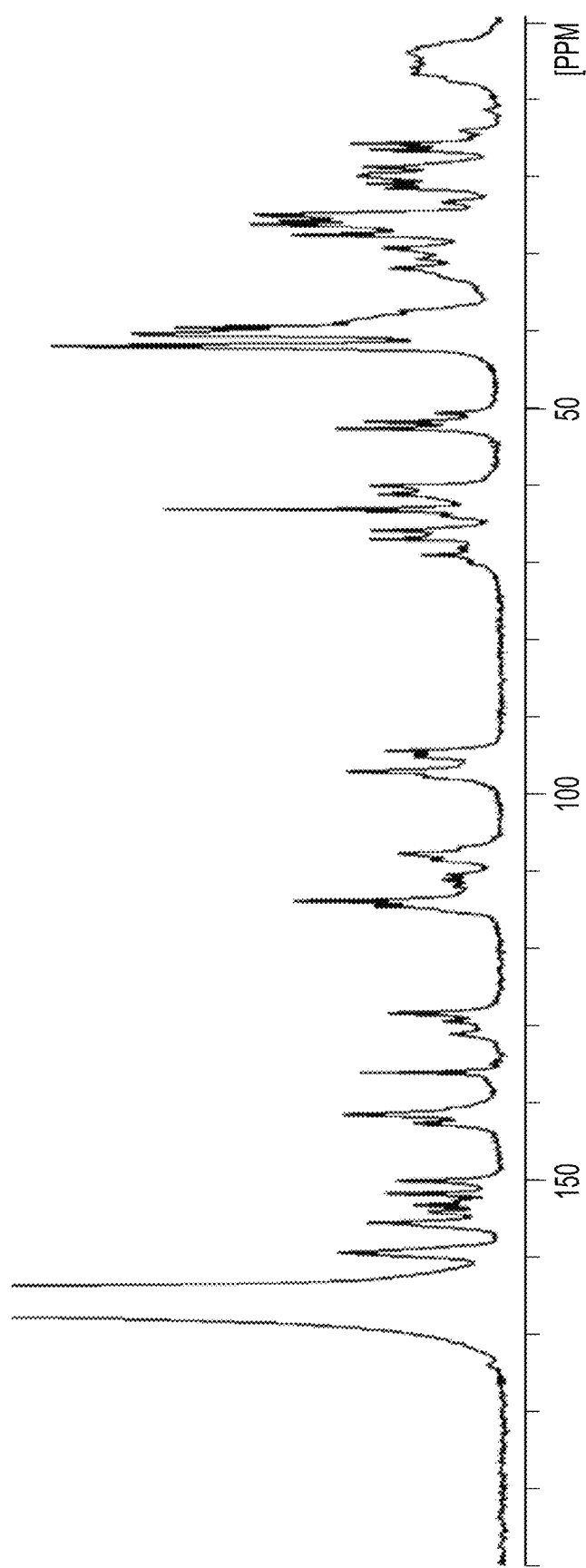
FIG. 48 shows a $^{13}$C solid state NMR spectrum of Compound I (free form) Form D.

In some embodiments, crystalline Compound I (free form) Form D is characterized by a $^{13}$C ssNMR spectrum substantially similar to FIG. 48.

Another aspect of the invention provides a method of making crystalline Compound I (free form) Form D comprising adding propanol to compound I (free form), concentrating the mixture under reduced pressure, and repeating the procedure using toluene.

Compound I Calcium Salt Hydrate Form A

Figure 6:
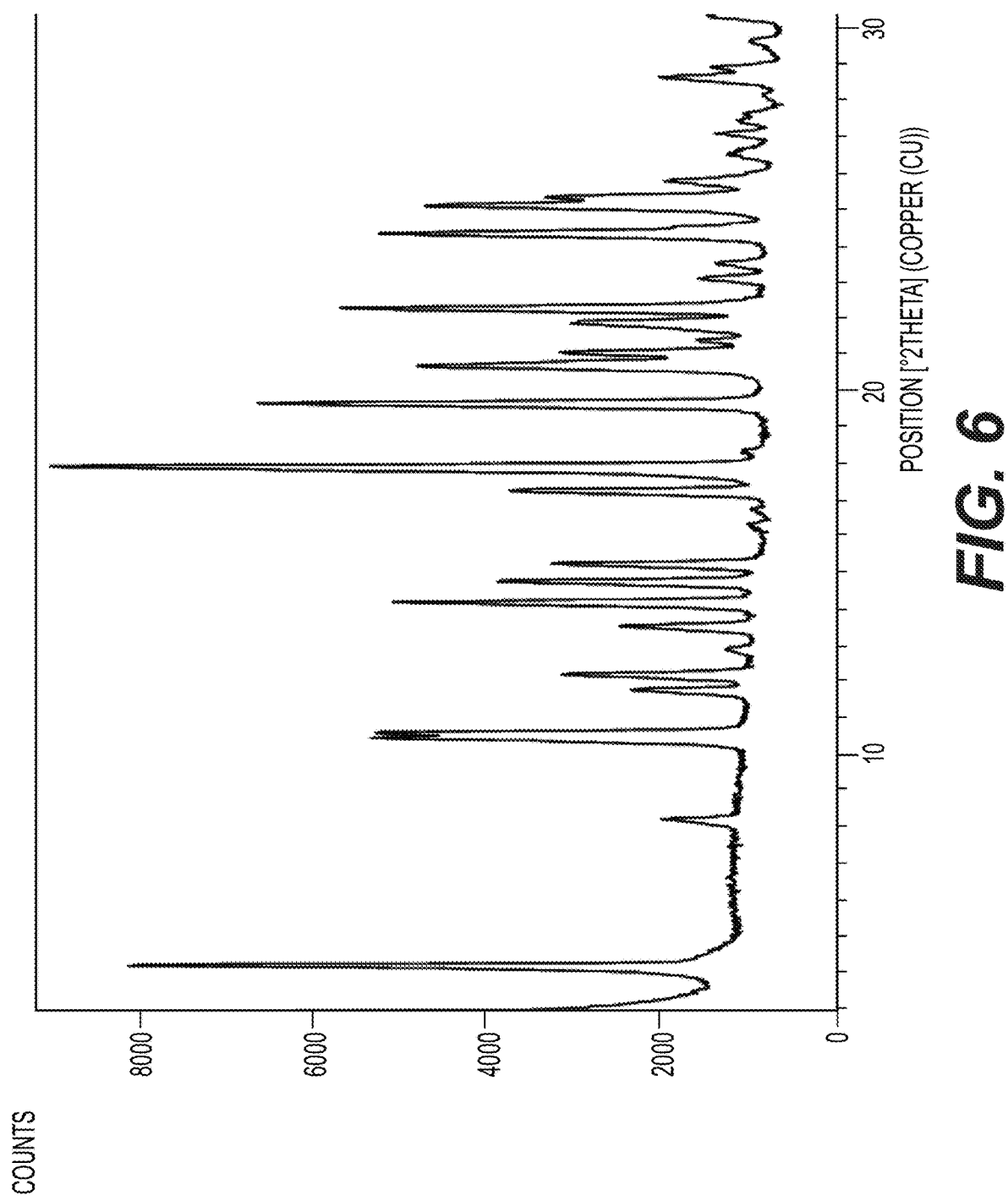
FIG. 6 provides an XRPD pattern of crystalline Compound I calcium salt hydrate Form A.

In some embodiments, the invention provides crystalline Compound I calcium salt hydrate Form A. FIG. 6 provides an X-ray powder diffractogram of Compound I calcium salt hydrate Form A at room temperature.

In some embodiments, Compound I calcium salt hydrate Form A is substantially pure crystalline. In some embodiments, Compound I calcium salt hydrate is substantially crystalline Form A. In some embodiments, Compound I calcium salt hydrate Form A is characterized by an X-ray powder diffractogram generated by an X-ray powder diffraction analysis with an incident beam of Cu Kα radiation.

In some embodiments, Compound I calcium salt hydrate Form A is characterized by an X-ray powder diffractogram having signals at 4.2±0.2 degrees two-theta, 18.0±0.2 degrees two-theta, and 19.7±0.2 degrees two-theta. In some embodiments, Compound I calcium salt hydrate Form A is characterized by an X-ray powder diffractogram having signals at (a) 4.2±0.2 degrees two-theta, 18.0±0.2 degrees two-theta, and 19.7±0.2 degrees two-theta; and (b) a signal at 10.5±0.2 degrees two-theta and/or 10.6±0.2 degrees two-theta.

In some embodiments Compound I calcium salt hydrate Form A is characterized by an X-ray powder diffractogram substantially similar to FIG. 6.

In some embodiments, Compound I calcium salt hydrate Form A is characterized as having a $^{13}$C ssNMR spectrum with a peak at 17.0±0.2 ppm or 7.8±0.2 ppm. In some embodiments, Compound I calcium salt hydrate Form A is characterized as having a $^{13}$C ssNMR spectrum with peaks at 17.0±0.2 ppm and 7.8±0.2 ppm. In some embodiments, Compound I calcium salt hydrate Form A is characterized as having a 13 C ssNMR spectrum with (a) peaks at one or both of 17.0±0.2 ppm and 7.8±0.2 ppm, and (b) one or more peaks selected from 178.3±0.2 ppm, 136.8±0.2 ppm, 93.6±0.2 ppm, and 26.4±0.2 ppm.

In some embodiments, Compound I calcium salt hydrate Form A is characterized as having a $^{13}$C ssNMR spectrum with (a) peaks at one or both of 17.0±0.2 ppm and 7.8±0.2 ppm, and (b) two or more peaks selected from 178.3±0.2 ppm, 136.8±0.2 ppm, 93.6±0.2 ppm, and 26.4±0.2 ppm. In some embodiments, Compound I calcium salt hydrate Form A is characterized as having a $^{13}$C ssNMR spectrum with (a) peaks at one or both of 17.0±0.2 ppm and 7.8±0.2 ppm, and (b) three or more peaks selected from 178.3±0.2 ppm, 136.8±0.2 ppm, 93.6±0.2 ppm, and 26.4±0.2 ppm. In some embodiments, Compound I calcium salt hydrate Form A is characterized as having a $^{13}$C ssNMR spectrum with peaks at 178.3±0.2 ppm, 136.8±0.2 ppm, 93.6±0.2 ppm, 26.4±0.2 ppm, 17.0±0.2 ppm, and 7.8±0.2 ppm.

Figure 7:
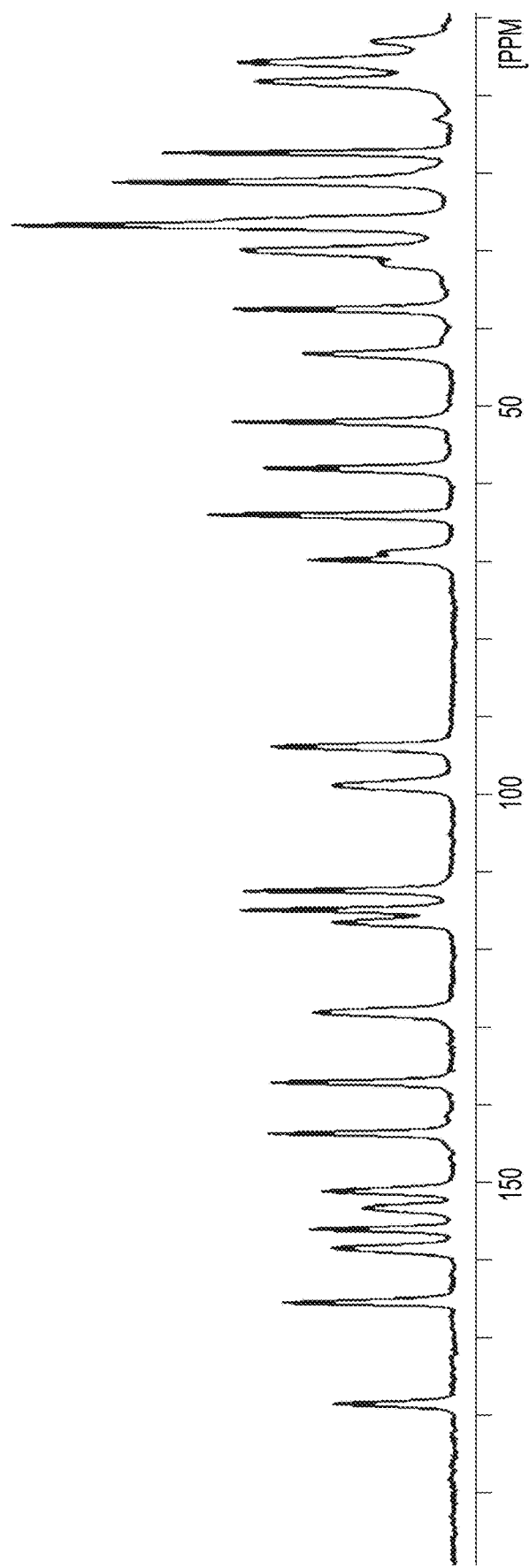
FIG. 7 shows a $^{13}$C solid state NMR spectrum of Compound I calcium salt hydrate Form A.

In some embodiments, Compound I calcium salt hydrate Form A is characterized by a $^{13}$C ssNMR spectrum substantially similar to FIG. 7.

In some embodiments, Compound I calcium salt hydrate Form A is characterized by a monoclinic crystal system, a C2 space group, and the following unit cell dimensions measured at 100 K on a Bruker diffractometer equipped with Cu K$_\alpha$ radiation (λ=1.5478 Å) and a CCD detector:

| a | 11.13 ± .01 Å | α | 90° |
| b | 13.77 ± .01 Å | β | 101.93 ± .01° |
| c | 22.21 ± .01 Å | γ | 90° |

In some embodiments, Compound I calcium salt hydrate Form A is characterized by a monoclinic crystal system, a C2 space group, and the following unit cell dimensions measured at 298 K on a Bruker diffractometer equipped with Cu K$_\alpha$ radiation (λ=1.5478 Å) and a CCD detector:

| a | 11.19 ± .01 Å | α | 90° |
| b | 13.88 ± .01 Å | β | 101.48 ± .01° |
| c | 22.41 ± .01 Å | γ | 90°. |

Another aspect of the invention provides a method of making Compound I calcium salt hydrate Form A comprising charging Compound I (free form) Form A and Ca(OMe)$_2$ with IPA/H$_2$O at 70° C. to provide Compound I calcium salt hydrate Form A.

Compound I Calcium Salt Hydrate Form B

Figure 8:
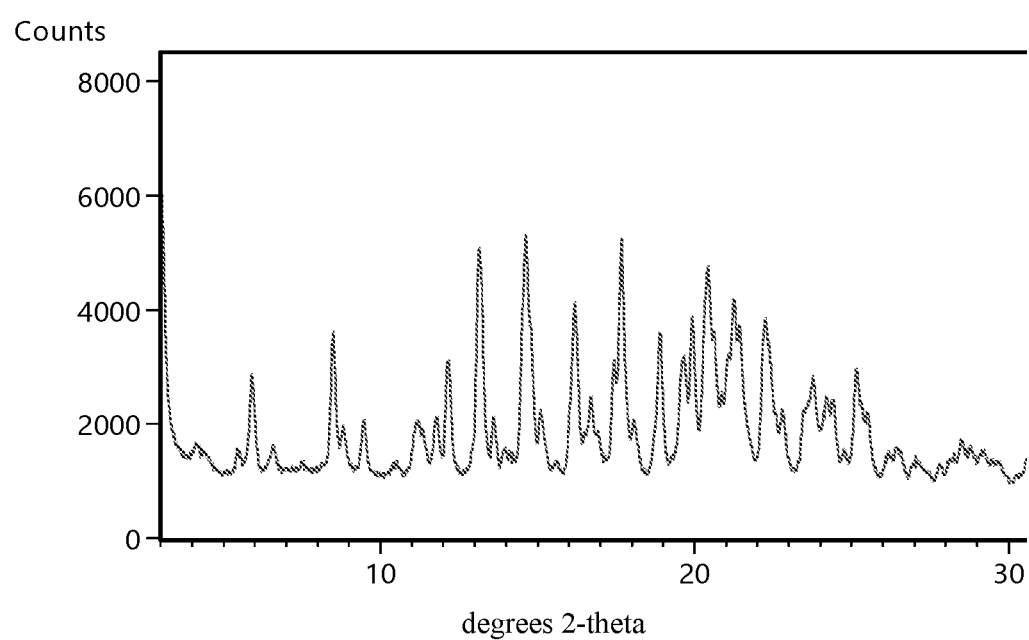
FIG. 8 provides an XRPD pattern of crystalline Compound I calcium salt hydrate Form B.

In some embodiments, the invention provides crystalline Compound I calcium salt hydrate Form B. FIG. 8 provides an X-ray powder diffractogram of Compound I calcium salt hydrate Form B at room temperature.

In some embodiments, Compound I calcium salt hydrate Form B is substantially pure crystalline. In some embodiments, Compound I calcium salt hydrate is substantially crystalline Form B. In some embodiments, Compound I calcium salt hydrate Form B is characterized by an X-ray powder diffractogram generated by an X-ray powder diffraction analysis with an incident beam of Cu Kα radiation.

In some embodiments, Compound I calcium salt hydrate Form B is characterized by an X-ray powder diffractogram having signals at 13.1±0.2 degrees two-theta, 14.6±0.2 degrees two-theta, and 17.7±0.2 degrees two-theta. In some embodiments, Compound I calcium salt hydrate Form B is characterized by an X-ray powder diffractogram having signals at 12.2±0.2 degrees two-theta, 13.1±0.2 degrees two-theta, 14.6±0.2 degrees two-theta, and 17.7±0.2 degrees two-theta. In some embodiments, Compound I calcium salt hydrate Form B is characterized by an X-ray powder diffractogram having (a) signals at 12.2±0.2 degrees two-theta, 13.1±0.2 degrees two-theta, 14.6±0.2 degrees two-theta, and 17.7±0.2 degrees two-theta; and (b) one or more signals selected from 16.2±0.2 degrees two-theta, 20.4±0.2 degrees two-theta, and 21.3±0.2 degrees two-theta.

In some embodiments, Compound I calcium salt hydrate Form B is characterized by an X-ray powder diffractogram having (a) signals at 12.2±0.2 degrees two-theta, 13.1±0.2 degrees two-theta, 14.6±0.2 degrees two-theta, and 17.7±0.2 degrees two-theta; and (b) one, two, three, or four signals selected from 16.2±0.2 degrees two-theta, 18.1±0.2 degrees two-theta, 20.4±0.2 degrees two-theta, and 21.3±0.2 degrees two-theta. In some embodiments, Compound I calcium salt hydrate Form B is characterized by an X-ray powder diffractogram having signals at 12.2±0.2 degrees two-theta, 14.6±0.2 degrees two-theta, 16.2±0.2 degrees two-theta, 17.7±0.2 degrees two-theta, 18.1±0.2 degrees two-theta, 20.4±0.2 degrees two-theta, and 21.3±0.2 degrees two-theta.

In some embodiments Compound I calcium salt hydrate Form B is characterized by an X-ray powder diffractogram substantially similar to FIG. 8.

In some embodiments, Compound I calcium salt hydrate Form B is characterized as having a $^{13}$C solid state nuclear magnetic resonance ($^{13}$C ssNMR) spectrum with a peak at 119.6±0.2 ppm and/or 48.7±0.2 ppm. In some embodiments, Compound I calcium salt hydrate Form B is characterized as having a $^{13}$C solid state nuclear magnetic resonance ($^{13}$C ssNMR) spectrum with (a) a peak at 119.6±0.2 ppm and/or 48.7±0.2 ppm; and (b) one or more peaks selected from 164.7±0.2 ppm, 148.9±0.2 ppm, 114.3±0.2 ppm, 97.7±0.2 ppm, and 25.9±0.2 ppm. In some embodiments, Compound I calcium salt hydrate Form B is characterized as having a $^{13}$C solid state nuclear magnetic resonance ($^{13}$C ssNMR) spectrum with (a) a peak at 119.6±0.2 ppm and/or 48.7±0.2 ppm; and (b) two or more peaks selected from 164.7±0.2 ppm, 148.9±0.2 ppm, 114.3±0.2 ppm, 97.7±0.2 ppm, and 25.9±0.2 ppm. In some embodiments, Compound I calcium salt hydrate Form B is characterized as having a $^{13}$C solid state nuclear magnetic resonance ($^{13}$C ssNMR) spectrum with (a) a peak at 119.6±0.2 ppm and/or 48.7±0.2 ppm; and (b) three or more peaks selected from: 164.7±0.2 ppm, 148.9±0.2 ppm, 114.3±0.2 ppm, 97.7±0.2 ppm, and 25.9±0.2 ppm. In some embodiments, Compound I calcium salt hydrate Form B is characterized as having a $^{13}$C solid state nuclear magnetic resonance ($^{13}$C ssNMR) spectrum with peaks at 119.6±0.2 ppm, 48.7±0.2 ppm, 164.7±0.2 ppm, 148.9±0.2 ppm, 114.3±0.2 ppm, 97.7±0.2 ppm, and 25.9±0.2 ppm. In some embodiments, Compound I calcium salt hydrate Form B is characterized as having a $^{13}$C solid state nuclear magnetic resonance ($^{13}$C ssNMR) spectrum with (a) one or more peaks selected from: 175.8±0.2 ppm, 119.6±0.2 ppm, 48.7±0.2 ppm, 24.4±0.2 ppm, and 22.5±0.2 ppm, and (b) peaks at 164.7±0.2 ppm, 148.9±0.2 ppm, 114.3±0.2 ppm, 97.7±0.2 ppm, and 25.9±0.2 ppm In some embodiments, Compound I calcium salt hydrate Form B is characterized by a $^{13}$C ssNMR spectrum substantially similar to FIG. 9.

In some embodiments, isomorphic solvates, solvate/hydrate, and hydrate share the same XRPD pattern as Compound I calcium salt hydrate Form B. The solvents can be MeOH, EtOH, IPA, and/or water.

In some embodiments, Compound I calcium salt hydrate/solvate Form B with MeOH is characterized as having a $^{13}$C ssNMR spectrum with a peak at 32.9±0.2 ppm and/or 23.3±0.2 ppm. In some embodiments, Compound I calcium salt hydrate/solvate Form B with MeOH is characterized as having a $^{13}$C ssNMR spectrum with (a) a peak at 32.9±0.2 ppm and/or 23.3±0.2 ppm; and (b) one or more peaks selected from 176.1±0.2 ppm, 164.7±0.2 ppm, 148.9±0.2 ppm, 49.3±0.2 ppm, and 25.9±0.2 ppm. In some embodiments, Compound I calcium salt hydrate/solvate Form B with MeOH is characterized as having a $^{13}$C ssNMR spectrum with (a) a peak at 32.9±0.2 ppm and 23.3±0.2 ppm; and (b) one or more peaks selected from 176.1±0.2 ppm, 164.7±0.2 ppm, 148.9±0.2 ppm, 49.3±0.2 ppm, and 25.9±0.2 ppm. In some embodiments, Compound I calcium salt hydrate/solvate Form B with MeOH is characterized as having a $^{13}$C ssNMR spectrum with peaks at 32.9±0.2 ppm 23.3±0.2 ppm, 176.1±0.2 ppm, 164.7±0.2 ppm, 148.9±0.2 ppm, 49.3±0.2 ppm, and 25.9±0.2 ppm.

Figure 10:
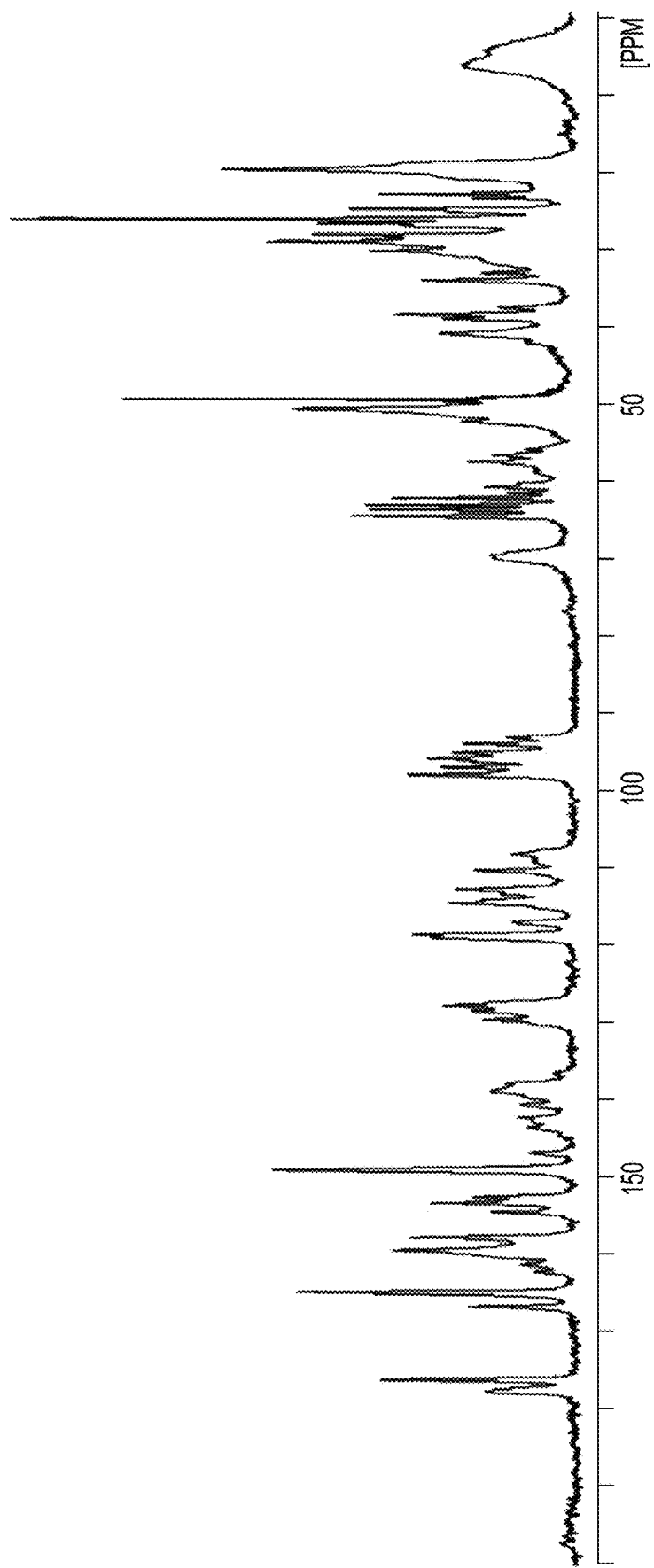
FIG. 10 shows a $^{13}$C solid state NMR spectrum of Compound I calcium salt hydrate/solvate Form B with MeOH.

In some embodiments, Compound I calcium salt hydrate/solvate Form B with MeOH is characterized by a $^{13}$C ssNMR spectrum substantially similar to FIG. 10.

In some embodiments, Compound I calcium salt hydrate/solvate Form B with MeOH is characterized by a monoclinic crystal system, a P2$_1$ space group, and the following unit cell dimensions measured at 100 K on a Bruker diffractometer equipped with Cu K$_\alpha$ radiation (λ=1.5478 Å) and a CCD detector:

| a | 18.52 ± .01 Å | α | 90° |
|---|---|---|---|
| b | 13.01 ± .01 Å | β | 106.87 ± .01° |
| c | 31.22 ± .01 Å | γ | 90°. |

Another aspect of the invention provides a method of making Compound I calcium salt hydrate Form B comprising slurrying Compound I calcium salt in EtOH/water. In some embodiments, the invention provides a method of making Compound I calcium salt hydrate/solvate Form B with MeOH comprising adding MeOH to Compound I calcium salt hydrate Form B.

Compound I Calcium Salt Hydrate Form C

Figure 11:
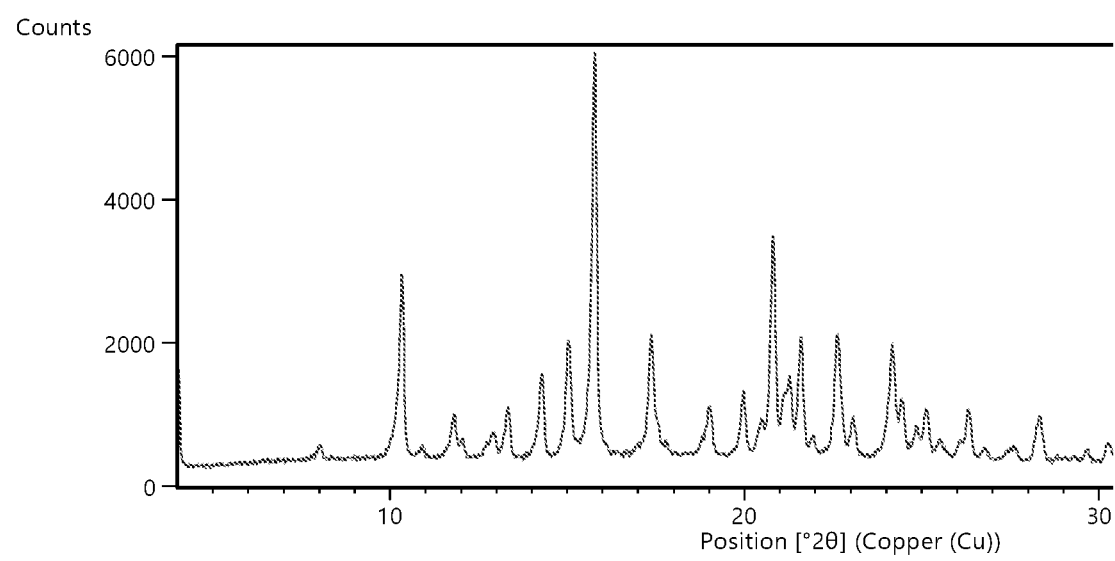
FIG. 11 provides an XRPD pattern of crystalline Compound I calcium salt hydrate Form C.

In some embodiments, the invention provides crystalline Compound I calcium salt hydrate Form C. FIG. 11 provides an X-ray powder diffractogram of Compound I calcium salt hydrate Form C at room temperature.

In some embodiments, Compound I calcium salt hydrate Form C is substantially pure crystalline. In some embodiments, Compound I calcium salt hydrate is substantially crystalline Form C. In some embodiments, Compound I calcium salt hydrate Form C is characterized by an X-ray powder diffractogram generated by an X-ray powder diffraction analysis with an incident beam of Cu Kα radiation.

In some embodiments, Compound I calcium salt hydrate Form C is characterized by an X-ray powder diffractogram having signals at 10.3±0.2 degrees two-theta, 15.8±0.2 degrees two-theta, and 20.8±0.2 degrees two-theta. In some embodiments, Compound I calcium salt hydrate Form C is characterized by an X-ray powder diffractogram having signals at 4.0±0.2 degrees two-theta, 10.3±0.2 degrees two-theta, 15.8±0.2 degrees two-theta, and 20.8±0.2 degrees two-theta. In some embodiments, Compound I calcium salt hydrate Form C is characterized by an X-ray powder diffractogram having (a) signals at 4.0±0.2 degrees two-theta, 10.3±0.2 degrees two-theta, 15.8±0.2 degrees two-theta, and 20.8±0.2 degrees two-theta; and (b) one or more signals selected from 13.3±0.2 degrees two-theta, 14.3±0.2 degrees two-theta, and 19.0±0.2 degrees two-theta. In some embodiments, Compound I calcium salt hydrate Form C is characterized by an X-ray powder diffractogram having (a) signals at 4.0±0.2 degrees two-theta, 10.3±0.2 degrees two-theta, 15.8±0.2 degrees two-theta, and 20.8±0.2 degrees two-theta; and (b) two or more signals selected from: 13.3±0.2 degrees two-theta, 14.3±0.2 degrees two-theta, and 19.0±0.2 degrees two-theta. In some embodiments, Compound I calcium salt hydrate Form C is characterized by an X-ray powder diffractogram having signals at 4.0±0.2 degrees two-theta, 10.3±0.2 degrees two-theta, 13.3±0.2 degrees two-theta, 14.3±0.2 degrees two-theta, 15.8±0.2 degrees two-theta, 19.0±0.2 degrees two-theta, and 20.8±0.2 degrees two-theta.

In some embodiments Compound I calcium salt hydrate Form C is characterized by an X-ray powder diffractogram substantially similar to FIG. 11.

In some embodiments, Compound I calcium salt hydrate Form C is characterized as having a $^{13}$C ssNMR spectrum with one or more peaks selected from 115.7±0.2 ppm, 65.9±0.2 ppm, 52.7±0.2 ppm, and 21.4±0.2 ppm. In some embodiments, Compound I calcium salt hydrate Form C is characterized as having a 13 C ssNMR spectrum with two or more peaks selected from 115.7±0.2 ppm, 65.9±0.2 ppm, 52.7±0.2 ppm, and 21.4±0.2 ppm. In some embodiments, Compound I calcium salt hydrate Form C is characterized as having a $^{13}$C ssNMR spectrum with three or more peaks selected from: 115.7±0.2 ppm, 65.9±0.2 ppm, 52.7±0.2 ppm, and 21.4±0.2 ppm. In some embodiments, Compound I calcium salt hydrate Form C is characterized as having a $^{13}$C ssNMR spectrum with four or more peaks selected from: 115.7±0.2 ppm, 65.9±0.2 ppm, 52.7±0.2 ppm, and 21.4±0.2 ppm. In some embodiments, Compound I calcium salt hydrate Form C is characterized as having a $^{13}$C ssNMR spectrum with peaks at 115.7±0.2 ppm, 65.9±0.2 ppm, 52.7±0.2 ppm, and 21.4±0.2 ppm.

In some embodiments, Compound I calcium salt hydrate Form C is characterized as having a $^{13}$C ssNMR spectrum with (a) one or more peaks selected from: 115.7±0.2 ppm, 65.9±0.2 ppm, 52.7±0.2 ppm, and 21.4±0.2 ppm, and (b) one or more peaks selected from 178.3±0.2 ppm, 155.9±0.2 ppm, 137.7±0.2 ppm, 129.6±0.2 ppm, 112.0±0.2 ppm, 100.0±0.2 ppm, 37.8±0.2 ppm, 26.4±0.2 ppm, and 19.9±0.2 ppm. In some embodiments, Compound I calcium salt hydrate Form C is characterized as having a $^{13}$C ssNMR spectrum with (a) one or more peaks selected from: 115.7±0.2 ppm, 96.0±0.2 ppm, 65.9±0.2 ppm, 52.7±0.2 ppm, and 21.4±0.2 ppm, and (b) two, three, four, five, six or more peaks selected from 178.3±0.2 ppm, 155.9±0.2 ppm, 137.7±0.2 ppm, 129.6±0.2 ppm, 112.0±0.2 ppm, 100.0±0.2 ppm, 37.8±0.2 ppm, 26.4±0.2 ppm, and 19.9±0.2 ppm.

Figure 12:
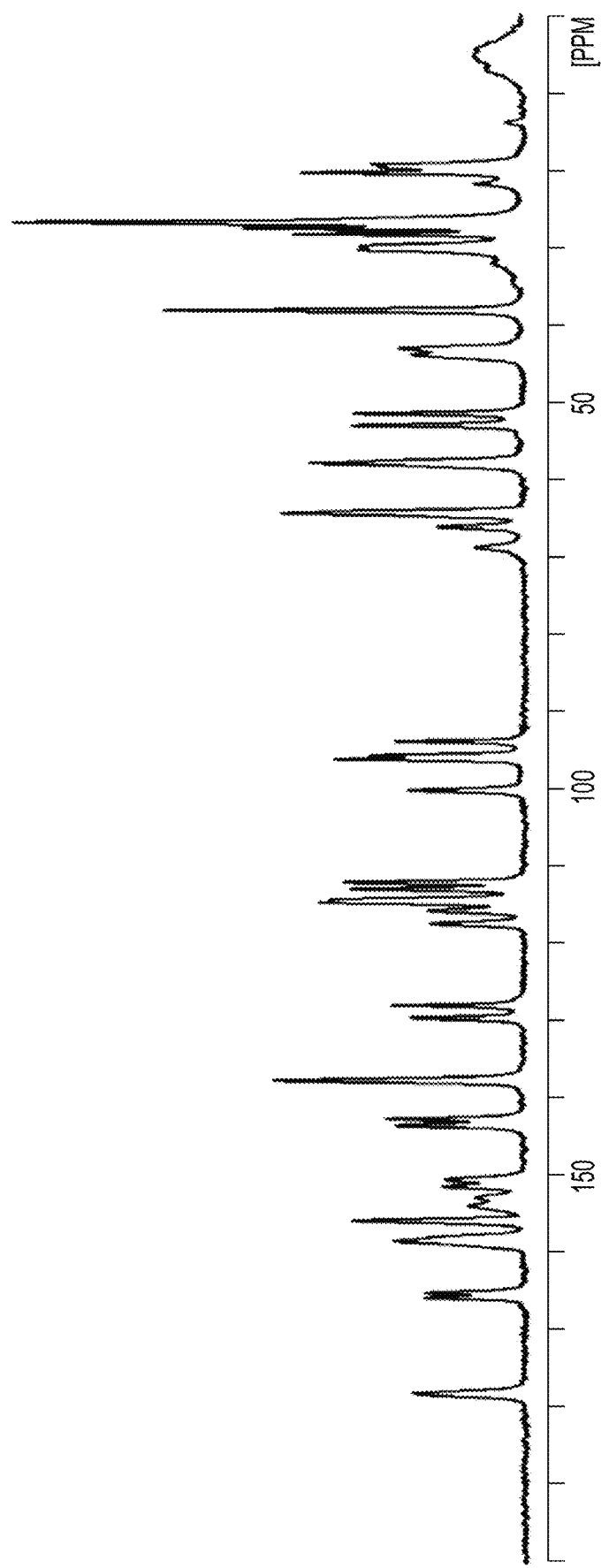
FIG. 12 shows a $^{13}$C solid state NMR spectrum of Compound I calcium salt hydrate Form C.

In some embodiments, Compound I calcium salt hydrate Form C is characterized by a $^{13}$C ssNMR spectrum substantially similar to FIG. 12.

Another aspect of the invention provides a method of making Compound I calcium salt hydrate Form C comprising stirring Compound I (free form) Form A with calcium methoxide (Ca((OMe)$_2$) in DCM (with 10% water) and isolating and drying the solid.

Compound I Calcium Salt Hydrate Form D

Figure 13:
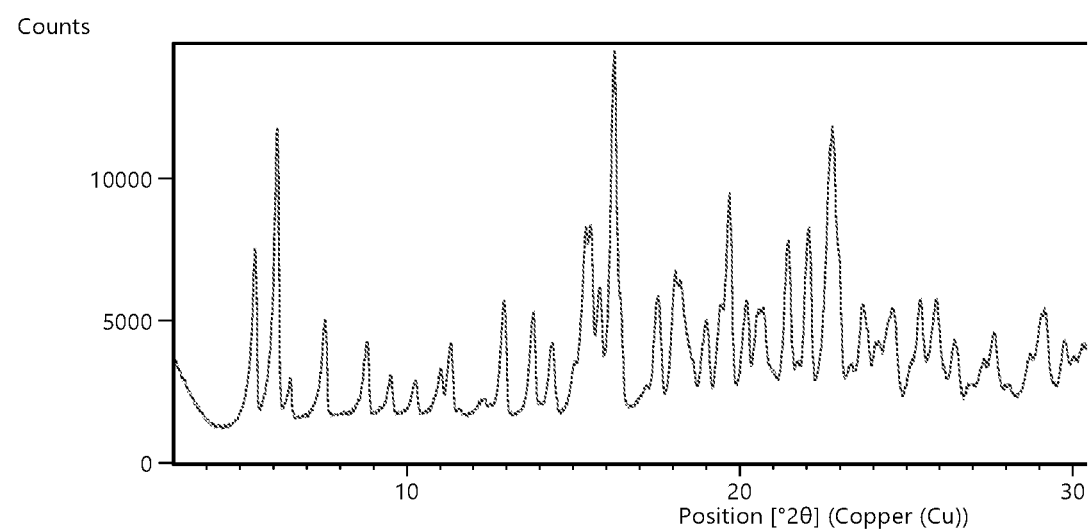
FIG. 13 provides an XRPD pattern of crystalline Compound I calcium salt hydrate Form D.

In some embodiments, the invention provides crystalline Compound I calcium salt hydrate Form D. FIG. 13 provides an X-ray powder diffractogram of Compound I calcium salt hydrate Form D at room temperature.

In some embodiments, Compound I calcium salt hydrate Form D is substantially pure crystalline. In some embodiments, Compound I calcium salt hydrate is substantially crystalline Form D. In some embodiments, Compound I calcium salt hydrate Form D is characterized by an X-ray powder diffractogram generated by an X-ray powder diffraction analysis with an incident beam of Cu Kα radiation.

In some embodiments, Compound I calcium salt hydrate Form D is characterized by an X-ray powder diffractogram having signals at 6.1±0.2 degrees two-theta, 16.2±0.2 degrees two-theta, and 22.8±0.2 degrees two-theta. In some embodiments, Compound I calcium salt hydrate Form D is characterized by an X-ray powder diffractogram having (a) signals at 6.1±0.2 degrees two-theta, 16.2±0.2 degrees two-theta, and 22.8±0.2 degrees two-theta; and (b) one or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta.

In some embodiments, Compound I calcium salt hydrate Form D is characterized by an X-ray powder diffractogram having (a) signals at 6.1±0.2 degrees two-theta, 16.2±0.2 degrees two-theta, and 22.8±0.2 degrees two-theta; and (b) two or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta. In some embodiments, Compound I calcium salt hydrate Form D is characterized by an X-ray powder diffractogram having (a) signals at 6.1±0.2 degrees two-theta, 16.2±0.2 degrees two-theta, and 22.8±0.2 degrees two-theta; and (b) three or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta. In some embodiments, Compound I calcium salt hydrate Form D is characterized by an X-ray powder diffractogram having (a) signals at 6.1±0.2 degrees two-theta, 16.2±0.2 degrees two-theta, and 22.8±0.2 degrees two-theta; and (b) four or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta.

In some embodiments, Compound I calcium salt hydrate Form D is characterized by an X-ray powder diffractogram having signals at 6.1±0.2 degrees two-theta, 16.2±0.2 degrees two-theta, and 22.8±0.2 degrees two-theta, and 27.6±0.2 degrees two-theta. In some embodiments, Compound I calcium salt hydrate Form D is characterized by an X-ray powder diffractogram having signals at 6.1±0.2 degrees two-theta, 15.5±0.2 degrees two-theta, 16.2±0.2 degrees two-theta, 19.7±0.2 degrees two-theta, 22.8±0.2 degrees two-theta, and 27.6±0.2 degrees two-theta.

In some embodiments Compound I calcium salt hydrate Form D is characterized by an X-ray powder diffractogram substantially similar to FIG. 13.

In some embodiments, Compound I calcium salt hydrate Form D is characterized as having a $^{13}$C ssNMR spectrum with one or more peaks selected from: 179.8±0.2 ppm, 130.2±0.2 ppm, 125.6±0.2 ppm, 120.9±0.2 ppm, 55.2±0.2 ppm, 44.3±0.2 ppm, 35.0±0.2 ppm, and 1.6±0.2 ppm. In some embodiments, Compound I calcium salt hydrate Form D is characterized as having a $^{13}$C ssNMR spectrum with two or more peaks selected from 179.8±0.2 ppm, 130.2±0.2 ppm, 125.6±0.2 ppm, 120.9±0.2 ppm, 55.2±0.2 ppm, 44.3±0.2 ppm, 35.0±0.2 ppm, and 1.6±0.2 ppm. In some embodiments, Compound I calcium salt hydrate Form D is characterized as having a 13 C ssNMR spectrum with three or more peaks selected from 179.8±0.2 ppm, 130.2±0.2 ppm, 125.6±0.2 ppm, 120.9±0.2 ppm, 55.2±0.2 ppm, 44.3±0.2 ppm, 35.0±0.2 ppm, and 1.6±0.2 ppm. In some embodiments, Compound I calcium salt hydrate Form D is characterized as having a $^{13}$C ssNMR spectrum with four or more peaks selected from: 179.8±0.2 ppm, 130.2±0.2 ppm, 125.6±0.2 ppm, 120.9±0.2 ppm, 55.2±0.2 ppm, 44.3±0.2 ppm, 35.0±0.2 ppm, and 1.6±0.2 ppm. In some embodiments, Compound I calcium salt hydrate Form D is characterized as having a $^{13}$C ssNMR spectrum with five or more peaks selected from 179.8±0.2 ppm, 130.2±0.2 ppm, 125.6±0.2 ppm, 120.9±0.2 ppm, 55.2±0.2 ppm, 44.3±0.2 ppm, 35.0±0.2 ppm, and 1.6±0.2 ppm. In some embodiments, Compound I calcium salt hydrate Form D is characterized as having a 13 C ssNMR spectrum with six or more peaks selected from 179.8±0.2 ppm, 130.2±0.2 ppm, 125.6±0.2 ppm, 120.9±0.2 ppm, 55.2±0.2 ppm, 44.3±0.2 ppm, 35.0±0.2 ppm, and 1.6±0.2 ppm.

In some embodiments, Compound I calcium salt hydrate Form D is characterized as having a $^{13}$C ssNMR spectrum with one or more peaks selected from 130.2±0.2 ppm, 125.6±0.2 ppm, and 35.0±0.2 ppm. In some embodiments, Compound I calcium salt hydrate Form D is characterized as having a $^{13}$C ssNMR spectrum with two or more peaks selected from 130.2±0.2 ppm, 125.6±0.2 ppm, and 35.0±0.2 ppm. In some embodiments, Compound I calcium salt hydrate Form D is characterized as having a $^{13}$C ssNMR spectrum with peaks at 130.2±0.2 ppm, 125.6±0.2 ppm, and 35.0±0.2 ppm.

In some embodiments, Compound I calcium salt hydrate Form D is characterized as having a $^{13}$C solid state nuclear magnetic resonance ($^{13}$C ssNMR) spectrum with (a) a peak at 130.2±0.2 ppm, 125.6±0.2 ppm, and/or 35.0±0.2 ppm; and (b) a peak at 176.9±0.2 ppm, 160.9±0.2 ppm, 142.0±0.2 ppm, and/or 98.6±0.2 ppm. In some embodiments, Compound I calcium salt hydrate Form D is characterized as having a $^{13}$C ssNMR spectrum with (a) a peak at 130.2±0.2 ppm, 125.6±0.2 ppm, and/or 35.0±0.2 ppm; and (b) peaks at 176.9±0.2 ppm, 160.9±0.2 ppm, 142.0±0.2 ppm, and 98.6±0.2 ppm. In some embodiments, Compound I calcium salt hydrate Form D is characterized as having a $^{13}$C ssNMR spectrum with (a) peaks at 130.2±0.2 ppm, 125.6±0.2 ppm, and 35.0±0.2 ppm; and (b) a peak at 176.9±0.2 ppm, 160.9±0.2 ppm, 142.0±0.2 ppm, and/or 98.6±0.2 ppm. In some embodiments, Compound I calcium salt hydrate Form D is characterized as having a $^{13}$C ssNMR spectrum with peaks at 130.2±0.2 ppm, 125.6±0.2 ppm, 35.0±0.2 ppm, 176.9±0.2 ppm, 160.9±0.2 ppm, 142.0±0.2 ppm, and 98.6±0.2 ppm.

Figure 14:
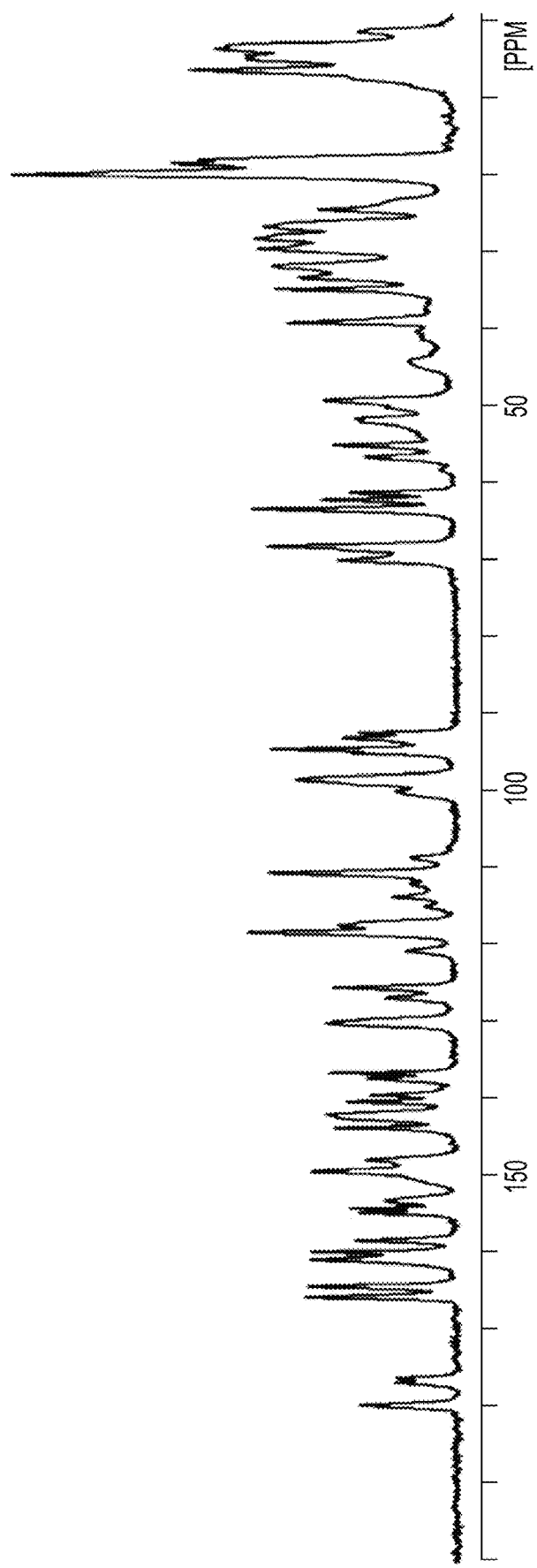
FIG. 14 shows a $^{13}$C solid state NMR spectrum of Compound I calcium salt hydrate Form D.

In some embodiments, Compound I calcium salt hydrate Form D is characterized by a $^{13}$C ssNMR spectrum substantially similar to FIG. 14.

In some embodiments, Compound I calcium salt hydrate Form D is characterized by a triclinic crystal system, a P1 space group, and the following unit cell dimensions measured at by 100 K on a Bruker diffractometer equipped with Cu Kα radiation (λ=1.5478 Å) and a Complementary metal-oxide-semiconductor (CMOS) detector:

| a | 12.78 ± .01 Å | α | 64.93 ± .02° |
|---|---|---|---|
| b | 16.64 ± .01 Å | β | 75.10 ± .02° |
| c | 18.19 ± .01 Å | γ | 68.22 ± .02°. |

Another aspect of the invention provides a method of making Compound I calcium salt hydrate Form D comprising charging Compound I calcium salt hydrate Form A with EtOH/water and heating to 65° C.

Compound I Calcium Salt Hydrate Form E

Figure 15:
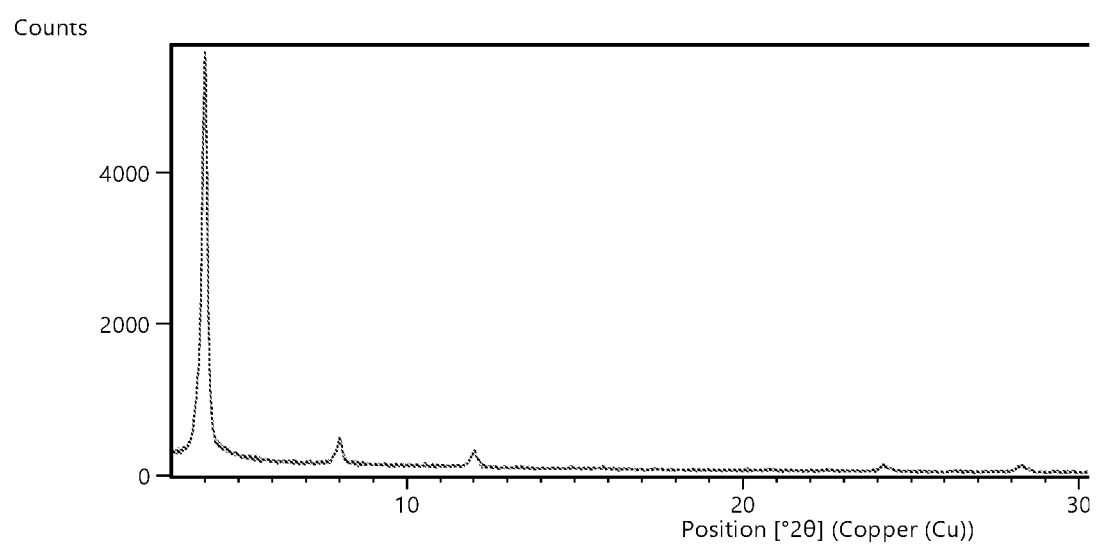
FIG. 15 provides an XRPD pattern of crystalline Compound I calcium salt hydrate Form E.

In some embodiments, the invention provides crystalline Compound I calcium salt hydrate Form E. FIG. 15 provides an X-ray powder diffractogram of Compound I calcium salt hydrate Form E at room temperature.

In some embodiments, Compound I calcium salt hydrate Form E is substantially pure crystalline. In some embodiments, Compound I calcium salt hydrate is substantially crystalline Form E. In some embodiments, Compound I calcium salt hydrate Form E is characterized by an X-ray powder diffractogram generated by an X-ray powder diffraction analysis with an incident beam of Cu Kα radiation.

In some embodiments, Compound I calcium salt hydrate Form E is characterized by an X-ray powder diffractogram having signals at 8.0±0.2 degrees two-theta, 12.0±0.2 degrees two-theta and 24.2±0.2 degrees two-theta. In some embodiments, Compound I calcium salt hydrate Form E is characterized by an X-ray powder diffractogram having signals at 4.0±0.2 degrees two-theta, 8.0±0.2 degrees two-theta, 12.0±0.2 degrees two-theta, and 24.2±0.2 degrees two-theta. In some embodiments, Compound I calcium salt hydrate Form E is characterized by an X-ray powder diffractogram having signals at 4.0±0.2 degrees two-theta, 8.0±0.2 degrees two-theta, 12.0±0.2 degrees two-theta, 24.2±0.2 degrees two-theta, and 28.3±0.2 degrees two-theta.

In some embodiments Compound I calcium salt hydrate Form E is characterized by an X-ray powder diffractogram substantially similar to FIG. 15.

Another aspect of the invention provides a method of making Compound I calcium salt hydrate Form E comprising subjecting Compound I calcium salt hydrate Form A to solid vapor diffusion in EtOAc.

Compound I Form F

Figure 16:
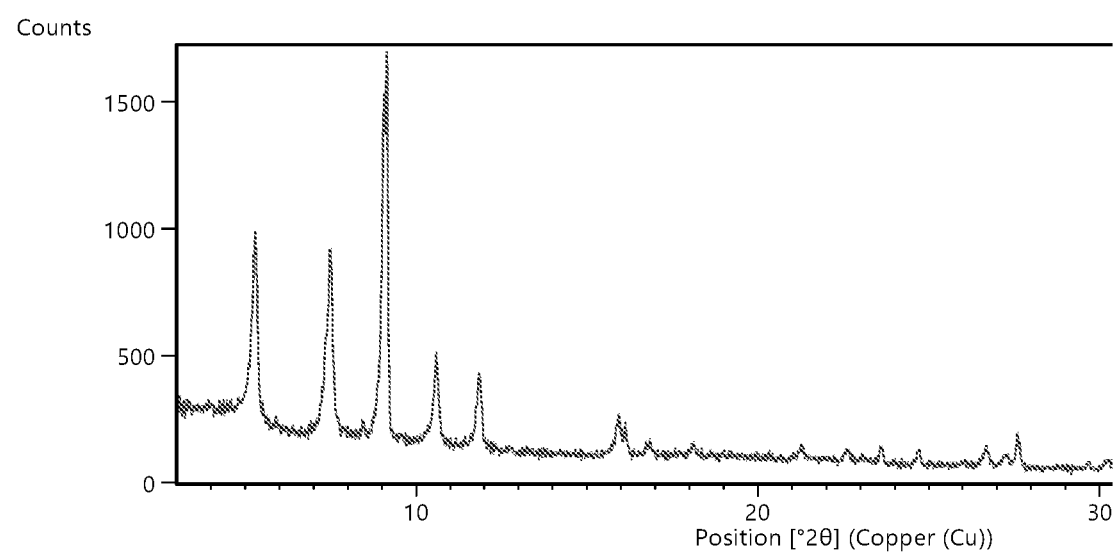
FIG. 16 provides an XRPD pattern of crystalline Compound I Form F.

Elemental analysis data of two batches of Compound I Form F revealed the presence of both Ca and Na, indicating Compound I Form F could be a mixed Ca—Na salt of Compound I or a mixture of Compound I Ca salt and Na salt. In some embodiments, the invention provides Compound I crystalline Form F. FIG. 16 provides an X-ray powder diffractogram of Compound I calcium salt hydrate Form F at room temperature.

In some embodiments, Compound I Form F is substantially pure crystalline. In some embodiments, Compound I is substantially crystalline Form F. In some embodiments, Compound I Form F is characterized by an X-ray powder diffractogram generated by an X-ray powder diffraction analysis with an incident beam of Cu Kα radiation.

In some embodiments, Compound I Form F is characterized by an X-ray powder diffractogram having signals at 5.3±0.2 degrees two-theta, 7.5±0.2 degrees two-theta, and 9.1±0.2 degrees two-theta. In some embodiments, Compound I is characterized by an X-ray powder diffractogram having signals at 5.3±0.2 degrees two-theta, 9.1±0.2 degrees two-theta, and 11.9±0.2 degrees two-theta. In some embodiments, Compound I Form F is characterized by an X-ray powder diffractogram having signals at 7.5±0.2 degrees two-theta, 9.1±0.2 degrees two-theta, and 11.9±0.2 degrees two-theta. In some embodiments, Compound I Form F is characterized by an X-ray powder diffractogram having signals at 5.3±0.2 degrees two-theta, 7.5±0.2 degrees two-theta, 9.1±0.2 degrees two-theta, and 11.9±0.2 degrees two-theta.

In some embodiments, Compound I Form F is characterized by an X-ray powder diffractogram having signals at 5.3±0.2 degrees two-theta, 7.5±0.2 degrees two-theta, 9.1±0.2 degrees two-theta, 10.6±0.2 degrees two-theta, and 11.9±0.2 degrees two-theta.

In some embodiments Compound I Form F is characterized by an X-ray powder diffractogram substantially similar to FIG. 16.

In some embodiments Compound I Form F is characterized by the following:

| Batch # | Ca | Compound I:Ca ratio | Na | Compound I:Na ratio |
|---|---|---|---|---|
| 1 | 14% | 1:2 | 5% | 1:1 |
| 2 | 7% | 1:1 | 3% | 1:0.8 |

Compound I Calcium Salt Hydrate Form G

Figure 17:
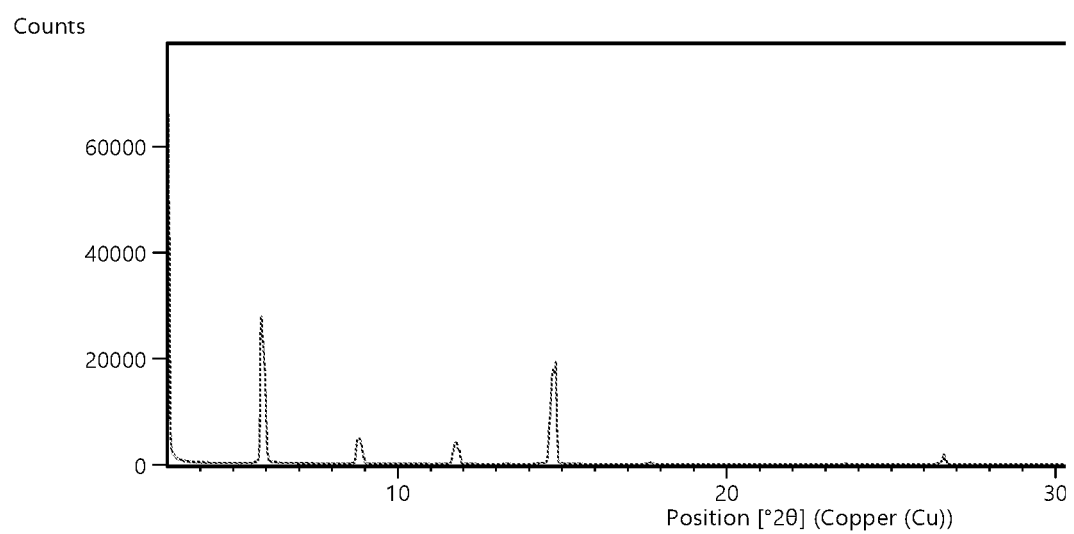
FIG. 17 provides an XRPD pattern of crystalline Compound I calcium salt hydrate Form G.

In some embodiments, the invention provides crystalline Compound I calcium salt hydrate Form G. FIG. 17 provides an X-ray powder diffractogram of Compound I calcium salt hydrate Form G at room temperature.

In some embodiments, Compound I calcium salt hydrate Form G is substantially pure crystalline. In some embodiments, Compound I calcium salt hydrate is substantially crystalline Form G. In some embodiments, Compound I calcium salt hydrate Form G is characterized by an X-ray powder diffractogram generated by an X-ray powder diffraction analysis with an incident beam of Cu Kα radiation.

In some embodiments, Compound I calcium salt hydrate Form G is characterized by an X-ray powder diffractogram having signals at 5.9±0.2 degrees two-theta, 8.8±0.2 degrees two-theta, and 26.6±0.2 degrees two-theta. In some embodiments, Compound I calcium salt hydrate Form G is characterized by an X-ray powder diffractogram having (a) signals at 5.9±0.2 degrees two-theta, 8.8±0.2 degrees two-theta, and 26.6±0.2 degrees two-theta; and (b) one or more signals selected from 6.0±0.2 degrees two-theta, 11.8±0.2 degrees two-theta, 11.9±0.2 degrees two-theta, 14.8 0.2 degrees two-theta, and 14.7±0.2 degrees two-theta. In some embodiments, Compound I calcium salt hydrate Form G is characterized by an X-ray powder diffractogram having signals at 5.9±0.2 degrees two-theta, 6.0±0.2 degrees two-theta, 8.8±0.2 degrees two-theta, 11.8±0.2 degrees two-theta, 11.9±0.2 degrees two-theta, 14.8±0.2 degrees two-theta, 14.7±0.2 degrees two-theta, and 26.6±0.2 degrees two-theta.

In some embodiments Compound I calcium salt hydrate Form G is characterized by an X-ray powder diffractogram substantially similar to FIG. 17.

Another aspect of the invention provides a method of making Compound I calcium salt hydrate Form G comprising fast cooling a solution of Compound I calcium salt hydrate Form A in EtOH:H$_2$O (90:10).

Compound I Calcium Salt Form H

Figure 45:
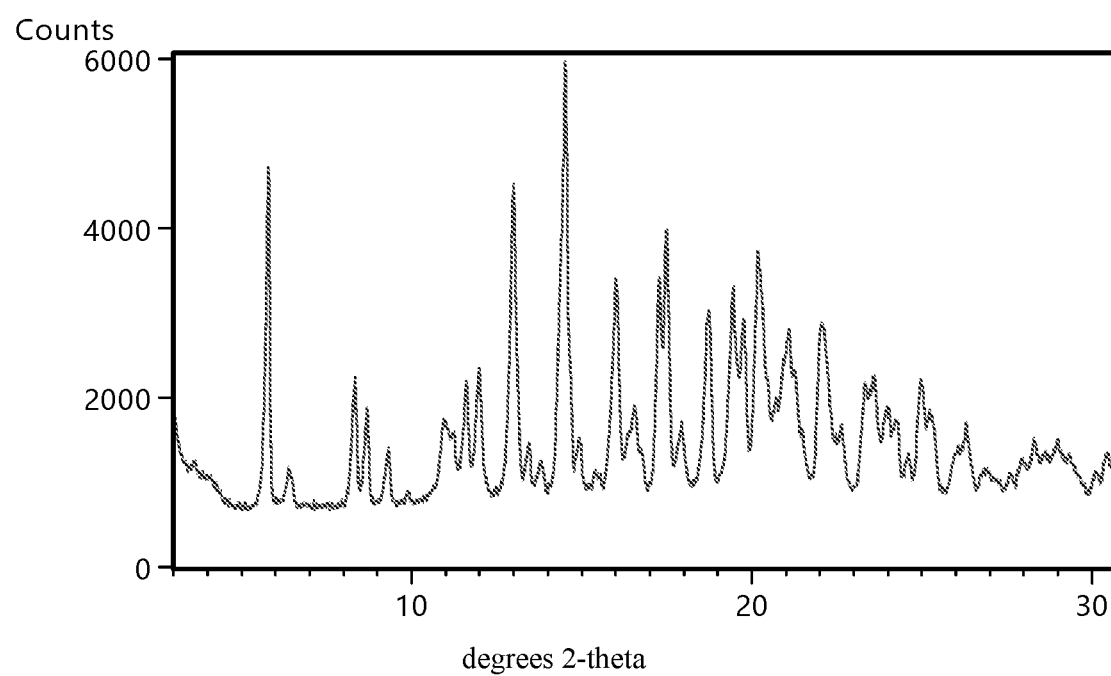
FIG. 45 provides an XRPD pattern of crystalline Compound I calcium salt hydrate Form H.

In some embodiments, the invention provides crystalline Compound I calcium salt Form H. FIG. 45 provides an X-ray powder diffractogram of Compound I calcium salt Form H at room temperature.

In some embodiments, Compound I is substantially pure crystalline calcium salt Form H. In some embodiments, Compound I is substantially crystalline calcium salt Form H. In some embodiments, Compound I calcium salt Form H is characterized by an X-ray powder diffractogram generated by an X-ray powder diffraction analysis with an incident beam of Cu Kα radiation.

In some embodiments, Compound I calcium salt Form H is characterized by an X-ray powder diffractogram having signals at 5.8±0.2 degrees two-theta, 13.0±0.2 degrees two-theta, and 14.5±0.2 degrees two-theta. In some embodiments, Compound I calcium salt Form H is characterized by an X-ray powder diffractogram having (a) signals at 5.8±0.2 degrees two-theta, 13.0±0.2 degrees two-theta, and 14.5±0.2 degrees two-theta; and (b) one or more signals selected from 8.3±0.2 degrees two-theta, 12.0±0.2 degrees two-theta, 19.5±0.2 degrees two-theta, and 27.9±0.2 degrees two-theta. In some embodiments, Compound I calcium salt Form H is characterized by an X-ray powder diffractogram having signals at 5.8±0.2 degrees two-theta, 12.0±0.2 degrees two-theta, 13.0±0.2 degrees two-theta, and 14.5±0.2 degrees two-theta, and 27.9±0.2 degrees two-theta.

In some embodiments Compound I calcium salt Form H is characterized by an X-ray powder diffractogram substantially similar to FIG. 45.

In some embodiments, Compound I calcium salt Form H is characterized as having a $^{13}$C solid state nuclear magnetic resonance ($^{13}$C ssNMR) spectrum with peaks at 148.9±0.2 ppm, 27.2±0.2 ppm, and 4.8±0.2 ppm. In some embodiments, Compound I calcium salt Form H is characterized as having a $^{13}$C solid state nuclear magnetic resonance ($^{13}$C ssNMR) spectrum with (a) peaks at 148.9±0.2 ppm, 27.2±0.2 ppm, and 4.8±0.2 ppm; and (b) one or more peaks selected from 164.7±0.2 ppm, 128.3±0.2 ppm, 117.0±0.2 ppm, and 19.4±0.2 ppm. In some embodiments, Compound I calcium salt Form H is characterized as having a $^{13}$C solid state nuclear magnetic resonance ($^{13}$C ssNMR) spectrum with (a) peaks at 148.9±0.2 ppm, 27.2±0.2 ppm, and 4.8±0.2 ppm; and (b) two, three, or four peaks selected from 164.7±0.2 ppm, 128.3±0.2 ppm, 117.0 0.2 ppm, and 19.4±0.2 ppm.

Figure 46:
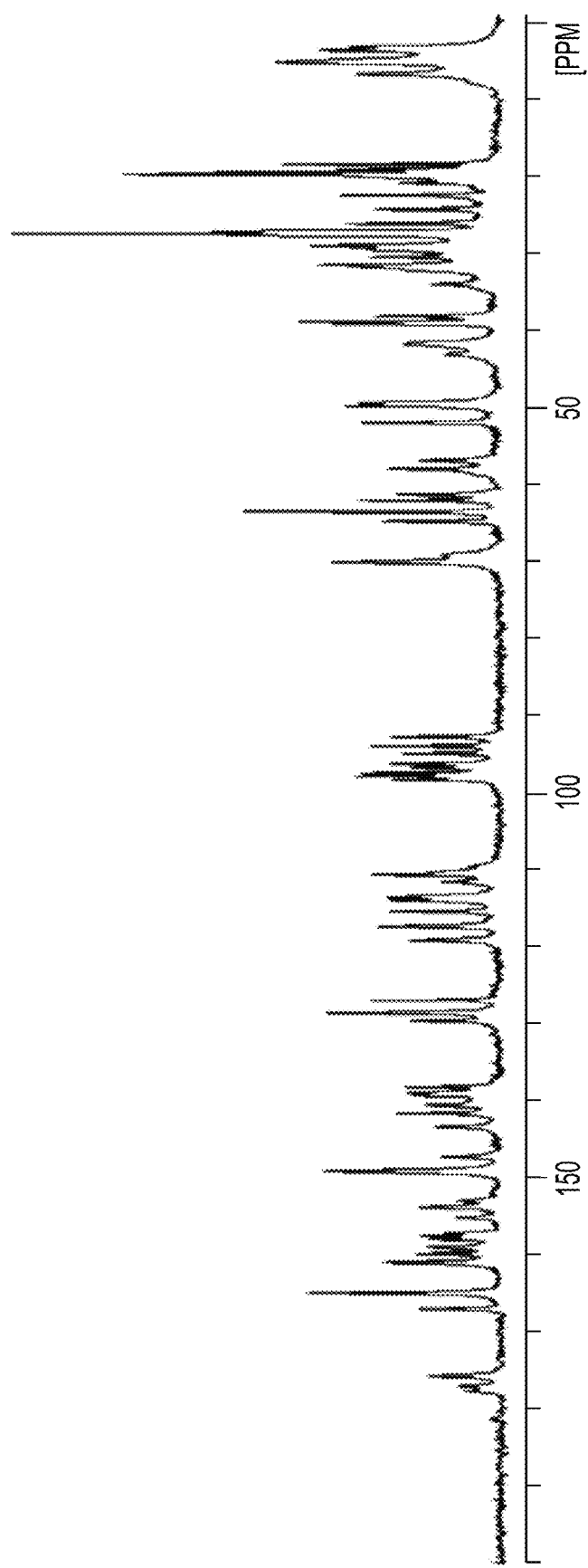
FIG. 46 shows a $^{13}$C solid state NMR spectrum of Compound I calcium salt hydrate Form H.

In some embodiments, Compound I calcium salt Form H is characterized by a $^{13}$C ssNMR spectrum substantially similar to FIG. 46.

In some embodiments, Compound I calcium salt Form H is characterized by a triclinic crystal system, a P1 space group, and the following unit cell dimensions measured at 100 K on a Bruker diffractometer utilizing synchrotron radiation (0.7288 Å) and CMOS detector:

| a | 8.65 ± .01 Å | α | 82.47 ± .01° |
|---|---|---|---|
| b | 17.78 ± .01 Å | β | 86.95 ± .01° |
| c | 24.07 ± .01 Å | γ | 86.56 ± .01°. |

Another aspect of the invention provides a method of making Compound I calcium salt Form H comprising mixing Compound I calcium salt hydrate Form B in IPA/water.

Compound I Calcium Salt EtOH Solvate Form A

Figure 18:
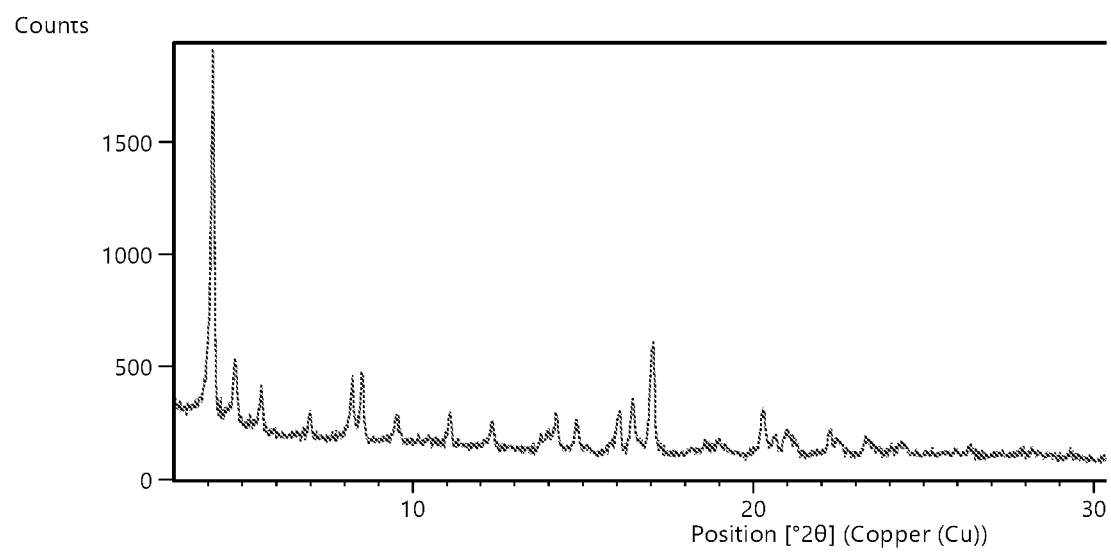
FIG. 18 provides an XRPD pattern of crystalline Compound I calcium salt EtOH solvate Form A.

In some embodiments, the invention provides crystalline Compound I calcium salt EtOH solvate Form A. FIG. 18 provides an X-ray powder diffractogram of Compound I calcium salt EtOH Solvate Form A at room temperature.

In some embodiments, Compound I calcium salt EtOH solvate Form A is substantially pure crystalline. In some embodiments, Compound I calcium salt EtOH solvate Form A is substantially crystalline. In some embodiments, Compound I calcium salt EtOH solvate Form A is characterized by an X-ray powder diffractogram generated by an X-ray powder diffraction analysis with an incident beam of Cu Kα radiation.

In some embodiments, Compound I calcium salt EtOH solvate Form A is characterized by an X-ray powder diffractogram having signals at 4.1±0.2 degrees two-theta, 8.2±0.2 degrees two-theta, and 17.1±0.2 degrees two-theta. In some embodiments, Compound I calcium salt EtOH solvate Form A is characterized by an X-ray powder diffractogram having (a) signals at 4.1±0.2 degrees two-theta, 8.2±0.2 degrees two-theta, and 17.1±0.2 degrees two-theta; and (b) a signal at 8.5±0.2 degrees two-theta and/or 16.5±0.2 degrees two-theta.

In some embodiments, Compound I calcium salt EtOH solvate Form A is characterized by an X-ray powder diffractogram having at least two signals selected from 8.2±0.2 degrees two-theta, 8.5±0.2 degrees two-theta, 16.5±0.2 degrees two-theta and 17.1±0.2 degrees two-theta. In some embodiments, Compound I calcium salt EtOH solvate Form A is characterized by an X-ray powder diffractogram having signals at 8.2±0.2 degrees two-theta, 8.5±0.2 degrees two-theta, 16.5±0.2 degrees two-theta, and 17.1±0.2 degrees two-theta.

In some embodiments, Compound I calcium salt EtOH solvate Form A is characterized by an X-ray powder diffractogram having (a) a signal at 8.2±0.2 degrees two-theta, 8.5±0.2 degrees two-theta, 16.5±0.2 degrees two-theta and/or 17.1±0.2 degrees two-theta, and (b) at least one signal selected from 4.1±0.2 degrees two-theta, 4.8±0.2 degrees two-theta, 5.6±0.2 degrees two-theta, and 20.3±0.2 degrees two-theta.

In some embodiments Compound I calcium salt EtOH solvate Form A is characterized by an X-ray powder diffractogram substantially similar to FIG. 18.

Another aspect of the invention provides a method of making Compound I calcium salt EtOH solvate Form A comprising fast cooling a solution of Compound I calcium salt in EtOH:H$_2$O (85:15).

Compound I Calcium Salt EtOH Solvate Form B

Figure 19:
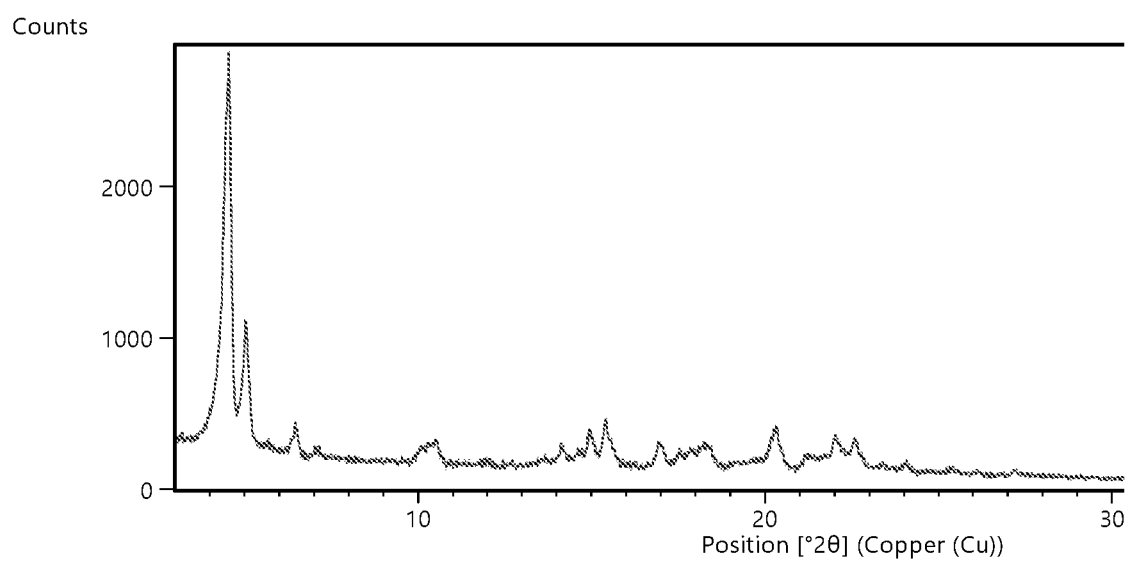
FIG. 19 provides an XRPD pattern of crystalline Compound I calcium salt EtOH solvate Form B.

In some embodiments, the invention provides crystalline Compound I calcium salt EtOH solvate Form B. FIG. 19 provides an X-ray powder diffractogram of Compound I calcium salt EtOH Solvate Form B at room temperature.

In some embodiments, Compound I calcium salt EtOH solvate Form B is substantially pure crystalline. In some embodiments, Compound I calcium salt EtOH solvate Form B is substantially crystalline. In some embodiments, Compound I calcium salt EtOH solvate Form B is characterized by an X-ray powder diffractogram generated by an X-ray powder diffraction analysis with an incident beam of Cu Kαradiation.

In some embodiments, Compound I calcium salt EtOH solvate Form B is characterized by an X-ray powder diffractogram having a signal at 15.4±0.2 degrees two-theta. In some embodiments, Compound I calcium salt EtOH solvate Form B is characterized by an X-ray powder diffractogram having (a) a signal at 15.4±0.2 degrees two-theta; and (b) a signal signal at 4.5±0.2 degrees two-theta and/or 5.0±0.2 degrees two-theta. In some embodiments, Compound I calcium salt EtOH solvate Form B is characterized by an X-ray powder diffractogram having (a) a signal at 15.4±0.2 degrees two-theta; and (b) at least two signals selected from 4.5±0.2 degrees two-theta, 5.0±0.2 degrees two-theta, and 20.3±0.2 degrees two-theta. In some embodiments, Compound I calcium salt EtOH solvate Form B is characterized by an X-ray powder diffractogram having signals at 4.5±0.2 degrees two-theta, 5.0±0.2 degrees two-theta, 15.4±0.2 degrees two-theta, and 20.3±0.2 degrees two-theta.

In some embodiments Compound I calcium salt EtOH solvate Form B is characterized by an X-ray powder diffractogram substantially similar to FIG. 19.

Another aspect of the invention provides a method of making Compound I calcium salt EtOH solvate Form B comprising temperature cycling between 60° C. and 5° C. with cooling rate of 0.2° C./min of Compound I calcium salt hydrate Form A in EtOH:n-heptane (1:1).

Compound I Calcium Salt EtOH Solvate Form C

Figure 20:
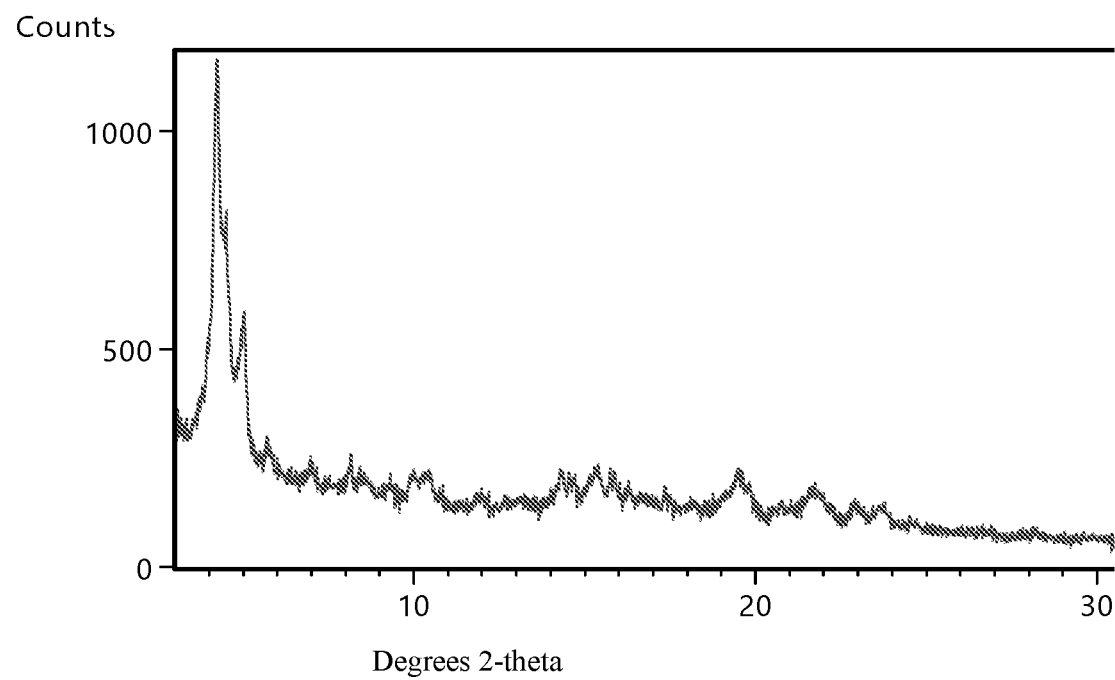
FIG. 20 provides an XRPD pattern of crystalline Compound I calcium salt EtOH solvate Form C.

In some embodiments, the invention provides crystalline Compound I calcium salt EtOH solvate Form C. FIG. 20 provides an X-ray powder diffractogram of Compound I calcium salt EtOH Solvate Form C at room temperature.

In some embodiments, Compound I calcium salt EtOH solvate Form C is substantially pure crystalline. In some embodiments, Compound I calcium salt EtOH solvate Form C is substantially crystalline. In some embodiments, Compound I calcium salt EtOH solvate Form C is characterized by an X-ray powder diffractogram generated by an X-ray powder diffraction analysis with an incident beam of Cu Kαradiation.

In some embodiments, Compound I calcium salt EtOH solvate Form C is characterized by an X-ray powder diffractogram having signals at 4.2±0.2 degrees two-theta, 5.0±0.2 degrees two-theta, and 5.7±0.2 degrees two-theta.

In some embodiments Compound I calcium salt EtOH solvate Form C is characterized by an X-ray powder diffractogram substantially similar to FIG. 20.

Another aspect of the invention provides a method of making Compound I calcium salt EtOH solvate Form C comprising making a slurry of amorphous Compound I calcium salt with EtOH:H$_2$O (9:1) at room temperature.

Compound I Sodium Salt Hydrate Form A

Figure 34:
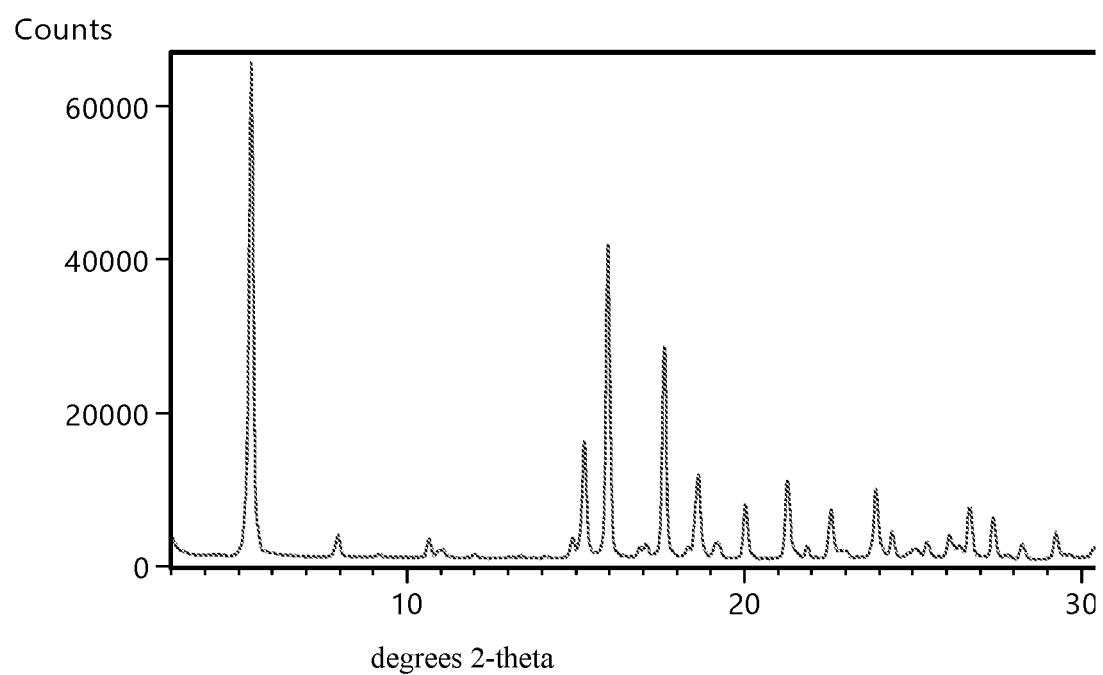
FIG. 34 provides an XRPD pattern of crystalline Compound I sodium salt hydrate Form A.

In some embodiments, the invention provides crystalline Compound I sodium salt hydrate Form A. FIG. 34 provides an X-ray powder diffractogram of Compound I sodium salt hydrate Form A at room temperature.

In some embodiments, Compound I sodium salt hydrate Form A is substantially pure crystalline. In some embodiments, Compound I sodium salt hydrate Form A is substantially crystalline. In some embodiments, Compound I sodium salt hydrate Form A is characterized by an X-ray powder diffractogram generated by an X-ray powder diffraction analysis with an incident beam of Cu Kαradiation.

In some embodiments, Compound I sodium salt hydrate Form A is characterized by an X-ray powder diffractogram having signals at 5.4±0.2 degrees two-theta, 15.9±0.2 degrees two-theta, and 17.6±0.2 degrees two-theta. In some embodiments, Compound I sodium salt hydrate Form A is characterized by an X-ray powder diffractogram having (a) signals at 5.4±0.2 degrees two-theta, 15.9±0.2 degrees two-theta, and 17.6±0.2 degrees two-theta; and (b) at least one, at least two, at least three, at least four, or at least five signals selected from 15.3±0.2 degrees two-theta, 18.6±0.2 degrees two-theta, 21.3±0.2 degrees two-theta, 23.9±0.2 degrees two-theta, 20.0±0.2 degrees two-theta, and 26.7±0.2 degrees two-theta. In some embodiments, Compound I sodium salt hydrate Form A is characterized by an X-ray powder diffractogram having signals at 5.4±0.2 degrees two-theta, 15.9±0.2 degrees two-theta, 17.6±0.2 degrees two-theta, 15.3±0.2 degrees two-theta, 18.6±0.2 degrees two-theta, 21.3±0.2 degrees two-theta, 23.9±0.2 degrees two-theta, 20.0±0.2 degrees two-theta, and 26.7±0.2 degrees two-theta.

In some embodiments Compound I sodium salt hydrate Form A is characterized by an X-ray powder diffractogram substantially similar to FIG. 34.

In some embodiments, Compound I sodium salt hydrate Form A is characterized as having a $^{13}$C ssNMR spectrum with at least one peak selected from: 177.0±0.2 ppm, 159.6±0.2 ppm, 138.5±0.2 ppm, 107.0±0.2 ppm, 96.4±0.2 ppm, 38.3±0.2 ppm, and 28.9±0.2 ppm. In some embodiments, Compound I sodium salt hydrate Form A is characterized as having a $^{13}$C ssNMR spectrum with at least two peaks selected from: 177.0±0.2 ppm, 159.6±0.2 ppm, 138.5±0.2 ppm, 107.0±0.2 ppm, 96.4±0.2 ppm, 38.3±0.2 ppm, and 28.9±0.2 ppm. In some embodiments, Compound I sodium salt hydrate Form A is characterized as having a $^{13}$C ssNMR spectrum with at least three peaks selected from: 177.0±0.2 ppm, 159.6±0.2 ppm, 138.5±0.2 ppm, 107.0±0.2 ppm, 96.4±0.2 ppm, 38.3±0.2 ppm, and 28.9±0.2 ppm. In some embodiments, Compound I sodium salt hydrate Form A is characterized as having a $^{13}$C ssNMR spectrum with at least four peaks selected from: 177.0±0.2 ppm, 159.6±0.2 ppm, 138.5±0.2 ppm, 107.0±0.2 ppm, 96.4±0.2 ppm, 38.3±0.2 ppm, and 28.9±0.2 ppm. In some embodiments, Compound I sodium salt hydrate Form A is characterized as having a $^{13}$C ssNMR spectrum with at least five peaks selected from: 177.0±0.2 ppm, 159.6±0.2 ppm, 138.5±0.2 ppm, 107.0±0.2 ppm, 96.4±0.2 ppm, 38.3±0.2 ppm, and 28.9±0.2 ppm. In some embodiments, Compound I sodium salt hydrate Form A is characterized as having a $^{13}$C ssNMR spectrum with peaks at 177.0±0.2 ppm, 159.6±0.2 ppm, 138.5 0.2 ppm, 107.0±0.2 ppm, 96.4±0.2 ppm, 38.3±0.2 ppm, and 28.9 0.2 ppm.

Figure 35:
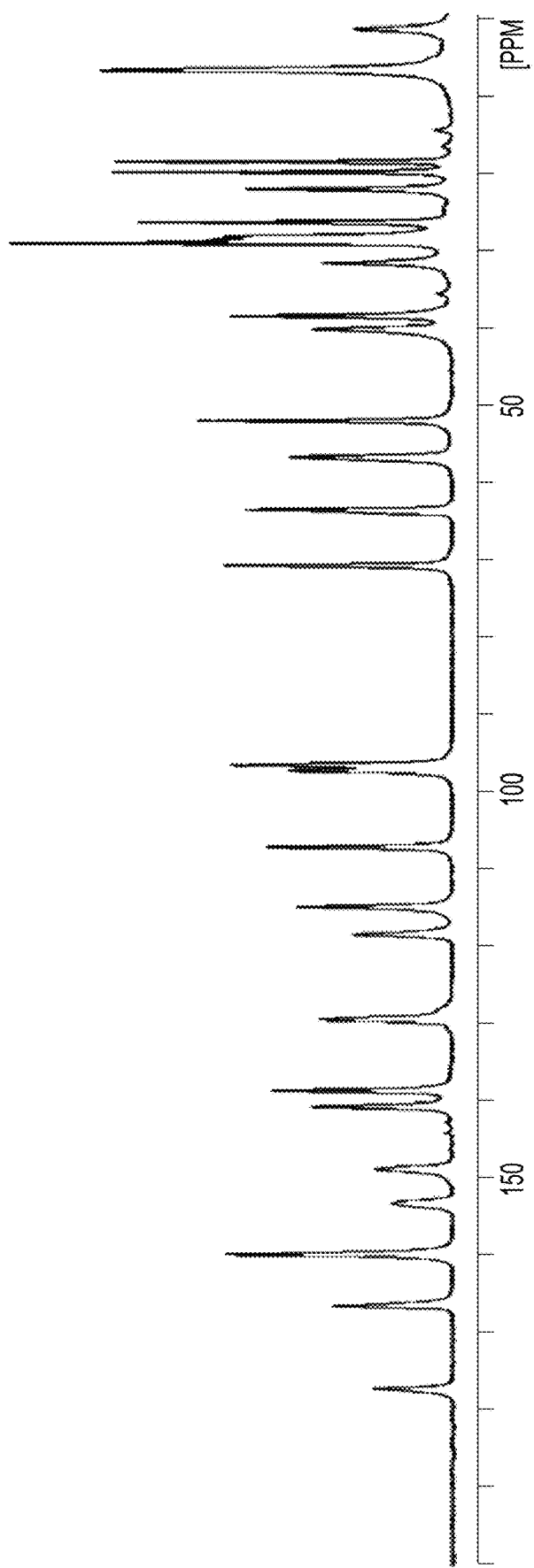
FIG. 35 shows a $^{13}$C solid state NMR spectrum of Compound I sodium salt hydrate Form A.

In some embodiments, Compound I sodium salt hydrate Form A is characterized by a $^{13}$C ssNMR spectrum substantially similar to FIG. 35.

In some embodiments, Compound I sodium salt hydrate Form A is characterized by an orthorhombic crystal system, a P212121 space group, and the following unit cell dimensions measured at 100 K on a Bruker diffractometer utilizing synchrotron radiation (0.7288 Å):

| a | 8.23 ± .01 Å | α | 90° |
|---|---|---|---|
| b | 11.85 ± .01 Å | β | 90° |
| c | 33.09 ± .01 Å | γ | 90°. |

Another aspect of the invention provides a method of making Compound I sodium salt hydrate Form A comprising mixing amorphous Compound I sodium salt with IPA/water at room temperature for two weeks.

Compound I Sodium Salt Neat Form B

Figure 36:
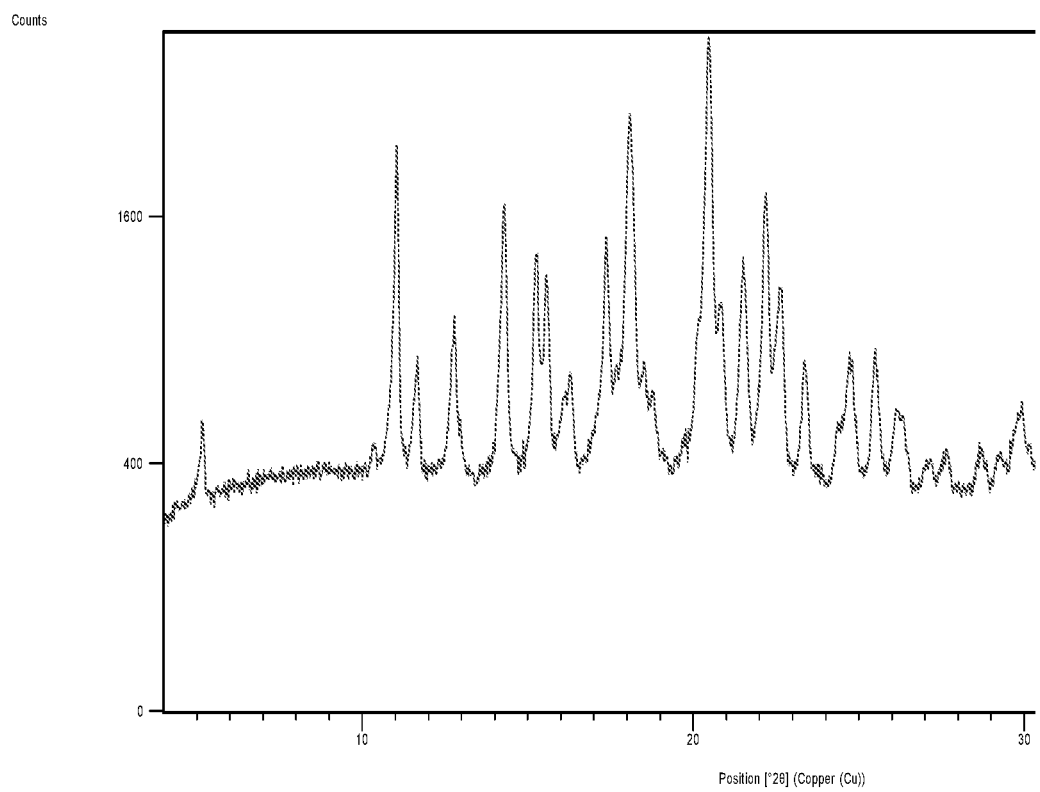
FIG. 36 provides an XRPD pattern of crystalline Compound I sodium salt neat Form B.

In some embodiments, the invention provides crystalline Compound I sodium salt neat Form B. FIG. 36 provides an X-ray powder diffractogram of Compound I sodium salt neat Form B at room temperature.

In some embodiments, Compound I sodium salt neat Form B is substantially pure crystalline. In some embodiments, Compound I sodium salt neat Form B is substantially crystalline. In some embodiments, Compound I sodium salt neat Form B is characterized by an X-ray powder diffractogram generated by an X-ray powder diffraction analysis with an incident beam of Cu Kα radiation.

In some embodiments, Compound I sodium salt neat Form B is characterized by an X-ray powder diffractogram having a signal at 11.0±0.2 degrees two-theta, 18.1 0.2 degrees two-theta, and 20.5±0.2 degrees two-theta. In some embodiments, Compound I sodium salt neat Form B is characterized by an X-ray powder diffractogram having a signal at 12.8±0.2 degrees two-theta. In some embodiments, Compound I sodium salt neat Form B is characterized by an X-ray powder diffractogram having (a) a signal at 12.8±0.2 degrees two-theta; and (b) having a signal at 11.0±0.2 degrees two-theta, 18.1±0.2 degrees two-theta, and/or 20.5±0.2 degrees two-theta. In some embodiments, Compound I sodium salt neat Form B is characterized by an X-ray powder diffractogram having a signal at 11.0±0.2 degrees two-theta, 12.8±0.2 degrees two-theta, 18.1±0.2 degrees two-theta, and 20.5±0.2 degrees two-theta.

In some embodiments Compound I sodium salt neat Form B is characterized by an X-ray powder diffractogram substantially similar to FIG. 36.

Another aspect of the invention provides a method of making Compound I sodium salt neat Form B comprising desolvating/dehydrating Compound I sodium salt hydrate Form C.

Compound I Sodium Salt Hydrate Form C

Figure 37:
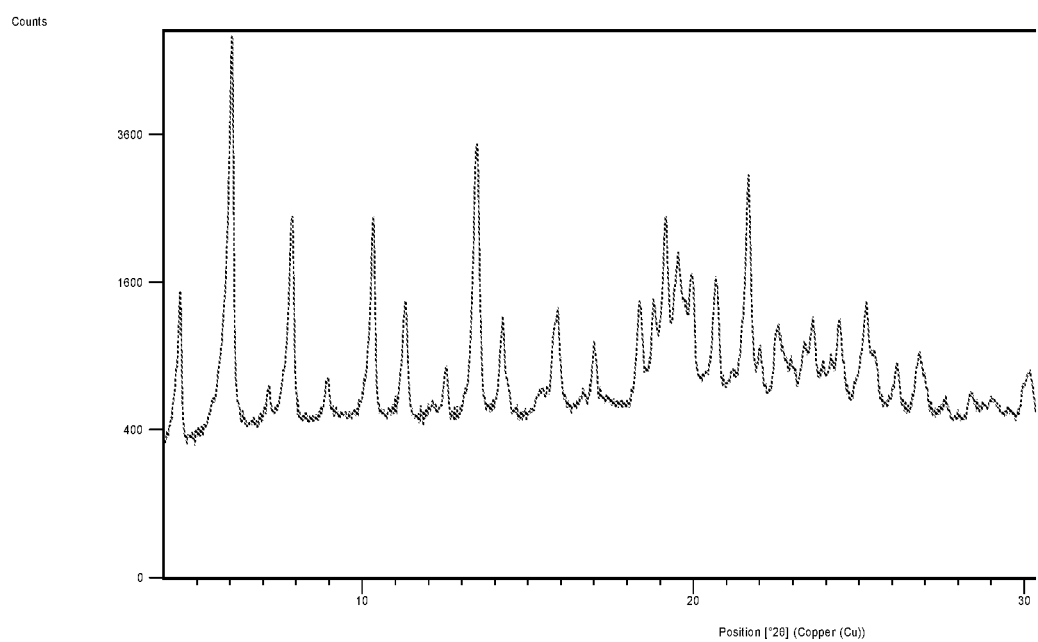
FIG. 37 provides an XRPD pattern of crystalline Compound I sodium salt hydrate Form C.

In some embodiments, the invention provides crystalline Compound I sodium salt hydrate Form C. FIG. 37 provides an X-ray powder diffractogram of Compound I sodium salt hydrate Form C at room temperature.

In some embodiments, Compound I sodium salt hydrate Form C is substantially pure crystalline. In some embodiments, Compound I sodium salt hydrate Form C is substantially crystalline. In some embodiments, Compound I sodium salt hydrate Form C is characterized by an X-ray powder diffractogram generated by an X-ray powder diffraction analysis with an incident beam of Cu Kα radiation.

In some embodiments, Compound I sodium salt hydrate Form C is characterized by an X-ray powder diffractogram having signals at 6.1±0.2 degrees two-theta, 13.4±0.2 degrees two-theta, and 19.2±0.2 degrees two-theta. In some embodiments, Compound I sodium salt hydrate Form C is characterized by an X-ray powder diffractogram having a signal at 4.5±0.2 degrees two-theta and/or 10.3±0.2 degrees two-theta. In some embodiments, Compound I sodium salt hydrate Form C is characterized by an X-ray powder diffractogram having (a) a signal at 4.5±0.2 degrees two-theta and/or 10.3±0.2 degrees two-theta; and (b) having a signal at 6.1±0.2 degrees two-theta, 13.4±0.2 degrees two-theta, and/or 19.2±0.2 degrees two-theta. In some embodiments, Compound I sodium salt hydrate Form C is characterized by an X-ray powder diffractogram having a signal at 4.5±0.2 degrees two-theta, 6.1±0.2 degrees two-theta, 10.3±0.2 degrees two-theta, 13.4±0.2 degrees two-theta, and 19.2±0.2 degrees two-theta.

In some embodiments Compound I sodium salt hydrate Form C is characterized by an X-ray powder diffractogram substantially similar to FIG. 37.

Another aspect of the invention provides a method of making Compound I sodium salt hydrate Form C comprising stirring Compound I amorphous sodium salt with ACN at room temperature.

Compound I Sodium Salt Hydrate Form D

Figure 38:
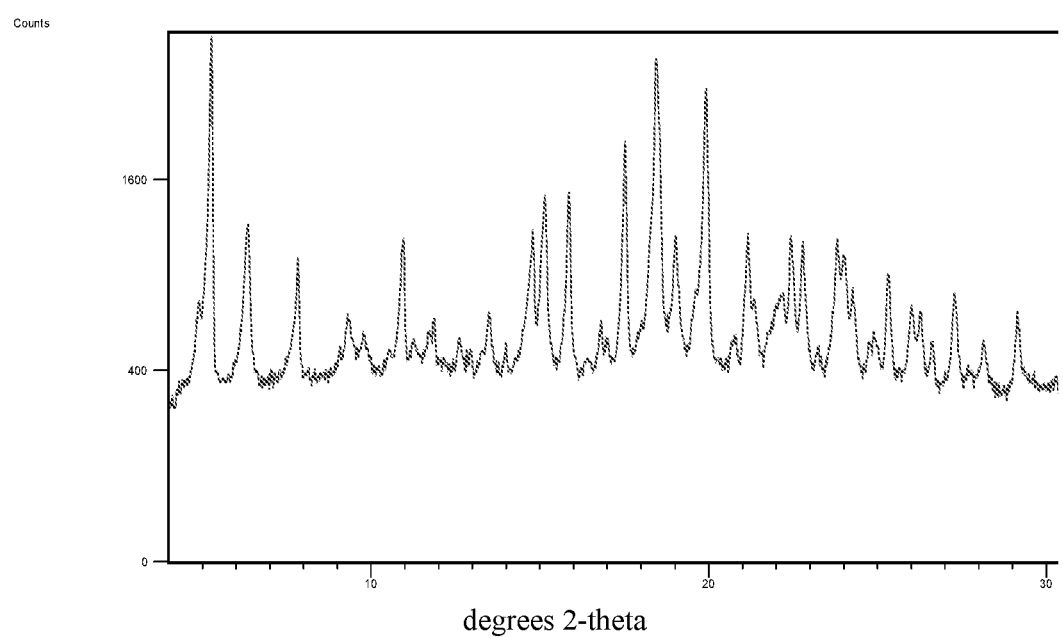
FIG. 38 provides an XRPD pattern of crystalline Compound I sodium salt hydrate Form D.

In some embodiments, the invention provides crystalline Compound I sodium salt hydrate Form D. FIG. 38 provides an X-ray powder diffractogram of Compound I sodium salt hydrate Form D at room temperature.

In some embodiments, Compound I sodium salt hydrate Form D is substantially pure crystalline. In some embodiments, Compound I sodium salt hydrate Form D is substantially crystalline. In some embodiments, Compound I sodium salt hydrate Form D is characterized by an X-ray powder diffractogram generated by an X-ray powder diffraction analysis with an incident beam of Cu Kα radiation.

In some embodiments, Compound I sodium salt hydrate Form D is characterized by an X-ray powder diffractogram having signals at 7.8±0.2 degrees two-theta, 18.5±0.2 degrees two-theta, and 19.9±0.2 degrees two-theta. In some embodiments, Compound I sodium salt hydrate Form D is characterized by an X-ray powder diffractogram having a signal at 9.3±0.2 degrees two-theta, 14.8±0.2 degrees two-theta, 27.3±0.2 degrees two-theta, and/or 29.1±0.2 degrees two-theta. In some embodiments, Compound I sodium salt hydrate Form D is characterized by an X-ray powder diffractogram having (a) signals at 7.8±0.2 degrees two-theta, 18.5±0.2 degrees two-theta, and 19.9±0.2 degrees two-theta; and (b) a signal at 9.3±0.2 degrees two-theta, 14.8±0.2 degrees two-theta, and/or 27.3±0.2 degrees two-theta. In some embodiments, Compound I sodium salt hydrate Form D is characterized by an X-ray powder diffractogram having signals at 7.8±0.2 degrees two-theta, 9.3±0.2 degrees two-theta, 14.8±0.2 degrees two-theta, 18.5±0.2 degrees two-theta, and 19.9±0.2 degrees two-theta, and 27.3±0.2 degrees two-theta.

In some embodiments Compound I sodium salt hydrate Form D is characterized by an X-ray powder diffractogram substantially similar to FIG. 38.

Another aspect of the invention provides a method of making Compound I sodium salt hydrate Form D comprising drying Compound I sodium salt hydrate Form C under vacuum at 80° C.

Compound I Sodium Salt Hydrate Form E

Figure 49:
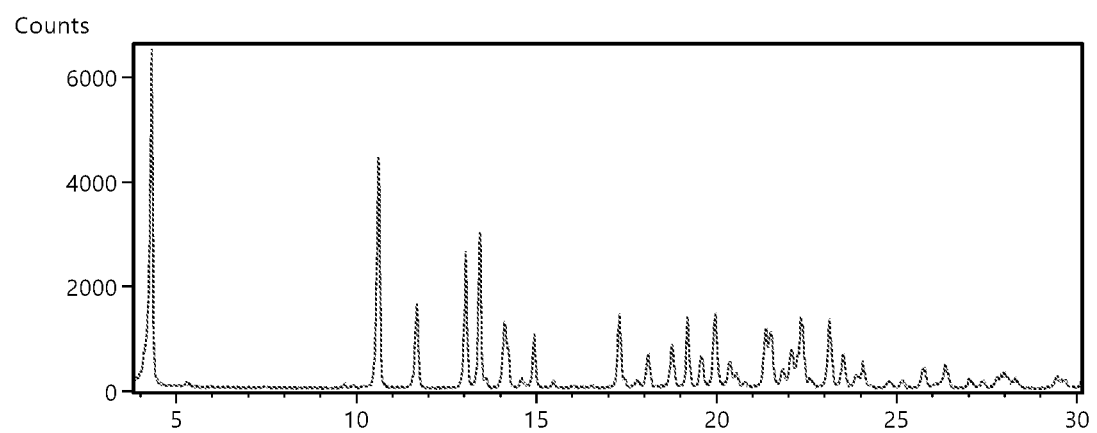
FIG. 49 provides an XRPD pattern of crystalline Compound I sodium salt hydrate Form E.

In some embodiments, the invention provides crystalline Compound I sodium salt hydrate Form E. FIG. 49 provides an X-ray powder diffractogram of Compound I sodium salt hydrate Form E at room temperature.

In some embodiments, Compound I sodium salt hydrate Form E is substantially pure crystalline. In some embodiments, Compound I sodium salt hydrate Form E is substantially crystalline. In some embodiments, Compound I sodium salt hydrate Form E is characterized by an X-ray powder diffractogram generated by an X-ray powder diffraction analysis with an incident beam of Cu Kα radiation.

In some embodiments, Compound I sodium salt hydrate Form E is characterized by an X-ray powder diffractogram having signals at 4.3±0.2 degrees two-theta, 13.0±0.2 degrees two-theta, and 14.9±0.2 degrees two-theta. In some embodiments, Compound I sodium salt hydrate Form E is characterized by an X-ray powder diffractogram having (a) signals at 4.3±0.2 degrees two-theta, 13.0±0.2 degrees two-theta, and 14.9±0.2 degrees two-theta; and (b) at least one signal selected from signals at 10.6±0.2 degrees two-theta, 11.7±0.2 degrees two-theta, 13.4±0.2 degrees two-theta, 14.1±0.2 degrees two-theta, 14.2±0.2 degrees two-theta, 17.3±0.2 degrees two-theta, 18.1±0.2 degrees two-theta, 18.8±0.2 degrees two-theta, 19.2±0.2 degrees two-theta, 20.0±0.2 degrees two-theta, 21.4±0.2 degrees two-theta, 21.5±0.2 degrees two-theta, 22.3±0.2 degrees two-theta, and 23.1±0.2 degrees two-theta. In some embodiments, Compound I sodium salt hydrate Form E is characterized by an X-ray powder diffractogram having (a) signals at 4.3±0.2 degrees two-theta, 13.0±0.2 degrees two-theta, and 14.9±0.2 degrees two-theta; and (b) at least two, at least three, or at least four signals selected from signals at 10.6±0.2 degrees two-theta, 11.7±0.2 degrees two-theta, 13.4±0.2 degrees two-theta, 14.1±0.2 degrees two-theta, 14.2±0.2 degrees two-theta, 17.3±0.2 degrees two-theta, 18.1±0.2 degrees two-theta, 18.8±0.2 degrees two-theta, 19.2±0.2 degrees two-theta, 20.0±0.2 degrees two-theta, 21.4±0.2 degrees two-theta, 21.5±0.2 degrees two-theta, 22.3±0.2 degrees two-theta, and 23.1±0.2 degrees two-theta.

In some embodiments, Compound I sodium salt hydrate Form E is characterized by an X-ray powder diffractogram having signals at 4.3±0.2 degrees two-theta, 13.0±0.2 degrees two-theta, and 23.1±0.2 degrees two-theta.

In some embodiments Compound I sodium salt hydrate Form E is characterized by an X-ray powder diffractogram substantially similar to FIG. 49.

In some embodiments, Compound I sodium salt hydrate Form E is characterized as having a $^{13}$C ssNMR spectrum with at least one peak selected from: 165.2±0.2 ppm, 155.4±0.2 ppm, 142.7±0.2 ppm, 128.4±0.2 ppm, 121.3±0.2 ppm, 101.0±0.2 ppm, 93.1±0.2 ppm, 69.5±0.2 ppm, 62.6±0.2 ppm, 55.0±0.2 ppm, 50.6±0.2 ppm, 50.0±0.2 ppm, 21.1±0.2 ppm, 17.2±0.2 ppm, 7.2±0.2 ppm, and 2.1±0.2 ppm. In some embodiments, Compound I sodium salt hydrate Form E is characterized as having a $^{13}$C ssNMR spectrum with two, three, four, five, six, seven, or more peaks selected from: 165.2±0.2 ppm, 155.4±0.2 ppm, 142.7±0.2 ppm, 128.4±0.2 ppm, 121.3±0.2 ppm, 101.0 0.2 ppm, 93.1±0.2 ppm, 69.5±0.2 ppm, 62.6±0.2 ppm, 55.2 0.2 ppm, 50.6±0.2 ppm, 50.0±0.2 ppm, 21.1±0.2 ppm, 17.2±0.2 ppm, 7.2±0.2 ppm, and 2.1±0.2 ppm. In some embodiments, Compound I sodium salt hydrate Form E is characterized as having a $^{13}$C ssNMR spectrum peaks at: 165.2±0.2 ppm, 155.4±0.2 ppm, 142.7±0.2 ppm, 128.4±0.2 ppm, 121.3±0.2 ppm, 101.0±0.2 ppm, 93.1±0.2 ppm, 69.5±0.2 ppm, 62.6±0.2 ppm, 55.2 0.2 ppm, 50.6±0.2 ppm, 50.0 0.2 ppm, 21.1±0.2 ppm, 17.2±0.2 ppm, 7.2±0.2 ppm, and 2.1±0.2 ppm.

In some embodiments, Compound I sodium salt hydrate Form E is characterized as having $^{13}$C ssNMR spectrum peaks at: 177.4±0.2 ppm, 165.2±0.2 ppm, 155.4±0.2 ppm, 142.7±0.2 ppm, 128.4±0.2 ppm, 121.3±0.2 ppm, 101.0±0.2 ppm, 69.5±0.2 ppm, 62.6±0.2 ppm, 55.2±0.2 ppm, 50.0±0.2 ppm, 30.9±0.2 ppm, 30.2±0.2 ppm, 27.8±0.2 ppm, 21.1±0.2 ppm, 17.2±0.2 ppm, 7.2±0.2 ppm, and 2.1±0.2 ppm.

Figure 50:
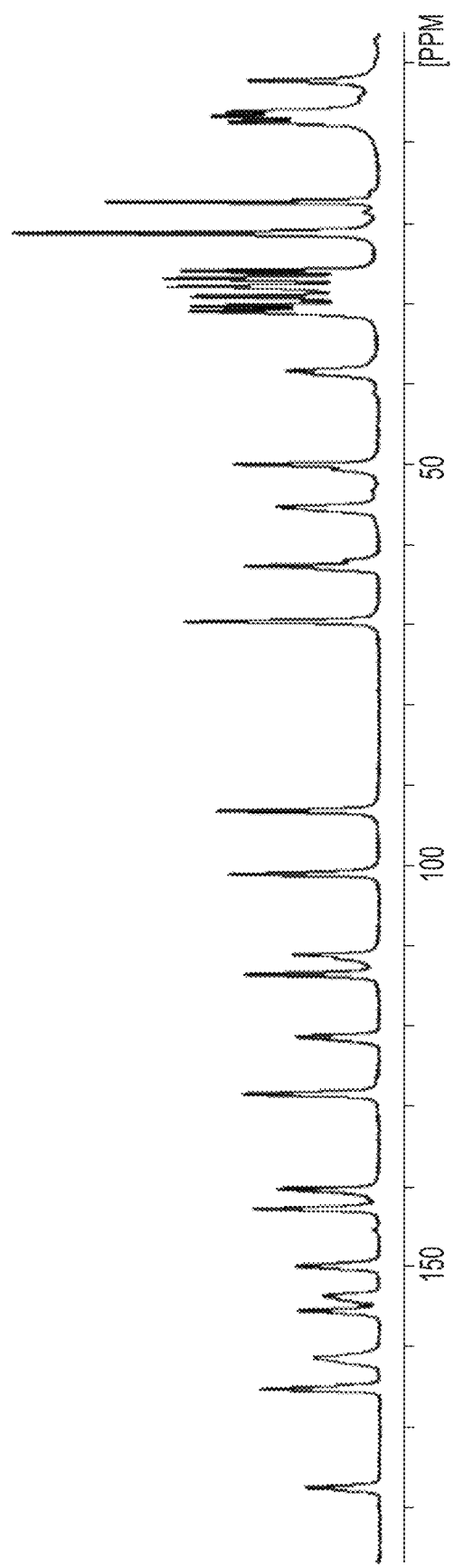
FIG. 50 shows a $^{13}$C solid state NMR spectrum of crystalline Compound I sodium salt hydrate Form E.

In some embodiments, Compound I sodium salt hydrate Form E is characterized by a $^{13}$C ssNMR spectrum substantially similar to FIG. 50.

In some embodiments, Compound I sodium salt hydrate Form E is characterized by a orthorhombic crystal system, a C222$_1$ space group, and unit cell dimensions measured at 100 K on a Bruker diffractometer equipped Cu K$_\alpha$ radiation (λ=1.54178 Å) of:

| a | 12.66 ± .01 Å | α | 90° |
|---|---|---|---|
| b | 13.16 ± .01 Å | β | 90° |
| c | 39.93 ± .01 Å | γ | 90° |

Another aspect of the invention provides a method of making Compound I sodium salt hydrate Form E comprising heating Compound I sodium salt hydrate Form A in IPA and water at 65° C., cooling the mixture to 45° C., seeding with Compound I sodium salt hydrate Form A crystals, cooling the mixture to 20° C., collecting and then washing the solids with IPA:water (1:3 v:v), air drying, then adding IPA, NaOH, and water to the solid, heating to 73° C., polish filtering the solution, cooling to 58° C., adding water, seeding with Compound I sodium salt hydrate Form E crystals at 40° C., cooling to 5° C., collecting the solids, washing the solids with a mixture of water and IPA, and drying under vacuum at 40° C. to provide Compound I sodium salt hydrate Form E.

Another aspect of the invention provides a method of making Compound I sodium salt hydrate Form E comprising dissolving Compound I sodium salt hydrate Form A in IPA/water at 65° C., cooling the solution to 45° C., seeding with a mixture of Compound I sodium salt hydrate Form A and Form E, adding water, cooling to 20° C., collecting the solids, washing the solids with a mixture of water and IPA, and drying under vacuum to provide Compound I sodium salt hydrate Form E.

Compound I Sodium Salt IPA (Wet) Solvate Form A

Figure 51:
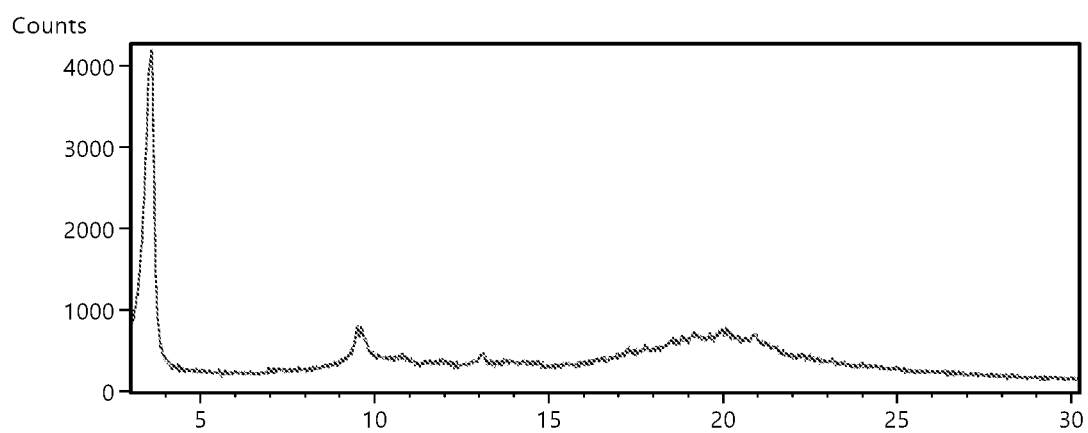
FIG. 51 provides an XRPD pattern of crystalline Compound I sodium salt IPA solvate (wet) Form A.

In some embodiments, the invention provides Compound I sodium salt IPA (wet) solvate Form A. FIG. 51 provides an X-ray powder diffractogram of Compound I sodium salt IPA (wet) solvate Form A at room temperature.

In some embodiments, Compound I sodium salt IPA (wet) solvate Form A is substantially pure crystalline. In some embodiments, Compound I sodium salt IPA (wet) solvate Form A is substantially crystalline. In some embodiments, Compound I sodium salt IPA (wet) solvate Form A is characterized by an X-ray powder diffractogram generated by an X-ray powder diffraction analysis with an incident beam of Cu Kα radiation.

In some embodiments, Compound I sodium salt IPA (wet) solvate Form A is characterized by an X-ray powder diffractogram having a signal at 3.5±0.2 degrees two-theta and/or a signal at 3.6±0.2 degrees two-theta. In some embodiments, Compound I sodium salt IPA (wet) solvate Form A is characterized by an X-ray powder diffractogram having (a) a signal at 3.5±0.2 degrees two-theta and/or a signal at 3.6±0.2 degrees two-theta and (b) a signal 9.5±0.2 degrees two-theta.

In some embodiments, Compound I sodium salt IPA (wet) solvate Form A is characterized by an X-ray powder diffractogram having signals at 3.6±0.2 degrees two-theta, 3.5±0.2 degrees two-theta, and 9.5±0.2 degrees two-theta.

In some embodiments Compound I sodium salt IPA (wet) solvate Form A is characterized by an X-ray powder diffractogram substantially similar to FIG. 51.

Another aspect of the invention provides a method of making Compound I sodium salt IPA (wet) solvate Form A comprising comprising slurrying amorphous Compound I sodium salt hydrate Form A in IPA.

Compound I Sodium Salt IPA (Dry) Solvate Form B

Figure 52:
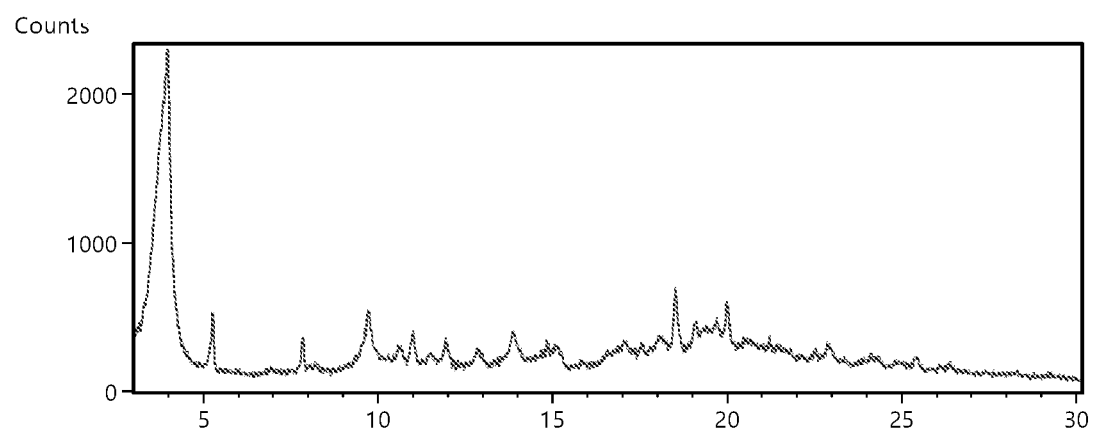
FIG. 52 provides an XRPD pattern of crystalline Compound I sodium salt IPA solvate (dry) Form B.

In some embodiments, the invention provides Compound I sodium salt IPA (dry) solvate Form B. FIG. 52 provides an X-ray powder diffractogram of Compound I sodium salt IPA (dry) solvate Form B at room temperature.

In some embodiments, Compound I sodium salt IPA (dry) solvate Form B is substantially pure crystalline. In some embodiments, Compound I sodium salt IPA (dry) solvate Form B is substantially crystalline. In some embodiments, Compound I sodium salt IPA (dry) solvate Form B is characterized by an X-ray powder diffractogram generated by an X-ray powder diffraction analysis with an incident beam of Cu Kα radiation.

In some embodiments, Compound I sodium salt IPA (dry) solvate Form B is characterized by an X-ray powder diffractogram having a signal at 4.0±0.2 degrees two-theta and 5.3±0.2 degrees two-theta. In some embodiments, Compound I sodium salt IPA (dry) solvate Form B is characterized by an X-ray powder diffractogram having (a) signals at 4.0±0.2 degrees two-theta and 5.3±0.2 degrees two-theta; and (b) at least one signal selected from signals at 7.9±0.2 degrees two-theta, 9.7±0.2 degrees two-theta, 11.0±0.2 degrees two-theta, 13.9±0.2 degrees two-theta, 18.5±0.2 degrees two-theta, and 20.0±0.2 degrees two-theta. In some embodiments, Compound I sodium salt IPA (dry) solvate Form B is characterized by an X-ray powder diffractogram having (a) signals at 4.0±0.2 degrees two-theta and 5.3±0.2 degrees two-theta; and (b) a signal at one, two, three, or four of 7.9±0.2 degrees two-theta, 9.7±0.2 degrees two-theta, 11.0±0.2 degrees two-theta, 13.9±0.2 degrees two-theta, 18.5±0.2 degrees two-theta, and 20.0±0.2 degrees two-theta.

In some embodiments, Compound I sodium salt IPA (dry) solvate Form B is characterized by an X-ray powder diffractogram having signals at 4.0±0.2 degrees two-theta, 7.9±0.2 degrees two-theta, and 9.7±0.2 degrees two-theta.

In some embodiments Compound I sodium salt IPA (dry) solvate Form B is characterized by an X-ray powder diffractogram substantially similar to FIG. 52.

In some embodiments, Compound I sodium salt IPA (dry) solvate Form B is characterized as having a $^{13}$C ssNMR spectrum with at least one peak selected from: 180.3±0.2 ppm, 178.7±0.2 ppm, 164.7±0.2 ppm, 135.9±0.2 ppm, 127.0±0.2 ppm, 117.0±0.2 ppm, 105.4±0.2 ppm, 95.5±0.2 ppm, 94.4±0.2 ppm, 68.9±0.2 ppm, 67.6±0.2 ppm, 64.1±0.2 ppm, 59.5±0.2 ppm, 54.5±0.2 ppm, 53.6±0.2 ppm, 32.7±0.2 ppm, 24.6±0.2 ppm, 20.2±0.2 ppm, 5.1±0.2 ppm, 3.6±0.2 ppm. In some embodiments, Compound I sodium salt IPA (dry) solvate Form B is characterized as having a 13 C ssNMR spectrum with two, three, four, five, six, seven, or more peaks selected from: 180.3±0.2 ppm, 178.7±0.2 ppm, 164.7±0.2 ppm, 135.9±0.2 ppm, 127.0±0.2 ppm, 117.0±0.2 ppm, 105.4±0.2 ppm, 95.5±0.2 ppm, 94.4±0.2 ppm, 68.9±0.2 ppm, 67.6±0.2 ppm, 64.1±0.2 ppm, 59.5±0.2 ppm, 54.5±0.2 ppm, 53.6±0.2 ppm, 32.7±0.2 ppm, 24.6±0.2 ppm, 20.2±0.2 ppm, 5.1±0.2 ppm, 3.6±0.2 ppm. In some embodiments, Compound I sodium salt IPA (dry) solvate Form B is characterized as having a $^{13}$C ssNMR spectrum peaks at: 180.3 0.2 ppm, 178.7 0.2 ppm, 164.7 0.2 ppm, 135.9±0.2 ppm, 127.0±0.2 ppm, 117.0 0.2 ppm, 105.4±0.2 ppm, 95.5±0.2 ppm, 94.4±0.2 ppm, 68.9±0.2 ppm, 67.6±0.2 ppm, 64.1±0.2 ppm, 59.5±0.2 ppm, 54.5±0.2 ppm, 53.6±0.2 ppm, 32.7±0.2 ppm, 24.6±0.2 ppm, 20.2±0.2 ppm, 5.1 0.2 ppm, 3.6±0.2 ppm.

In some embodiments, Compound I sodium salt IPA (dry) solvate Form B is characterized as having $^{13}$C ssNMR spectrum peaks at: 180.3±0.2 ppm, 178.7±0.2 ppm, 164.7±0.2 ppm, 135.9±0.2 ppm, 127.0±0.2 ppm, 117.0±0.2 ppm, 105.4±0.2 ppm, 95.5±0.2 ppm, 94.4±0.2 ppm, 67.6±0.2 ppm, 59.5±0.2 ppm, 53.6±0.2 ppm, 32.7±0.2 ppm, 27.2±0.2 ppm, 24.6±0.2 ppm, and 3.6±0.2 ppm.

Figure 53:
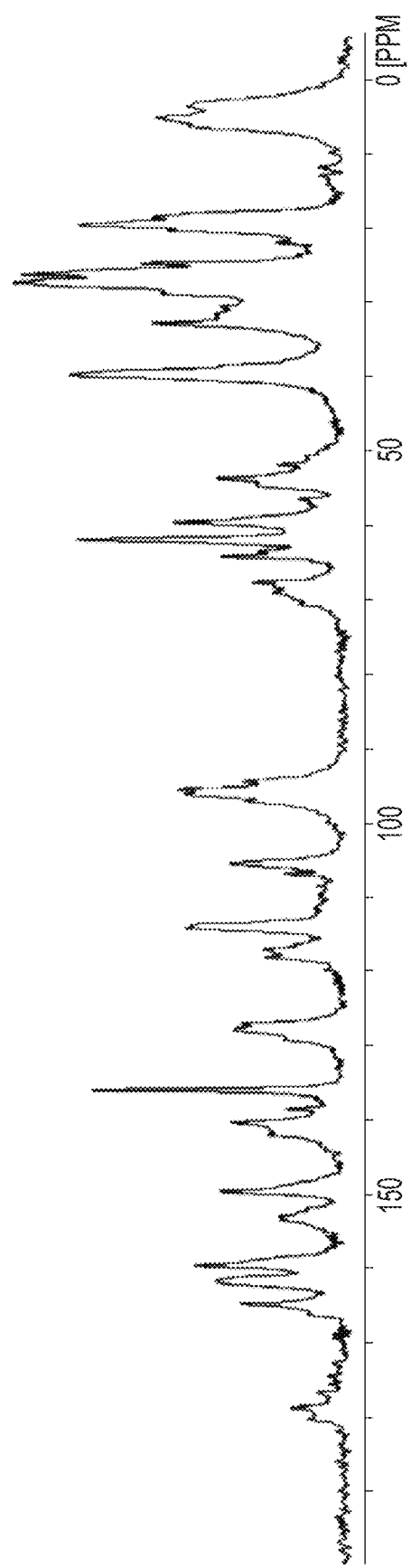
FIG. 53 shows a $^{13}$C solid state NMR spectrum of crystalline Compound I sodium salt IPA solvate (dry) Form B.

In some embodiments, Compound I sodium salt IPA (dry) solvate Form B is characterized by a $^{13}$C ssNMR spectrum substantially similar to FIG. 53.

Another aspect of the invention provides a method of making Compound I sodium salt IPA (dry) solvate Form B comprising comprising slurrying amorphous Compound I sodium salt hydrate Form A in IPA, then drying under vacuum at 40° C. to provide Compound I sodium salt IPA (dry) solvate Form B.

Compound I Potassium Salt Hydrate Form A

Figure 39:
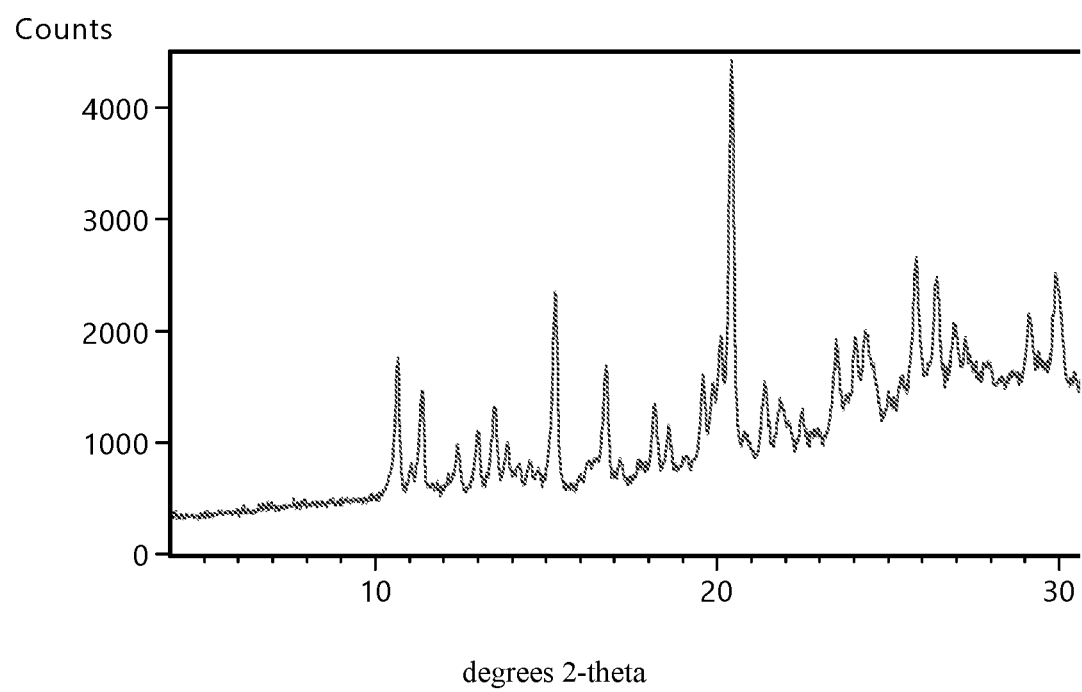
FIG. 39 provides an XRPD pattern of crystalline Compound I potassium salt hydrate Form A.

In some embodiments, the invention provides crystalline Compound I potassium salt hydrate Form A. FIG. 39 provides an X-ray powder diffractogram of Compound I potassium salt hydrate Form A at room temperature.

In some embodiments, Compound I potassium salt hydrate Form A is substantially pure crystalline. In some embodiments, Compound I potassium salt hydrate Form A is substantially crystalline. In some embodiments, Compound I potassium salt hydrate Form A is characterized by an X-ray powder diffractogram generated by an X-ray powder diffraction analysis with an incident beam of Cu Kαradiation.

In some embodiments, Compound I potassium salt hydrate Form A is characterized by an X-ray powder diffractogram having a signal at 10.7±0.2 degrees two-theta. In some embodiments, Compound I potassium salt hydrate Form A is characterized by an X-ray powder diffractogram having a signal at 10.7±0.2 degrees two-theta and a signal at 15.3±0.2 degrees two-theta and/or 20.4±0.2 degrees two-theta. In some embodiments, Compound I potassium salt hydrate Form A is characterized by an X-ray powder diffractogram having a signal at 10.7±0.2 degrees two-theta, 15.3±0.2 degrees two-theta and 20.4±0.2 degrees two-theta.

In some embodiments, Compound I potassium salt hydrate Form A is characterized by an X-ray powder diffractogram having (a) a signal at 10.7±0.2 degrees two-theta; and (b) one or more signals selected from 15.3±0.2 degrees two-theta, 20.4±0.2 degrees two-theta, and 29.1±0.2 degrees two-theta. In some embodiments, Compound I potassium salt hydrate Form A is characterized by an X-ray powder diffractogram having a signal at 10.7±0.2 degrees two-theta, 15.3±0.2 degrees two-theta, 20.4±0.2 degrees two-theta, and 29.1±0.2 degrees two-theta.

In some embodiments Compound I potassium salt hydrate Form A is characterized by an X-ray powder diffractogram substantially similar to FIG. 39.

Another aspect of the invention provides a method of making Compound I potassium salt hydrate Form A comprising reacting Compound I (free form) Form A with potassium hydride/water and subjecting to two heating and cooling cycles from 60° C. to room temperature.

Compound I Potassium Salt Hydrate Form B

Figure 40:
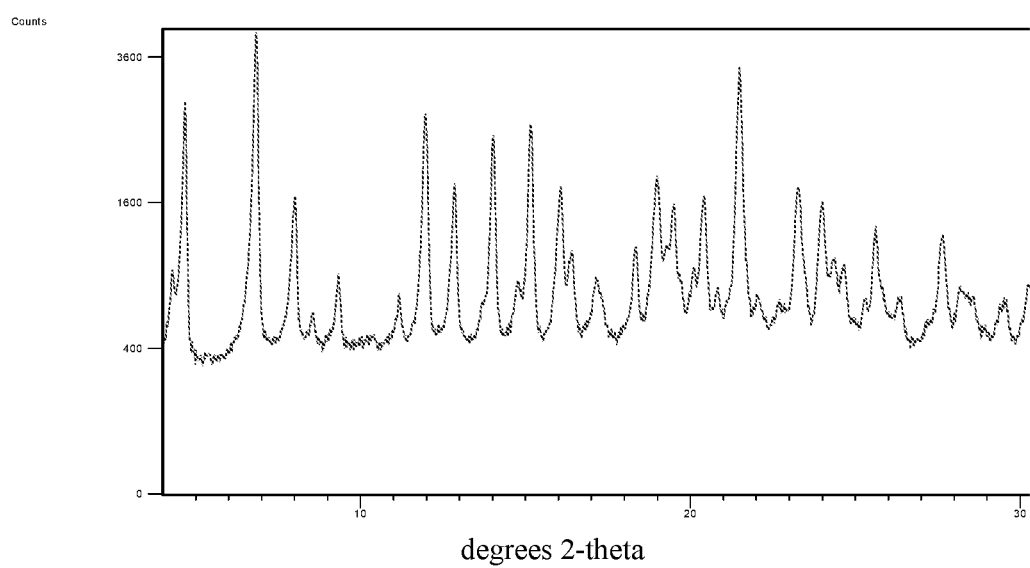
FIG. 40 provides an XRPD pattern of crystalline Compound I potassium salt hydrate Form B.

In some embodiments, the invention provides crystalline Compound I potassium salt hydrate Form B. FIG. 40 provides an X-ray powder diffractogram of Compound I potassium salt hydrate Form B at room temperature.

In some embodiments, Compound I potassium salt hydrate Form B is substantially pure crystalline. In some embodiments, Compound I potassium salt hydrate Form B is substantially crystalline. In some embodiments, Compound I potassium salt hydrate Form B is characterized by an X-ray powder diffractogram generated by an X-ray powder diffraction analysis with an incident beam of Cu Kα radiation.

In some embodiments, Compound I potassium salt hydrate Form B is characterized by an X-ray powder diffractogram having signals at 4.7±0.2 degrees two-theta, 6.8±0.2 degrees two-theta, and 21.5±0.2 degrees two-theta. In some embodiments, Compound I potassium salt hydrate Form B is characterized by an X-ray powder diffractogram having signals at 4.7±0.2 degrees two-theta, 6.8±0.2 degrees two-theta, 14.8±0.2 degrees two-theta, and 21.5±0.2 degrees two-theta.

In some embodiments, Compound I potassium salt hydrate Form B is characterized by an X-ray powder diffractogram having (a) 4.7±0.2 degrees two-theta, 6.8±0.2 degrees two-theta, and 21.5±0.2 degrees two-theta; and (b) at least one signal selected from 14.8±0.2 degrees two-theta, 15.2±0.2 degrees two-theta, 16.1±0.2 degrees two-theta, and 19.0±0.2 degrees two-theta. In some embodiments, Compound I potassium salt hydrate Form B is characterized by an X-ray powder diffractogram having signals at 4.7±0.2 degrees two-theta, 6.8±0.2 degrees two-theta, 14.8±0.2 degrees two-theta, 15.2±0.2 degrees two-theta, 16.1±0.2 degrees two-theta, 19.0±0.2 degrees two-theta, and 21.5±0.2 degrees two-theta.

In some embodiments Compound I potassium salt hydrate Form B is characterized by an X-ray powder diffractogram substantially similar to FIG. 40.

Another aspect of the invention provides a method of making Compound I potassium salt hydrate Form B comprising making a slurry of Compound I amorphous potassium salt with ACN at room temperature and then at 60° C.

Compound I Potassium Salt Hydrate Form C

Figure 41:
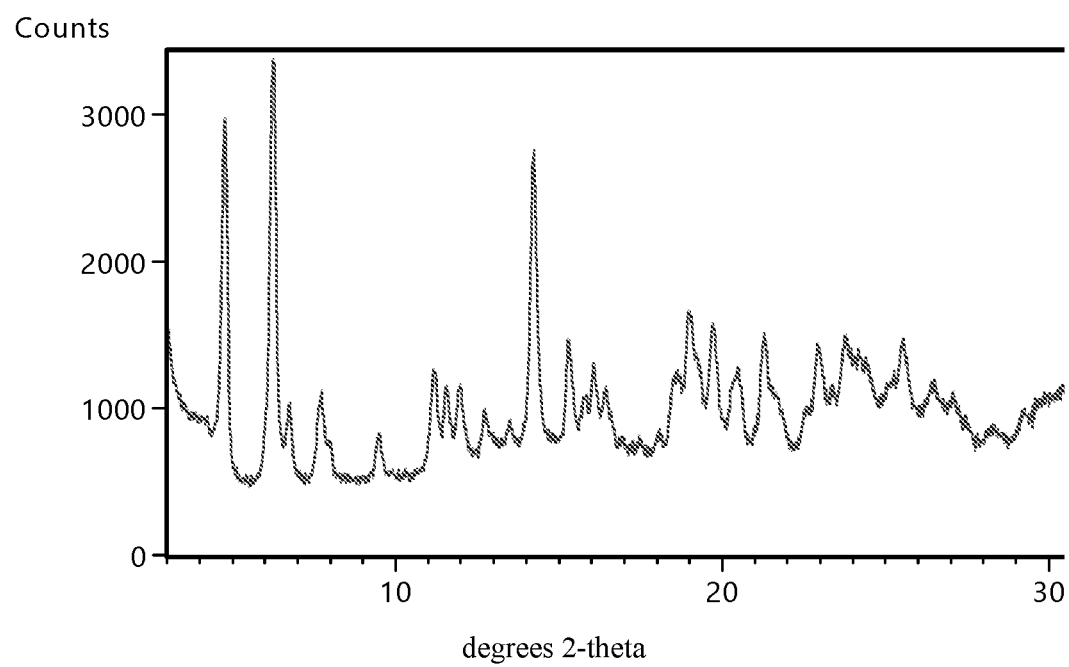
FIG. 41 provides an XRPD pattern of crystalline Compound I potassium salt hydrate Form C.

In some embodiments, the invention provides crystalline Compound I potassium salt hydrate Form C. FIG. 41 provides an X-ray powder diffractogram of Compound I potassium salt hydrate Form C at room temperature.

In some embodiments, Compound I potassium salt hydrate Form C is substantially pure crystalline. In some embodiments, Compound I potassium salt hydrate Form C is substantially crystalline. In some embodiments, Compound I potassium salt hydrate Form C is characterized by an X-ray powder diffractogram generated by an X-ray powder diffraction analysis with an incident beam of Cu Kα radiation.

In some embodiments, Compound I potassium salt hydrate Form C is characterized by an X-ray powder diffractogram having a signal at 4.8±0.2 degrees two-theta, 6.3±0.2 degrees two-theta, and 14.2±0.2 degrees two-theta. In some embodiments, Compound I potassium salt hydrate Form C is characterized by an X-ray powder diffractogram having a signal at 4.8±0.2 degrees two-theta, 6.3±0.2 degrees two-theta, 14.2±0.2 degrees two-theta, 13.5±0.2 degrees two-theta, and 27.1±0.2 degrees two-theta. In some embodiments, Compound I potassium salt hydrate Form C is characterized by an X-ray powder diffractogram having (a) a signal at 6.3 0.2 degrees two-theta, 4.8±0.2 degrees two-theta, 14.2±0.2 degrees two-theta, 13.5±0.2 degrees two-theta, and 27.1±0.2 degrees two-theta; and (b) a signal at 19.0±0.2 degrees two-theta and/or 15.8±0.2 degrees two-theta. In some embodiments, Compound I potassium salt hydrate Form C is characterized by an X-ray powder diffractogram having signals at 6.3±0.2 degrees two-theta, 4.8±0.2 degrees two-theta, 14.2±0.2 degrees two-theta, 13.5±0.2 degrees two-theta, 27.1±0.2 degrees two-theta, 19.0±0.2 degrees two-theta, and 15.8±0.2 degrees two-theta.

In some embodiments Compound I potassium salt hydrate Form C is characterized by an X-ray powder diffractogram substantially similar to FIG. 41.

Another aspect of the invention provides a method of making Compound I potassium salt hydrate Form C comprising mixing amorphous Compound I potassium salt with ACN at room temperature.

Compound I Potassium Salt Hydrate Form D

Figure 42:
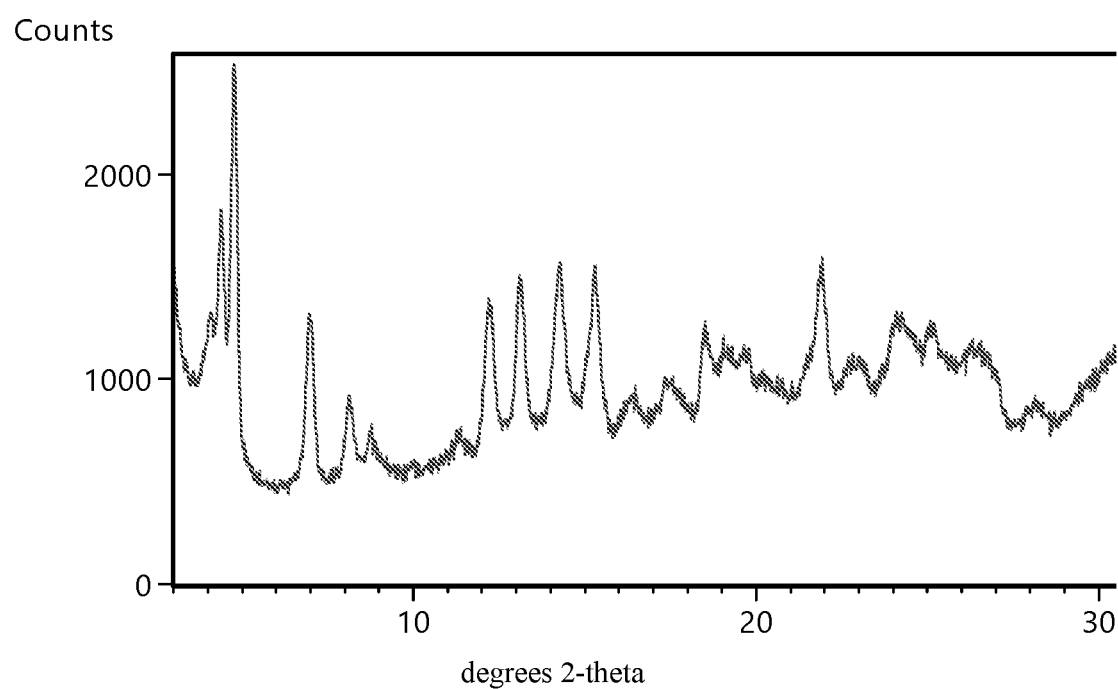
FIG. 42 provides an XRPD pattern of crystalline Compound I potassium salt hydrate Form D.

In some embodiments, the invention provides crystalline Compound I potassium salt hydrate Form D. FIG. 42 provides an X-ray powder diffractogram of Compound I potassium salt hydrate Form D at room temperature.

In some embodiments, Compound I potassium salt hydrate Form D is substantially pure crystalline. In some embodiments, Compound I potassium salt hydrate Form D is substantially crystalline. In some embodiments, Compound I potassium salt hydrate Form D is characterized by an X-ray powder diffractogram generated by an X-ray powder diffraction analysis with an incident beam of Cu Kα radiation.

In some embodiments, Compound I potassium salt hydrate Form D is characterized by an X-ray powder diffractogram having signals at 4.4±0.2 degrees two-theta, 15.3±0.2 degrees two-theta, and 13.1±0.2 degrees two-theta.

In some embodiments, Compound I potassium salt hydrate Form D is characterized by an X-ray powder diffractogram having (a) signals at 4.4±0.2 degrees two-theta, 15.3±0.2 degrees two-theta, and 13.1±0.2 degrees two-theta and (b) a signal at 8.8±0.2 degrees two-theta. In some embodiments, Compound I potassium salt hydrate Form D is characterized by an X-ray powder diffractogram having signals at 4.4±0.2 degrees two-theta, 8.8±0.2 degrees two-theta, 13.1±0.2 degrees two-theta, and 15.3±0.2 degrees two-theta.

In some embodiments, Compound I potassium salt hydrate Form D is characterized by an X-ray powder diffractogram having (a) 4.4±0.2 degrees two-theta, 8.8±0.2 degrees two-theta, 13.1±0.2 degrees two-theta, and 15.3±0.2 degrees two-theta; and (b) at least one signal selected from 7.0±0.2 degrees two-theta, 8.1±0.2 degrees two-theta, and 21.9±0.2 degrees two-theta. In some embodiments, Compound I potassium salt hydrate Form D is characterized by an X-ray powder diffractogram having signals at 4.4±0.2 degrees two-theta, 7.0±0.2 degrees two-theta, 8.1±0.2 degrees two-theta, 8.8±0.2 degrees two-theta, 13.1±0.2 degrees two-theta, and 15.3±0.2 degrees two-theta, and 21.9±0.2 degrees two-theta.

In some embodiments Compound I potassium salt hydrate Form D is characterized by an X-ray powder diffractogram substantially similar to FIG. 42.

Another aspect of the invention provides a method of making Compound I potassium salt hydrate Form D comprising mixing amorphous Compound I potassium salt with ACN at room temperature and drying at 29° C. under vacuum.

Compound I Ammonia Salt Hydrate Form A

Figure 44:
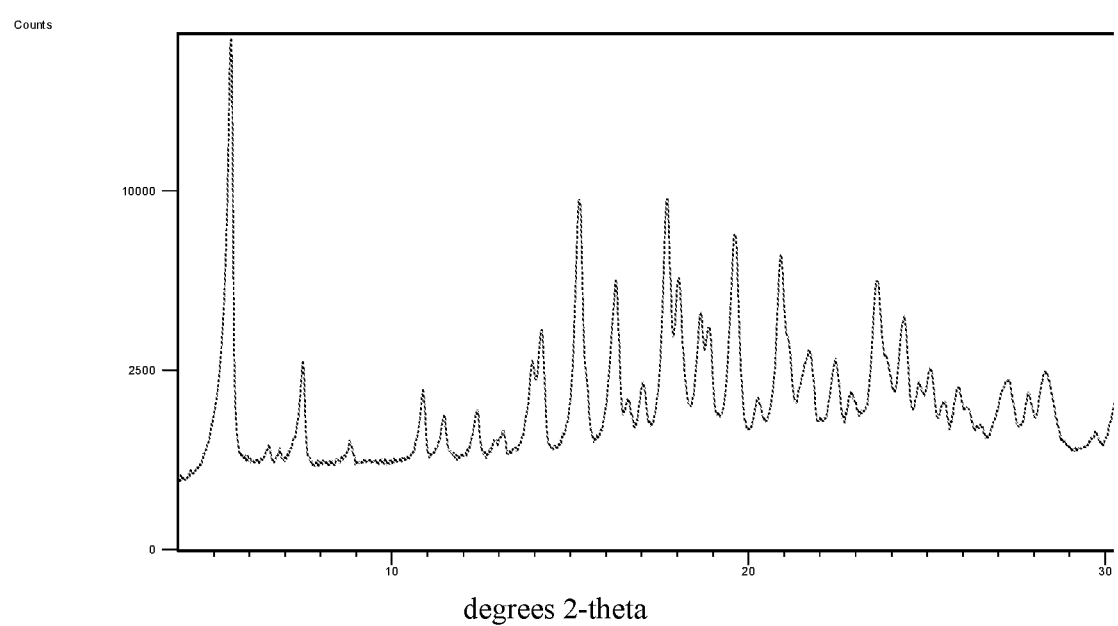
FIG. 44 provides an XRPD pattern of crystalline Compound I ammonia salt hydrate Form A.

In some embodiments, the invention provides crystalline Compound I ammonia salt hydrate Form A. FIG. 44 provides an X-ray powder diffractogram of Compound I ammonia salt hydrate Form A at room temperature.

In some embodiments, Compound I ammonia salt hydrate Form A is substantially pure crystalline. In some embodiments, Compound I ammonia salt hydrate Form A is substantially crystalline. In some embodiments, Compound I ammonia salt hydrate Form A is characterized by an X-ray powder diffractogram generated by an X-ray powder diffraction analysis with an incident beam of Cu Kα radiation.

In some embodiments, Compound I ammonia salt hydrate Form A is characterized by an X-ray powder diffractogram having a signal at 5.5±0.2 degrees two-theta. In some embodiments, Compound I ammonia salt hydrate Form A is characterized by an X-ray powder diffractogram having a signal at 15.3±0.2 degrees two-theta. In some embodiments, Compound I ammonia salt hydrate Form A is characterized by an X-ray powder diffractogram having a signal at 17.7±0.2 degrees two-theta. In some embodiments, Compound I ammonia salt hydrate Form A is characterized by an X-ray powder diffractogram having signals at 5.5±0.2 degrees two-theta, 15.3±0.2 degrees two-theta, and/or 17.7±0.2 degrees two-theta. In some embodiments, Compound I ammonia salt hydrate Form A is characterized by an X-ray powder diffractogram having signals at 5.5±0.2 degrees two-theta, 15.3±0.2 degrees two-theta, and 17.7±0.2 degrees two-theta.

In some embodiments, Compound I ammonia salt hydrate Form A is characterized by an X-ray powder diffractogram having (a) signals at 5.5±0.2 degrees two-theta, 15.3±0.2 degrees two-theta, and/or 17.7±0.2 degrees two-theta; and (b) at least one signal selected from 19.6±0.2 degrees two-theta, 20.9±0.2 degrees two-theta, and 18.0±0.2 degrees two-theta. In some embodiments, Compound I ammonia salt hydrate Form A is characterized by an X-ray powder diffractogram having (a) signals at 5.5±0.2 degrees two-theta, 15.3±0.2 degrees two-theta, and/or 17.7±0.2 degrees two-theta; and (b) signals at 18.0±0.2 degrees two-theta, 19.6±0.2 degrees two-theta, and/or 20.9±0.2 degrees two-theta. In some embodiments, Compound I ammonia salt hydrate Form A is characterized by an X-ray powder diffractogram having signals at 5.5±0.2 degrees two-theta, 15.3±0.2 degrees two-theta, 17.7±0.2 degrees two-theta, 18.0±0.2 degrees two-theta, 19.6±0.2 degrees two-theta, and 20.9±0.2 degrees two-theta.

In some embodiments Compound I ammonia salt hydrate Form A is characterized by an X-ray powder diffractogram substantially similar to FIG. 44.

Another aspect of the invention provides a method of making Compound I ammonia salt hydrate Form A comprising mixing amorphous Compound I (free form) Form A with ammonium hydroxide in water.

Methods of Treatment

Compound I, in amorphous form or in any one of the pharmaceutically acceptable crystalline forms disclosed herein acts as a CFTR modulator, i.e., it modulates CFTR activity in the body. Individuals suffering from a mutation in the gene encoding CFTR may benefit from receiving a CFTR modulator. A CFTR mutation may affect the CFTR quantity, i.e., the number of CFTR channels at the cell surface, or it may impact CFTR function, i.e., the functional ability of each channel to open and transport ions. Mutations affecting CFTR quantity include mutations that cause defective synthesis (Class I defect), mutations that cause defective processing and trafficking (Class II defect), mutations that cause reduced synthesis of CFTR (Class V defect), and mutations that reduce the surface stability of CFTR (Class VI defect). Mutations that affect CFTR function include mutations that cause defective gating (Class III defect) and mutations that cause defective conductance (Class IV defect). Some CFTR mutations exhibit characteristics of multiple classes. Certain mutations in the CFTR gene result in cystic fibrosis.

Thus, in some embodiments, the invention provides methods of treating, lessening the severity of, or symptomatically treating cystic fibrosis in a patient comprising administering to the patient an effective amount of Compound I as an amorphous solid or in any one of the pharmaceutically acceptable crystalline forms disclosed herein, alone or in combination with another active ingredient, such as another CFTR modulating agent. In some embodiments, the patient has an F508del/minimal function (MF) genotype, F508del/F508del genotype (homozygous for the F508del mutation), F508del/gating genotype, or F508del/residual function (RF) genotype. In some embodiments the patient is heterozygous and has one F508del mutation. In some embodiments the patient is homozygous for the N1303K mutation.

In some embodiments, the patient is heterozygous and has an F508del mutation on one allele and a mutation on the other allele selected from Table 1:

TABLE 1

CFTR Mutations
Mutation

| | | | | |
|---|---|---|---|---|
| Q2X | L218X | Q525X | R792X | E1104X |
| S4X | Q220X | G542X | E822X | W1145X |
| W19X | Y275X | G550X | W882X | R1158X |
| G27X | C276X | Q552X | W846X | R1162X |
| Q39X | Q290X | R553X | Y849X | S1196X |
| W57X | G330X | E585X | R851X | W1204X |
| E60X | W401X | G673X | Q890X | L1254X |
| R75X | Q414X | Q685X | S912X | S1255X |
| L88X | S434X | R709X | Y913X | W1282X |
| E92X | S466X | K710X | Q1042X | Q1313X |
| Q98X | S489X | Q715X | W1089X | Q1330X |
| Y122X | Q493X | L732X | Y1092X | E1371X |

TABLE 1-continued

CFTR Mutations
Mutation

| | | | | |
|---|---|---|---|---|
| E193X | W496X | R764X | W1098X | Q1382X |
| W216X | C524X | R785X | R1102X | Q1411X |
| 185 + 1G→T | 711 + 5G→A | 1717 − 8G→A | 2622 + 1G→A | 3 + −1G→A |
| 296 + 1G→A | 712 − 1G→T | 1717 − 1G→A | 2790 − 1G→C | 3500 − 2A→G |
| 296 + 1G→T | 1248 + 1G→A | 1811 + 1G→C | 3040G→C | 3600 + 2insT |
| 405 + 1G→A | 1249 − 1G→A | 1811 + 1.6kbA→G | (G970R) | 3850 − 1G→A |
| 405 + 3A→C | 1341 + 1G→A | 1811 + 1643G→T | 3120G→A | 4005 + 1G→A |
| 406 − 1G→A | 1525 − 2A→G | 1812 − 1G→A | 3120 + 1G→A | 4374 + 1G→T |
| 621 + 1G→T | 1525 − 1G→A | 1898 + 1G→A | 3121 − 2A→G | |
| 711 + 1G→T | | 1898 + 1G→C | | |
| 182delT | 1078delT | 1677delTA | 2711delT | 3737delA |
| 306insA | 1119delA | 1782delA | 2732insA | 3791delC |
| 306delTAGA | 1138insG | 1824delA | 2869insG | 3821delT |
| 365–366insT | 1154insTC | 1833delT | 2896delAG | 3876delA |
| 394delTT | 1161delC | 2043delG | 2942insT | 3878delG |
| 442delA | 1213delT | 2143delT | 2957delT | 3905insT |
| 444delA | 1259insA | 2183AA→G | 3007delG | 4016insT |
| 457TAT→G | 1288insTA | 2184delA | 3028delA | 4021dupT |
| 541delC | 1343delG | 2184insA | 3171delC | 4022insT |
| 574delA | 1471delA | 2307insA | 3171insC | 4040delA |
| 663delT | 1497delGG | 2347delG | 3271delGG | 4279insA |
| 849delG | 1548delG | 2585delT | 3349insT | 4326delTC |
| 935delA | 1609del CA | 2594delGT | 3659delC | |
| CFTRdele1 | | CFTRdele16–17b | 1461ins4 | |
| CFTRdele2 | | CFTRdele17a,17b | 1924del7 | |
| CFTRdele2,3 | | CFTRdele17a–18 | 2055del9→A | |
| CFTRdele2–4 | | CFTRdele19 | 2105–2117del13insAGAAA | |
| CFTRdele3–10,14b–16 | | CFTRdele19–21 | 2372del8 | |
| CFTRdele4–7 | | CFTRdele21 | 2721del11 | |
| CFTRdele4–11 | | CFTRdele22–24 | 2991del32 | |
| CFTR50kbdel | | CFTRdele22,23 | 3667ins4 | |
| CFTRdup6b–10 | | 124del23bp | 4010del4 | |
| CFTRdele11 | | 602del14 | 4209TGTT→AA | |
| CFTRdele13,14a | | 852del22 | | |
| CFTRdele14b–17b | | 991del5 | | |
| A46D | V520F | Y569D | N1303K | |
| G85E | A559T | L1065P | | |
| R347P | R560T | R1066C | | |
| L467P | R560S | L1077P | | |
| I507del | A561E | M1101K | | |

In some embodiments, the invention provides methods of treating, lessening the severity of, or symptomatically treating cystic fibrosis in a patient comprising administering to the patient an effective amount of Compound I as crystalline free form Compound I, Form A. In some embodiments, the method employs crystalline free form Compound I, Form B. In some embodiments, method employs crystalline free form Compound I, Form C.

In some embodiments, the invention provides methods of treating, lessening the severity of, or symptomatically treating cystic fibrosis in a patient comprising administering to the patient an effective amount of crystalline Compound I in the form of a calcium salt hydrate. In some embodiments, the crystalline form of Compound I is calcium salt hydrate Form A. In some embodiments, the crystalline form of Compound I is calcium salt hydrate Form B. In some embodiments, the crystalline form of Compound I is calcium salt hydrate Form C. In some embodiments, the crystalline form of Compound I is calcium salt hydrate Form D. In some embodiments, the crystalline form of Compound I is calcium salt hydrate Form E. In some embodiments, the crystalline form of Compound I is Form F. In some embodiments, the crystalline form of Compound I is calcium salt hydrate Form G. In some embodiments, the crystalline form of Compound I is calcium salt Form H.

In some embodiments, the invention provides methods of treating, lessening the severity of, or symptomatically treating cystic fibrosis in a patient comprising administering to the patient an effective amount of a crystalline form of Compound I, wherein the crystalline form is a calcium salt solvate. In some embodiments, the crystalline Compound I is calcium salt EtOH solvate Form A. In some embodiments, the crystalline Compound I is calcium salt EtOH solvate Form B. In some embodiments, the crystalline Compound I is calcium salt EtOH solvate Form C.

In some embodiments the invention provides methods of treating, lessening the severity of, or symptomatically treating cystic fibrosis in a patient comprising administering to the patient an effective amount of a crystalline form of Compound I, wherein the crystalline form is sodium salt hydrate Form A. In some embodiments, the crystalline form of Compound I is sodium salt neat Form B. In some embodiments the crystalline form of Compound I is sodium salt hydrate Form C. In some embodiments the crystalline form of Compound I is sodium salt hydrate Form D.

In some embodiments the methods of treating, lessening the severity of, or symptomatically treating cystic fibrosis in a patient comprise administering to the patient an effective amount of a crystalline form of Compound I, wherein the crystalline form is potassium salt hydrate Form A. In some embodiments the crystalline form of Compound I is potassium salt hydrate Form A.

In some embodiments the crystalline form of Compound I used in the methods of treating, lessening the severity of, or symptomatically treating cystic fibrosis of the invention is potassium salt hydrate Form C. In some embodiments the crystalline form of Compound I used in the methods of treating, lessening the severity of, or symptomatically treating cystic fibrosis of the invention is potassium salt hydrate Form D.

In some embodiments the crystalline form of Compound I used in the methods of treating, lessening the severity of, or symptomatically treating cystic fibrosis of the invention is ammonia salt hydrate Form A.

Combination Therapies

One aspect disclosed herein provides methods of treating cystic fibrosis and other CFTR-mediated diseases with Compound I in combination with other pharmaceutically active agents, including CFTR modulating agents. In some embodiments, Compound I is in amorphous form and can be administered in combination with at least one additional active pharmaceutical ingredient, such as, e.g., a CFTR modulating agent. In some embodiments, the at least one additional active pharmaceutical ingredient is selected from (a) Compound II and pharmaceutically acceptable salts thereof; and (b) Compound III or Compound III-d and pharmaceutically acceptable salts of Compound III or Compound III-d. Thus, in some embodiments, the combination therapies provided herein comprise amorphous Compound I and at least one compound selected from Compound II, (Compound III or III-d), and pharmaceutically acceptable salts thereof. In some embodiments, the combination therapies provided herein comprise at least one compound selected from amorphous Compound I and pharmaceutically acceptable salts thereof; and at least one compound selected from (Compound III or III-d), Compound IV, and/or pharmaceutically acceptable salts thereof.

In some embodiments, at least one compound selected from Compound I in any one of the pharmaceutically acceptable crystalline forms disclosed herein is administered in combination with at least one compound selected from Compound II and pharmaceutically acceptable salts thereof. In some embodiments, at least one compound selected from Compound I in any one of the pharmaceutically acceptable crystalline forms disclosed herein is administered in combination with at least one compound selected from Compound III and pharmaceutically acceptable salts thereof. In some embodiments, at least one compound selected from Compound I in any one of the pharmaceutically acceptable crystalline forms disclosed herein is administered in combination with at least one compound selected from Compound III-d and pharmaceutically acceptable salts thereof. In some embodiments, at least one compound selected from Compound I in any one of the pharmaceutically acceptable crystalline forms disclosed herein is administered in combination with Compounds II or a pharmaceutically acceptable salt thereof and at least one compound selected from Compound III and pharmaceutically acceptable salts thereof. In some embodiments, at least one compound selected from Compound I in any one of the pharmaceutically acceptable crystalline forms disclosed herein is administered in combination with at least one compound selected from Compound II and pharmaceutically acceptable salts thereof and at least one compound selected from Compound III-d and pharmaceutically acceptable salts thereof.

Each of Compounds I (in any one of the pharmaceutically acceptable crystalline forms disclosed herein), II, and III or III-d, and their pharmaceutically acceptable salts thereof independently can be administered once daily, twice daily, or three times daily. In some embodiments, at least one compound selected from Compound I in any one of the pharmaceutically acceptable crystalline forms disclosed herein is administered once daily. In some embodiments, at least one compound selected from Compound I in any one of the pharmaceutically acceptable crystalline forms disclosed herein is administered twice daily. In some embodiments, at least one compound selected from Compound I in any one of the pharmaceutically acceptable crystalline forms disclosed herein and at least one compound selected from Compound II and pharmaceutically acceptable salts thereof are administered once daily. In some embodiments, at least one compound selected from Compound I in any one of the pharmaceutically acceptable crystalline forms disclosed herein and at least one compound selected from Compound II and pharmaceutically acceptable salts thereof are administered twice daily. In some embodiments, at least one compound selected from Compound I in any one of the pharmaceutically acceptable crystalline forms disclosed herein and at least one compound selected from Compound III or III-d and pharmaceutically acceptable salts thereof are administered once daily. In some embodiments, at least one compound selected from Compound I in any one of the pharmaceutically acceptable crystalline forms disclosed herein and at least one compound selected from Compound III or III-d and pharmaceutically acceptable salts thereof are administered twice daily.

In some embodiments, at least one compound selected from Compound I in any one of the pharmaceutically acceptable crystalline forms disclosed herein, at least one compound selected from Compound II and pharmaceutically acceptable salts thereof, and at least one compound selected from Compound III or III-d and pharmaceutically acceptable salts thereof are administered once daily. In some embodiments, at least one compound selected from Compound I in any one of the pharmaceutically acceptable crystalline forms disclosed herein, at least one compound selected from Compound III or III-d and pharmaceutically acceptable salts thereof, and at least one compound selected from Compound IV and pharmaceutically acceptable salts thereof, are administered once daily. In some embodiments, at least one compound selected from Compound I in any one of the pharmaceutically acceptable crystalline forms disclosed herein, at least one compound selected from Compound II and pharmaceutically acceptable salts thereof, and at least one compound selected from Compound III or III-d and pharmaceutically acceptable salts thereof are administered twice daily. In some embodiments, at least one compound selected from Compound I in any one of the pharmaceutically acceptable crystalline forms disclosed herein, at least one compound selected from Compound III or III-d and pharmaceutically acceptable salts thereof, and at least one compound selected from Compound IV and pharmaceutically acceptable salts thereof, are administered twice daily.

In some embodiments, at least one compound selected from Compound I in any one of the pharmaceutically acceptable crystalline forms disclosed herein and at least one compound selected from Compound II and pharmaceutically acceptable salts thereof, are administered once daily and at least one compound selected from Compound III-d and pharmaceutically acceptable salts thereof, are administered twice daily. In some embodiments, at least one compound selected from Compound I in any one of the pharmaceutically acceptable crystalline forms disclosed herein and at least one compound selected from Compound IV and pharmaceutically acceptable salts thereof, are administered once daily and at least one compound selected from Compound III-d and pharmaceutically acceptable salts thereof, are administered twice daily.

In some embodiments, at least one compound selected from Compound I in any one of the pharmaceutically acceptable crystalline forms disclosed herein is administered in an amount of 5 mg to 100 mg. In some embodiments, at least one compound selected from Compound I in any one of the pharmaceutically acceptable crystalline forms disclosed herein is administered in an amount of 5 mg, 10 mg, 15 mg, or 20 mg daily. In some embodiments, at least one compound selected from Compound I in any one of the pharmaceutically acceptable crystalline forms disclosed herein is administered in an amount of 5 mg, 10 mg, or 20 mg once daily. In some embodiments, 5 mg, or 10 mg of Compound I in any one of the pharmaceutically acceptable crystalline forms disclosed herein are administered twice daily.

Compounds I (in any one of the pharmaceutically acceptable crystalline forms disclosed herein), II, (III or III-d), and their pharmaceutically acceptable salts thereof can be administered in a single pharmaceutical composition or separate pharmaceutical compositions. Such pharmaceutical compositions can be administered once daily or multiple times daily, such as twice daily. As used herein, the phrase that a given amount of API (e.g., Compound I, II, (III, III-d) or a pharmaceutically acceptable salt thereof) is administered once or twice daily or per day means that said given amount is administered per dosing once or twice daily. For example, the phrase that 50 mg of Compound II or a pharmaceutically acceptable salt thereof is administered twice daily or per day means that 50 mg of Compound II or an equivalent amount of a pharmaceutically acceptable salt thereof is administerd per dosing twice per day (e.g., 50 mg of Compound II or an equivalent amount of a pharmaceutically acceptable salt thereof is administerd in the morning and 50 mg of Compound II or an equivalent amount of a pharmaceutically acceptable salt thereof is administered in the evening).

In some embodiments, at least one compound selected from Compound I in any one of the pharmaceutically acceptable crystalline forms disclosed herein is administered in a first pharmaceutical composition; at least one compound selected from Compound II and pharmaceutically acceptable salts thereof is administered in a second pharmaceutical composition; and at least one compound selected from Compound III and pharmaceutically acceptable salts thereof is administered in a third pharmaceutical composition.

In some embodiments, at least one compound selected from Compound I in any one of the pharmaceutically acceptable crystalline forms disclosed herein is administered in a first pharmaceutical composition; at least one compound selected from Compound II and pharmaceutically acceptable salts thereof is administered in a second pharmaceutical composition; at least one compound selected from Compound III-d and pharmaceutically acceptable salts thereof is administered in a third pharmaceutical composition.

In some embodiments, at least one compound selected from Compound I in any one of the pharmaceutically acceptable crystalline forms disclosed herein is administered in a first pharmaceutical composition; at least one compound selected from Compound III or III-d and pharmaceutically acceptable salts thereof is administered in a second pharmaceutical composition; at least one compound selected from Compound IV and pharmaceutically acceptable salts thereof is administered in a third pharmaceutical composition.

In some embodiments, at least one compound selected from Compound I in any one of the pharmaceutically acceptable crystalline forms disclosed herein is administered in a first pharmaceutical composition; and at least one compound selected from Compound II and pharmaceutically acceptable salts thereof and at least one compound selected from Compound III or III-d, and pharmaceutically acceptable salts thereof are administered in a second pharmaceutical composition. In some embodiments, the second pharmaceutical composition comprises a half of a daily dose of said at least one compound selected from Compound III, III-d, and pharmaceutically acceptable salts thereof, and the other half of said at least one compound selected from Compound III, III-d, and pharmaceutically acceptable salts thereof is administered in a third pharmaceutical composition.

In some embodiments, at least one compound selected from Compound I in any one of the pharmaceutically acceptable crystalline forms disclosed herein; at least one compound selected from Compound II and pharmaceutically acceptable salts thereof and at least one compound selected from Compound III, III-d, and pharmaceutically acceptable salts thereof are administered in a first pharmaceutical composition. In some embodiments, the first pharmaceutical composition is administered to the patient twice daily. In some embodiments the first pharmaceutical composition is administered once daily. In some embodiments the first pharmaceutical composition is administered once daily and a second composition comprising only Compound III is administered once daily.

Any suitable pharmaceutical compositions known in the art can be used for Compound I (in any one of the pharmaceutically acceptable crystalline forms disclosed herein), Compound II, Compound III, Compound III-d, and pharmaceutically acceptable salts thereof. Some exemplary pharmaceutical compositions for Compound I and its pharmaceutically acceptable salts are described in the Examples. Some exemplary pharmaceutical compositions for Compound II and its pharmaceutically acceptable salts can be found in WO 2011/119984 and WO 2014/014841, incorporated herein by reference. Some exemplary pharmaceutical compositions for Compound III and its pharmaceutically acceptable salts can be found in WO 2007/134279, WO 2010/019239, WO 2011/019413, WO 2012/027731, and WO 2013/130669, and some exemplary pharmaceutical compositions for Compound III-d and its pharmaceutically acceptable salts can be found in U.S. Pat. Nos. 8,865,902, 9,181,192, 9,512,079, WO 2017/053455, and WO 2018/080591, all of which are incorporated herein by reference. Some exemplary pharmaceutical compositions for Compound IV and its pharmaceutically acceptable salts can be found in WO 2010/037066, WO 2011/127421, and WO 2014/071122, incorporated herein by reference.

In some embodiments, the crystalline form of Compound I used in the combination therapies of the invention is free form Compound I, Form A. In some embodiments, the combination therapy employs crystalline free form Compound I, Form B. In some embodiments, combination therapy employs crystalline free form Compound I, Form C.

In some embodiments, the crystalline form of Compound I employed in the combination therapy of the invention is a calcium salt hydrate. In some embodiments, the crystalline form of Compound I is calcium salt hydrate Form A. In some embodiments, the crystalline form of Compound I is calcium salt hydrate Form B. In some embodiments, the crystalline form of Compound I is calcium salt hydrate Form C. In some embodiments, the crystalline form of Compound I is calcium salt hydrate Form D. In some embodiments, the crystalline form of Compound I is calcium salt hydrate Form E. In some embodiments, the crystalline form of Compound I is Form F. In some embodiments, the crystalline form of Compound I is calcium salt hydrate Form G. In some embodiments, the crystalline form of Compound I is calcium salt Form H.

In some embodiments, the combination therapy of the invention employs a crystalline form of Compound I, wherein the crystalline form is a calcium salt solvate. In some embodiments, the crystalline Compound I is calcium salt EtOH solvate Form A. In some embodiments, the crystalline Compound I is calcium salt EtOH solvate Form B. In some embodiments, the crystalline Compound I is calcium salt EtOH solvate Form C.

In some embodiments the combination therapy of the invention comprises a crystalline form of Compound I, wherein the crystalline form is sodium salt hydrate Form A. In some embodiments, the crystalline form of Compound I is sodium salt neat Form B. In some embodiments the crystalline form of Compound I is sodium salt hydrate Form C. In some embodiments the crystalline form of Compound I is sodium salt hydrate Form D.

In some embodiments the combination therapy of the invention comprises a crystalline form of Compound I, wherein the crystalline form is potassium salt hydrate Form A. In some embodiments the crystalline form of Compound I is potassium salt hydrate Form B.

In some embodiments the crystalline form of Compound I used in the combination therapy of the invention is potassium salt hydrate Form C. In some embodiments the crystalline form of Compound I used in the combination therapy of the invention is potassium salt hydrate Form D.

In some embodiments the crystalline form of Compound I used in the combination therapy of the invention is ammonia salt hydrate Form A.

Coordination Structure of Certain Crystalline Forms

Certain crystalline forms involve Compound I coordinated to Ca ions. The local coordination has a chemical structure depicted as:

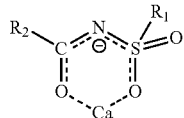

wherein R1 and R2 are the remaining parts of Compound I.

In each case, the calcium ion is coordinated by either 6, 7 or 8 atoms where at least two atoms are two oxygen atoms from Compound I, the other atoms in the coordination sphere may include other atoms from a Compound I molecule, atoms from a different Compound I molecule, water, or alcohol solvents.

Pharmaceutical Compositions

Another aspect of the invention provides pharmaceutical compositions comprising Compound I as an amorphous solid, or as any one of the pharmaceutically acceptable crystalline forms disclosed herein. In some embodiments, the invention provides pharmaceutical compositions comprising Compound I as an amorphous solid, or as any one of the pharmaceutically acceptable crystalline forms disclosed herein in combination with at least one additional active pharmaceutical ingredient. In some embodiments, the at least one additional active pharmaceutical ingredient is a CFTR modulator. In some embodiments, the at least one additional active pharmaceutical ingredient is a CFTR corrector. In some embodiments, the at least one additional active pharmaceutical ingredient is a CFTR potentiator. In some embodiments, the pharmaceutical composition comprises Compound I as an amorphous solid, or as any one of the pharmaceutically acceptable crystalline forms disclosed herein and at least two additional active pharmaceutical ingredients, one of which is a CFTR corrector and one of which is a CFTR potentiator.

In some embodiments, at least one additional active pharmaceutical ingredient is selected from mucolytic agents, bronchodilators, antibiotics, anti-infective agents, and anti-inflammatory agents.

In some embodiments, the invention provides a pharmaceutical composition comprising at least one compound selected from Compound I as an amorphous solid or as any one of the pharmaceutically acceptable crystalline forms disclosed herein, and at least one pharmaceutically acceptable carrier.

In some embodiments, the invention provides a pharmaceutical composition comprising (a) 5 mg to 20 mg of Compound I, wherein Compound I is any one of the pharmaceutically acceptable crystalline forms disclosed herein, (b) at least one compound selected from Compound II and pharmaceutically acceptable salts thereof, and (c) at least one pharmaceutically acceptable carrier.

In some embodiments, the disclosure provides a pharmaceutical composition comprising (a) 5 mg to 20 mg of Compound I, wherein Compound I is any one of the pharmaceutically acceptable crystalline forms disclosed herein, (b) at least one compound selected from Compound III, III-d, and pharmaceutically acceptable salts thereof, and (c) at least one pharmaceutically acceptable carrier.

In some embodiments, the disclosure provides a pharmaceutical composition comprising (a) 5 mg to 20 mg of Compound I, wherein Compound I is any one of the pharmaceutically acceptable crystalline forms disclosed herein, (b) at least one compound selected from Compound II and pharmaceutically acceptable salts thereof, (c) at least one compound selected from Compound III and pharmaceutically acceptable salts thereof, and (d) at least one pharmaceutically acceptable carrier.

In some embodiments, the disclosure provides a pharmaceutical composition comprising (a) 5 mg to 20 mg of Compound I, wherein Compound I is any one of the pharmaceutically acceptable crystalline forms disclosed herein, (b) at least one compound selected from Compound II and pharmaceutically acceptable salts thereof, (c) at least one compound selected from Compound III-d and pharmaceutically acceptable salts thereof, and (d) at least one pharmaceutically acceptable carrier.

In some embodiments, the disclosure provides a pharmaceutical composition comprising (a) 5 mg to 20 mg of Compound I, wherein Compound I is any one of the pharmaceutically acceptable crystalline forms disclosed herein, (b) at least one compound selected from Compound III or III-d and pharmaceutically acceptable salts thereof, (c) at least one compound selected from Compound IV and pharmaceutically acceptable salts thereof, and (d) at least one pharmaceutically acceptable carrier.

In some embodiments, the disclosure provides a pharmaceutical composition comprising 5 mg to 20 mg of Compound I, wherein Compound I is any one of the pharmaceutically acceptable crystalline forms disclosed herein, and optionally comprising one or more additional CFTR modulating agents. In some embodiments, the composition comprises about 5 mg, about 10 mg, or about 20 mg of Compound I and pharmaceutically acceptable salts thereof, and optionally comprise one or more additional CFTR modulating agents. In some embodiments, the composition comprises (a) 5 mg to 20 mg of at least one compound selected from Compound I, wherein Compound I is any one of the pharmaceutically acceptable crystalline forms disclosed herein, (b) 50 mg to 100 mg of Compound II, and (c) 150 mg to 300 mg of Compound III or 50 mg to 150 mg of Compound III-d. In some embodiments the composition comprises (a) 5 mg to 20 mg of Compound I, wherein Compound I is any one of the pharmaceutically acceptable crystalline forms disclosed herein, (b) 100 mg of Compound II, and (c) 150 mg of Compound III or 150 mg of Compound III-d.

In some embodiments, the disclosure provides a pharmaceutical composition comprising 5 mg of Compound I, wherein Compound I is any one of the pharmaceutically acceptable crystalline forms disclosed herein, and optionally comprising one or more additional CFTR modulating agents. In some embodiments, the composition comprises 10 mg of Compound I, wherein Compound I is any one of the pharmaceutically acceptable crystalline forms disclosed herein, and optionally comprises one or more additional CFTR modulating agents. In some embodiments, the disclosure provides a pharmaceutical composition comprising 20 mg of Compound I, wherein Compound I is any one of the pharmaceutically acceptable crystalline forms disclosed herein, and optionally comprising one or more additional CFTR modulating agents. In some embodiments, the composition comprises (a) 5 mg, 10 mg, or 20 mg of Compound I, wherein Compound I is any one of the pharmaceutically acceptable crystalline forms disclosed herein, (b) 50 mg or 100 mg of Compound II, and (c) 150 mg or 300 mg of Compound III or 50 mg, 75 mg, 100 mg, 125 mg, or 150 mg of Compound III-d.

Any pharmaceutical composition disclosed herein may comprise at least one pharmaceutically acceptable carrier. In some embodiments, the at least one pharmaceutically acceptable carrier is selected from pharmaceutically acceptable vehicles and pharmaceutically acceptable adjuvants. In some embodiments, the at least one pharmaceutically acceptable is selected from pharmaceutically acceptable fillers, disintegrants, surfactants, binders, lubricants.

In some embodiments, the crystalline form of Compound I in the pharmaceutical compositions of the invention is free form Compound I, Form A. In some embodiments, the pharmaceutical compositions comprise crystalline free form Compound I, Form B. In some embodiments, the pharmaceutical compositions comprise crystalline free form Compound I, Form C.

In some embodiments, the crystalline form of Compound I in the pharmaceutical composition of the invention is a calcium salt hydrate. In some embodiments, the crystalline form of Compound I is calcium salt hydrate Form A. In some embodiments, the crystalline form of Compound I is calcium salt hydrate Form B. In some embodiments, the crystalline form of Compound I is calcium salt hydrate Form C. In some embodiments, the crystalline form of Compound I is calcium salt hydrate Form D. In some embodiments, the crystalline form of Compound I is calcium salt hydrate Form E. In some embodiments, the crystalline form of Compound I is Form F. In some embodiments, the crystalline form of Compound I is calcium salt hydrate Form G. In some embodiments, the crystalline form of Compound I is calcium salt Form H.

In some embodiments, the pharmaceutical compositions of the invention comprise a crystalline form of Compound I, wherein the crystalline form is a calcium salt solvate. In some embodiments, the crystalline Compound I is calcium salt EtOH solvate Form A. In some embodiments, the crystalline Compound I is calcium salt EtOH solvate Form B. In some embodiments, the crystalline Compound I is calcium salt EtOH solvate Form C.

In some embodiments the pharmaceutical compositions of the invention comprise a crystalline form of Compound I, wherein the crystalline form is sodium salt hydrate Form A. In some embodiments, the crystalline form of Compound I is sodium salt neat Form B. In some embodiments the crystalline form of Compound I is sodium salt hydrate Form C. In some embodiments the crystalline form of Compound I is sodium salt hydrate Form D.

In some embodiments the pharmaceutical compositions of the invention comprise a crystalline form of Compound I, wherein the crystalline form is potassium salt hydrate Form A. In some embodiments the crystalline form of Compound I is potassium salt hydrate Form B.

In some embodiments the crystalline form of Compound I in the pharmaceutical compositions of the invention is potassium salt hydrate Form C. In some embodiments the crystalline form of Compound I in the pharmaceutical compositions of the invention is potassium salt hydrate Form D.

In some embodiments the crystalline form of Compound I in the pharmaceutical compositions of the invention is ammonia salt hydrate Form A.

The pharmaceutical compositions described herein are useful for treating cystic fibrosis and other CFTR-mediated diseases.

As described above, pharmaceutical compositions disclosed herein may optionally further comprise at least one pharmaceutically acceptable carrier. The at least one pharmaceutically acceptable carrier may be selected from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as tsodium lauryl sulfate and magnesium stearate), coloring agents, releasing agents, coating agents, sweetening agents, flavoring agents, perfuming agents, preservatives, and antioxidants.

EXEMPLARY EMBODIMENTS

1. Compound I (free form)

(Compound I)

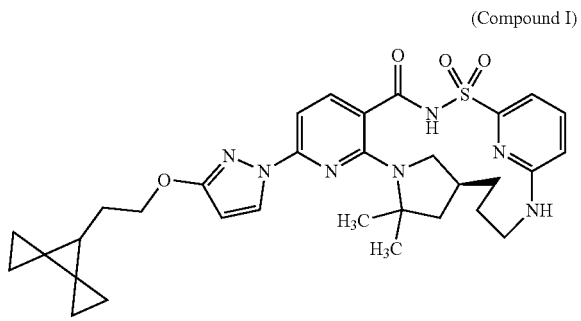 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]

wherein Compound I is substantially crystalline Form A (i.e., wherein less than 15% of Compound I is in amorphous form, wherein less than 10% of Compound I is in amorphous form, wherein less than 5% of Compound I is in amorphous form).

2. The Compound I of Embodiment 1, wherein Compound I is 100% crystalline Form A.

3. The Compound I of Embodiment 1 or Embodiment 2, wherein Compound I (free form) Form A is characterized by an X-ray powder diffractogram having a signal at 9.2±0.2 degrees two-theta, 11.3±0.2 degrees two-theta, 14.0±0.2 degrees two-theta, and/or 22.9±0.2 degrees two-theta.

4. The Compound I of Embodiment 1 or Embodiment 2, wherein Compound I (free form) Form A is characterized by an X-ray powder diffractogram having a signal at 9.2±0.2 degrees two-theta, 16.6±0.2 degrees two-theta, and 20.0±0.2 degrees two-theta.

5. The Compound I of Embodiment 1 or Embodiment 2, wherein Compound I (free form) Form A is characterized by an X-ray powder diffractogram having (a) signals at 9.2±0.2 degrees two-theta, 16.6±0.2 degrees two-theta, and 20.0 0.2 degrees two-theta; and (b) a signal at 11.3 0.2 degrees two-theta, 14.0±0.2 degrees two-theta, 22.9±0.2 degrees two-theta, 23.1±0.2 degrees two-theta, and/or 23.3±0.2 degrees two-theta.

6. The Compound I of Embodiment 1 or Embodiment 2, wherein Compound I (free form) Form A is characterized by an X-ray powder diffractogram substantially similar to FIG. 1.

7. The Compound I (free form) Form A of any one of Embodiments 1-6, characterized by a monoclinic crystal system, a $P2_1$ space group, and unit cell dimensions measured at 298 K on a Bruker diffractometer equipped with Mo $K_\alpha$ radiation ($\lambda$=0.71073 Å) of:

| a | 15.48 ± .01 Å | α | 90° |
| b | 12.74 ± .01 Å | β | 99.35 ± .01° |
| c | 16.37 ± .01 Å | γ | 90° |

8. The Compound I (free form) Form A of any one of Embodiments 1-7, wherein Compound I (free form) Form A is characterized by a $^{13}C$ solid state nuclear magnetic resonance ($^{13}C$ ssNMR) spectrum with one, two, three, four, five, six, seven, or more peaks selected from 163.2±0.2 ppm, 130.2±0.2 ppm, 104.6±0.2 ppm, 103.9±0.2 ppm, 58.3±0.2 ppm, 49.7±0.2 ppm, 43.3±0.2 ppm, and 37.0 0.2 ppm.

9. The Compound I (free form) Form A of any one of Embodiments 1-7, wherein Compound I (free form) Form A is characterized by a $^{13}C$ ssNMR spectrum with peaks at 163.2±0.2 ppm, 130.2±0.2 ppm, 104.6±0.2 ppm, 103.9±0.2 ppm, 58.3±0.2 ppm, 49.7±0.2 ppm, 43.3±0.2 ppm, and 37.0±0.2 ppm.

10. The Compound I (free form) Form A of any one of Embodiments 1-7, wherein Compound I (free form) Form A is characterized by a $^{13}C$ ssNMR substantially similar to FIG. 2.

11. The Compound I (free form) Form A of any one of Embodiments 1-10, prepared by a process comprising crystallizing amorphous Compound I in toluene and drying under vacuum to provide Compound I (free form) crystalline Form A.

12. A pharmaceutical composition comprising the Compound I (free form) Form A of any one of Embodiments 1-11, and optionally further comprising one or more additional CFTR modulating compounds.

13. The pharmaceutical composition of Embodiment 12, wherein the one or more additional CFTR modulating compounds are
  a. (a) Compound III or Compound III-d; or
  b. (i) Compound II and (ii) Compound III or Compound III-d.

14. The Compound I (free form) Form A of any one of Embodiments 1-11 or the pharmaceutical composition of Embodiment 12 or Embodiment 13 for use in the treatment of cystic fibrosis.

15. Use of the Compound I (free form) Form A of any one of Embodiments 1-11 or the compositions of Embodiment 12 or Embodiment 13 in the manufacture of a medicament for the treatment of cystic fibrosis.

16. A method of treating cystic fibrosis comprising administering the Compound I (free form) Form A of any one of Embodiments 1-11 or the pharmaceutical composition of Embodiment 12 or Embodiment 13 to a subject in need thereof.

17. The compound of use of Embodiment 14, the use of Embodiment 15, or the method of Embodiment 19, wherein the Compound I (free form) Form A of any one of Embodiments 1-11 is administered in combination with at least one additional CFTR modulating compound.

18. The compound, use, or method of Embodiment 17, wherein the Compound I (free form) Form A of any one of Embodiments 1-11 is administered in combination with
  a. (a) Compound III or Compound III-d;
  b. (i) Compound II and (ii) Compound III or Compound III-d; or
  c. (i) Compound IV and (ii) Compound III or Compound III-d.

19. The composition, method, use, or compound of any one of Embodiments 13-18, wherein Compound II and/or Compound III are in the form of a solid dispersion.

20. A method of preparing Compound I (free form) Form A of any one of Embodiments 1-10, comprising crystallizing amorphous Compound I in toluene and drying under vacuum to provide Compound I (free form) crystalline Form A.

21. Compound I (free form) wherein Compound I is substantially crystalline Form B (i.e., wherein less than 15% of Compound I is in amorphous form, wherein less than 10% of Compound I is in amorphous form, wherein less than 5% of Compound I is in amorphous form).

22. The Compound I of Embodiment 21, wherein Compound I is 100% crystalline Form B.

23. The Compound I of Embodiment 21 or Embodiment 22, wherein Compound I (free form) Form B is characterized by an X-ray powder diffractogram having a signal at 16.3±0.2 degrees two-theta and/or 17.7±0.2 degrees two-theta.

24. The Compound I of Embodiment 21 or Embodiment 22, wherein Compound I (free form) Form B is characterized by an X-ray powder diffractogram having (a) a signal at 16.3 0.2 degrees two-theta and/or 17.7±0.2 degrees two-theta; and (b) a signal at 5.5±0.2 degrees two-theta.

25. The Compound I of Embodiment 21 or Embodiment 22, wherein Compound I (free form) Form B is characterized by an X-ray powder diffractogram substantially similar to FIG. 3.

26. The Compound I of any one of Embodiments 21-25, wherein Compound I (free form) Form B is characterized by a $^{13}$C solid state nuclear magnetic resonance ($^{13}$C ssNMR) spectrum with one, two, three, or four peaks selected from 142.8±0.2 ppm, 97.8±0.2 ppm, 18.1±0.2 ppm, and 2.3±0.2 ppm.

27. The Compound I of any one of Embodiments 21-25, wherein Compound I (free form) Form B is characterized by a $^{13}$C ssNMR spectrum with (a) one, two, three, or four peaks selected from 142.8±0.2 ppm, 97.8±0.2 ppm, 18.1±0.2 ppm, and 2.3±0.2 ppm; and (b) one, two, three, four, five or six peaks selected from 166.3±0.2 ppm, 137.2±0.2 ppm, 108.1±0.2 ppm, 37.6±0.2 ppm, 25.3±0.2 ppm, and 20.1±0.2 ppm.

28. The Compound I of any one of Embodiments 21-25, wherein Compound I (free form) Form B is characterized by a $^{13}$C ssNMR spectrum with peaks at 142.8±0.2 ppm, 108.1±0.2 ppm, 97.8±0.2 ppm, 37.6±0.2 ppm, 18.1±0.2 ppm, and 2.3±0.2 ppm.

29. The Compound I of any one of Embodiments 21-25, wherein Compound I (free form) Form B is characterized by a $^{13}$C ssNMR spectrum with peaks at 142.8±0.2 ppm, 166.3±0.2 ppm, 137.2±0.2 ppm, 25.3±0.2 ppm, and 20.1±0.2 ppm.

30. The Compound I of any one of Embodiments 21-25, wherein Compound I (free form) Form B is characterized by a $^{13}$C ssNMR spectrum with peaks at 37.6±0.2 ppm, 166.3±0.2 ppm, 137.2±0.2 ppm, 25.3±0.2 ppm, and 20.1±0.2 ppm.

31. The Compound I of any one of Embodiments 21-25, wherein Compound I (free form) Form B is characterized by a $^{13}$C ssNMR substantially similar to FIG. 4.

32. The Compound I (free form) Form B of any one of Embodiments 21-31, prepared by a process comprising stirring Compound I calcium salt hydrate Form D in fed state simulated intestinal fluid.

33. A method of preparing Compound I (free form) Form B of any one of Embodiments 21-31, comprising stirring Compound I calcium salt hydrate Form D in fed state simulated intestinal fluid.

34. A pharmaceutical composition comprising the Compound I (free form) Form B of any one of Embodiments 21-32, optionally further comprising one or more additional CFTR modulating compounds.

35. The pharmaceutical composition of Embodiment 34, wherein the one or more additional CFTR modulating compounds are
   a. Compound III or Compound III-d; or
   b. (i) Compound II and (ii) Compound III or Compound III-d.

36. The Compound I (free form) Form B of any one of Embodiments 21-32 or the pharmaceutical composition of Embodiment 34 or Embodiment 35 for use in the treatment of cystic fibrosis.

37. Use of the Compound I (free form) Form B of any one of Embodiments 21-32 or the pharmaceutical composition of Embodiment 34 or Embodiment 35 in the manufacture of a medicament for the treatment of cystic fibrosis.

38. A method of treating cystic fibrosis comprising administering the Compound I (free form) Form B of any one of Embodiments 21-32 or the pharmaceutical composition of Embodiment 34 or Embodiment 35 to a subject in need thereof.

39. The compound for use of Embodiment 36, the use of Embodiment 37, or the method of Embodiment 38, wherein the Compound I of any one of Embodiments 21-32 is administered in combination with
   a. Compound III or Compound III-d;
   b. (i) Compound II and (ii) Compound III or Compound III-d; or
   c. (i) Compound IV and (ii) Compound III or Compound III-d.

40. The composition, use, method or compound of any one of Embodiments 35-39, wherein Compound II and/or Compound III are in the form of a solid dispersion.

41. Compound I (free form) wherein Compound I is substantially crystalline Form C (i.e., wherein less than 15% of Compound I is in amorphous form, wherein less than 10% of Compound I is in amorphous form, wherein less than 5% of Compound I is in amorphous form).

42. The Compound I of Embodiment 41, wherein Compound I is 100% crystalline Form C.

43. The Compound I of Embodiments 41 or Embodiment 42, wherein Compound I (free form) Form C is characterized by an X-ray powder diffractogram having a signal at 6.3±0.2 degrees two-theta.

44. The Compound I of Embodiments 41 or Embodiment 42, wherein Compound I (free form) Form C is characterized by an X-ray powder diffractogram having signals at 6.3±0.2 degrees two-theta, 14.8±0.2 degrees two-theta, and 20.4±0.2 degrees two-theta.

45. The Compound I of Embodiments 41 or Embodiment 42, wherein Compound I (free form) Form C is characterized by an X-ray powder diffractogram having (a) a signal at 6.3±0.2 degrees two-theta; and (b) one, two, three, four, five, six, or more signals selected from 14.8±0.2 degrees two-theta, 15.5±0.2 degrees two-theta, 18.5±0.2 degrees two-theta, 19.2±0.2 degrees two-theta, 20.1±0.2 degrees two-theta, 20.4±0.2 degrees two-theta, 23.8±0.2 degrees two-theta, and 26.4 degrees two-theta.

46. The Compound I of any one of Embodiments 41 or Embodiment 42, wherein Compound I (free form) Form C is characterized by an X-ray powder diffractogram substantially similar to FIG. 5.

47. The Compound I (free form) Form C of any one of Embodiments 41-46, prepared by a process comprising stirring Compound I (free form) Form A in IPA/H$_2$O at 25° C.

48. A method of preparing Compound I (free form) Form C of any one of Embodiments 41-46 comprising stirring Compound I (free form) Form A in IPA/H$_2$O at 25° C.

49. A pharmaceutical composition comprising the Compound I (free form) Form C of any one of Embodiments 41-47, optionally further comprising one or more additional CFTR modulating compounds.

50. The pharmaceutical composition of Embodiment 49, wherein the one or more additional CFTR modulating compounds are
    a. Compound III or Compound III-d; or
    b. (i) Compound II and (ii) Compound III or Compound III-d.

51. The Compound I of any one of Embodiments 41-47 or the pharmaceutical composition of Embodiment 49 or Embodiment 50 for use in the treatment of cystic fibrosis.

52. Use of the Compound I (free form) Form C of any one of Embodiments 41-47 or the pharmaceutical composition of Embodiment 49 or Embodiment 50 in the manufacture of a medicament for the treatment of cystic fibrosis.

53. A method of treating cystic fibrosis comprising administering the Compound I (free form) Form C of any one of Embodiments 41-47 or the pharmaceutical composition of Embodiment 49 or Embodiment 50 to a subject in need thereof.

54. The compound for use of Embodiment 51, the use of Embodiment 52, or the method of Embodiment 53, wherein the Compound I (free form) Form C of any one of Embodiments 41-47 is administered in combination with at least one additional CFTR modulating compound.

55. The compound, use, or method of Embodiment 54, wherein the Compound I (free form) Form C of any one of Embodiments 41-47 is administered in combination with
    a. Compound III or Compound III-d;
    b. (i) Compound II and (ii) Compound III or Compound III-d; or
    c. (i) Compound IV and (ii) Compound III or Compound III-d.

56. The composition, use, method or compound of any one of Embodiments 50-55, wherein Compound II and/or Compound III are in the form of a solid dispersion.

57. Compound I (free form) wherein Compound I is substantially crystalline Form D (i.e., wherein less than 15% of Compound I is in amorphous form, wherein less than 10% of Compound I is in amorphous form, wherein less than 5% of Compound I is in amorphous form).

58. The Compound I of Embodiment 57, wherein Compound I is 100% crystalline Form D.

59. The Compound I of Embodiment 57 or Embodiment 58, wherein Compound I (free form) Form D is characterized by an X-ray powder diffractogram having a signal at 3.7±0.2 degrees two-theta, 7.4±0.2 degrees two-theta, and/or 12.2±0.2 degrees two-theta.

60. The Compound I of Embodiment 57 or Embodiment 58, wherein Compound I (free form) Form D is characterized by an X-ray powder diffractogram having signals at 3.7±0.2 degrees two-theta, 7.4±0.2 degrees two-theta, and 17.3±0.2 degrees two-theta.

61. The Compound I of any one of Embodiment 57 or Embodiment 58, wherein Compound I (free form) Form D is characterized by an X-ray powder diffractogram substantially similar to FIG. 47.

62. The Compound I of any one of Embodiments 57-61, wherein Compound I (free form) Form D is characterized by a $^{13}$C solid state nuclear magnetic resonance ($^{13}$C ssNMR) spectrum with two, three, four, five, six, seven, or eight peaks selected from 164.6±0.2 ppm, 149.6±0.2 ppm, 135.7±0.2 ppm, 113.6±0.2 ppm, 63.0±0.2 ppm, 38.9±0.2 ppm, 27.6±0.2 ppm, and 15.7±0.2 ppm.

63. The Compound I of any one of Embodiments 57-61, wherein Compound I (free form) Form D is characterized by a $^{13}$C ssNMR substantially similar to FIG. 48.

64. The Compound I (free form) Form D of any one of Embodiments 57-63, prepared by a process comprising adding propanol to compound I (free form) and concentrating the mixture under reduced pressure, repeating the procedure using toluene.

65. A method of preparing Compound I (free form) Form D of any one of Embodiments 57-63 comprising adding propanol to compound I (free form) and concentrating the mixture under reduced pressure, repeating the procedure using toluene.

66. A pharmaceutical composition comprising the Compound I (free form) Form D of any one of Embodiments 57-64, optionally further comprising one or more additional CFTR modulating compounds.

67. The pharmaceutical composition of Embodiment 64, wherein the one or more additional CFTR modulating compounds are
    a. Compound III or Compound III-d; or
    b. (i) Compound II and (ii) Compound III or Compound III-d.

68. The Compound I (free form) Form D of any one of Embodiments 57-64 or the pharmaceutical composition of Embodiment 66 or Embodiment 67 for use in the treatment of cystic fibrosis.

69. Use of the Compound I (free form) Form D of any one of Embodiments 57-64 or the pharmaceutical composition of Embodiment 66 or Embodiment 67 in the manufacture of a medicament for the treatment of cystic fibrosis.

70. A method of treating cystic fibrosis comprising administering the Compound I (free form) Form D of any one of Embodiments 57-64 or the pharmaceutical composition of Embodiment 66 or Embodiment 67 to a subject in need thereof.

71. The compound for use of Embodiment 68, the use of Embodiment 69, or the method of Embodiment 70, wherein the Compound I (free form) Form D of any one of Embodiments 57-64 is administered in combination with at least one additional CFTR modulating compound.

72. The compound, use, or method of Embodiment 71, wherein the Compound I (free form) Form D of any one of Embodiments 57-64 is administered in combination with
  a. Compound III or Compound III-d;
  b. (i) Compound II and (ii) Compound III or Compound III-d; or
  c. (i) Compound IV and (ii) Compound III or Compound III-d.

73. The composition, use, method or compound of any one of Embodiments 67-72, wherein Compound II and/or Compound III are in the form of a solid dispersion.

74. Substantially crystalline Compound I calcium salt hydrate Form A (i.e., wherein less than 15% of Compound I is in amorphous form).

75. The substantially crystalline Compound I calcium salt hydrate Form A of Embodiment 74, wherein less than 10% is in amorphous form.

76. The substantially crystalline Compound I calcium salt hydrate Form A of Embodiment 74, wherein less than 5% is in amorphous form.

77. Crystalline Compound I calcium salt hydrate Form A.

78. The crystalline Compound I calcium salt hydrate Form A of any one of Embodiments 74-77, characterized by an X-ray powder diffractogram having signals at 4.2±0.2 degrees two-theta, 18.0±0.2 degrees two-theta, and 19.7 0.2 degrees two-theta.

79. The crystalline Compound I calcium salt hydrate Form A of any one of Embodiments 74-77, characterized by an X-ray powder diffractogram having (a) signals at 4.2±0.2 degrees two-theta, 18.0±0.2 degrees two-theta, and 19.7±0.2 degrees two-theta; and (b) signals at one or more of 10.5±0.2 degrees two-theta, 10.6±0.2 degrees two-theta, and 17.8±0.2 degrees two-theta.

80. The crystalline Compound I calcium salt hydrate Form A of any one of Embodiments 74-77, characterized by an X-ray powder diffractogram having (a) signals at 4.2±0.2 degrees two-theta, 18.0±0.2 degrees two-theta, and 19.7±0.2 degrees two-theta; and (b) signals at two or more of 10.5±0.2 degrees two-theta, 10.6±0.2 degrees two-theta, and 17.8±0.2 degrees two-theta.

81. The crystalline Compound I calcium salt hydrate Form A of any one of Embodiments 74-77, characterized by an X-ray powder diffractogram having (a) signals at 4.2±0.2 degrees two-theta, 18.0±0.2 degrees two-theta, and 19.7±0.2 degrees two-theta; and (b) signals at 10.5±0.2 degrees two-theta, 10.6±0.2 degrees two-theta, and 17.8±0.2 degrees two-theta.

82. The crystalline Compound I calcium salt hydrate Form A of any one of Embodiments 74-77, characterized by an X-ray powder diffractogram having (a) signals at 4.2±0.2 degrees two-theta, 18.0±0.2 degrees two-theta, and 19.7±0.2 degrees two-theta; and (b) one or more signals selected from 10.5±0.2 degrees two-theta, 10.6±0.2 degrees two-theta, 17.8±0.2 degrees two-theta, 20.7±0.2 degrees two-theta, and 25.1±0.2 degrees two-theta.

83. The crystalline Compound I calcium salt hydrate Form A of any one of Embodiments 74-77, characterized by an X-ray powder diffractogram having (a) signals at 4.2±0.2 degrees two-theta, 18.0±0.2 degrees two-theta, and 19.7±0.2 degrees two-theta; and (b) two or more signals selected from 10.5±0.2 degrees two-theta, 10.6±0.2 degrees two-theta, 17.8±0.2 degrees two-theta, 20.7±0.2 degrees two-theta, and 25.1±0.2 degrees two-theta.

84. The crystalline Compound I calcium salt hydrate Form A of any one of Embodiments 74-77, characterized by an X-ray powder diffractogram having (a) signals at 4.2±0.2 degrees two-theta, 18.0±0.2 degrees two-theta, and 19.7±0.2 degrees two-theta; and (b) three or more signals selected from 10.5±0.2 degrees two-theta, 10.6±0.2 degrees two-theta, 17.8±0.2 degrees two-theta, 20.7±0.2 degrees two-theta, and 25.1±0.2 degrees two-theta.

85. The crystalline Compound I calcium salt hydrate Form A of any one of Embodiments 74-77, characterized by an X-ray powder diffractogram having (a) signals at 4.2±0.2 degrees two-theta, 18.0±0.2 degrees two-theta, and 19.7±0.2 degrees two-theta; and (b) four or more signals selected from 10.5±0.2 degrees two-theta, 10.6±0.2 degrees two-theta, 17.8±0.2 degrees two-theta, 20.7±0.2 degrees two-theta, and 25.1±0.2 degrees two-theta.

86. The crystalline Compound I calcium salt hydrate Form A of any one of Embodiments 74-77, characterized by an X-ray powder diffractogram having (a) signals at 4.2±0.2 degrees two-theta, 18.0±0.2 degrees two-theta, and 19.7±0.2 degrees two-theta; and (b) one or more signals selected from 10.6±0.2 degrees two-theta, 14.8±0.2 degrees two-theta, 17.8±0.2 degrees two-theta, 19.6±0.2 degrees two-theta, 20.7±0.2 degrees two-theta, 24.4±0.2 degrees two-theta, and 25.1±0.2 degrees two-theta.

87. The crystalline Compound I calcium salt hydrate Form A of any one of Embodiments 74-77, characterized by an X-ray powder diffractogram having (a) signals at 4.2±0.2 degrees two-theta, 18.0±0.2 degrees two-theta, and 19.7±0.2 degrees two-theta; and (b) two or more signals selected from 10.6±0.2 degrees two-theta, 14.8±0.2 degrees two-theta, 17.8±0.2 degrees two-theta, 19.6±0.2 degrees two-theta, 20.7±0.2 degrees two-theta, 24.4±0.2 degrees two-theta, and 25.1±0.2 degrees two-theta.

88. The crystalline Compound I calcium salt hydrate Form A of any one of Embodiments 74-77, characterized by an X-ray powder diffractogram having (a) signals at 4.2±0.2 degrees two-theta, 18.0±0.2 degrees two-theta, and 19.7±0.2 degrees two-theta; and (b) three or more signals selected from 10.6±0.2 degrees two-theta, 14.8±0.2 degrees two-theta, 17.8±0.2 degrees two-theta, 19.6±0.2 degrees two-theta, 20.7±0.2 degrees two-theta, 24.4±0.2 degrees two-theta, and 25.1±0.2 degrees two-theta.

89. The crystalline Compound I calcium salt hydrate Form A of any one of Embodiments 74-77, characterized by an X-ray powder diffractogram having (a) signals at 4.2±0.2 degrees two-theta, 18.0±0.2 degrees two-theta, and 19.7±0.2 degrees two-theta; and (b) four or more signals selected from 10.6±0.2 degrees two-theta, 14.8±0.2 degrees two-theta, 17.8±0.2 degrees two-theta, 19.6±0.2 degrees two-theta, 20.7±0.2 degrees two-theta, 24.4±0.2 degrees two-theta, and 25.1±0.2 degrees two-theta.

90. The crystalline Compound I calcium salt hydrate Form A of any one of Embodiments 74-77, characterized by an X-ray powder diffractogram having (a) signals at 4.2±0.2 degrees two-theta, 18.0±0.2 degrees two-theta, and 19.7±0.2 degrees two-theta; and (b) five or more signals selected from 10.6±0.2 degrees two-theta, 14.8±0.2 degrees two-theta, 17.8±0.2 degrees two-theta, 19.6±0.2 degrees two-theta, 20.7±0.2 degrees two-theta, 24.4±0.2 degrees two-theta, and 25.1±0.2 degrees two-theta.

91. The crystalline Compound I calcium salt hydrate Form A of any one of Embodiments 74-77, characterized by an X-ray powder diffractogram substantially similar to FIG. 6.

92. The crystalline Compound I calcium salt hydrate Form A of any one of Embodiments 74-91, characterized by a monoclinic crystal system, a C2 space group, and unit cell dimensions measured at 100 K on a Bruker diffractometer equipped with Cu Kα radiation (λ=1.5478 Å) of

| a | 11.13 ± .01 Å | α | 90° |
|---|---|---|---|
| b | 13.77 ± .01 Å | β | 101.93 ± .01° |
| c | 22.21 ± .01 Å | γ | 90°. |

93. The crystalline Compound I calcium salt hydrate Form A of any one of Embodiments 74-92, characterized by a monoclinic crystal system, a C2 space group, and the following unit cell dimensions measured at 298 K on a Bruker diffractometer equipped with Cu $K_\alpha$ radiation (λ=1.5478 Å) and a CCD detector:

| a | 11.19 ± .01 Å | α | 90° |
|---|---|---|---|
| b | 13.88 ± .01 Å | β | 101.48 ± .01° |
| c | 22.41 ± .01 Å | γ | 90°. |

94. The crystalline Compound I calcium salt hydrate Form A of any one of Embodiments 74-93, characterized by a $^{13}$C ssNMR spectrum with a peak at 17.0 0.2 ppm.

95. The crystalline Compound I calcium salt hydrate Form A of any one of Embodiments 74-93, characterized by a $^{13}$C ssNMR spectrum with a peak at 7.8 0.2 ppm.

96. The crystalline Compound I calcium salt hydrate Form A of any one of Embodiments 74-93, characterized by a $^{13}$C ssNMR spectrum with peaks at 17.0 0.2 ppm and 7.8±0.2 ppm.

97. The crystalline Compound I calcium salt hydrate Form A of any one of Embodiments 74-93, characterized by a $^{13}$C ssNMR spectrum with (a) a peak at 17.0±0.2 ppm and/or a peak at 7.8±0.2 ppm; and (b) one or more peaks selected from 178.3±0.2 ppm, 136.8±0.2 ppm, 93.6±0.2 ppm, and 26.4±0.2 ppm.

98. The crystalline Compound I calcium salt hydrate Form A of any one of Embodiments 74-93, characterized by a $^{13}$C ssNMR spectrum with (a) a peak at 17.0±0.2 ppm and/or a peak at 7.8±0.2 ppm; and (b) two or more peaks selected from 178.3±0.2 ppm, 136.8±0.2 ppm, 93.6±0.2 ppm, and 26.4±0.2 ppm.

99. The crystalline Compound I calcium salt hydrate Form A of any one of Embodiments 74-93, characterized by a $^{13}$C ssNMR spectrum with (a) a peak at 17.0±0.2 ppm and/or a peak at 7.8±0.2 ppm; and (b) three or more peaks selected from 178.3±0.2 ppm, 136.8±0.2 ppm, 93.6±0.2 ppm, and 26.4±0.2 ppm.

100. The crystalline Compound I calcium salt hydrate Form A of any one of Embodiments 74-93, characterized by a $^{13}$C ssNMR spectrum with (a) a peak at 17.0±0.2 ppm and/or a peak at 7.8±0.2 ppm; and (b) peaks at 178.3±0.2 ppm, 136.8±0.2 ppm, 93.6±0.2 ppm, and 26.4±0.2 ppm.

101. The crystalline Compound I calcium salt hydrate Form A of any one of Embodiments 74-93, characterized by a $^{13}$C ssNMR spectrum with peaks at 17.0 0.2 ppm, 7.8±0.2 ppm, 178.3±0.2 ppm, 136.8±0.2 ppm, 93.6±0.2 ppm, and 26.4±0.2 ppm.

102. The crystalline Compound I calcium salt hydrate Form A of any one of Embodiments 74-93, characterized by a $^{13}$C ssNMR substantially similar to FIG. 7.

103. The crystalline Compound I calcium salt hydrate Form A of any one of Embodiments 74-102, prepared by a process comprising charging Compound I (free form) Form A and Ca(OMe)$_2$ with IPA/H$_2$O at 70° C.

104. A method of preparing the crystalline Compound I calcium salt hydrate Form A of any one of Embodiments 74-102, comprising charging Compound I (free form) Form A and Ca(OMe)$_2$ with IPA/H$_2$O at 70° C.

105. A pharmaceutical composition comprising the crystalline Compound I calcium salt hydrate Form A of any one of Embodiments 74-103.

106. The pharmaceutical composition of Embodiment 105, further comprising one or more additional CFTR modulating compounds.

107. The pharmaceutical composition of Embodiment 105 or Embodiment 106, further comprising Compound III or Compound III-d.

108. The pharmaceutical composition of Embodiment 105 or Embodiment 106, further comprising (a) Compound II and (b) Compound III or Compound III-d.

109. The crystalline Compound I calcium salt hydrate Form A of any one of Embodiments 74-103 or the pharmaceutical composition of any one of Embodiments 105-108 for use in the treatment of cystic fibrosis.

110. Use of the crystalline Compound I calcium salt hydrate Form A of any one of Embodiments 74-103 or the composition of any one of embodiments 105-108 in the manufacture of a medicament for the treatment of cystic fibrosis.

111. A method of treating cystic fibrosis comprising administering the crystalline Compound I calcium salt hydrate Form A of any one of Embodiments 74-103 or the pharmaceutical composition of any one of Embodiments 105-108 to a subject in need thereof.

112. The method of Embodiment 111, wherein the crystalline Compound I calcium salt hydrate Form A of any one of Embodiments 74-103 is administered in combination with at least one additional CFTR modulating compound.

113. The method of Embodiment 112, wherein the crystalline Compound I calcium salt hydrate Form A of any one of Embodiments 74-103 is administered in combination with Compound III or Compound III-d.

114. The method of Embodiment 112, wherein the crystalline Compound I calcium salt hydrate Form A of any one of Embodiments 74-103 is administered in combination with (a) Compound II and (b) Compound III or Compound III-d.

115. The method of Embodiment 112, wherein the crystalline Compound I calcium salt hydrate Form A of any one of Embodiments 74-103 is administered in combination with (a) Compound IV and (b) Compound III or Compound III-d.

116. The method of any one of Embodiments 107, 108, and 113-115, wherein Compound II and/or Compound III are in the form of a solid dispersion.

117. Substantially crystalline Compound I calcium salt hydrate Form B (i.e., wherein less than 15% of Compound I is in amorphous form, wherein less than 10% of Compound I is in amorphous form, wherein less than 5% of Compound I is in amorphous form).

118. Compound I of Embodiment 117, wherein Compound I is 100% crystalline calcium salt hydrate Form B.

119. The crystalline Compound I calcium salt hydrate Form B of Embodiment 117 or Embodiment 118, characterized by an X-ray powder diffractogram having signals at 13.1±0.2 degrees two-theta, 14.6±0.2 degrees two-theta, and 17.7±0.2 degrees two-theta.

120. The crystalline Compound I calcium salt hydrate Form B of Embodiment 117 or Embodiment 118, characterized by an X-ray powder diffractogram having (a) signals at 12.2±0.2 degrees two-theta, 13.1±0.2 degrees two-theta, 14.6±0.2 degrees two-theta, and 17.7±0.2; and (b) a signal at one, two, three, or four of 16.2±0.2 degrees two-theta, 18.1±0.2 degrees two-theta, 20.4±0.2 degrees two-theta, and 21.3±0.2 degrees two-theta.

121. The crystalline Compound I calcium salt hydrate Form B of Embodiment 117 or Embodiment 118, characterized by an X-ray powder diffractogram substantially similar to FIG. 8.

122. The crystalline Compound I calcium salt hydrate Form B of any one of Embodiments 117-121, characterized by a $^{13}$C ssNMR spectrum with a peak at one, two, three, four, or five of 175.8±0.2 ppm, 119.6±0.2 ppm, 48.7±0.2 ppm, 24.4±0.2 ppm, 22.5±0.2 ppm.

123. The crystalline Compound I calcium salt hydrate Form B of any one of Embodiments 117-121, characterized by a $^{13}$C ssNMR spectrum with (a) a peak at one, two, three, four, or five of 175.8±0.2 ppm, 119.6±0.2 ppm, 48.7±0.2 ppm, 24.4±0.2 ppm, and 22.5±0.2 ppm; and (b) one, two, three or four peaks selected from 164.7±0.2 ppm, 148.9±0.2 ppm, 97.7±0.2 ppm, and 25.9±0.2 ppm.

124. The crystalline Compound I calcium salt hydrate Form B of any one of Embodiments 117-121, characterized by a $^{13}$C ssNMR substantially similar to FIG. 9.

125. A crystalline Compound I calcium salt hydrate/solvate Form B with MeOH, characterized by a $^{13}$C ssNMR spectrum with a peak at 32.9±0.2 ppm and/or a peak at 23.3±0.2 ppm.

126. The crystalline Compound I calcium salt hydrate/solvate Form B with MeOH of Embodiment 125, characterized by a $^{13}$C ssNMR spectrum with (a) a peak at 32.9±0.2 ppm and/or a peak at 23.3±0.2 ppm; and (b) one, two, three, four or five peaks selected from 176.1±0.2 ppm, 164.7±0.2 ppm, 148.9±0.2 ppm, 49.3±0.2 ppm, and 25.9±0.2 ppm.

127. The crystalline Compound I calcium salt hydrate/solvate Form B with MeOH of Embodiment 125, characterized by a $^{13}$C ssNMR substantially similar to FIG. 10.

128. The crystalline Compound I calcium salt hydrate/solvate Form B with MeOH of any one of Embodiments 125-127, characterized by a monoclinic crystal system, a P2$_1$ space group, and the following unit cell dimensions measured at 100 K on a Bruker diffractometer equipped with Cu K$_\alpha$ radiation (λ=1.5478 Å) and a CCD detector:

| a | 18.52 ± .01 Å | α | 90° |
|---|---|---|---|
| b | 13.01 ± .01 Å | β | 106.87 ± .01° |
| c | 31.21 ± .01 Å | γ | 90°. |

129. The crystalline Compound I calcium salt hydrate Form B of any one of Embodiments 117-125, prepared by a process comprising slurrying Compound I calcium salt in EtOH/water or the crystalline Compound I calcium salt hydrate/solvate Form B with MeOH of any one of Embodiments 126-128, prepared by a process of adding MeOH to Compound I calcium salt hydrate Form B.

130. A method of preparing the crystalline Compound I calcium salt hydrate Form B of any one of Embodiments 117-125, comprising slurrying Compound I calcium salt in EtOH/water or the crystalline Compound I calcium salt hydrate/solvate Form B with MeOH of any one of Embodiments 126-128, comprising adding MeOH to Compound I calcium salt hydrate Form B.

131. A pharmaceutical composition comprising the crystalline Compound I calcium salt hydrate Form B or the crystalline Compound I calcium salt hydrate/solvate Form B with MeOH of any one of Embodiments 117-129, optionally further comprising one or more additional CFTR modulating compounds.

132. The pharmaceutical composition of Embodiment 131, wherein the one or more additional CFTR modulating compounds are
  a. Compound III or Compound III-d; or
  b. (i) Compound II and (ii) Compound III or Compound III-d.

133. The Compound I calcium salt hydrate Form B or the crystalline Compound I calcium salt hydrate/solvate Form B with MeOH of any one of Embodiments 117-129 or the pharmaceutical composition of Embodiment 131 or Embodiment 132 for use in the treatment of cystic fibrosis.

134. Use of the Compound I calcium salt hydrate Form B or the crystalline Compound I calcium salt hydrate/solvate Form B with MeOH of any one of Embodiments 117-129 or the pharmaceutical composition of Embodiment 131 or Embodiment 132 in the manufacture of a medicament for the treatment of cystic fibrosis.

135. A method of treating cystic fibrosis comprising administering the Compound I calcium salt hydrate Form B or the crystalline Compound I calcium salt hydrate/solvate Form B with MeOH of any one of Embodiments 117-129 or the pharmaceutical composition of Embodiment 131 or Embodiment 132 to a subject in need thereof.

136. The compound for use of Embodiment 133, the use of Embodiment 134, or the method of Embodiment 135, wherein the Compound I calcium salt hydrate Form B of any one of Embodiments 117-129 is administered in combination with at least one additional CFTR modulating compound.

137. The compound, use, or method of Embodiment 136, wherein the Compound I calcium salt hydrate Form B or the crystalline Compound I calcium salt hydrate/solvate Form B with MeOH of any one of Embodiments 117-129 is administered in combination with
  a. Compound III or Compound III-d;
  b. (i) Compound II and (ii) Compound III or Compound III-d; or c. (i) Compound IV and (ii) Compound III or Compound III-d.
138. The composition, use, method or compound of any one of Embodiments 132-137, wherein Compound II and/or Compound III are in the form of a solid dispersion.
139. Substantially crystalline Compound I calcium salt hydrate Form C (i.e., wherein less than 15% of Compound I is in amorphous form, wherein less than 10% of Compound I is in amorphous form, wherein less than 5% of Compound I is in amorphous form).
140. Compound I of Embodiment 139, wherein Compound I is 100% crystalline calcium salt hydrate Form C.
141. The crystalline Compound I calcium salt hydrate Form C of Embodiment 139 or Embodiment 140, characterized by an X-ray powder diffractogram having signals at 10.3±0.2 degrees two-theta, 15.8±0.2 degrees two-theta, and 20.8±0.2 degrees two-theta.
142. The crystalline Compound I calcium salt hydrate Form C of Embodiment 139 or Embodiment 140, characterized by an X-ray powder diffractogram having (a) signals at 4.0±0.2 degrees two-theta, 10.3±0.2 degrees two-theta, 15.8±0.2 degrees two-theta, and 20.8±0.2 degrees two-theta; and (b) one or more signals at 19.0±0.2 degrees two-theta, 14.3±0.2 degrees two-theta, and 13.3±0.2 degrees two-theta.
143. The crystalline Compound I calcium salt hydrate Form C of Embodiment 139 or Embodiment 140, characterized by an X-ray powder diffractogram substantially similar to FIG. 11.
144. The crystalline Compound I calcium salt hydrate Form C of any one of Embodiments 139-143, characterized by a $^{13}$C ssNMR spectrum with a peak at 115.7±0.2 ppm, 65.9±0.2 ppm, 52.7±0.2 ppm, and/or 21.4±0.2 ppm.
145. The crystalline Compound I calcium salt hydrate Form C of any one of Embodiments 139-143, characterized by a $^{13}$C ssNMR spectrum with (a) a peak at 115.7±0.2 ppm, 65.9±0.2 ppm, 52.7±0.2 ppm, and/or 21.4±0.2 ppm; and (b) a peak at 178.3±0.2 ppm, 155.9±0.2 ppm, 137.7±0.2 ppm, 129.6±0.2 ppm, 112.0±0.2 ppm, 100.0±0.2 ppm, 37.8±0.2 ppm, 26.4±0.2 ppm, and/or 19.9 0.2 ppm.
146. The crystalline Compound I calcium salt hydrate Form C of Embodiment 139 or Embodiment 140, characterized by a $^{13}$C ssNMR substantially similar to FIG. 12.
147. The crystalline Compound I calcium salt hydrate Form C of any one of Embodiments 139-146, prepared by a process comprising stirring Compound I (free form) Form A with calcium methoxide in dichloromethane (with 10% water) and isolating and drying the solid.
148. A method of preparing the crystalline Compound I calcium salt hydrate Form C of any one of Embodiments 139-146, prepared by a process comprising stirring Compound I (free form) Form A with calcium methoxide in dichloromethane (with 10% water) and isolating and drying the solid.
149. A pharmaceutical composition comprising the crystalline Compound I calcium salt hydrate Form C of any one of Embodiments 139-147, optionally further comprising one or more additional CFTR modulating compounds.
150. The pharmaceutical composition of Embodiment 149, wherein the one or more additional CFTR modulating compounds are
a. Compound III or Compound III-d; or
b. (i) Compound II and (ii) Compound III or Compound III-d.
151. The Compound I calcium salt hydrate Form C of any one of Embodiments 139-147 or the pharmaceutical composition of Embodiment 149 or Embodiment 150 for use in the treatment of cystic fibrosis.
152. Use of the Compound I calcium salt hydrate Form C of any one of Embodiments 139-147 or the pharmaceutical composition of Embodiment 149 or Embodiment 150 in the manufacture of a medicament for the treatment of cystic fibrosis.
153. A method of treating cystic fibrosis comprising administering the Compound I calcium salt hydrate Form C of any one of Embodiments 117-129 or the pharmaceutical composition of Embodiment 149 or Embodiment 150 to a subject in need thereof.
154. The compound for use of Embodiment 151, the use of Embodiment 152, or the method of Embodiment 153, wherein the Compound I calcium salt hydrate Form C of any one of Embodiments 139-147 is administered in combination with at least one additional CFTR modulating compound.
155. The compound, use, or method of Embodiment 154, wherein the Compound I calcium salt hydrate Form C of any one of Embodiments 139-147 is administered in combination with
a. Compound III or Compound III-d;
b. (i) Compound II and (ii) Compound III or Compound III-d; or
c. (i) Compound IV and (ii) Compound III or Compound III-d.
156. The composition, use, method or compound of any one of Embodiments 150-155, wherein Compound II and/or Compound III are in the form of a solid dispersion.
157. Substantially crystalline Compound I calcium salt hydrate Form D (i.e., wherein less than 15% of Compound I is in amorphous form).
158. The substantially crystalline Compound I calcium salt hydrate Form D of Embodiment 74, wherein less than 10% is in amorphous form.
159. The substantially crystalline Compound I calcium salt hydrate Form D of Embodiment 74, wherein less than 5% is in amorphous form.
160. Crystalline Compound I calcium salt hydrate Form D.
161. The crystalline Compound I calcium salt hydrate Form D of any one of Embodiments 157-160, characterized by an X-ray powder diffractogram having signals at 6.1±0.2 degrees two-theta, 16.2±0.2 degrees two-theta, and 22.8±0.2 degrees two-theta.
162. The crystalline Compound I calcium salt hydrate Form D of any one of Embodiments 157-160, characterized by an X-ray powder diffractogram having (a) signals at 6.1±0.2 degrees two-theta, 16.2±0.2 degrees two-theta, and 22.8±0.2 degrees two-theta; and (b) one or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta.
163. The crystalline Compound I calcium salt hydrate Form D of any one of Embodiments 157-160, characterized by an X-ray powder diffractogram having (a) signals at 6.1±0.2 degrees two-theta, 16.2±0.2 degrees two-theta, and 22.8±0.2 degrees two-theta; and (b) two or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta.

164. The crystalline Compound I calcium salt hydrate Form D of any one of Embodiments 157-160, characterized by an X-ray powder diffractogram having (a) signals at 6.1±0.2 degrees two-theta, 16.2±0.2 degrees two-theta, and 22.8±0.2 degrees two-theta; and (b) three or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta.

165. The crystalline Compound I calcium salt hydrate Form D of any one of Embodiments 157-160, characterized by an X-ray powder diffractogram having (a) signals at 6.1±0.2 degrees two-theta, 16.2±0.2 degrees two-theta, and 22.8±0.2 degrees two-theta; and (b) four or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta.

166. The crystalline Compound I calcium salt hydrate Form D of any one of Embodiments 157-160, characterized by an X-ray powder diffractogram having (a) signals at 6.1±0.2 degrees two-theta, 16.2±0.2 degrees two-theta, and 22.8±0.2 degrees two-theta; and (b) five or more signals selected from 5.5±0.2 degrees two-theta, 15.5±0.2 degrees two-theta, 19.7±0.2 degrees two-theta, 21.5±0.2 degrees two-theta, 22.1±0.2 degrees two-theta, 23.0±0.2 degrees two-theta, and 27.6±0.2 degrees two-theta.

167. The crystalline Compound I calcium salt hydrate Form D of any one of Embodiments 157-160, characterized by an X-ray powder diffractogram having signals at 6.1±0.2 degrees two-theta, 16.2±0.2 degrees two-theta, and 22.8±0.2 degrees two-theta, and 27.6±0.2 degrees two-theta.

168. The crystalline Compound I calcium salt hydrate Form D of any one of Embodiments 157-160, characterized by an X-ray powder diffractogram having signals at 6.1±0.2 degrees two-theta, 15.5±0.2 degrees two-theta, 16.2±0.2 degrees two-theta, 19.7±0.2 degrees two-theta, 22.8±0.2 degrees two-theta, and 27.6±0.2 degrees two-theta.

169. The crystalline Compound I calcium salt hydrate Form D of any one of Embodiments 157-160, characterized by an X-ray powder diffractogram substantially similar to FIG. 13.

170. The crystalline Compound I calcium salt hydrate Form D of any one of Embodiments 157-169, characterized by a triclinic crystal system, a P1 space group, and unit cell dimensions measured at 100 K on a Bruker diffractometer equipped with Cu Kα radiation (λ=1.5478 Å) of

| a | 12.78 ± .01 Å | α | 64.93 ± .02° |
|---|---|---|---|
| b | 16.64 ± .01 Å | β | 75.10 ± .02° |
| c | 18.19 ± .01 Å | γ | 68.22 ± .02°. |

171. The crystalline Compound I calcium salt hydrate Form D of any one of Embodiments 157-170, characterized by a $^{13}C$ ssNMR spectrum with a peak at 130.2±0.2 ppm.

172. The crystalline Compound I calcium salt hydrate Form D of any one of Embodiments 157-170, characterized by a $^{13}C$ ssNMR spectrum with a peak at 125.6±0.2 ppm.

173. The crystalline Compound I calcium salt hydrate Form D of any one of Embodiments 157-170, characterized by a $^{13}C$ ssNMR spectrum with a peak at 35.0±0.2 ppm.

174. The crystalline Compound I calcium salt hydrate Form D of any one of Embodiments 157-170, characterized by a $^{13}C$ ssNMR spectrum with a peak at 130.2±0.2 ppm, 125.6±0.2 ppm, and/or 35.0±0.2 ppm.

175. The crystalline Compound I calcium salt hydrate Form D of any one of Embodiments 157-170, characterized by a $^{13}C$ ssNMR spectrum with (a) a peak at 130.2±0.2 ppm, 125.6±0.2 ppm, and/or 35.0±0.2 ppm; and (b) a peak at 176.9±0.2 ppm, 160.9±0.2 ppm, 142.0±0.2 ppm, and/or 98.6±0.2 ppm.

176. The crystalline Compound I calcium salt hydrate Form D of any one of Embodiments 157-170, characterized by a $^{13}C$ ssNMR spectrum with (a) a peak at 130.2±0.2 ppm, 125.6±0.2 ppm, and 35.0±0.2 ppm; and (b) a peak at 176.9 0.2 ppm, 160.9±0.2 ppm, 142.0±0.2 ppm, and/or 98.6±0.2 ppm.

177. The crystalline Compound I calcium salt hydrate Form D of any one of Embodiments 157-170, characterized by a $^{13}C$ ssNMR spectrum with (a) a peak at 130.2±0.2 ppm, 125.6±0.2 ppm, and/or 35.0±0.2 ppm; and (b) a peak at 176.9±0.2 ppm, 160.9±0.2 ppm, 142.0±0.2 ppm, and 98.6±0.2 ppm.

178. The crystalline Compound I calcium salt hydrate Form D of any one of Embodiments 157-170, characterized by a $^{13}C$ ssNMR spectrum with (a) a peak at 35.0±0.2 ppm; and (b) peaks at 176.9±0.2 ppm, 160.9±0.2 ppm, 142.0±0.2 ppm, and 98.6±0.2 ppm.

179. The crystalline Compound I calcium salt hydrate Form D of any one of Embodiments 157-170, characterized by a $^{13}C$ ssNMR substantially similar to FIG. 14.

180. The crystalline Compound I calcium salt hydrate Form D of any one of Embodiments 157-179, prepared by a process comprising charging Compound I calcium salt hydrate Form A with EtOH/water and heating to 65° C.

181. A method of preparing the crystalline Compound I calcium salt hydrate Form D of any one of Embodiments 157-179, comprising charging Compound I calcium salt hydrate Form A with EtOH/water and heating to 65° C.

182. A pharmaceutical composition comprising the crystalline Compound I calcium salt hydrate Form D of any one of Embodiments 157-180.

183. The pharmaceutical composition of Embodiment 182, further comprising one or more additional CFTR modulating compounds.

184. The pharmaceutical composition of Embodiment 182 or Embodiment 183, further comprising Compound III or Compound III-d.

185. The pharmaceutical composition of Embodiment 182 or Embodiment 183, further comprising (a) Compound II and (b) Compound III or Compound III-d.

186. The crystalline Compound I calcium salt hydrate Form D of any one of Embodiments 157-180 or the pharmaceutical composition of any one of Embodiments 182-185 for use in the treatment of cystic fibrosis.

187. Use of the crystalline Compound I calcium salt hydrate Form D of any one of Embodiments 157-180 or the composition of any one of embodiments 182-185 in the manufacture of a medicament for the treatment of cystic fibrosis.

188. A method of treating cystic fibrosis comprising administering the crystalline Compound I calcium salt hydrate Form D of any one of Embodiments 157-180 or the pharmaceutical composition of any one of Embodiments 182-185 to a subject in need thereof.

189. The method of Embodiment 188, wherein the crystalline Compound I calcium salt hydrate Form D of any one of Embodiments 157-180 is administered in combination with at least one additional CFTR modulating compound.

190. The method of Embodiment 189, wherein the crystalline Compound I calcium salt hydrate Form D of any one of Embodiments 157-180 is administered in combination with Compound III or Compound III-d.

191. The method of Embodiment 189, wherein the crystalline Compound I calcium salt hydrate Form D of any one of Embodiments 157-180 is administered in combination with (a) Compound II and (b) Compound III or Compound III-d.

192. The method of Embodiment 189, wherein the crystalline Compound I calcium salt hydrate Form D of any one of Embodiments 157-180 is administered in combination with (a) Compound IV and (b) Compound III or Compound III-d.

193. The method of any one of Embodiments 184, 185, and 190-192, wherein Compound II and/or Compound III are in the form of a solid dispersion.

194. Substantially crystalline Compound I calcium salt hydrate Form E (i.e., wherein less than 15% of Compound I is in amorphous form, wherein less than 10% of Compound I is in amorphous form, wherein less than 5% of Compound I is in amorphous form).

195. Compound I of Embodiment 194, wherein Compound I is 100% crystalline calcium salt hydrate Form E.

196. The crystalline Compound I calcium salt hydrate Form E of Embodiment 194 or Embodiment 195, characterized by an X-ray powder diffractogram having signals at 8.0±0.2 degrees two-theta, 12.0±0.2 degrees two-theta, and 24.2±0.2 degrees two-theta.

197. The crystalline Compound I calcium salt hydrate Form E of Embodiment 194 or Embodiment 195, characterized by an X-ray powder diffractogram having (a) signals at 8.0±0.2 degrees two-theta, 12.0±0.2 degrees two-theta, and 24.2 0.2 degrees two-theta; and (b) a signal at 4.0±0.2 degrees two-theta and/or 28.3±0.2 degrees two-theta.

198. The crystalline Compound I calcium salt hydrate Form E of Embodiment 194 or Embodiment 195, characterized by an X-ray powder diffractogram having signals at 8.0±0.2 degrees two-theta, 12.0±0.2 degrees two-theta, 24.2±0.2 degrees two-theta, and 4.0±0.2 degrees two-theta.

199. The crystalline Compound I calcium salt hydrate Form E of of Embodiment 194 or Embodiment 195, characterized by an X-ray powder diffractogram substantially similar to FIG. 15.

200. The crystalline Compound I calcium salt hydrate Form E of any one of Embodiments 195-199, prepared by a process comprising subjecting Compound I calcium salt hydrate Form A to solid vapor diffusion in EtOAc.

201. A method of preparing the crystalline Compound I calcium salt hydrate Form E of any one of Embodiments 195-199, prepared by a process comprising subjecting Compound I calcium salt hydrate Form A to solid vapor diffusion in EtOAc.

202. A pharmaceutical composition comprising the crystalline Compound I calcium salt hydrate Form E of any one of Embodiments 195-200, optionally further comprising one or more additional CFTR modulating compounds.

203. The pharmaceutical composition of Embodiment 202, wherein the one or more additional CFTR modulating compounds are
  a. Compound III or Compound III-d; or
  b. (i) Compound II and (ii) Compound III or Compound III-d.

204. The Compound I calcium salt hydrate Form E of any one of Embodiments 195-200 or the pharmaceutical composition of Embodiment 202 or Embodiment 203 for use in the treatment of cystic fibrosis.

205. Use of the Compound I calcium salt hydrate Form E of any one of Embodiments 195-200 or the pharmaceutical composition of Embodiment 202 or Embodiment 203 in the manufacture of a medicament for the treatment of cystic fibrosis.

206. A method of treating cystic fibrosis comprising administering the Compound I calcium salt hydrate Form E of any one of Embodiments 195-200 or the pharmaceutical composition of Embodiment 202 or Embodiment 203 to a subject in need thereof.

207. The compound for use of Embodiment 204, the use of Embodiment 205, or the method of Embodiment 206, wherein the Compound I calcium salt hydrate Form E of any one of Embodiments 195-200 is administered in combination with at least one additional CFTR modulating compound.

208. The compound, use, or method of Embodiment 207, wherein the Compound I calcium salt hydrate Form E of any one of Embodiments 195-200 is administered in combination with
  a. Compound III or Compound III-d;
  b. (i) Compound II and (ii) Compound III or Compound III-d; or
  c. (i) Compound IV and (ii) Compound III or Compound III-d.

209. The composition, use, method or compound of any one of Embodiments 203-208, wherein Compound II and/or Compound III are in the form of a solid dispersion.

210. Substantially crystalline Compound I Form F (i.e., wherein less than 15% of Compound I is in amorphous form, wherein less than 10% of Compound I is in amorphous form, wherein less than 5% of Compound I is in amorphous form).

211. Compound I of Embodiment 210, wherein Compound I is 100% crystalline Form F.

212. The crystalline Compound I Form F of Embodiment 210 or Embodiment 211, characterized by an X-ray powder diffractogram having signals at 5.3±0.2 degrees two-theta, 7.5±0.2 degrees two-theta, and 9.14±0.2 degrees two-theta.

213. The crystalline Compound I F of Embodiment 210 or Embodiment 211, characterized by an X-ray powder diffractogram having (a) signals at 5.3±0.2 degrees two-theta, 7.5±0.2 degrees two-theta, and 9.1±0.2 degrees two-theta; and (b) a signal at 10.6±0.2 degrees two-theta and/or 11.9±0.2 degrees two-theta.
214. The crystalline Compound I Form F of of Embodiment 210 or Embodiment 211, characterized by an X-ray powder diffractogram substantially similar to FIG. 16.
215. The crystalline Compound I Form F of any one of Embodiments 210-214, prepared by a process comprising mixing Compound I calcium salt hydrate Form A with MEK at room temperature.
216. A method of preparing the crystalline Compound I Form F of any one of Embodiments 210-214, prepared by a process comprising mixing Compound I calcium salt hydrate Form A with MEK at room temperature.
217. A pharmaceutical composition comprising the crystalline Compound I Form F of any one of Embodiments 210-215, optionally further comprising one or more additional CFTR modulating compounds.
218. The pharmaceutical composition of Embodiment 217, wherein the one or more additional CFTR modulating compounds are
  a. Compound III or Compound III-d; or
  b. (i) Compound II and (ii) Compound III or Compound III-d.
219. The Compound I Form F of any one of Embodiments 210-215 or the pharmaceutical composition of Embodiment 217 or Embodiment 218 for use in the treatment of cystic fibrosis.
220. Use of the Compound I Form F of any one of Embodiments 210-215 or the pharmaceutical composition of Embodiment 217 or Embodiment 218 in the manufacture of a medicament for the treatment of cystic fibrosis.
221. A method of treating cystic fibrosis comprising administering the Compound I Form F of any one of Embodiments 210-215 or the pharmaceutical composition of Embodiment 217 or Embodiment 218 to a subject in need thereof.
222. The compound for use of Embodiment 219, the use of Embodiment 220, or the method of Embodiment 221, wherein the Compound I Form F of any one of Embodiments 210-215 is administered in combination with at least one additional CFTR modulating compound.
223. The compound, use, or method of Embodiment 222, wherein the Compound I Form F of any one of Embodiments 210-215 is administered in combination with
  a. Compound III or Compound III-d;
  b. (i) Compound II and (ii) Compound III or Compound III-d; or
  c. (i) Compound IV and (ii) Compound III or Compound III-d.
224. The composition, use, method or compound of any one of Embodiments 218-223, wherein Compound II and/or Compound III are in the form of a solid dispersion.
225. Substantially crystalline Compound I calcium salt hydrate Form G (i.e., wherein less than 15% of Compound I is in amorphous form, wherein less than 10% of Compound I is in amorphous form, wherein less than 5% of Compound I is in amorphous form).
226. Compound I of Embodiment 225, wherein Compound I is 100% crystalline calcium salt hydrate Form G.
227. The crystalline Compound I calcium salt hydrate Form G of Embodiment 225 or Embodiment 226, characterized by an X-ray powder diffractogram having signals at 5.9±0.2 degrees two-theta, 8.8±0.2 degrees two-theta, and 26.6±0.2 degrees two-theta.
228. The crystalline Compound I calcium salt hydrate Form G of of Embodiment 225 or Embodiment 226, characterized by an X-ray powder diffractogram substantially similar to FIG. 17.
229. The crystalline Compound I calcium salt hydrate Form G of any one of Embodiments 225-228, prepared by a process comprising subjecting Compound I calcium salt hydrate Form A to solid vapor diffusion in EtOAc.
230. A method of preparing the crystalline Compound I calcium salt hydrate Form G of any one of Embodiments 225-228, prepared by a process comprising subjecting Compound I calcium salt hydrate Form A to solid vapor diffusion in EtOAc.
231. A pharmaceutical composition comprising the crystalline Compound I calcium salt hydrate Form G of any one of Embodiments 225-229, optionally further comprising one or more additional CFTR modulating compounds.
232. The pharmaceutical composition of Embodiment 231, wherein the one or more additional CFTR modulating compounds are
  a. Compound III or Compound III-d; or
  b. (i) Compound II and (ii) Compound III or Compound III-d.
233. The Compound I calcium salt hydrate Form G of any one of Embodiments 225-229 or the pharmaceutical composition of Embodiment 231 or Embodiment 232 for use in the treatment of cystic fibrosis.
234. Use of the Compound I calcium salt hydrate Form G of any one of Embodiments 225-229 or the pharmaceutical composition of Embodiment 231 or Embodiment 232 in the manufacture of a medicament for the treatment of cystic fibrosis.
235. A method of treating cystic fibrosis comprising administering the Compound I calcium salt hydrate Form G of any one of Embodiments 225-229 or the pharmaceutical composition of Embodiment 231 or Embodiment 232 to a subject in need thereof.
236. The compound for use of Embodiment 233, the use of Embodiment 234, or the method of Embodiment 235, wherein the Compound I calcium salt hydrate Form G of any one of Embodiments 225-229 is administered in combination with at least one additional CFTR modulating compound.
237. The compound, use, or method of Embodiment 236, wherein the Compound I calcium salt hydrate Form G of any one of Embodiments 225-229 is administered in combination with
  a. Compound III or Compound III-d;
  b. (i) Compound II and (ii) Compound III or Compound III-d; or
  c. (i) Compound IV and (ii) Compound III or Compound III-d.
238. The composition, use, method or compound of any one of Embodiments 232-237, wherein Compound II and/or Compound III are in the form of a solid dispersion.
239. Substantially crystalline Compound I calcium salt hydrate Form H (i.e., wherein less than 15% of Compound I is in amorphous form, wherein less than 10% of Compound I is in amorphous form, wherein less than 5% of Compound I is in amorphous form).

240. Compound I of Embodiment 239, wherein Compound I is 100% crystalline calcium salt hydrate Form H.

241. The crystalline Compound I calcium salt hydrate Form H of Embodiment 239 or Embodiment 240, characterized by an X-ray powder diffractogram having signals at 5.8±0.2 degrees two-theta, 13.0±0.2 degrees two-theta, and 14.5±0.2 degrees two-theta.

242. The crystalline Compound I calcium salt hydrate Form H of Embodiment 239 or Embodiment 240, characterized by an X-ray powder diffractogram having (a) signals at 5.8±0.2 degrees two-theta, 13.0±0.2 degrees two-theta, and 14.5±0.2 degrees two-theta; and (b) one or more signals selected from 8.3±0.2 degrees two-theta, 12.0±0.2 degrees two-theta, 19.5±0.2 degrees two-theta, and 27.9 0.2 degrees two-theta.

243. The crystalline Compound I calcium salt hydrate Form H of Embodiment 239 or Embodiment 240 characterized by an X-ray powder diffractogram substantially similar to FIG. 45.

244. The crystalline Compound I calcium salt hydrate Form H of any one of Embodiments 239-243, characterized by a triclinic crystal system, a P1 space group, and unit cell dimensions measured at 100 K on a Bruker diffractometer utilizing synchrotron radiation ($\lambda$=0.7288 Å) of:

| a | 8.65 ± .01 Å | α | 82.47 ± .01° |
|---|---|---|---|
| b | 17.78 ± .01 Å | β | 86.95 ± .01° |
| c | 24.07 ± .01 Å | γ | 86.56 ± .01°. |

245. The crystalline Compound I calcium salt hydrate Form H of any one of Embodiments 239-244, characterized by a $^{13}$C ssNMR spectrum with a peak at 148.9±0.2 ppm, 27.2±0.2 ppm, and 4.8±0.2 ppm.

246. The crystalline Compound I calcium salt hydrate Form H of any one of Embodiments 239-244, characterized by a $^{13}$C ssNMR spectrum with (a) peaks at 148.9±0.2 ppm, 27.2±0.2 ppm, and 4.8±0.2 ppm; and (b) a peak at 164.7±0.2 ppm, 128.3±0.2 ppm, 117.0±0.2 ppm, and/or 19.4±0.2 ppm.

247. The crystalline Compound I calcium salt hydrate Form H of any one of Embodiments 239-244, characterized by a $^{13}$C ssNMR substantially similar to FIG. 46.

248. The crystalline Compound I calcium salt hydrate Form H of any one of Embodiments 239-244, prepared by a process comprising mixing Compound I calcium salt Form A in IPA/H$_2$O.

249. A method of preparing the crystalline Compound I calcium salt hydrate Form H of any one of Embodiments 239-244, comprising mixing Compound I calcium salt in IPA/H$_2$O.

250. A pharmaceutical composition comprising the crystalline Compound I calcium salt hydrate Form H of any one of Embodiments 239-245, optionally further comprising one or more additional CFTR modulating compounds.

251. The pharmaceutical composition of Embodiment 250, wherein the one or more additional CFTR modulating compounds are
  a. Compound III or Compound III-d; or
  b. (i) Compound II and (ii) Compound III or Compound III-d.

252. The Compound I calcium salt hydrate Form H of any one of Embodiments 239-245 or the pharmaceutical composition of Embodiment 250 or Embodiment 251 for use in the treatment of cystic fibrosis.

253. Use of the Compound I calcium salt hydrate Form H of any one of Embodiments 239-245 or the pharmaceutical composition of Embodiment 250 or Embodiment 251 in the manufacture of a medicament for the treatment of cystic fibrosis.

254. A method of treating cystic fibrosis comprising administering the Compound I calcium salt hydrate Form H of any one of Embodiments 239-245 or the pharmaceutical composition of Embodiment 250 or Embodiment 251 to a subject in need thereof.

255. The compound for use of Embodiment 252, the use of Embodiment 253, or the method of Embodiment 254, wherein the Compound I calcium salt hydrate Form H of any one of Embodiments 239-245 is administered in combination with at least one additional CFTR modulating compound.

256. The compound, use, or method of Embodiment 255, wherein the Compound I calcium salt hydrate Form H of any one of Embodiments 239-245 is administered in combination with
  a. Compound III or Compound III-d;
  b. (i) Compound II and (ii) Compound III or Compound III-d; or
  c. (i) Compound IV and (ii) Compound III or Compound III-d.

257. The composition, use, method or compound of any one of Embodiments 251-256, wherein Compound II and/or Compound III are in the form of a solid dispersion.

258. Substantially crystalline Compound I calcium salt EtOH solvate Form A (i.e., wherein less than 15% of Compound I is in amorphous form, wherein less than 10% of Compound I is in amorphous form, wherein less than 5% of Compound I is in amorphous form).

259. Compound I of Embodiment 258, wherein Compound I is 100% crystalline calcium salt EtOH solvate Form A.

260. The crystalline Compound I calcium salt EtOH solvate Form A of Embodiment 258 or Embodiment 259, characterized by an X-ray powder diffractogram having signals at 4.1±0.2 degrees two-theta, 8.2±0.2 degrees two-theta, and 17.1±0.2 degrees two-theta.

261. The crystalline Compound I calcium salt EtOH solvate Form A of Embodiment 258 or Embodiment 259, characterized by an X-ray powder diffractogram having (a) signals at 4.1±0.2 degrees two-theta, 8.2 0.2 degrees two-theta, and 17.1±0.2 degrees two-theta; and (b) a signal at 8.5±0.2 degrees two-theta and/or 16.5 0.2 degrees two-theta.

262. The crystalline Compound I calcium salt EtOH solvate Form A of Embodiment 258 or Embodiment 259, characterized by an X-ray powder diffractogram having (a) signals at 4.1±0.2 degrees two-theta, 8.2±0.2 degrees two-theta, and 17.1±0.2 degrees two-theta; and (b) one or more signals at 4.1±0.2 degrees two-theta, 4.8±0.2 degrees two-theta, 5.6±0.2 degrees two-theta, 8.5±0.2 degrees two-theta, 16.5±0.2 degrees two-theta and 20.3±0.2 degrees two-theta.

263. The crystalline Compound I calcium salt EtOH solvate Form A of of Embodiment 258 or Embodiment 259, characterized by an X-ray powder diffractogram substantially similar to FIG. 18.

264. The crystalline Compound I calcium salt EtOH solvate Form A of any one of Embodiments 258-263, prepared by a process comprising fast cooling a solution of Compound I calcium salt in EtOH:H$_2$O (85:15).

265. A method of preparing the crystalline Compound I calcium salt EtOH solvate Form A of any one of Embodiments 225-228, prepared by a process comprising fast cooling a solution of Compound I calcium salt in EtOH:H$_2$O (85:15).

266. A pharmaceutical composition comprising the crystalline Compound I calcium salt EtOH solvate Form A of any one of Embodiments 258-264, optionally further comprising one or more additional CFTR modulating compounds.

267. The pharmaceutical composition of Embodiment 266, wherein the one or more additional CFTR modulating compounds are
   a. Compound III or Compound III-d; or
   b. (i) Compound II and (ii) Compound III or Compound III-d.

268. The Compound I calcium salt EtOH solvate Form A of any one of Embodiments 258-264 or the pharmaceutical composition of Embodiment 266 or Embodiment 267 for use in the treatment of cystic fibrosis.

269. Use of the Compound I calcium salt EtOH solvate Form A any one of Embodiments 258-264 or the pharmaceutical composition of Embodiment 266 or Embodiment 267 in the manufacture of a medicament for the treatment of cystic fibrosis.

270. A method of treating cystic fibrosis comprising administering the Compound I calcium salt EtOH solvate Form A of any one of Embodiments 258-264 or the pharmaceutical composition of Embodiment 266 or Embodiment 267 to a subject in need thereof.

271. The compound for use of Embodiment 268, the use of Embodiment 269, or the method of Embodiment 270, wherein the Compound I calcium salt EtOH solvate Form A of any one of Embodiments 258-264 is administered in combination with at least one additional CFTR modulating compound.

272. The compound, use, or method of Embodiment 271, wherein the Compound I calcium salt EtOH solvate Form A of any one of Embodiments 258-264 is administered in combination with
   a. Compound III or Compound III-d;
   b. (i) Compound II and (ii) Compound III or Compound III-d; or
   c. (i) Compound IV and (ii) Compound III or Compound III-d.

273. The composition, use, method or compound of any one of Embodiments 267-272, wherein Compound II and/or Compound III are in the form of a solid dispersion.

274. Substantially crystalline Compound I calcium salt EtOH solvate Form B (i.e., wherein less than 15% of Compound I is in amorphous form, wherein less than 10% of Compound I is in amorphous form, wherein less than 5% of Compound I is in amorphous form).

275. Compound I of Embodiment 274, wherein Compound I is 100% crystalline calcium salt EtOH solvate Form B.

276. The crystalline Compound I calcium salt EtOH solvate Form B of Embodiment 274 or Embodiment 275, characterized by an X-ray powder diffractogram having signals at 15.4±0.2 degrees two-theta.

277. The crystalline Compound I calcium salt EtOH solvate Form B of Embodiment 274 or Embodiment 175, characterized by an X-ray powder diffractogram having signals at 4.5±0.2 degrees two-theta, 5.0±0.2 degrees two-theta, and 15.4±0.2 degrees two-theta.

278. The crystalline Compound I calcium salt EtOH solvate Form B of of Embodiment 274 or Embodiment 175, characterized by an X-ray powder diffractogram substantially similar to FIG. 19.

279. The crystalline Compound I calcium salt EtOH solvate Form B of any one of Embodiments 274-278, prepared by a process comprising temperature cycling between 60° C. and 5° C. with cooling rate of 0.2° C./min of Compound I calcium salt hydrate Form A in EtOH:n-heptane (1:1).

280. A method of preparing the crystalline Compound I calcium salt EtOH solvate Form B of any one of Embodiments 274-278, prepared by a process comprising temperature cycling between 60° C. and 5° C. with cooling rate of 0.2° C./min of Compound I calcium salt hydrate Form A in EtOH:n-heptane (1:1).

281. A pharmaceutical composition comprising the crystalline Compound I calcium salt EtOH solvate Form B of any one of Embodiments 274-279, optionally further comprising one or more additional CFTR modulating compounds.

282. The pharmaceutical composition of Embodiment 281, wherein the one or more additional CFTR modulating compounds are
   a. Compound III or Compound III-d; or
   b. (i) Compound II and (ii) Compound III or Compound III-d.

283. The Compound I calcium salt EtOH solvate Form B of any one of Embodiments 274-279 or the pharmaceutical composition of Embodiment 281 or Embodiment 282 for use in the treatment of cystic fibrosis.

284. Use of the Compound I calcium salt EtOH solvate Form B any one of Embodiments 274-279 or the pharmaceutical composition of Embodiment 281 or Embodiment 282 in the manufacture of a medicament for the treatment of cystic fibrosis.

285. A method of treating cystic fibrosis comprising administering the Compound I calcium salt EtOH solvate Form B of any one of Embodiments 274-279 or the pharmaceutical composition of Embodiment 281 or Embodiment 282 to a subject in need thereof.

286. The compound for use of Embodiment 283, the use of Embodiment 284, or the method of Embodiment 285, wherein the Compound I calcium salt EtOH solvate Form B of any one of Embodiments 274-279 is administered in combination with at least one additional CFTR modulating compound.

287. The compound, use, or method of Embodiment 286, wherein the Compound I calcium salt EtOH solvate Form B of any one of Embodiments 274-279 is administered in combination with
   a. Compound III or Compound III-d;
   b. (i) Compound II and (ii) Compound III or Compound III-d; or
   c. (i) Compound IV and (ii) Compound III or Compound III-d.

288. The composition, use, method or compound of any one of Embodiments 282-287, wherein Compound II and/or Compound III are in the form of a solid dispersion.

289. Substantially crystalline Compound I calcium salt EtOH solvate Form C (i.e., wherein less than 15% of Compound I is in amorphous form, wherein less than 10% of Compound I is in amorphous form, wherein less than 5% of Compound I is in amorphous form).

290. Compound I of Embodiment 289, wherein Compound I is 100% crystalline calcium salt EtOH solvate Form C.

291. The crystalline Compound I calcium salt EtOH solvate Form C of Embodiment 289 or Embodiment 290, characterized by an X-ray powder diffractogram having signals 4.2±0.2 degrees two-theta, 5.0±0.2 degrees two-theta, and at 5.7±0.2 degrees two-theta.

292. The crystalline Compound I calcium salt EtOH solvate Form C of of Embodiment 289 or Embodiment 290, characterized by an X-ray powder diffractogram substantially similar to FIG. 20.

293. The crystalline Compound I calcium salt EtOH solvate Form C of any one of Embodiments 289-292, prepared by a process comprising making a slurry of amorphous Compound I calcium salt with EtOH:$H_2O$ (9:1) at room temperature.

294. A method of preparing the crystalline Compound I calcium salt EtOH solvate Form C of any one of Embodiments 289-292, prepared by a process comprising making a slurry of amorphous Compound I calcium salt with EtOH:$H_2O$ (9:1) at room temperature.

295. A pharmaceutical composition comprising the crystalline Compound I calcium salt EtOH solvate Form C of any one of Embodiments 289-293, optionally further comprising one or more additional CFTR modulating compounds.

296. The pharmaceutical composition of Embodiment 295, wherein the one or more additional CFTR modulating compounds are
   a. Compound III or Compound III-d; or
   b. (i) Compound II and (ii) Compound III or Compound III-d.

297. The Compound I calcium salt EtOH solvate Form C of any one of Embodiments 289-293 or the pharmaceutical composition of Embodiment 295 or Embodiment 296 for use in the treatment of cystic fibrosis.

298. Use of the Compound I calcium salt EtOH solvate Form C any one of Embodiments 289-293 or the pharmaceutical composition of Embodiment 295 or Embodiment 296 in the manufacture of a medicament for the treatment of cystic fibrosis.

299. A method of treating cystic fibrosis comprising administering the Compound I calcium salt EtOH solvate Form C of any one of Embodiments 289-293 or the pharmaceutical composition of Embodiment 295 or Embodiment 296 to a subject in need thereof.

300. The compound for use of Embodiment 297, the use of Embodiment 298, or the method of Embodiment 299, wherein the Compound I calcium salt EtOH solvate Form C of any one of Embodiments 289-293 is administered in combination with at least one additional CFTR modulating compound.

301. The compound, use, or method of Embodiment 300, wherein the Compound I calcium salt EtOH solvate Form C of any one of Embodiments 289-293 is administered in combination with
   a. Compound III or Compound III-d;
   b. (i) Compound II and (ii) Compound III or Compound III-d; or
   c. (i) Compound IV and (ii) Compound III or Compound III-d.

302. The composition, use, method or compound of any one of Embodiments 296-301, wherein Compound II and/or Compound III are in the form of a solid dispersion.

303. Substantially crystalline Compound I sodium salt hydrate Form A (i.e., wherein less than 15% of Compound I is in amorphous form, wherein less than 10% of Compound I is in amorphous form, wherein less than 5% of Compound I is in amorphous form).

304. Compound I of Embodiment 303, wherein Compound I is 100% crystalline sodium salt hydrate Form A.

305. The crystalline Compound I sodium salt hydrate Form A of Embodiment 303 or Embodiment 304, characterized by an X-ray powder diffractogram having signals at 5.4±0.2 degrees two-theta, 15.9±0.2 degrees two-theta, and 17.6±0.2 degrees two-theta.

306. The crystalline Compound I sodium salt hydrate Form A of Embodiment 303 or Embodiment 304, characterized by an X-ray powder diffractogram having (a) signals at 5.4±0.2 degrees two-theta, 15.9±0.2 degrees two-theta, and 17.6±0.2 degrees two-theta; and (b) a signal at 15.3±0.2 degrees two-theta, 18.6±0.2 degrees two-theta, 20.0±0.2 degrees two-theta, 21.3±0.2 degrees two-theta, 23.9±0.2 degrees two-theta, and/or 26.7±0.2 degrees two-theta.

307. The crystalline Compound I sodium salt hydrate Form A of Embodiment 303 or Embodiment 304, characterized by an X-ray powder diffractogram substantially similar to FIG. 34.

308. The crystalline Compound I sodium salt hydrate Form A of any one of Embodiments 303-307, characterized by a $^{13}C$ ssNMR spectrum with a peak at 177.0±0.2 ppm, 159.6±0.2 ppm, 138.5±0.2 ppm, 107.0±0.2 ppm, 96.4±0.2 ppm, 38.3±0.2 ppm, and/or 28.9±0.2 ppm.

309. The crystalline Compound I sodium salt hydrate Form A of any one of Embodiments 303-307, characterized by a $^{13}C$ ssNMR substantially similar to FIG. 35.

309(a) The crystalline Compound I sodium salt hydrate Form A of any one of Embodiments 303-309, characterized by an orthorhombic crystal system, a $P2_12_12_1$ space group, and unit cell dimensions measured at 100 K on a Bruker diffractometer utilizing synchrotron radiation ($\lambda$=0.7288 Å) of:

| | | | |
|---|---|---|---|
| a | 8.23 ± .01 Å | α | 90° |
| b | 11.85 ± .01 Å | β | 90° |
| c | 33.09 ± .01 Å | γ | 90°. |

310. The crystalline Compound I sodium salt hydrate Form A of any one of Embodiments 303-309, prepared by a process comprising mixing amorphous Compound I sodium salt with IPA/water at room temperature for two weeks.

311. A method of preparing the crystalline Compound I sodium salt hydrate Form A of any one of Embodiments 303-309, prepared by a process comprising mixing amorphous Compound I sodium salt with IPA/water at room temperature for two weeks.

312. A pharmaceutical composition comprising the crystalline Compound I sodium salt hydrate Form A of any one of Embodiments 303-310, optionally further comprising one or more additional CFTR modulating compounds.

313. The pharmaceutical composition of Embodiment 312, wherein the one or more additional CFTR modulating compounds are
  a. Compound III or Compound III-d; or
  b. (i) Compound II and (ii) Compound III or Compound III-d.
314. The Compound I sodium salt hydrate Form A of any one of Embodiments 303-310 or the pharmaceutical composition of Embodiment 312 or Embodiment 313 for use in the treatment of cystic fibrosis.
315. Use of the Compound I sodium salt hydrate Form A of any one of Embodiments 303-310 or the pharmaceutical composition of Embodiment 312 or Embodiment 313 in the manufacture of a medicament for the treatment of cystic fibrosis.
316. A method of treating cystic fibrosis comprising administering the Compound I sodium salt hydrate Form A of any one of Embodiments 303-310 or the pharmaceutical composition of Embodiment 312 or Embodiment 313 to a subject in need thereof.
317. The compound for use of Embodiment 314, the use of Embodiment 315, or the method of Embodiment 316, wherein the Compound I sodium salt hydrate Form A of any one of Embodiments 303-310 is administered in combination with at least one additional CFTR modulating compound.
318. The compound, use, or method of Embodiment 317, wherein the Compound I sodium salt hydrate Form A of any one of Embodiments 303-310 is administered in combination with
  a. Compound III or Compound III-d;
  b. (i) Compound II and (ii) Compound III or Compound III-d; or
  c. (i) Compound IV and (ii) Compound III or Compound III-d.
319. The composition, use, method, or compound of any one of Embodiments 313-318, wherein Compound II and/or Compound III are in the form of a solid dispersion.
320. Substantially crystalline Compound I sodium salt neat Form B (i.e., wherein less than 15% of Compound I is in amorphous form, wherein less than 10% of Compound I is in amorphous form, wherein less than 5% of Compound I is in amorphous form).
321. Compound I of Embodiment 320, wherein Compound I is 100% crystalline sodium salt neat Form B.
322. The crystalline Compound I sodium salt neat Form B of Embodiment 320 or Embodiment 321, characterized by an X-ray powder diffractogram having a signal at 11.0±0.2 degrees two-theta, 18.1±0.2 degrees two-theta, and 20.5±0.2 degrees two-theta.
323. The crystalline Compound I sodium salt neat Form B of Embodiment 320 or Embodiment 321, characterized by an X-ray powder diffractogram having (a) a signal at 12.8±0.2 degrees two-theta; and (b) a signal at 20.5±0.2 degrees two-theta, 18.1±0.2 degrees two-theta, and/or 11.0±0.2 degrees two-theta.
324. The crystalline Compound I sodium salt neat Form B of Embodiment 320 or Embodiment 321, characterized by an X-ray powder diffractogram substantially similar to FIG. 36.
325. The crystalline Compound I sodium salt neat Form B of any one of Embodiments 320-324, prepared by a process comprising desolvating/dehydrating Compound I sodium salt hydrate Form C.
326. A method of preparing the crystalline Compound I sodium salt neat Form B of any one of Embodiments 320-324, prepared by a process comprising desolvating/dehydrating Compound I sodium salt hydrate Form C.
327. A pharmaceutical composition comprising the crystalline Compound I sodium salt neat Form B of any one of Embodiments 320-325, optionally further comprising one or more additional CFTR modulating compounds.
328. The pharmaceutical composition of Embodiment 327, wherein the one or more additional CFTR modulating compounds are
  a. Compound III or Compound III-d; or
  b. (i) Compound II and (ii) Compound III or Compound III-d.
329. The Compound I sodium salt neat Form B of any one of Embodiments 320-325 or the pharmaceutical composition of Embodiment 327 or Embodiment 328 for use in the treatment of cystic fibrosis.
330. Use of the Compound I sodium salt neat Form B of any one of Embodiments 320-325 or the pharmaceutical composition of Embodiment 327 or Embodiment 328 in the manufacture of a medicament for the treatment of cystic fibrosis.
331. A method of treating cystic fibrosis comprising administering the Compound I sodium salt neat Form B of any one of Embodiments 320-325 or the pharmaceutical composition of Embodiment 327 or Embodiment 328 to a subject in need thereof.
332. The compound for use of Embodiment 329, the use of Embodiment 330, or the method of Embodiment 331, wherein the Compound I sodium salt neat Form B of any one of Embodiments 320-325 is administered in combination with at least one additional CFTR modulating compound.
333. The compound, use, or method of Embodiment 332, wherein the Compound I sodium salt neat Form B of any one of Embodiments 320-325 is administered in combination with
  a. Compound III or Compound III-d;
  b. (i) Compound II and (ii) Compound III or Compound III-d; or
  c. (i) Compound IV and (ii) Compound III or Compound III-d.
334. The composition, use, method, or compound of any one of Embodiments 328-333, wherein Compound II and/or Compound III are in the form of a solid dispersion.
335. Substantially crystalline Compound I sodium salt hydrate Form C (i.e., wherein less than 15% of Compound I is in amorphous form, wherein less than 10% of Compound I is in amorphous form, wherein less than 5% of Compound I is in amorphous form).
336. Compound I of Embodiment 335, wherein Compound I is 100% crystalline sodium salt hydrate Form C.
337. The crystalline Compound I sodium salt hydrate Form C of Embodiment 335 or Embodiment 336, characterized by an X-ray powder diffractogram having signals at 6.1±0.2 degrees two-theta, 13.4±0.2 degrees two-theta, and 19.2±0.2 degrees two-theta.
338. The crystalline Compound I sodium salt hydrate Form C of Embodiment 335 or Embodiment 336, characterized by an X-ray powder diffractogram having (a) a signal at 10.3±0.2 degrees two-theta and/or 4.5±0.2 degrees two-theta; and (b) a signal at 19.2±0.2 degrees two-theta, 13.4±0.2 degrees two-theta, and/or 6.1 0.2 degrees two-theta 339. The crystalline Compound I sodium salt hydrate Form C of Embodiment 335 or Embodiment 336, characterized by an X-ray powder diffractogram substantially similar to FIG. 37.
340. The crystalline Compound I sodium salt hydrate Form C of any one of Embodiments 335-339, prepared by a process comprising stirring Compound I amorphous sodium salt with ACN at room temperature.
341. A method of preparing the crystalline Compound I sodium salt hydrate Form C of any one of Embodiments 335-339, prepared by a process comprising stirring Compound I amorphous sodium salt with ACN at room temperature.
342. A pharmaceutical composition comprising the crystalline Compound I sodium salt hydrate Form C of any one of Embodiments 335-340, optionally further comprising one or more additional CFTR modulating compounds.
343. The pharmaceutical composition of Embodiment 342, wherein the one or more additional CFTR modulating compounds are
   a. Compound III or Compound III-d; or
   b. (i) Compound II and (ii) Compound III or Compound III-d.
344. The Compound I sodium salt hydrate Form C of any one of Embodiments 335-340 or the pharmaceutical composition of Embodiment 342 or Embodiment 343 for use in the treatment of cystic fibrosis.
345. Use of the Compound I sodium salt hydrate Form C of any one of Embodiments 335-340 or the pharmaceutical composition of Embodiment 342 or Embodiment 343 in the manufacture of a medicament for the treatment of cystic fibrosis.
346. A method of treating cystic fibrosis comprising administering the Compound I sodium salt hydrate Form C of any one of Embodiments 335-340 or the pharmaceutical composition of Embodiment 342 or Embodiment 343 to a subject in need thereof.
347. The compound for use of Embodiment 344, the use of Embodiment 345, or the method of Embodiment 346, wherein the Compound I sodium salt hydrate Form C of any one of Embodiments 335-340 is administered in combination with at least one additional CFTR modulating compound.
348. The compound, use, or method of Embodiment 347, wherein the Compound I sodium salt hydrate Form C of any one of Embodiments 335-340 is administered in combination with
   a. Compound III or Compound III-d;
   b. (i) Compound II and (ii) Compound III or Compound III-d; or
   c. (i) Compound IV and (ii) Compound III or Compound III-d.
349. The composition, use, method, or compound of any one of Embodiments 343-348, wherein Compound II and/or Compound III are in the form of a solid dispersion.
350. Substantially crystalline Compound I sodium salt hydrate Form D (i.e., wherein less than 15% of Compound I is in amorphous form, wherein less than 10% of Compound I is in amorphous form, wherein less than 5% of Compound I is in amorphous form).
351. Compound I of Embodiment 350, wherein Compound I is 100% crystalline sodium salt hydrate Form D.
352. The crystalline Compound I sodium salt hydrate Form D of Embodiment 350 or Embodiment 351, characterized by an X-ray powder diffractogram having a signal at 7.8±0.2 degrees two-theta, 18.5±0.2 degrees two-theta, and 19.9±0.2 degrees two-theta.
353. The crystalline Compound I sodium salt hydrate Form D of Embodiment 350 or Embodiment 351, characterized by an X-ray powder diffractogram having (a) signals at 7.8±0.2 degrees two-theta, 18.5±0.2 degrees two-theta, and 19.9±0.2 degrees two-theta; and (b) a signal at 9.3±0.2 degrees two-theta, 14.8±0.2 degrees two-theta, and/or 27.3±0.2 degrees two-theta.
354. The crystalline Compound I sodium salt hydrate Form D of Embodiment 350 or Embodiment 351, characterized by an X-ray powder diffractogram substantially similar to FIG. 38.
355. The crystalline Compound I sodium salt hydrate Form D of any one of Embodiments 350-354, prepared by a process comprising drying Compound I sodium salt hydrate Form C under vacuum at 80° C.
356. A method of preparing the crystalline Compound I sodium salt hydrate Form D of any one of Embodiments 350-354, prepared by a process comprising drying Compound I sodium salt hydrate Form C under vacuum at 80° C.
357. A pharmaceutical composition comprising the crystalline Compound I sodium salt hydrate Form D of any one of Embodiments 350-355, optionally further comprising one or more additional CFTR modulating compounds.
358. The pharmaceutical composition of Embodiment 357, wherein the one or more additional CFTR modulating compounds are
   a. Compound III or Compound III-d; or
   b. (i) Compound II and (ii) Compound III or Compound III-d.
359. The Compound I sodium salt hydrate Form D of any one of Embodiments 350-355 or the pharmaceutical composition of Embodiment 357 or Embodiment 358 for use in the treatment of cystic fibrosis.
360. Use of the Compound I sodium salt hydrate Form D of any one of Embodiments 350-355 or the pharmaceutical composition of Embodiment 357 or Embodiment 358 in the manufacture of a medicament for the treatment of cystic fibrosis.
361. A method of treating cystic fibrosis comprising administering the Compound I sodium salt hydrate Form D of any one of Embodiments 350-355 or the pharmaceutical composition of Embodiment 357 or Embodiment 358 to a subject in need thereof.
362. The compound for use of Embodiment 359, the use of Embodiment 360, or the method of Embodiment 361, wherein the Compound I sodium salt hydrate Form D of any one of Embodiments 350-355 is administered in combination with at least one additional CFTR modulating compound.
363. The compound, use, or method of Embodiment 362, wherein the Compound I sodium salt hydrate Form D of any one of Embodiments 350-355 is administered in combination with
   a. Compound III or Compound III-d;
   b. (i) Compound II and (ii) Compound III or Compound III-d; or
   c. (i) Compound IV and (ii) Compound III or Compound III-d.
364. The composition, use, method, or compound of any one of Embodiments 358-363, wherein Compound II and/or Compound III are in the form of a solid dispersion.

365. Substantially crystalline Compound I potassium salt hydrate Form A (i.e., wherein less than 15% of Compound I is in amorphous form, wherein less than 10% of Compound I is in amorphous form, wherein less than 5% of Compound I is in amorphous form).

366. Compound I of Embodiment 365, wherein Compound I is 100% crystalline potassium salt hydrate Form A.

367. The crystalline Compound I potassium salt hydrate Form A of Embodiment 365 or Embodiment 366, characterized by an X-ray powder diffractogram having a signal at 10.7±0.2 degrees two-theta.

368. The crystalline Compound I potassium salt hydrate Form A of Embodiment 365 or Embodiment 366, characterized by an X-ray powder diffractogram having (a) a signal at 10.7±0.2 degrees two-theta; and (b) a signal at 15.3±0.2 degrees two-theta and/or 20.4±0.2 degrees two-theta.

369. The crystalline Compound I potassium salt hydrate Form A of Embodiment 365 or Embodiment 366, characterized by an X-ray powder diffractogram substantially similar to FIG. 39.

370. The crystalline Compound I potassium salt hydrate Form A of any one of Embodiments 365-369, prepared by a process comprising reacting Compound I (free form) Form A with potassium hydride/H$_2$O and subjecting to two cycles of heating and cooling from 60° C. to room temperature.

371. A method of preparing the crystalline Compound I potassium salt hydrate Form A of any one of Embodiments 365-369, prepared by a process comprising reacting Compound I (free form) Form A with potassium hydride/H$_2$O and subjecting to two cycles of heating and cooling from 60° C. to room temperature.

372. A pharmaceutical composition comprising the crystalline Compound I potassium salt hydrate Form A of any one of Embodiments 365-370, optionally further comprising one or more additional CFTR modulating compounds.

373. The pharmaceutical composition of Embodiment 372, wherein the one or more additional CFTR modulating compounds are
    a. Compound III or Compound III-d; or
    b. (i) Compound II and (ii) Compound III or Compound III-d.

374. The Compound I potassium salt hydrate Form A of any one of Embodiments 365-370 or the pharmaceutical composition of Embodiment 372 or Embodiment 373 for use in the treatment of cystic fibrosis.

375. Use of the Compound I potassium salt hydrate Form A of any one of Embodiments 365-370 or the pharmaceutical composition of Embodiment 372 or Embodiment 373 in the manufacture of a medicament for the treatment of cystic fibrosis.

376. A method of treating cystic fibrosis comprising administering the Compound I potassium salt hydrate Form A of any one of Embodiments 365-370 or the pharmaceutical composition of Embodiment 372 or Embodiment 373 to a subject in need thereof.

377. The compound for use of Embodiment 374, the use of Embodiment 375, or the method of Embodiment 376, wherein the Compound I potassium salt hydrate Form A of any one of Embodiments 365-370 is administered in combination with at least one additional CFTR modulating compound.

378. The compound, use, or method of Embodiment 377, wherein the Compound I potassium salt hydrate Form A of any one of Embodiments 365-370 is administered in combination with
    a. Compound III or Compound III-d;
    b. (i) Compound II and (ii) Compound III or Compound III-d; or
    c. (i) Compound IV and (ii) Compound III or Compound III-d.

379. The composition, use, method, or compound of any one of Embodiments 374-378, wherein Compound II and/or Compound III are in the form of a solid dispersion.

380. Substantially crystalline Compound I potassium salt hydrate Form B (i.e., wherein less than 15% of Compound I is in amorphous form, wherein less than 10% of Compound I is in amorphous form, wherein less than 5% of Compound I is in amorphous form).

381. Compound I of Embodiment 380, wherein Compound I is 100% crystalline potassium salt hydrate Form B.

382. The crystalline Compound I potassium salt hydrate Form B of Embodiment 380 or Embodiment 381, characterized by an X-ray powder diffractogram having a signal at 14.8±0.2 degrees two-theta.

383. The crystalline Compound I potassium salt hydrate Form B of Embodiment 380 or Embodiment 381, characterized by an X-ray powder diffractogram having signals at 4.7±0.2 degrees two-theta, 6.8±0.2 degrees two-theta, and 21.5±0.2 degrees two-theta.

384. The crystalline Compound I potassium salt hydrate Form B of Embodiment 380 or Embodiment 381, characterized by an X-ray powder diffractogram having (a) signals at 4.7±0.2 degrees two-theta, 6.8±0.2 degrees two-theta, 14.8 0.2 degrees two-theta, 21.5±0.2 degrees two-theta; and (b) a signal at 15.2 0.2 degrees two-theta, 16.1±0.2 degrees two-theta, and/or 19.0±0.2 degrees two-theta.

385. The crystalline Compound I potassium salt hydrate Form B of Embodiment 380 or Embodiment 381, characterized by an X-ray powder diffractogram substantially similar to FIG. 40.

386. The crystalline Compound I potassium salt hydrate Form B of any one of Embodiments 380-385, prepared by a process comprising making a slurry of Compound I amorphous potassium salt with ACN at room temperature and then at 60° C.

387. A method of preparing the crystalline Compound I potassium salt hydrate Form B of any one of Embodiments 380-385, prepared by a process comprising making a slurry of Compound I amorphous potassium salt with ACN at room temperature and then at 60° C.

388. A pharmaceutical composition comprising the crystalline Compound I potassium salt hydrate Form B of any one of Embodiments 380-386, optionally further comprising one or more additional CFTR modulating compounds.

389. The pharmaceutical composition of Embodiment 388, wherein the one or more additional CFTR modulating compounds are
    a. Compound III or Compound III-d; or
    b. (i) Compound II and (ii) Compound III or Compound III-d.

390. The Compound I potassium salt hydrate Form B of any one of Embodiments 380-386 or the pharmaceutical composition of Embodiment 388 or Embodiment 389 for use in the treatment of cystic fibrosis.

391. Use of the Compound I potassium salt hydrate Form B of any one of Embodiments 380-386 or the pharmaceutical composition of Embodiment 388 or Embodiment 389 in the manufacture of a medicament for the treatment of cystic fibrosis.

392. A method of treating cystic fibrosis comprising administering the Compound I potassium salt hydrate Form B of any one of Embodiments 380-386 or the pharmaceutical composition of Embodiment 388 or Embodiment 389 to a subject in need thereof.

393. The compound for use of Embodiment 390, the use of Embodiment 391, or the method of Embodiment 392, wherein the Compound I potassium salt hydrate Form B of any one of Embodiments 380-386 is administered in combination with at least one additional CFTR modulating compound.

394. The compound, use, or method of Embodiment 393, wherein the Compound I potassium salt hydrate Form B of any one of Embodiments 380-386 is administered in combination with
  a. Compound III or Compound III-d;
  b. (i) Compound II and (ii) Compound III or Compound III-d; or
  c. (i) Compound IV and (ii) Compound III or Compound III-d.

395. The composition, use, method, or compound of any one of Embodiments 389-394, wherein Compound II and/or Compound III are in the form of a solid dispersion.

396. Substantially crystalline Compound I potassium salt hydrate Form C (i.e., wherein less than 15% of Compound I is in amorphous form, wherein less than 10% of Compound I is in amorphous form, wherein less than 5% of Compound I is in amorphous form).

397. Compound I of Embodiment 396, wherein Compound I is 100% crystalline potassium salt hydrate Form C.

398. The crystalline Compound I potassium salt hydrate Form C of Embodiment 396 or Embodiment 397 characterized by an X-ray powder diffractogram having signals at at 4.8±0.2 degrees two-theta, 6.3±0.2 degrees two-theta, and 14.2±0.2 degrees two-theta.

399. The crystalline Compound I potassium salt hydrate Form C of Embodiment 396 or Embodiment 397, characterized by an X-ray powder diffractogram having (a) signals at 4.8±0.2 degrees two-theta, 6.3±0.2 degrees two-theta, and 14.2±0.2 degrees two-theta; and (b) one or more signals selected from 13.5±0.2 degrees two-theta, 14.2±0.2 degrees two-theta, 15.8±0.2 degrees two-theta, 19.0±0.2 degrees two-theta, and 27.1±0.2 degrees two-theta.

400. The crystalline Compound I potassium salt hydrate Form C of Embodiment 396 or Embodiment 397, characterized by an X-ray powder diffractogram substantially similar to FIG. 41.

401. The crystalline Compound I potassium salt hydrate Form C of any one of Embodiments 396-400, prepared by a process comprising mixing amorphous Compound I potassium salt with ACN at room temperature.

402. A method of preparing the crystalline Compound I potassium salt hydrate Form C of any one of Embodiments 396-400, prepared by a process comprising mixing amorphous Compound I potassium salt with ACN at room temperature.

403. A pharmaceutical composition comprising the crystalline Compound I potassium salt hydrate Form C of any one of Embodiments 396-401, optionally further comprising one or more additional CFTR modulating compounds.

404. The pharmaceutical composition of Embodiment 403, wherein the one or more additional CFTR modulating compounds are
  a. Compound III or Compound III-d; or
  b. (i) Compound II and (ii) Compound III or Compound III-d.

405. The Compound I potassium salt hydrate Form C of any one of Embodiments 396-401 or the pharmaceutical composition of Embodiment 403 or Embodiment 404 for use in the treatment of cystic fibrosis.

406. Use of the Compound I potassium salt hydrate Form C of any one of Embodiments 396-401 or the pharmaceutical composition of Embodiment 403 or Embodiment 404 in the manufacture of a medicament for the treatment of cystic fibrosis.

407. A method of treating cystic fibrosis comprising administering the Compound I potassium salt hydrate Form C of any one of Embodiments 396-401 or the pharmaceutical composition of Embodiment 403 or Embodiment 404 to a subject in need thereof.

408. The compound for use of Embodiment 405, the use of Embodiment 406, or the method of Embodiment 407, wherein the Compound I potassium salt hydrate Form C of any one of Embodiments 396-401 is administered in combination with at least one additional CFTR modulating compound.

409. The compound, use, or method of Embodiment 408, wherein the Compound I potassium salt hydrate Form C of any one of Embodiments 396-401 is administered in combination with
  a. Compound III or Compound III-d;
  b. (i) Compound II and (ii) Compound III or Compound III-d; or
  c. (i) Compound IV and (ii) Compound III or Compound III-d.

410. The composition, use, method, or compound of any one of Embodiments 404-409, wherein Compound II and/or Compound III are in the form of a solid dispersion.

411. Substantially crystalline Compound I potassium salt hydrate Form D (i.e., wherein less than 15% of Compound I is in amorphous form, wherein less than 10% of Compound I is in amorphous form, wherein less than 5% of Compound I is in amorphous form).

412. Compound I of Embodiment 411, wherein Compound I is 100% crystalline potassium salt hydrate Form D.

413. The crystalline Compound I potassium salt hydrate Form D of Embodiment 411 or Embodiment 412 characterized by an X-ray powder diffractogram having signals at 4.4±0.2 degrees two-theta, 13.1±0.2 degrees two-theta, and 15.3±0.2 degrees two-theta.

414. The crystalline Compound I potassium salt hydrate Form D of Embodiment 411 or Embodiment 412, characterized by an X-ray powder diffractogram having (a) a signal at 8.8±0.2 degrees two-theta; and (b) a signal at 4.4±0.2 degrees two-theta, 13.1±0.2 degrees two-theta, and 15.3±0.2 degrees two-theta.

415. The crystalline Compound I potassium salt hydrate Form D of Embodiment 411 or Embodiment 412, characterized by an X-ray powder diffractogram having (a) signals at 4.4±0.2 degrees two-theta, 8.8±0.2 degrees two-theta, 13.1±0.2 degrees two-theta, and 15.3±0.2 degrees two-theta; and (b) a signal at 7.0±0.2 degrees two-theta, 8.1±0.2 degrees two-theta, and/or 21.9±0.2 degrees two-theta.

416. The crystalline Compound I potassium salt hydrate Form D of Embodiment 411 or Embodiment 412, characterized by an X-ray powder diffractogram substantially similar to FIG. 42.

417. The crystalline Compound I potassium salt hydrate Form D of any one of Embodiments 411-416, prepared by a process comprising mixing amorphous Compound I potassium salt with ACN at room temperature and drying at 29° C. under vacuum.

418. A method of preparing the crystalline Compound I potassium salt hydrate Form D of any one of Embodiments 411-416, prepared by a process comprising mixing amorphous Compound I potassium salt with ACN at room temperature and drying at 29° C. under vacuum.

419. A pharmaceutical composition comprising the crystalline Compound I potassium salt hydrate Form D of any one of Embodiments 411-417, optionally further comprising one or more additional CFTR modulating compounds.

420. The pharmaceutical composition of Embodiment 419, wherein the one or more additional CFTR modulating compounds are
  a. Compound III or Compound III-d; or
  b. (i) Compound II and (ii) Compound III or Compound III-d.

421. The Compound I potassium salt hydrate Form D of any one of Embodiments 411-417 or the pharmaceutical composition of Embodiment 419 or Embodiment 420 for use in the treatment of cystic fibrosis.

422. Use of the Compound I potassium salt hydrate Form D of any one of Embodiments 411-417 or the pharmaceutical composition of Embodiment 419 or Embodiment 420 in the manufacture of a medicament for the treatment of cystic fibrosis.

423. A method of treating cystic fibrosis comprising administering the Compound I potassium salt hydrate Form D of any one of Embodiments 411-417 or the pharmaceutical composition of Embodiment 419 or Embodiment 420 to a subject in need thereof.

424. The compound for use of Embodiment 421, the use of Embodiment 422, or the method of Embodiment 423, wherein the Compound I potassium salt hydrate Form D of any one of Embodiments 411-417 is administered in combination with at least one additional CFTR modulating compound.

425. The compound, use, or method of Embodiment 408, wherein the Compound I potassium salt hydrate Form D of any one of Embodiments 411-417 is administered in combination with
  a. Compound III or Compound III-d;
  b. (i) Compound II and (ii) Compound III or Compound III-d; or
  c. (i) Compound IV and (ii) Compound III or Compound III-d.

426. The composition, use, method, or compound of any one of Embodiments 420-425, wherein Compound II and/or Compound III are in the form of a solid dispersion.

427. Substantially crystalline Compound I ammonia salt hydrate Form A (i.e., wherein less than 15% of Compound I is in amorphous form, wherein less than 10% of Compound I is in amorphous form, wherein less than 5% of Compound I is in amorphous form).

428. Compound I of Embodiment 427, wherein Compound I is 100% crystalline ammonia salt hydrate Form A.

429. The crystalline Compound I ammonia salt hydrate Form A of Embodiment 427 or Embodiment 428 characterized by an X-ray powder diffractogram having a signal at 5.5±0.2 degrees two-theta, 15.3±0.2 degrees two-theta, and/or 17.7±0.2 degrees two-theta.

430. The crystalline Compound I ammonia salt hydrate Form A of Embodiment 427 or Embodiment 428, characterized by an X-ray powder diffractogram having (a) a signal at 5.5±0.2 degrees two-theta, 15.3±0.2 degrees two-theta, and/or 17.7 0.2 degrees two-theta; and (b) a signal at 18.0±0.2 degrees two-theta, 19.6±0.2 degrees two-theta, and/or 20.9±0.2 degrees two-theta.

431. The crystalline Compound I ammonia salt hydrate Form A of Embodiment 427 or Embodiment 428, characterized by an X-ray powder diffractogram substantially similar to FIG. 44.

432. The crystalline Compound I ammonia salt hydrate Form A of any one of Embodiments 427-431, prepared by a process comprising mixing amorphous Compound I (free form) Form A with ammonium hydroxide in water.

433. A method of preparing the crystalline Compound I ammonia salt hydrate Form A of any one of Embodiments 427-431, prepared by a process comprising mixing amoprhous Compound I (free form) Form A with ammonium hydroxide in water.

434. A pharmaceutical composition comprising the crystalline Compound I ammonia salt hydrate Form A of any one of Embodiments 427-432, optionally further comprising one or more additional CFTR modulating compounds.

435. The pharmaceutical composition of Embodiment 434, wherein the one or more additional CFTR modulating compounds are
  a. Compound III or Compound III-d; or
  b. (i) Compound II and (ii) Compound III or Compound III-d.

436. The Compound I ammonia salt hydrate Form A of any one of Embodiments 427-432 or the pharmaceutical composition of Embodiment 434 or Embodiment 435 for use in the treatment of cystic fibrosis.

437. Use of the Compound I ammonia salt hydrate Form A of any one of Embodiments 427-432 or the pharmaceutical composition of Embodiment 434 or Embodiment 435 in the manufacture of a medicament for the treatment of cystic fibrosis.

438. A method of treating cystic fibrosis comprising administering the Compound I ammonia salt hydrate Form A of any one of Embodiments 427-432 or the pharmaceutical composition of Embodiment 434 or Embodiment 435 to a subject in need thereof.

439. The compound for use of Embodiment 436, the use of Embodiment 437, or the method of Embodiment 438, wherein the Compound I ammonia salt hydrate Form A of any one of Embodiments 427-432 is administered in combination with at least one additional CFTR modulating compound.

440. The compound, use, or method of Embodiment 439, wherein the Compound I ammonia salt hydrate Form A of any one of Embodiments 427-432 is administered in combination with
  a. Compound III or Compound III-d;
  b. (i) Compound II and (ii) Compound III or Compound III-d; or c. (i) Compound IV and (ii) Compound III or Compound III-d.

441. The composition, use, method, or compound of any one of Embodiments 435-440, wherein Compound II and/or Compound III are in the form of a solid dispersion.

442. Substantially crystalline Compound I sodium salt hydrate Form E.

443. The Compound I sodium salt hydrate Form E according to Embodiment 442, characterized by an X-ray powder diffractogram having signals at 4.3±0.2 degrees two-theta, 13.0±0.2 degrees two-theta, and 14.9±0.2 degrees two-theta.

444. The Compound I sodium salt hydrate Form E according to Embodiment 442 or Embodiment 443, characterized by an X-ray powder diffractogram having
 (a) signals at 4.3±0.2 degrees two-theta, 13.0±0.2 degrees two-theta, and 14.9±0.2 degrees two-theta; and
 (b) a signal at one, two, three, or four of 10.6±0.2 degrees two-theta, 11.7 0.2 degrees two-theta, 13.4±0.2 degrees two-theta, 14.1±0.2 degrees two-theta, 14.2±0.2 degrees two-theta, 17.3±0.2 degrees two-theta, 18.1±0.2 degrees two-theta, 18.8±0.2 degrees two-theta, 19.2±0.2 degrees two-theta, 20.0±0.2 degrees two-theta, 21.4±0.2 degrees two-theta, 21.5±0.2 degrees two-theta, 22.3±0.2 degrees two-theta, and 23.1±0.2 degrees two-theta.

445. The Compound I sodium salt hydrate Form E according to Embodiment 442, characterized by an X-ray powder diffractogram having signals at 4.3±0.2 degrees two-theta, 13.0±0.2 degrees two-theta, and 23.1±0.2 degrees two-theta.

446. The Compound I sodium salt hydrate Form E according to any one of Embodiments 442-445, characterized by an X-ray powder diffractogram substantially similar to FIG. 49.

447. The Compound I sodium salt hydrate Form E according to any one of Embodiments 442-446, wherein Compound I sodium salt hydrate Form E is characterized by a $^{13}C$ solid state nuclear magnetic resonance ($^{13}C$ ssNMR) spectrum with one, two, three, four, five, six, seven, or more peaks selected from: 165.2±0.2 ppm, 155.4±0.2 ppm, 142.7±0.2 ppm, 128.4±0.2 ppm, 121.3 0.2 ppm, 101.0±0.2 ppm, 93.1±0.2 ppm, 69.5±0.2 ppm, 62.6±0.2 ppm, 55.2 0.2 ppm, 50.6±0.2 ppm, 50.0±0.2 ppm, 21.1±0.2 ppm, 17.2±0.2 ppm, 7.2±0.2 ppm, and 2.1±0.2 ppm.

448. The Compound I sodium salt hydrate Form E according to any one of Embodiments 442-447, wherein Compound I sodium salt hydrate Form E is characterized by a $^{13}C$ ssNMR spectrum with peaks at 165.2±0.2 ppm, 155.4±0.2 ppm, 142.7±0.2 ppm, 128.4±0.2 ppm, 121.3±0.2 ppm, 101.0±0.2 ppm, 93.1±0.2 ppm, 69.5±0.2 ppm, 62.6±0.2 ppm, 55.2±0.2 ppm, 50.6±0.2 ppm, 50.0±0.2 ppm, 21.1±0.2 ppm, 17.2±0.2 ppm, 7.2±0.2 ppm, and 2.1±0.2 ppm.

449. The Compound I sodium salt hydrate Form E according to any one of Embodiments 442-446, wherein Compound I sodium salt hydrate Form E is characterized by a $^{13}C$ solid state nuclear magnetic resonance ($^{13}C$ ssNMR) spectrum with peaks at 177.4±0.2 ppm, 165.2±0.2 ppm, 155.4±0.2 ppm, 142.7±0.2 ppm, 128.4±0.2 ppm, 121.3±0.2 ppm, 101.0±0.2 ppm, 69.5±0.2 ppm, 62.6±0.2 ppm, 55.2±0.2 ppm, 50.0±0.2 ppm, 30.9±0.2 ppm, 30.2±0.2 ppm, 27.8±0.2 ppm, 21.1±0.2 ppm, 17.2±0.2 ppm, 7.2±0.2 ppm, and 2.1±0.2 ppm.

450. The Compound I sodium salt hydrate Form E according to any one of Embodiments 442-449, characterized by a $^{13}C$ solid state NMR spectrum substantially similar to FIG. 50.

451. The Compound I sodium salt hydrate Form E according to any one of Embodiments 442-450, characterized by a orthorhombic crystal system, a $C222_1$ space group, and unit cell dimensions measured at 100 K on a Bruker diffractometer equipped Cu Kα radiation (λ=1.54178 Å) of:

| | | | |
|---|---|---|---|
| a | 12.66 ± .01 Å | α | 90° |
| b | 13.16 ± .01 Å | β | 90° |
| c | 39.93 ± .01 Å | γ | 90° |

452. The Compound I sodium salt hydrate Form E according to any one of Embodiments 442-451, prepared by a process comprising:
 i. heating Compound I sodium salt hydrate Form A in IPA and water at 65° C.,
 ii. cooling the mixture to 45° C.,
 iii. seeding with Compound I sodium salt hydrate Form A crystals,
 iv. cooling the mixture to 20° C.,
 v. collecting the solids,
 vi. washing the solids with IPA:water (1:3 v:v) and air drying,
 vii. adding IPA, NaOH, and water to the solids,
 viii. heating to 73° C.,
 ix. polish filtering the solution,
 x. cooling to 58° C.,
 xi. adding water,
 xii. seeding with Compound I sodium salt hydrate Form E crystals at 40° C.,
 xiii. cooling to 5° C.,
 xiv. collecting the solids,
 xv. washing the solids with a mixture of water and IPA, and
 xvi. drying under vacuum at 40° C., to provide Compound I sodium salt hydrate Form E.

453. A method of preparing Compound I sodium salt hydrate Form E according to any one of Embodiments 442-451, comprising:
 i. heating Compound I sodium salt hydrate Form A in IPA and water at 65° C.,
 ii. cooling the mixture to 45° C.,
 iii. seeding with Compound I sodium salt hydrate Form A crystals,
 iv. cooling the mixture to 20° C.,
 v. collecting the solids, then
 vi. washing the solids with IPA:water (1:3 v:v) and air drying,
 vii. adding IPA, NaOH, and water to the solids,
 viii. heating to 73° C.,
 ix. polish filtering the solution,
 x. cooling to 58° C.,
 xi. adding water,
 xii. seeding with Compound I sodium salt hydrate Form E crystals at 40° C.,
 xiii. cooling to 5° C.,
 xiv. collecting the solids,
 xv. washing the solids with a mixture of water and IPA, and
 xvi. drying under vacuum at 40° C.

454. The Compound I sodium salt hydrate Form E according to any one of Embodiments 442-451, prepared by a process comprising:
i. dissolving Compound I sodium salt hydrate Form A in IPA/water at 65° C.,
ii. cooling the solution to 45° C.,
iii. seeding with a mixture of Compound I sodium salt hydrate Form A and Form E,
iv. adding water,
v. cooling to 20° C.,
vi. collecting the solids,
vii. washing the solids with a mixture of water and IPA, and
viii. drying under vacuum to provide Compound I sodium salt hydrate Form E.

455. A method of preparing Compound I sodium salt hydrate Form E according to any one of Embodiments 442-451, comprising:
i. dissolving Compound I sodium salt hydrate Form A in IPA/water at 65° C.,
ii. cooling the solution to 45° C.,
iii. seeding with a mixture of Compound I sodium salt hydrate Form A and Form E,
iv. adding water,
v. cooling to 20° C.,
vi. collecting the solids,
vii. washing the solids with a mixture of water and IPA, and
viii. drying under vacuum.

456. Substantially crystalline Compound I sodium salt IPA (wet) solvate Form A.

457. The Compound I sodium salt IPA solvate (wet) Form A according to Embodiment 456, characterized by an X-ray powder diffractogram having a signal at 3.5±0.2 degrees two-theta and/or 3.6±0.2 degrees two-theta.

458. The Compound I sodium salt IPA solvate (wet) Form A according to Embodiment 456 or Embodiment 457, characterized by an X-ray powder diffractogram having
(a) a signal at 3.5±0.2 degrees two-theta and/or 3.6±0.2 degrees two-theta; and
(b) a signal at 9.5±0.2 degrees two-theta.

459. The Compound I sodium salt IPA solvate (wet) Form A according to any one of Embodiments 456-458, characterized by an X-ray powder diffractogram having signals at 3.6±0.2 degrees two-theta, 3.5±0.2 degrees two-theta, and 9.5±0.2 degrees two-theta.

460. The Compound I sodium salt IPA solvate (wet) Form A according to any one of Embodiments 456-459, characterized by an X-ray powder diffractogram substantially similar to FIG. 51.

461. The Compound I sodium salt IPA solvate (wet) Form A according to any one of Embodiments 456-460, prepared by a process comprising slurrying amorphous Compound I sodium salt hydrate Form A in IPA.

462. A method of preparing Compound I sodium salt IPA solvate (wet) Form A according to any one of Embodiments 456-460, comprising slurrying amorphous Compound I sodium salt hydrate Form A in IPA.

463. Substantially crystalline Compound I sodium salt IPA (dry) solvate Form B.

464. The Compound I sodium salt IPA solvate (dry) Form B according to Embodiment 463, characterized by an X-ray powder diffractogram having signals at 4.0±0.2 degrees two-theta and 5.3±0.2 degrees two-theta.

465. The Compound I sodium salt IPA solvate (dry) Form B according to Embodiment 463 or Embodiment 464, characterized by an X-ray powder diffractogram having
(a) signals at 4.0±0.2 degrees two-theta and 5.3±0.2 degrees two-theta; and
(b) a signal at one, two, three, or four of 7.9±0.2 degrees two-theta, 9.7±0.2 degrees two-theta, 11.0±0.2 degrees two-theta, 13.9±0.2 degrees two-theta, 18.5±0.2 degrees two-theta, and 20.0±0.2 degrees two-theta.

466. The Compound I sodium salt IPA solvate (dry) Form B according to Embodiment 463, characterized by an X-ray powder diffractogram having signals at 4.0±0.2 degrees two-theta, 7.9±0.2 degrees two-theta, and 9.7±0.2 degrees two-theta.

467. The Compound I sodium salt IPA solvate (dry) Form B according to any one of Embodiments 463-466, characterized by an X-ray powder diffractogram substantially similar to FIG. 52.

468. The Compound I sodium salt IPA solvate (dry) Form B any one of Embodiments 463-467, wherein Compound I sodium salt IPA solvate (dry) Form B is characterized by a $^{13}$C solid state nuclear magnetic resonance ($^{13}$C ssNMR) spectrum with one, two, three, four, five, six, seven, or more peaks selected from: 180.3±0.2 ppm, 178.7±0.2 ppm, 164.7±0.2 ppm, 135.9±0.2 ppm, 127.0 0.2 ppm, 117.0±0.2 ppm, 105.4±0.2 ppm, 95.5±0.2 ppm, 94.4±0.2 ppm, 68.9±0.2 ppm, 67.6±0.2 ppm, 64.1±0.2 ppm, 59.5±0.2 ppm, 54.5±0.2 ppm, 53.6±0.2 ppm, 32.7±0.2 ppm, 24.6±0.2 ppm, 20.2±0.2 ppm, 5.1±0.2 ppm, 3.6±0.2 ppm.

469. The Compound I sodium salt IPA solvate (dry) Form B according to any one of Embodiments 463-468, wherein Compound I sodium salt IPA solvate (dry) Form B is characterized by a $^{13}$C ssNMR spectrum with peaks at 180.3±0.2 ppm, 178.7±0.2 ppm, 164.7±0.2 ppm, 135.9±0.2 ppm, 127.0±0.2 ppm, 117.0±0.2 ppm, 105.4±0.2 ppm, 95.5±0.2 ppm, 94.4±0.2 ppm, 68.9±0.2 ppm, 67.6±0.2 ppm, 64.1±0.2 ppm, 59.5±0.2 ppm, 54.5±0.2 ppm, 53.6±0.2 ppm, 32.7±0.2 ppm, 24.6±0.2 ppm, 20.2±0.2 ppm, 5.1±0.2 ppm, 3.6±0.2 ppm.

470. The Compound I sodium salt IPA solvate (dry) Form B according to any one of Embodiments 463-467, wherein Compound I sodium salt IPA solvate (dry) Form B is characterized by a $^{13}$C ssNMR spectrum with peaks at 180.3±0.2 ppm, 178.7±0.2 ppm, 164.7±0.2 ppm, 135.9±0.2 ppm, 127.0±0.2 ppm, 117.0±0.2 ppm, 105.4±0.2 ppm, 95.5±0.2 ppm, 94.4±0.2 ppm, 67.6±0.2 ppm, 59.5±0.2 ppm, 53.6±0.2 ppm, 32.7±0.2 ppm, 27.2±0.2 ppm, 24.6±0.2 ppm, and 3.6±0.2 ppm.

471. The Compound I sodium salt IPA solvate (dry) Form B according to any one of Embodiments 463-470, characterized by a $^{13}$C solid state NMR spectrum substantially similar to FIG. 53.

472. The Compound I sodium salt IPA solvate (dry) Form B according to any one of Embodiments 463-471, prepared by a process comprising slurrying amorphous Compound I sodium salt hydrate Form A in IPA, then drying under vacuum at 40° C.

473. A method of preparing Compound I sodium salt IPA solvate (dry) Form B according to any one of Embodiments 463-471, comprising slurrying amorphous Compound I sodium salt hydrate Form A in IPA, then drying under vacuum at 40° C.

Methods of Preparing Compounds and Forms

General Experimental Procedures

The definitions of certain abbreviations for the Examples below are summarized below:

| Abbreviation | Chemical Name |
|---|---|
| ACN | acetonitrile |
| Boc$_2$O | di-tert-butyl dicarbonate; Boc anhydride |
| BuOH | butanol |
| CaCl$_2$ | calcium chloride |
| Ca(OCH$_3$)$_2$; Ca(OMe)$_2$ | calcium methoxide |
| CuI | copper iodide |
| DABCO | 1,4-diazabicyclo[2.2.2]octane |
| DCM | dichloromethane; methylene chloride |
| DMF | N,N-dimethylformamide |
| DMSO | dimethyl sulfoxide |
| EtOH | ethanol |
| H$_2$O | water |
| IPA | isopropanol |
| IPAc | isopropyl acetate |
| K$_2$CO$_3$ | potassium carbonate |
| KOH | potassium hydroxide |
| MeOH | methanol |
| MgCl$_2$ | magnesium chloride |
| NaOH | sodium hydroxide |
| Na(OCH$_3$) | sodium methoxide |
| NMP | N-methylpyrrolidone |
| NPA | N-propyl alcohol |
| Raney Ni | Raney Nickel |

Compounds II, III, III-d, and IV can be prepared by any suitable method in the art, for example, PCT Publication Nos. WO 2011/133751, WO 2011/133951, WO 2015/160787 and U.S. Pat. No. 8,865,902.

Solid State NMR experimental (applies to all crystalline forms): Bruker-Biospin 400 MHz wide-bore spectrometer equipped with Bruker-Biospin 4 mm HFX probe was used. Samples were packed into 4 mm rotors and spun under Magic Angle Spinning (MAS) condition with typical spinning speed of 12.5 kHz. The proton relaxation time was estimated from $^1$H MAS T$_1$ saturation recovery relaxation experiment and used to set up proper recycle delay of the $^{13}$C cross-polarization (CP) MAS experiment. The CP contact time of CPMAS experiments was set to 2 ms. A CP proton pulse with linear ramp (from 50% to 100%) was employed. All spectra were externally referenced by adjusting the magnetic field to set carbon resonance of adamantane to 29.5 ppm. TPPM15 proton decoupling sequence was used with the field strength of approximately 100 kHz.

Although certain crystalline forms of Compound I described in the examples are non-pharmaceutical, they are useful in the preparation of other forms. Thus, some embodiments of the invention provide crystalline Compound I calcium salt IPA solvate Form A (wet) or Form B (dry). In some embodiments, the crystalline Compound I is calcium salt NPA solvate Form A (wet) or Form B (dry). In some embodiments, the crystalline Compound I is calcium salt 2-BuOH solvate Form A (wet) or Form B (dry). In some embodiments, the crystalline Compound I is calcium salt acetone solvate Form A. In some embodiments, the crystalline Compound I is calcium salt DCM solvate Form A. In some embodiments, the crystalline Compound I is calcium salt ethylene glycol solvate Form A. In some embodiments, the crystalline Compound I is calcium salt ethylene glycol solvate Form B. In some embodiments, the crystalline Compound I is calcium salt 1,2-dimethoxyethane solvate Form A. In some embodiments, the crystalline Compound I is calcium salt 1,2-dimethoxyethane solvate Form B. In some embodiments, the crystalline Compound I is calcium salt CPME solvate Form A.

EXAMPLES

Example 1: Synthesis of (14S)-8-[3-(2-{dispiro [2.0.2.1]heptan-7-yl}ethoxy)-1H-pyrazol-1-yl]-12, 12-dimethyl-2λ6-thia-3,9,11,18,23-pentaazatetracyclo [17.3.1.1¹¹,¹⁴.0⁵,¹⁰]tetracosa-1(22),5,7,9,19 (23),20-hexaene-2,2,4-trione (Compound I)

Reagents and starting materials were obtained by commercial sources unless otherwise stated and were used without purification.

Proton and carbon NMR spectra (as applies to Example 1) were acquired on either of a Bruker Biospin DRX 400 MHz FTNMR spectrometer operating at a $^1$H and $^{13}$C resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters.

Part A: Synthesis of 2-Chloro-6-[3-(2-dispiro[2.0.2.1]heptan-7-ylethoxy)pyrazol-1-yl]pyridine-3-carboxylic acid

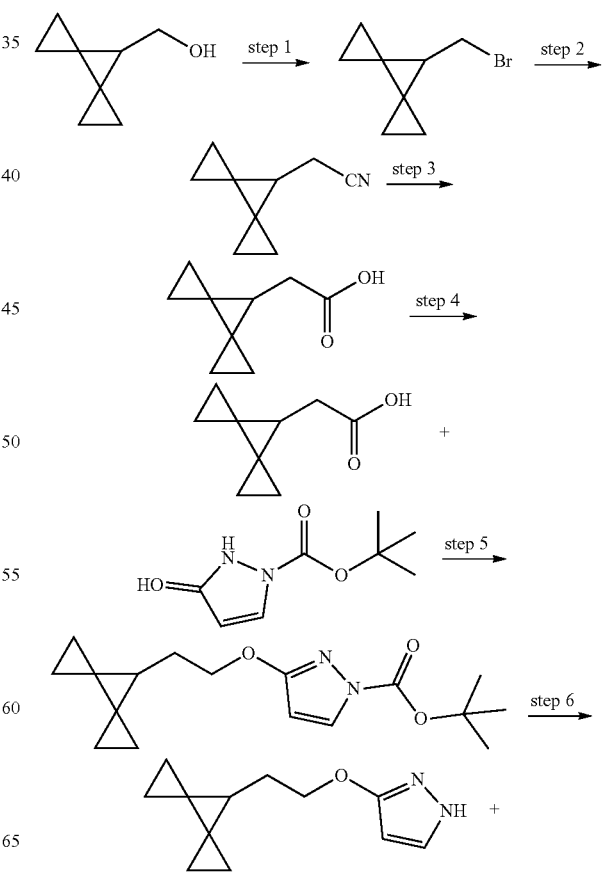

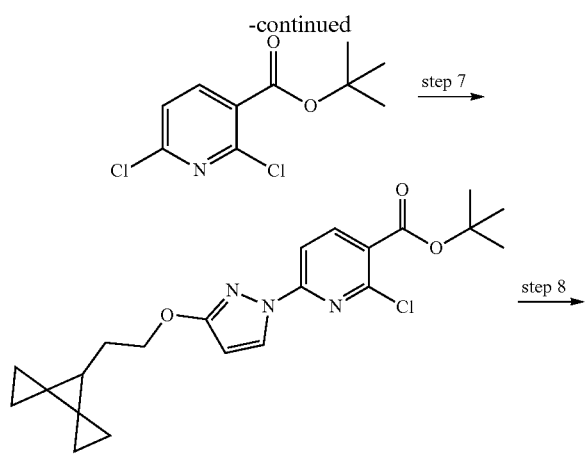

Step 1: 7-(Bromomethyl)dispiro[2.0.2.1]heptane

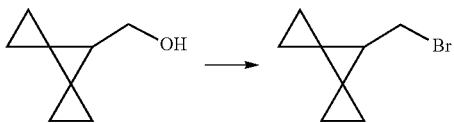 [SMILES: OCC1C2(CC2)C12CC2 ; BrCC1C2(CC2)C12CC2]

A 1000 mL, 3-neck round bottom flask was fitted with a mechanical stirrer, a cooling bath, an addition funnel, a J-Kem temperature probe and a nitrogen inlet/outlet. The vessel was charged under a nitrogen atmosphere with triphenylphosphine (102.7 mL, 443.2 mmol) and dichloromethane (1 L) which provided a clear colorless solution. Stirring was commenced and the cooling bath was charged with acetone. Dry ice was added in portions to the cooling bath until a pot temperature of −15° C. was obtained. The addition funnel was charged with a solution of bromine (22.82 mL, 443.0 mmol) in dichloromethane (220 mL, 10 mL/g) which was subsequently added dropwise over 1 h. Dry ice was added in portions to the cooling bath during the addition to maintain the pot temperature at −15° C. After the addition of bromine was completed, the pale yellow suspension was continued to stir at −15° C. for 15 min at which point the suspension was cooled to −30° C. The addition funnel was charged with a solution of dispiro[2.0.2.1]heptan-7-yl methanol (50 g, 402.6 mmol), pyridine (35.82 mL, 442.9 mmol) and dichloromethane (250 mL, 5 mL/g). The clear pale yellow solution was then added dropwise over 1.5 h maintaining the pot temperature at −30° C. The resulting clear light yellow reaction mixture was allowed to gradually warm to a pot temperature of −5° C. and then continued to stir at −5° C. for 1 h. The reaction mixture then was poured into hexane (2000 mL) which resulted in the formation of a precipitate. The suspension was stirred at room temperature for 30 min and then filtered through a glass frit Buchner funnel with a 20 mm layer of celite. The clear filtrate was concentrated under reduced pressure (water bath temperature at 20° C.) to provide a yellow oil with some precipitate present. The oil was diluted with some hexane, allowed to stand at room temperature for 15 min and then filtered through a glass frit Buchner funnel with a 20 mm layer of celite. The clear filtrate was concentrated under reduced pressure (water bath temperature at 20° C.) to provide 7-(bromomethyl)dispiro[2.0.2.1]heptane (70 g, 93%) as a clear yellow oil. $^1$H NMR (400 MHz, Chloroform-d) δ 3.49 (d, J=7.5 Hz, 2H), 1.90 (t, J=7.5 Hz, 1H), 1.06-0.84 (m, 4H), 0.71 (ddd, J=9.1, 5.1, 4.0 Hz, 2H), 0.54 (dddd, J=8.6, 4.8, 3.8, 1.0 Hz, 2H).

Step 2: 2-Dispiro[2.0.2.1]heptan-7-ylacetonitrile

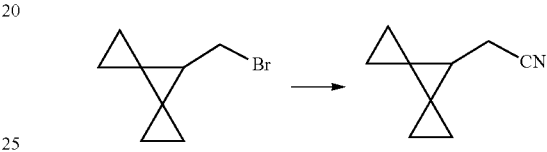

A 1000 mL, 3-neck round bottom flask was fitted with a mechanical stirrer, a cooling bath used as secondary containment, a J-Kem temperature probe and a nitrogen inlet/outlet. The vessel was charged under a nitrogen atmosphere with 7-(bromomethyl)dispiro[2.0.2.1]heptane (35 g, 187.1 mmol) and dimethyl sulfoxide (245 mL) which provided a clear amber solution. Stirring was commenced and the pot temperature was recorded at 19° C. The vessel was then charged with sodium cyanide (11.46 g, 233.8 mmol) added as a solid in one portion which resulted in a dark solution and a gradual exotherm to 49° C. over 15 min. After a few min the pot temperature began to decrease and the mixture was continued to stir at room temperature overnight (about 15 h). The dark reaction mixture was quenched with ice cold saturated sodium carbonate solution (500 mL) and then transferred to a separatory funnel and partitioned with diethyl ether (500 mL). The organic was removed and the residual aqueous was extracted with diethyl ether (2×250 mL). The combined organics were washed with water (500 mL), dried over sodium sulfate (200 g) and then filtered through a glass frit Buchner funnel. The clear amber filtrate was concentrated under reduced pressure (water bath temperature 20° C.) to provide 2-dispiro[2.0.2.1]heptan-7-ylacetonitrile (21 g, 84%) as a clear dark amber oil. $^1$H NMR (400 MHz, Chloroform-d) δ 2.42 (d, J=6.6 Hz, 2H), 1.69 (t, J=6.6 Hz, 1H), 1.02-0.88 (m, 4H), 0.79-0.70 (m, 2H), 0.66-0.55 (m, 2H).

Step 3: 2-Dispiro[2.0.2.1]heptan-7-ylacetic acid

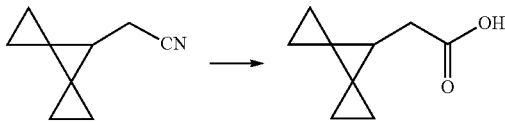 [SMILES: N#CCC1C2(CC2)C12CC2 ; O=C(O)CC1C2(CC2)C12CC2]

To a solution of 2-dispiro[2.0.2.1]heptan-7-ylacetonitrile (2.1 g, 14.19 mmol) in EtOH (32 mL) was added sodium hydroxide (5.12 g, 128.0 mmol) followed by water (13 mL)

and the resulting solution was stirred and heated to 70° C. overnight. The mixture was then cooled to room temperature, diluted with water and extracted with diethyl ether. The aqueous phase was adjusted to pH=1 by the addition of 6 N hydrochloric acid (resulting in a cloudy precipitate) and extracted with diethyl ether (3×). The organic phases were dried (magnesium sulfate), filtered and concentrated giving 2-dispiro[2.0.2.1]heptan-7-ylacetic acid (2.19 g, 99% yield, 98% purity) as an orange solid which was used in the next step without further purification. $^1$H NMR (400 MHz, Chloroform-d) δ 2.44 (d, J=6.9 Hz, 2H), 1.67 (t, J=6.9 Hz, 1H), 0.91 (ddd, J=9.0, 5.2, 3.9 Hz, 2H), 0.81 (dddd, J=8.9, 5.2, 3.9, 0.5 Hz, 2H), 0.69 (ddd, J=8.9, 5.2, 3.9 Hz, 2H), 0.56-0.44 (m, 2H).

Step 4: 2-Dispiro[2.0.2.1]heptan-7-ylethanol

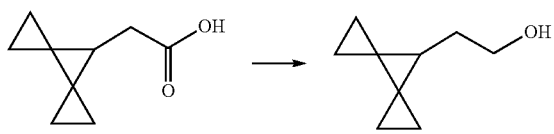

To lithium aluminum hydride (827.4 mg, 902.3 μL, 21.80 mmol) dissolved in tetrahydrofuran (33.71 mL) cooled in an ice/water bath was added 2-dispiro[2.0.2.1]heptan-7-ylacetic acid (2.552 g, 16.77 mmol) in tetrahydrofuran (7.470 mL) dropwise over 15 min keeping the reaction temperature <20° C. The mixture was allowed to stir a total of 18 h, gradually warming to ambient temperature. The mixture was cooled with an ice/water bath and sequentially quenched with slow addition of water (838.4 mg, 838.4 μL, 46.54 mmol), followed by sodium hydroxide (1.006 mL of 5 M, 5.031 mmol), then water (2.493 g, 2.493 mL, 138.4 mmol) affording a white, granular slurry which was filtered over celite. Washed the filtered solid with diethyl ether. The filtrate was concentrated in vacuo at ~300 mbar and 30° C. water bath. Diluted the residue with diethyl ether, dried (magnesium sulfate), filtered and concentrated in vacuo at ~300 mbar and 30° C. water bath followed by ~30 s under vacuum to give 2-dispiro[2.0.2.1]heptan-7-ylethanol (2.318 g, 100%) which was used directly in the ensuing step without further purification. $^1$H NMR (400 MHz, Chloroform-d) δ 3.64 (s, 2H), 1.68 (d, J=6.7 Hz, 2H), 1.39 (s, 1H), 1.31 (s, 1H), 0.82 (d, J=14.0 Hz, 4H), 0.65 (s, 2H), 0.50 (d, J=3.6 Hz, 2H).

Step 5: tert-Butyl 3-(2-dispiro[2.0.2.1]heptan-7-ylethoxy)pyrazole-1-carboxylate

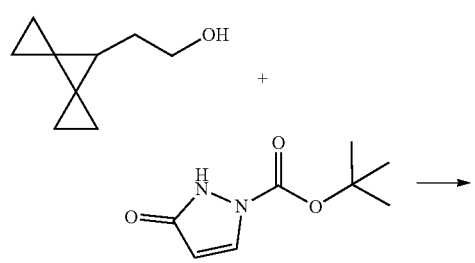

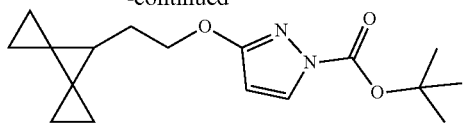

To a solution of tert-butyl 5-oxo-TH-pyrazole-2-carboxylate (2.942 g, 15.97 mmol) and 2-dispiro[2.0.2.1]heptan-7-ylethanol (2.318 g, 16.77 mmol) in tetrahydrofuran (36.78 mL) was added triphenylphosphine (4.399 g, 16.77 mmol). To the mixture was slowly added diisopropyl azodicarboxylate (3.391 g, 3.302 mL, 16.77 mmol) dropwise over 10 min (mild exotherm noted). The reaction mixture was stirred at room temperature for 30 min then at 50° C. for 30 min. The tetrahydrofuran was removed in vacuo. To the crude residue was added toluene (23.54 mL) and the mixture was stirred overnight as a precipitate gradually crystallized. Slurried with Celite then the precipitate was filtered off and washed with toluene (8.705 mL) and again with toluene (8.705 mL). The filtrate was concentrated in vacuo. The crude product was purified by silica gel chromatography using a shallow gradient from 100% hexanes to 100% ethyl acetate giving tert-butyl 3-(2-dispiro[2.0.2.1]heptan-7-ylethoxy)pyrazole-1-carboxylate (3.449 g, 71%). ESI-MS m/z calc. 304.17868, found 305.1 (M+1)$^+$; Retention time: 0.82 min (LC Method A).

Step 6: 3-(2-Dispiro[2.0.2.1]heptan-7-ylethoxy)-1H-pyrazole

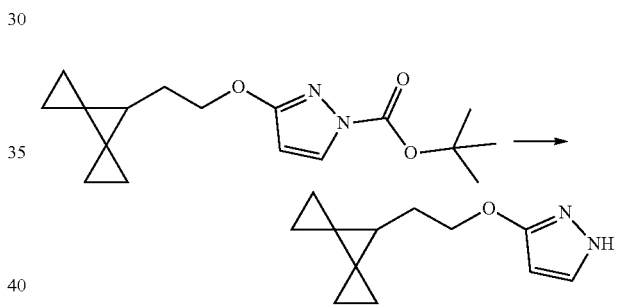

tert-Butyl 3-(2-dispiro[2.0.2.1]heptan-7-ylethoxy)pyrazole-1-carboxylate (5.304 g, 17.43 mmol) was dissolved in dichloromethane (53.04 mL) with trifluoroacetic acid (29.81 g, 20.14 mL, 261.4 mmol) and the reaction was stirred at room temperature for 120 min. The reaction was evaporated and the resulting oil was partitioned between ethyl acetate and a saturated sodium bicarbonate solution and the layers separated. The aqueous portion was extracted two additional times with ethyl acetate, then the organics were combined, washed with brine, dried over sodium sulfate, filtered and evaporated to give an oil, 3-(2-dispiro[2.0.2.1]heptan-7-ylethoxy)-1H-pyrazole (3.56 g, 100%). ESI-MS m/z calc. 204.12627, found 205.1 (M+1)$^+$; Retention time: 0.59 min (LC Method A).

Step 7: tert-Butyl 2-chloro-6-[3-(2-dispiro[2.0.2.1]heptan-7-ylethoxy)pyrazol-1-yl]pyridine-3-carboxylate

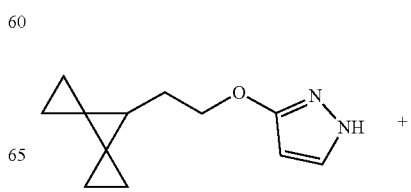

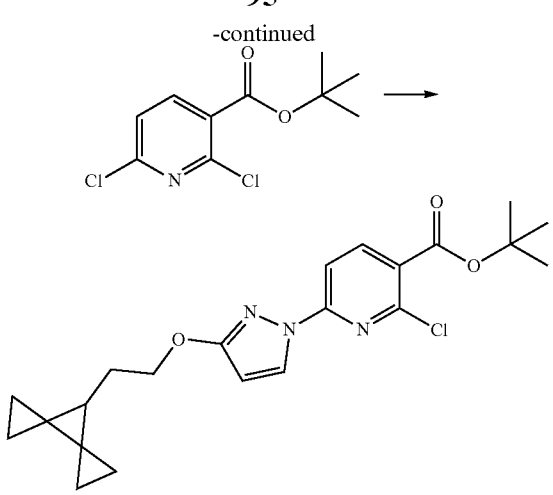

tert-Butyl 2,6-dichloropyridine-3-carboxylate (4.322 g, 17.42 mmol), 3-(2-dispiro[2.0.2.1]heptan-7-ylethoxy)-1H-pyrazole (3.559 g, 17.42 mmol) and potassium carbonate (2.891 g, 20.92 mmol) were combined in anhydrous dimethyl sulfoxide (71.18 mL). 1,4-Diazabicyclo[2.2.2]octane (391.1 mg, 3.487 mmol) was added and the mixture was stirred at room temperature under nitrogen for 16 h. The reaction mixture was diluted with water (136.9 mL) and stirred for 15 min. The resulting white solid was filtered and washed with water. The solid was dissolved in dichloromethane and dried over magnesium sulfate. The mixture was filtered and evaporated to give tert-butyl 2-chloro-6-[3-(2-dispiro[2.0.2.1]heptan-7-ylethoxy)pyrazol-1-yl]pyridine-3-carboxylate (5.69 g, 79%) as a white solid. $^1$H NMR (400 MHz, Chloroform-d) δ 8.35 (d, J=2.9 Hz, 1H), 8.18 (d, J=8.4 Hz, 1H), 7.69 (d, J=8.4 Hz, 1H), 5.94 (d, J=2.9 Hz, 1H), 4.25 (s, 2H), 1.90 (d, J=6.8 Hz, 2H), 1.62 (s, 9H), 1.49 (t, J=6.6 Hz, 1H), 0.85 (d, J=1.5 Hz, 4H), 0.65 (d, J=1.1 Hz, 2H). ESI-MS m/z calc. 415.16626, found 360.0 (M−tBu)+; Retention time: 2.09 min (LC Method B).

Step 8: 2-Chloro-6-[3-(2-dispiro[2.0.2.1]heptan-7-ylethoxy)pyrazol-1-yl]pyridine-3-carboxylic acid

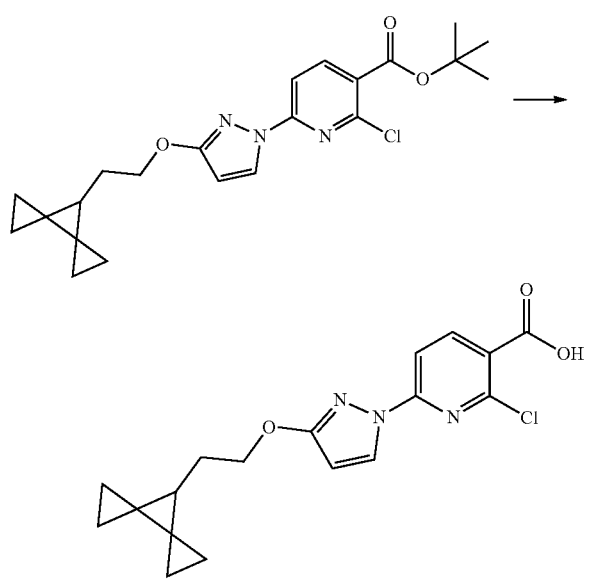

tert-Butyl 2-chloro-6-[3-(2-dispiro[2.0.2.1]heptan-7-ylethoxy)pyrazol-1-yl]pyridine-3-carboxylate (5.85 g, 14.07 mmol) was dissolved in dichloromethane (58.5 mL) with trifluoroacetic acid (16.26 mL, 211.1 mmol) and the reaction was stirred at room temperature for 16 h. The reaction was evaporated and to the resulting solid was added ether and then removed the ether under reduced pressure. This evaporation from ether was repeated twice more resulting in a white solid, 2-chloro-6-[3-(2-dispiro[2.0.2.1]heptan-7-ylethoxy)pyrazol-1-yl]pyridine-3-carboxylic acid (5.06 g, 100%). $^1$H NMR (400 MHz, Chloroform-d) δ 8.41 (d, J=8.5 Hz, 1H), 8.37 (d, J=2.9 Hz, 1H), 7.75 (d, J=8.5 Hz, 1H), 5.97 (d, J=2.9 Hz, 1H), 4.27 (s, 2H), 1.91 (d, J=6.7 Hz, 2H), 1.50 (s, 1H), 0.85 (d, J=1.5 Hz, 4H), 0.71-0.62 (m, 2H), 0.52 (d, J=1.1 Hz, 2H). ESI-MS m/z calc. 359.10367, found 360.2 (M+1)+; Retention time: 2.16 min (LC Method B).

Part B: Synthesis of tert-Butyl (4S)-2,2-dimethyl-4-[3-[(6-sulfamoyl-2-pyridyl)amino]propyl]pyrrolidine-1-carboxylate

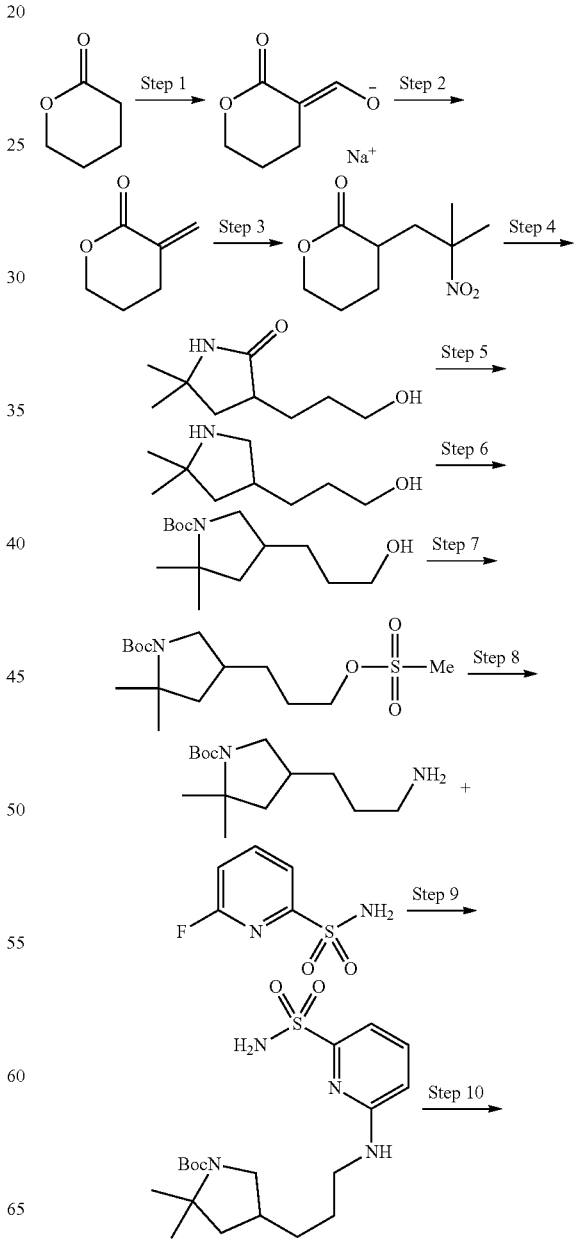

-continued

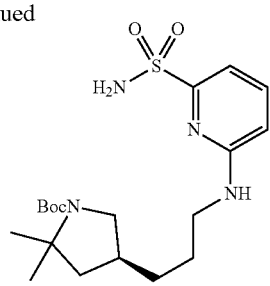

Step 1:
(E)-(2-Oxotetrahydropyran-3-ylidene)methanolate
(sodium salt)

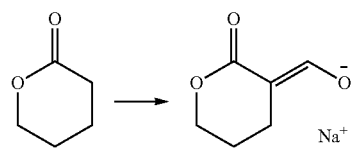 [SMILES: O=C1CCCCO1 ; O=C1OCCC/C1=C\[O-] ; [Na+]]

A 5 L, 3-neck round bottom flask was fitted with a mechanical stirrer, a heating mantle, an addition funnel, a J-Kem temperature probe/controller and a nitrogen inlet/outlet. The vessel was charged under a nitrogen atmosphere with sodium hydride (59.91 g of 60% w/w, 1.498 mol) followed by heptane (1.5 L) which provided a grey suspension. Stirring was commenced and the pot temperature was recorded at 19° C. The vessel was then charged with ethyl alcohol (3.451 g, 74.91 mmol) added via syringe which resulted in gas evolution. The addition funnel was charged with a clear pale yellow solution of tetrahydropyran-2-one (150 g, 1.498 mol) and ethyl formate (111 g, 1.50 mol). The solution was added dropwise over 1 h which resulted in gas evolution and a gradual exotherm to 45° C. The resulting thick white suspension was then heated to 65° C. for 2 h and then allowed to cool to room temperature. The mixture was continued to stir at room temperature overnight (about 10 h). The reaction mixture was vacuum filtered through a glass frit Buchner funnel (medium porosity) under a stream of nitrogen. The filter cake was displacement washed with heptane (2×250 mL) and pulled for a few min. The slightly heptane wet cake was transferred to a glass tray and dried in a vacuum oven at 45° C. for 15 h to provide a white solid (205 g, 1.36 mol, 91% yield) as the desired product, (E)-(2-oxotetrahydropyran-3-ylidene)methanolate (sodium salt).

Step 2: 3-Methylenetetrahydropyran-2-one

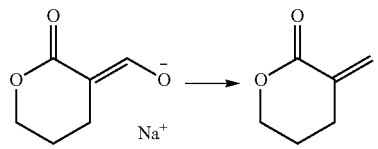

A 5 L, 3-neck round bottom flask was fitted with a mechanical stirrer, a heating mantle, an addition funnel, a J-Kem temperature probe/controller and a nitrogen inlet/outlet. The vessel was charged under a nitrogen atmosphere with (E)-(2-oxotetrahydropyran-3-ylidene)methanolate (sodium salt) (205 g, 1.366 mol) (205 g, 1.366 mol) and tetrahydrofuran (1640 mL) which provided a white suspension. Stirring was commenced and the pot temperature was recorded at 19° C. The vessel was then charged with paraformaldehyde (136.6 g, 4.549 mol) added as a solid in one portion. The resulting suspension was heated to 63° C. and the condition was maintained for 15 h. Upon heating the reaction mixture became slightly gelatinous. The white gelatinous mixture was concentrated under reduced pressure to remove most of the tetrahydrofuran. The remaining residue was partitioned with ethyl acetate (1000 mL), saturated sodium chloride (500 mL) and saturated sodium hydrogen carbonate (500 mL) in a separatory funnel. The organic was removed and the residual aqueous was extracted with ethyl acetate (5×300 mL). The combined organic was dried over sodium sulfate (500 g) and then vacuum filtered through a glass frit Buchner funnel with a 20 mm layer of celite. The filter cake was displacement washed with ethyl acetate (250 mL). The clear filtrate was concentrated under reduced pressure to provide a clear pale yellow oil (135 g) as the desired crude product. The material was purified by silica gel column flash chromatography (liquid load) eluting with a gradient of 100% hexane to 60% ethyl acetate in hexane over 1 h collecting 450 mL fractions. The product was detected by TLC analysis on silica gel eluting with 3:1 hexanes/ethyl acetate and visualized under UV. The product fractions were combined and concentrated under reduced pressure to provide a clear, colorless oil (132 g, 1.18 mol, 72% yield containing 16 wt % residual ethyl acetate by NMR) as the desired product, 3-methylenetetrahydropyran-2-one. 1H NMR (400 MHz, dimethyl sulfoxide-$d_6$) δ6.18 (q, J=1.9 Hz, 1H), 5.60 (q, J=1.9 Hz, 1H), 4.40-4.26 (m, 2H), 2.61 (ddt, J=7.0, 6.3, 2.0 Hz, 2H), 1.90-1.75 (m, 2H).

Step 3:
3-(2-Methyl-2-nitro-propyl)tetrahydropyran-2-one

A 5000 mL, 3-neck round bottom flask was fitted with a mechanical stirrer, a cooling bath used as secondary containment, a J-Kem temperature probe, an addition funnel and a nitrogen inlet/outlet. The vessel was charged under a nitrogen atmosphere with 2-nitropropane (104.9 g, 1.177 mol). Stirring was commenced and the pot temperature was recorded at 19° C. The vessel was then charged with 1,8-diazabicyclo[5.4.0]undec-7-ene (22.41 g, 147.2 mmol) added neat in one portion which resulted in a clear light yellow solution. No exotherm was observed. The addition funnel was charged with a solution of 3-methylenetetrahydropyran-2-one (110 g, 981.0 mmol) in acetonitrile (1100 mL) which was added dropwise over 1 h which resulted in a clear light yellow solution and a gradual exotherm to 24° C. The reaction mixture was continued to stir at room temperature for 3.5 h and then concentrated under reduced pressure. The remaining residue was dissolved in dichloromethane (1000 mL) and partitioned with 500 mL of a 3:2 mixture of 1 molar citric acid solution/saturated sodium chloride solution. The resulting organic phase was a clear pale blue solution and the aqueous phase was a slightly cloudy very pale blue solution. The organic was removed and the residual aqueous was extracted with dichloromethane (300 mL). The combined organic was washed with saturated sodium chloride solution (300 mL), dried over sodium sulfate (250 g) and then filtered through a glass frit Buchner funnel. The filtrate was concentrated under reduced pressure to a volume of about 200 mL. The clear pale blue dichloromethane solution was diluted with methyl tert-butyl ether (1500 mL) and the cloudy solution was concentrated under reduced pressure to a volume of about 200 mL which provided a suspension. The mixture was again diluted with methyl tert-butyl ether (1500 mL) and concentrated under reduced pressure to a volume of about 250 mL. The resulting suspension was allowed to stand at room temperature overnight (about 12 h). The solid was collected by vacuum filtration in a glass frit Buchner funnel and the filter cake was displacement washed with cold methyl tert-butyl ether (2×150 mL) and then pulled for 30 min. The material was further dried in a vacuum oven at 45° C. for 5 h to provide (160 g, 0.795 mol, 81% yield) of a white solid as the desired product, 3-(2-methyl-2-nitro-propyl)tetrahydropyran-2-one. $^1$H NMR (400 MHz, dimethyl sulfoxide-$d_6$) δ 4.34 (ddd, J=11.1, 9.3, 4.3 Hz, 1H), 4.20 (dt, J=11.1, 5.1 Hz, 1H), 2.75-2.62 (m, 1H), 2.56 (dd, J=14.9, 5.2 Hz, 1H), 2.01-1.89 (m, 2H), 1.89-1.67 (m, 2H), 1.55 (d, J=6.0 Hz, 6H), 1.44 (dddd, J=12.8, 11.5, 8.1, 6.6 Hz, 1H).

Step 4:
3-(3-Hydroxypropyl)-5,5-dimethyl-pyrrolidin-2-one

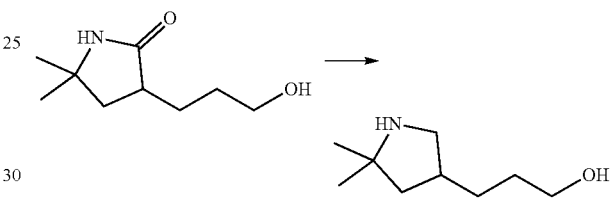

A 1000 mL, 3-neck round bottom flask was fitted with a Teflon stir bar, a heating mantle, a J-Kem temperature probe/controller and rubber septums. The vessel was charged with 3-(2-methyl-2-nitro-propyl)tetrahydropyran-2-one (25 g, 124.2 mmol) and ethyl alcohol (375 mL) which provided a white suspension. Stirring was commenced and the suspension was heated to 40° C. for 10 min which provided a clear colorless solution. The vessel was then fitted with a gas dispersion tube and the solution was degased with nitrogen for 15 min. The vessel was then charged with Raney Nickel (8.019 g of 50% w/w, 68.31 mmol) and the vessel was then fitted with the septums. The vessel was evacuated and placed under a hydrogen atmosphere. The process was repeated for three cycles. The vessel was then placed under 1 atmosphere hydrogen and the reaction mixture was gradually heated to 60° C. The reaction was continued to stir at 60° C. for 24 h. After cooling to room temperature, the vessel was fitted with a gas dispersion tube and the reaction mixture was degased with nitrogen for 15 min. The mixture was vacuum filtered through a glass frit Buchner funnel with a 20 mm layer of celite. The filter cake was displacement washed with ethanol (2×100 mL) and pulled until slightly ethyl alcohol wet, then wetted with water and the used Raney nickel catalyst was discarded under water. The clear pale amber filtrate was concentrated under reduced pressure to a clear viscous light amber oil. The oil was diluted with methyl tert-butyl ether (1500 mL) and the cloudy solution was concentrated under reduced pressure to a volume of about 150 mL which provided a suspension. The mixture was again diluted with methyl tert-butyl ether (1500 mL) and concentrated under reduced pressure to a volume of about 150 mL. The resulting suspension was allowed to stand at room temperature overnight (about 12 h). The solid was collected by vacuum filtration in a glass frit Buchner funnel and the filter cake was displacement washed with cold methyl tert-butyl ether (2×50 mL) and then pulled for 30 min. The material was further dried in a vacuum oven at 45° C. for 3 h to provide a white solid (19 g, 0.111 mol, 89% yield) as the product, 3-(3-hydroxypropyl)-5,5-dimethyl-pyrrolidin-2-one. $^1$H NMR (400 MHz, dimethyl sulfoxide-$d_6$) δ 7.63 (s, 1H), 3.38 (t, J=6.5 Hz, 2H), 2.37 (tdd, J=9.8, 8.5, 4.4 Hz, 1H), 2.02 (dd, J=12.3, 8.6 Hz, 1H), 1.72 (tdd, J=9.6, 7.5, 4.4 Hz, 1H), 1.52-1.32 (m, 3H), 1.28-1.03 (m, 7H).

Step 5: 3-(5,5-Dimethylpyrrolidin-3-yl)propan-1-ol

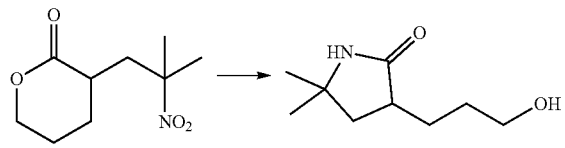

A 5 L, 3-neck round bottom flask was fitted with a mechanical stirrer, a heating mantle, an addition funnel, a J-Kem temperature probe/controller and a nitrogen inlet/outlet. The vessel was charged under a nitrogen atmosphere with lithium aluminum hydride pellets (19.39 g, 510.9 mmol). The vessel was then charged with tetrahydrofuran (500 mL, 20 mL/g). Stirring was commenced and the pot temperature was recorded at 20° C. The mixture was allowed to stir at room temperature for 0.5 h to allow the pellets to dissolve. The pot temperature of the resulting grey suspension was recorded at 24° C. The addition funnel was charged with a solution of 3-(3-hydroxypropyl)-5,5-dimethyl-pyrrolidin-2-one (25 g, 146.0 mmol) in tetrahydrofuran (500 mL) and the clear pale yellow solution was added dropwise over 90 min. Slight heating was required to achieve homogeneity. After the completed addition the pot temperature of the resulting greyish suspension was recorded at 24° C. The mixture was then heated to a pot temperature of 65° C. and the condition was maintained for 72 h. Analysis of the reaction mixture at this point indicated some residual starting material still remaining and no change in product formation. The reaction was subsequently stopped at this point. The heating mantle was removed and the vessel was fitted with a cooling bath. The suspension was cooled to 0° C. with a crushed ice/water cooling bath and then quenched by the very slow dropwise addition of water (19.93 mL), followed by 15 wt % sodium hydroxide solution (19.93 mL) and then finally with water (59.79 mL). The pot temperature of the resulting white suspension was recorded at 5° C. The cooling bath was removed and the vessel was again fitted with a heating mantle. The suspension was warmed to 60° C. and the condition was maintained for 30 min. The warm suspension was vacuum filtered through a glass frit Buchner funnel with a 20 mm layer of celite. The filter cake was then displacement washed with 60° C.

tetrahydrofuran (2×250 mL) and then pulled for 30 min. The clear filtrate was concentrated under reduced pressure to provide (23.5 g, 0.149 mol, 99% yield) of a clear light yellow viscous oil as the desired product, 3-(5,5-dimethylpyrrolidin-3-yl)propan-1-ol. $^1$H NMR (400 MHz, dimethyl sulfoxide-d$_6$) δ 3.37 (dt, J=8.3, 6.4 Hz, 3H), 2.95 (dd, J=10.6, 7.6 Hz, 1H), 2.40 (dd, J=10.7, 7.7 Hz, 1H), 2.04 (dt, J=16.1, 8.1 Hz, 1H), 1.69 (dd, J=12.2, 8.2 Hz, 1H), 1.50-1.24 (m, 5H), 1.11-0.94 (m, 7H).

Step 6: tert-Butyl 4-(3-hydroxypropyl)-2,2-dimethyl-pyrrolidine-1-carboxylate

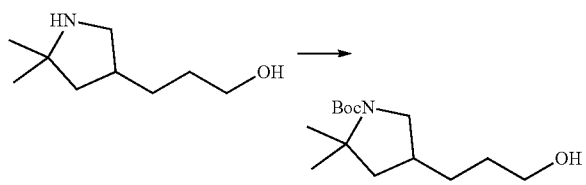

A 1 L, 3-neck round bottom flask was fitted with a mechanical stirrer, a cooling bath, an addition funnel, a J-Kem temperature probe and a nitrogen inlet/outlet. The vessel was charged under a nitrogen atmosphere with 3-(5,5-dimethylpyrrolidin-3-yl)propan-1-ol (15 g, 95.39 mmol) and dichloromethane (225 mL, 15 mL/g) which provided a clear light yellow solution. Stirring was commenced and the pot temperature was recorded at 19° C. The cooling bath was charged with crushed ice/water and the pot temperature was lowered to 0° C. The addition funnel was charged with triethylamine (12.55 g, 124.0 mmol) which was subsequently added neat dropwise over 5 min. No exotherm was observed. The addition funnel was then charged with di-tert-butyl dicarbonate (22.89 g, 104.9 mmol) dissolved in dichloromethane (225 mL). The clear pale yellow solution was then added dropwise over 30 min which resulted in gentle gas evolution. No exotherm was observed. The cooling bath was removed and the resulting clear light yellow solution was allowed to warm to room temperature and continue to stir at room temperature for 3 h. The reaction mixture was transferred to a separatory funnel and partitioned with water (75 mL). The organic was removed and washed with saturated sodium chloride solution (75 mL), dried over sodium sulfate (150 g) and then filtered through a glass frit Buchner funnel. The filtrate was concentrated under reduced pressure to provide (30 g) of a clear light yellow oil as the desired crude product. The material was purified by silica gel column flash chromatography (liquid load with dichloromethane) eluting with a gradient of 100% dichloromethane to 10% methyl alcohol in dichloromethane over 60 min collecting 50 mL fractions. The desired product fractions were combined and concentrated under reduced pressure to provide tert-butyl 4-(3-hydroxypropyl)-2,2-dimethyl-pyrrolidine-1-carboxylate (22 g, 0.0855 mol, 90% yield) as a clear pale yellow viscous oil. $^1$H NMR (400 MHz, DMSO-d$_6$) δ 4.38 (td, J=5.2, 1.4 Hz, 1H), 3.54 (dt, J=10.3, 6.7 Hz, 1H), 3.38 (td, J=6.6, 3.5 Hz, 2H), 2.76 (q, J=10.3 Hz, 1H), 2.07 (td, J=11.6, 5.7 Hz, 1H), 1.87 (ddd, J=16.7, 12.1, 6.0 Hz, 1H), 1.37 (dd, J=14.2, 10.4 Hz, 17H), 1.24 (s, 3H).

Step 7: tert-Butyl 2,2-dimethyl-4-(3-methylsulfonyl oxypropyl)pyrrolidine-1-carboxylate

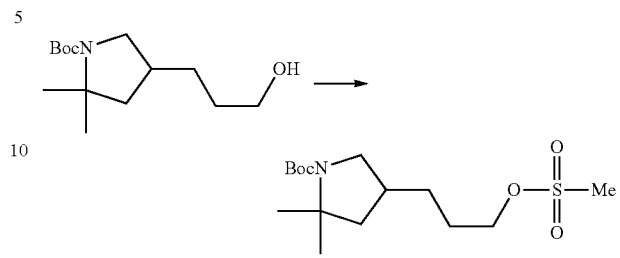

tert-Butyl 4-(3-hydroxypropyl)-2,2-dimethyl-pyrrolidine-1-carboxylate (50.5 g, 196.22 mmol) and triethylamine (39.711 g, 54.698 mL, 392.44 mmol) were dissolved in dichloromethane (500 mL) and the resulting solution was chilled in an ice water bath for 30 min. Mesyl chloride (24.725 g, 16.706 mL, 215.84 mmol) was added dropwise over a 30 min period, then the ice bath was removed and the mixture stirred at room temperature for one h. The reaction was then quenched with saturated sodium bicarbonate solution (200 mL). The phases were separated and the organic phase was extracted with saturated sodium bicarbonate (200 mL) and water (2×100 mL). The aqueous phases were discarded and the organic phase was dried over sodium sulfate, filtered and concentrated in vacuo to obtain tert-butyl 2,2-dimethyl-4-(3-methylsulfonyl oxypropyl)pyrrolidine-1-carboxylate (64.2 g, 93%) as a pale yellow oil. ESI-MS m/z calc. 335.1766, found 336.4 (M+1)$^+$; Retention time: 5.54 min (LC Method Q).

Step 8: tert-Butyl 4-(3-aminopropyl)-2,2-dimethyl-pyrrolidine-1-carboxylate

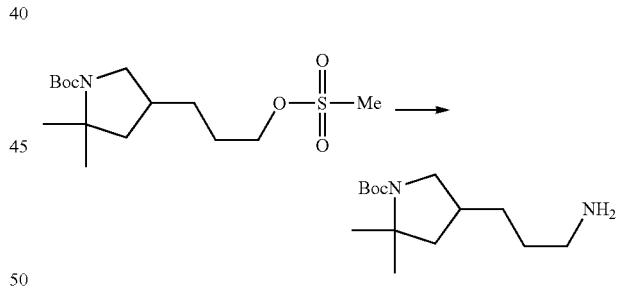

tert-Butyl 2,2-dimethyl-4-(3-methylsulfonyloxypropyl)pyrrolidine-1-carboxylate (64.2 g, 191.38 mmol) was dissolved in dioxane (650 mL) and then ammonium hydroxide (650 mL) was added and the resulting mixture heated to 45° C. for 18 h. After 18 h, the reaction was cooled to room temperature. The solution was diluted with 1M sodium hydroxide (200 mL) and then extracted with diethyl ether (3×650 mL). The aqueous phase was discarded and the combined organic phases were extracted with water (2×200 mL). The aqueous phases were discarded and the organic phase was dried over sodium sulfate, filtered and concentrated in vacuo to afford tert-butyl 4-(3-aminopropyl)-2,2-dimethyl-pyrrolidine-1-carboxylate (48.9 g, 95%) as a pale yellow oil. ESI-MS m/z calc. 256.2151, found 257.3 (M+1)$^+$; Retention time: 3.70 min (LC Method Q).

Step 9: tert-Butyl 2,2-dimethyl-4-[3-[(6-sulfamoyl-2-pyridyl)amino]propyl]pyrrolidine-1-carboxylate

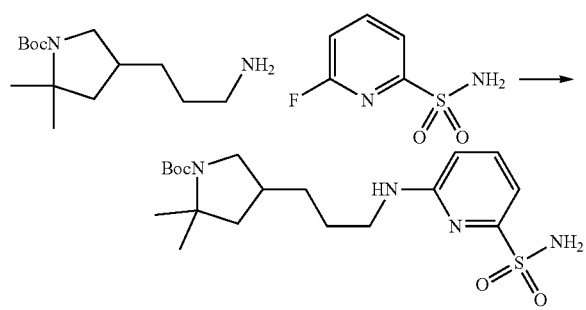

To tert-butyl 4-(3-aminopropyl)-2,2-dimethyl-pyrrolidine-1-carboxylate (8.91 g, 34.8 mmol) and 6-fluoropyridine-2-sulfonamide (6.13 g, 34.8 mmol) in dimethyl sulfoxide (75 mL) was added potassium carbonate (4.91 g, 35.5 mmol) and the mixture stirred at 100° C. for 12 h and then allowed to cool to ambient temperature and stirred for an additional 4 h (16 h total). The reaction mixture was slowly poured into hydrochloric acid (35 mL of 1 M, 35.00 mmol) in water (200 mL) (some foaming) and diluted with ethyl acetate (250 mL). The organic phase was separated and washed with 100 mL of brine. The organic phase was dried over magnesium sulfate, filtered over celite, and concentrated in vacuo to afford a dark yellow oil. The crude product was purified by silica gel chromatography eluting with 0%-100% ethyl acetate in hexanes. Collected both pure (9.0 g) and impure (3 g) fractions. Purified the impure fractions by silica gel chromatography eluting with 0%-100% ethyl acetate in hexanes affording, in total, tert-butyl 2,2-dimethyl-4-[3-[(6-sulfamoyl-2-pyridyl)amino]propyl]pyrrolidine-1-carboxylate (10.0 g, 69%). $^1$H NMR (400 MHz, dimethyl sulfoxide-$d_6$) δ 7.52 (dd, J=8.5, 7.2 Hz, 1H), 7.07 (s, 2H), 6.95 (dd, J=7.2, 0.7 Hz, 2H), 6.61 (d, J=8.5 Hz, 1H), 3.55 (q, J=9.1 Hz, 1H), 3.32-3.24 (m, 2H), 2.79 (q, J=10.0 Hz, 1H), 2.13 (d, J=16.1 Hz, 1H), 1.96-1.82 (m, 1H), 1.51 (dt, J=18.0, 9.3 Hz, 2H), 1.37 (dd, J=12.9, 10.6 Hz, 15H), 1.24 (s, 3H). ESI-MS m/z calc. 412.21442, found 413.1 (M+1)$^+$; Retention time: 2.34 min (LC Method D).

Step 10: tert-Butyl (4S)-2,2-dimethyl-4-[3-[(6-sulfamoyl-2-pyridyl)amino]propyl]pyrrolidine-1-carboxylate

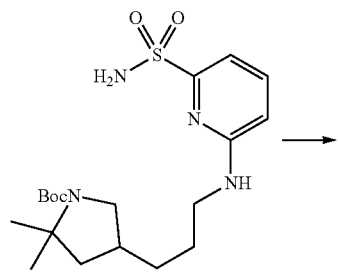

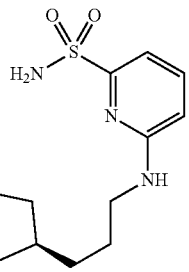

Subjected racemic tert-butyl 2,2-dimethyl-4-[3-[(6-sulfamoyl-2-pyridyl)amino]propyl]pyrrolidine-1-carboxylate (7 g, 16.97 mmol) to chiral separation by SFC chromatography using a ChiralPak IG (250×21.2 mm column, 5 μm particle size) with 40% methanol/60% carbon dioxide mobile phase at 70 mL/min over 11.0 min (injection volume=500 μL of 32 mg/mL solution in methanol) giving as the first peak to elute, tert-butyl (4S)-2,2-dimethyl-4-[3-[(6-sulfamoyl-2-pyridyl)amino]propyl]pyrrolidine-1-carboxylate (3.4481 g, 99%). ESI-MS m/z calc. 412.21442, found 413.2 (M+1)$^+$; Retention time: 0.63 min (LC Method A).

Part C: Synthesis of (14S)-8-[3-(2-{dispiro[2.0.2.1]heptan-7-yl}ethoxy)-1H-pyrazol-1-yl]-12,12-dimethyl-2λ6-thia-3,9,11,18,23-pentaazatetracyclo [17.3.1.1 11,14.0 5,10]tetracosa-1(22),5,7,9,19(23),20-hexaene-2,2,4-trione (Compound I)

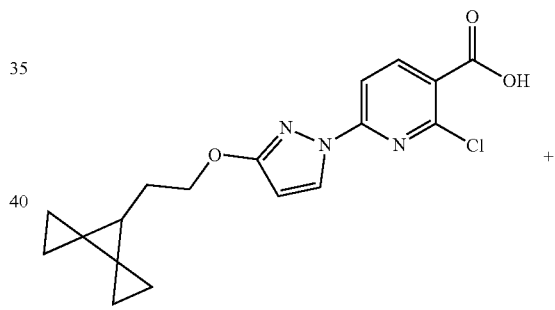

+

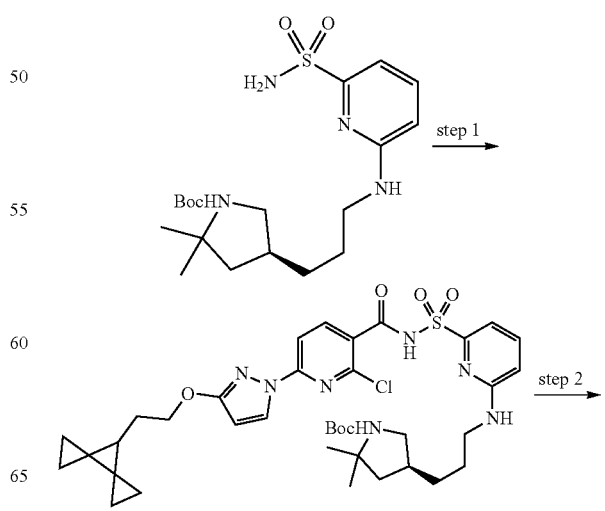

-continued

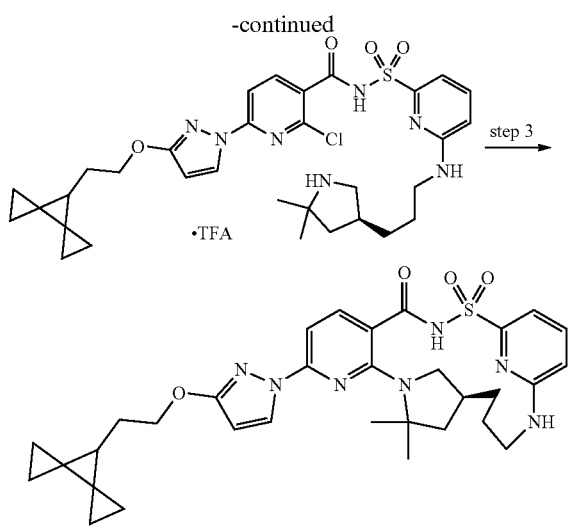

Step 1: tert-Butyl (4S)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate

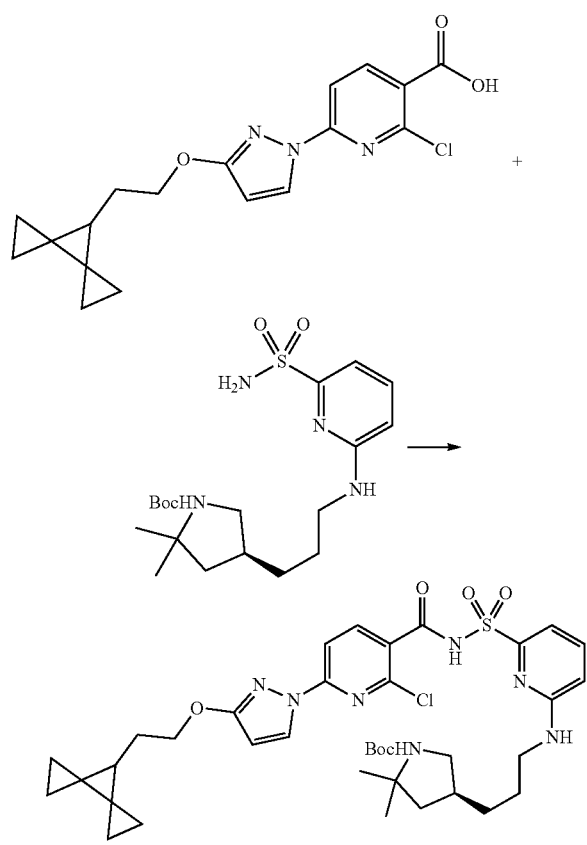

To a solution of 2-chloro-6-[3-(2-dispiro[2.0.2.1]heptan-7-ylethoxy)pyrazol-1-yl]pyridine-3-carboxylic acid (5.2 g, 14.45 mmol) in tetrahydrofuran (100 mL) was added carbonyl diimidazole (2.8 g, 16.51 mmol) and the mixture stirred at ambient temperature for 1 h. To this mixture was added tert-butyl (4S)-2,2-dimethyl-4-[3-[(6-sulfamoyl-2-pyridyl)amino]propyl]pyrrolidine-1-carboxylate (6.0 g, 14.54 mmol) in tetrahydrofuran (15 mL) followed by 1,8-diazabicyclo[5.4.0]undec-7-ene (6.5 mL, 43.47 mmol) and the mixture was stirred at ambient temperature for 16 h. The reaction was diluted with water (150 mL) and the mixture acidified with aqueous hydrochloric acid (15 mL of 6 M, 90.00 mmol). The mixture was extracted with ethyl acetate (300 mL) and the organic phase separated. The organic phase was washed with brine, dried over magnesium sulfate, filtered over Celite and concentrated in vacuo affording a white precipitate. The precipitate was slurried with acetonitrile and the solid collected by filtration using a medium glass frit and washed with acetonitrile. The filtrate was concentrated in vacuo affording a yellow oil. The crude oil was diluted with acetonitrile and some N-methyl-2-pyrrolidone and chromatographed on a 415 g reverse phase $C_{18}$ column eluting with 50%-100% acetonitrile in water giving tert-butyl (4S)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate (4.5 g, 41%). ESI-MS m/z calc. 753.30756, found 754.4 (M+1)⁺; Retention time: 3.79 min (LC Method D).

Step 2: 2-Chloro-N-[[6-[3-[(3S)-5,5-dimethylpyrrolidin-3-yl]propylamino]-2-pyridyl]sulfonyl]-6-[3-(2-dispiro[2.0.2.1]heptan-7-ylethoxy)pyrazol-1-yl]pyridine-3-carboxamide (trifluoroacetate salt)

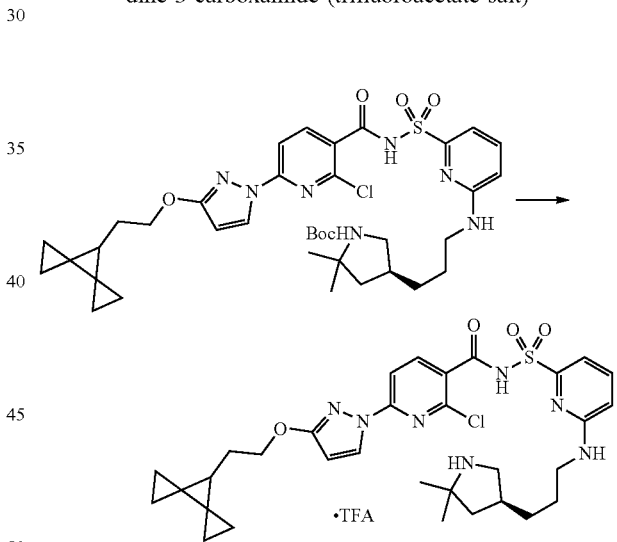

To a solution of tert-butyl (4S)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate (5.9 g, 7.821 mmol) in dichloromethane (30 mL) and toluene (15 mL) was added trifluoroacetic acid (6.0 mL, 77.88 mmol) and the mixture stirred at ambient temperature for 18 h. The solvent was removed in vacuo with the bath temp set at 45° C. affording a thick, yellow oil. The oil was diluted with toluene (125 mL) and the solvent removed in vacuo with the bath temp set at 45° C. The oil was diluted with toluene and the solvent removed in vacuo affording a thick, viscous yellow oil, 2-chloro-N-[[6-[3-[(3S)-5,5-dimethylpyrrolidin-3-yl]propylamino]-2-pyridyl]sulfonyl]-6-[3-(2-dispiro[2.0.2.1]heptan-7-ylethoxy)pyrazol-1-yl]pyridine-3-carboxamide (trifluoroacetate salt) (6.0 g, 100%) which was used in the next step without further purification. ESI-MS m/z calc. 653.2551, found 654.3 (M+1)+; Retention time: 2.6 min (LC Method B).

Step 3: (14S)-8-[3-(2-{Dispiro[2.0.2.1]heptan-7-yl}ethoxy)-1H-pyrazol-1-yl]-12,12-dimethyl-2λ6-thia-3,9,11,18,23-pentaazatetracyclo [17.3.1.111, 14.05,10]tetracosa-1(22),5,7,9,19(23),20-hexaene-2, 2,4-trione (Compound I)

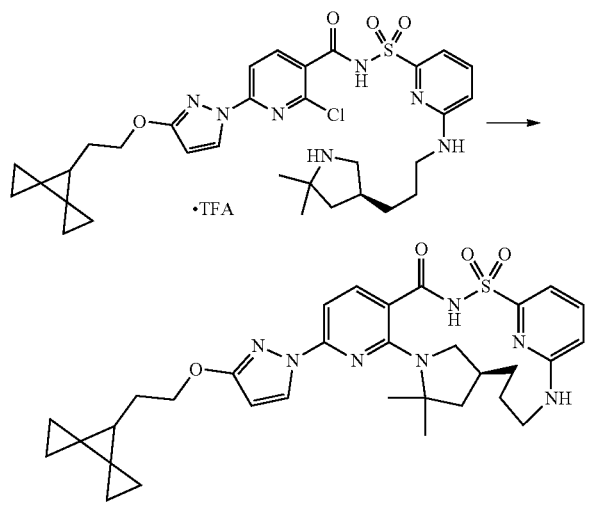

To a solution of 2-chloro-N-[[6-[3-[(3S)-5,5-dimethylpyrrolidin-3-yl]propylamino]-2-pyridyl]sulfonyl]-6-[3-(2-dispiro[2.0.2.1]heptan-7-ylethoxy)pyrazol-1-yl]pyridine-3-carboxamide (trifluoroacetate salt) (6.0 g, 7.810 mmol) in NMP (140 mL) was added potassium carbonate (5.3 g, 38.35 mmol). The mixture was purged with nitrogen for 5 min. The mixture was then heated at 150° C. for 22 h. The reaction mixture was cooled to room temperature and added to water (300 mL) affording an off-white solid precipitate. The mixture was carefully acidified with aqueous hydrochloric acid (12 mL of 6 M, 72.00 mmol) affording a foamy slurry. The solid was collected by filtration using a medium glass frit. The wet filter cake was dissolved in ethyl acetate (500 mL) and washed with 200 mL of brine. The aqueous phase was slightly cloudy so it was acidified with a small amount of 6N hydrochloric acid and returned to the organic phase. The aqueous phase was separated and the organic phase was dried over magnesium sulfate, filtered and concentrated in vacuo affording a light yellow oil. This crude product was diluted with acetonitrile and chromatographed on a 415 g Cis reverse phase column eluting with 50%-100% acetonitrile in water. The product was isolated as a cream colored foam. The foam was dried in vacuo at 45° C. for 48 h giving (14S)-8-[3-(2-{dispiro[2.0.2.1]heptan-7-yl}ethoxy)-1H-pyrazol-1-yl]-12,12-dimethyl-2λ6-thia-3,9,11,18,23-pentaazatetracyclo[17.3.1.111,14.05,10]tetracosa-1(22),5,7,9, 19(23),20-hexaene-2,2,4-trione (Compound I) (3.32 g, 68%). 1H NMR (400 MHz, dimethyl sulfoxide-d6) δ 12.48 (s, 1H), 8.20 (d, J=2.8 Hz, 1H), 7.81 (d, J=8.2 Hz, 1H), 7.57 (dd, J=8.5, 7.2 Hz, 1H), 7.05 (d, J=7.1 Hz, 1H), 6.97 (d, J=8.5 Hz, 1H), 6.91 (d, J=8.2 Hz, 1H), 6.71 (d, J=8.5 Hz, 1H), 6.08 (d, J=2.7 Hz, 1H), 4.21 (td, J=6.7, 1.3 Hz, 2H), 3.92 (d, J=12.0 Hz, 1H), 3.16 (s, 1H), 2.95 (d, J=13.3 Hz, 1H), 2.78-2.66 (m, 1H), 2.07 (s, 1H), 1.92-1.72 (m, 4H), 1.60 (s, 6H), 1.51 (s, 3H), 1.47 (t, J=6.5 Hz, 1H), 1.31 (q, J=12.2 Hz, 1H), 0.89-0.77 (m, 4H), 0.69-0.61 (m, 2H), 0.53-0.45 (m, 2H). ESI-MS m/z calc. 617.27844, found 618.4 (M+1)+; Retention time: 10.29 min (LC Method F).

Ca2+, Na+, and K+ salts of Compound I were made by mixing Compound I with Ca(OCH3)2, Na(OCH3), and KOH, respectively: mixing Compound I (1 g) and Ca(OCH3)2 (83 mg) in methanol (65 mL) at room temperature for 30 min and then at 65° C. for 30 min; mixing Compound I (0.6 g (1 mmol)) in MeOH (40 mL) with 25 wt % Na(OCH3) in MeOH (250 mL (1 molar equiv)) at 60° C. for 20 min; and mixing Compound I (0.6 g) in acetone (11 mL) with 1N KOH (1 molar equivalent) at 50° C. for 1 h. After filtration of the resulting hot solutions, the filtrates were evaporated to dryness to yield the desired amorphous salts, respectively.

Example 2: Compound I (Free Form) Form A

A reactor was equipped with an overhead stirrer, reflux condenser, N2 bubble line and outlet, and a temperature probe. A mixture of (14S)-8-bromo-12,12-dimethyl-2λ6-thia-3,9,11,18,23-pentaazatetracyclo [17.3.1.111, r40.05, r0]tetracosa-1(23),5,7,9,19,21-hexaene-2, 2,4-trione (120 g of 86% w/w with IPAc [103.2 g (14S)-8-bromo-12,12-dimethyl-2λ6-thia-3,9,11,18,23-pentaazatetracyclo[17.3.1.111, r40.05, r0]tetracosa-1(23),5,7,9,19,21-hexaene-2,2,4-trione], 0.21 mol, 1 equiv), 3-(2-(dispiro [2.0.24.13]heptan-7-yl)ethoxy)-1H-pyrazole (42.6 g, 0.21 mol, 1 equiv), 325 mesh K2CO3 (63.4 g, 0.46 mol, 2.2 equiv), CuI (3.3 g, 17.2 mmol, 0.083 equiv) and BuOAc (740 mL) were charged into a reactor. The mixture was stirred at ambient temperature. Then DMF (300 mL, 2.9 vol) and N,N'-dimethylcyclohexane-1,2-diamine (14.6 g or 16.2 ml, 0.1 mol, 0.49 equiv) were charged to the reactor and the mixture was purged with three N2/vacuum/N2 cycles. The mixture was then heated to 120° C. for 4 h, then allowed to cool to ambient temperature. 10% aq w/v oxalic acid (860 mL, 0.96 mol, 4.6 equiv) was added dropwise and the mixture stirred for at least 1 h. The mixture was then filtered to remove suspended solids. The removed solids were washed with (2×120 mL). The layers from the filtrate were separated. The organic layer was washed with 8% aq. w/v trisodium citrate (600 mL). Brine was added as necessary to aid phase separation. The organic layer was washed with 1:1 v/v water/brine (400 mL). The organic layer was filtered through a pad of Celite. The filter pad was washed with IPAc (150 mL). The filtrate was concentrated, then 800 mL of 1-PrOH (7.8 vol) was added and the mixture concentrated. This step was repeated one more time. Toluene (800 mL) was added and the mixture concentrated. This step was repeated one more time to afford a thick slurry. The crude mixture was concentrated to a volume of 300 mL (2.9 vol) of toluene. After stirring the slurry overnight, the solid was collected by filtration and washing the solid with toluene (2×100 mL, 0.97 vol). The solid was dried under vacuum with a nitrogen bleed at 50° C. until the loss on drying was no more than 1.0% to afford Compound I as a white/off-white solid (107.0 g, 83%, 94.5% (AUC) HPLC purity.

Recrystallization: Compound I Form A [22.2 g, 94.6% (AUC) Compound I Form A was suspended in toluene (440 mL, 20 vol based on Compound I Form A) and the mixture heated to reflux. After holding at reflux for NLT 2 h, the mixture was allowed to cool to ambient over 8 h. After stirring at ambient temperature overnight, the solid was collected by filtration washing the solid with toluene (40 mL, 1.8 vol). The solid was dried under vacuum with a nitrogen bleed at 50° C. until the loss on drying was no more than 1.0% to afford Compound I Form A as a white/off-white solid (18.8 g, 84%, 96.8% (AUC) HPLC purity).

Second Recrystallization: Compound I Form A [17.5 g, 97.0% (AUC) Compound I Form A] was suspended in toluene (350 mL, 20 vol based on Compound I Form A) and the mixture heated to reflux. After holding at reflux for no less than 2 h, the mixture was allowed to cool to ambient temperature over 8 h. After stirring at ambient temperature overnight, the solid was collected by filtration washing the solid with toluene (40 mL, 1.8 vol). The solid was dried under vacuum with a nitrogen bleed at 50° C. until the loss on drying was no more than 1.0% to afford Compound I Form A (free form) as a white/off-white solid (15.7 g, 89%, 98.4% (AUC) HPLC purity).

Compound I free Form A is the most stable polymorphic form at water activity ≤0.95 at ambient temperature.

A. X-Ray Powder Diffraction

The XRPD pattern was acquired at room temperature in reflection mode using a Bruker Advance equipped with Vantec-1 detector. A sample was analyzed on a silicon sample holder from 3-40° 2-theta on continuous mode with step size of 0.0144531° and time per step of 0.25 s. The sample was spinning at 15 rpm. The XRPD diffractogram for Compound I (free form) Form A is provided in FIG. 1 and the XRPD data are summarized below in Table 2.

TABLE 2

XRPD signals for crystalline Form A of Compound I (free form)

| XRPD Peaks | Angle (degrees 2-Theta ± 0.2) | Intensity % |
|---|---|---|
| 1 | 20.0 | 100.0 |
| 2 | 23.1 | 63.9 |
| 3 | 16.6 | 56.4 |
| 4 | 23.3 | 52.3 |
| 5 | 9.2 | 51.2 |
| 6 | 24.3 | 42.0 |
| 7 | 18.1 | 41.9 |
| 8 | 16.5 | 40.7 |
| 9 | 11.2 | 38.6 |
| 10 | 21.8 | 37.2 |
| 11 | 11.3 | 33.3 |
| 12 | 18.0 | 32.9 |
| 13 | 14.0 | 31.8 |
| 14 | 24.4 | 29.5 |
| 15 | 22.9 | 29.4 |
| 16 | 23.8 | 29.3 |
| 17 | 5.7 | 26.2 |
| 18 | 18.7 | 24.6 |
| 19 | 18.8 | 24.6 |
| 20 | 18.5 | 22.4 |
| 21 | 22.5 | 19.2 |
| 22 | 20.4 | 17.7 |
| 23 | 15.1 | 14.9 |
| 24 | 26.5 | 14.3 |
| 25 | 13.7 | 13.8 |
| 26 | 22.2 | 13.8 |
| 27 | 27.3 | 11.9 |
| 28 | 15.0 | 11.7 |
| 29 | 14.8 | 10.4 |

B. Single Crystal Elucidation

Single crystals having the Compound I (free form) Form A structure were grown from acetone/heptane. X-ray diffraction data were acquired at 298K on a Bruker diffractometer equipped with Mo K$_\alpha$ radiation (λ=0.71073 Å) and a CCD detector. The structure was solved and refined using SHELX programs (Sheldrick, G. M., Acta Cryst., (2008) A64, 112-122) and results are summarized in Table 3 below.

TABLE 3

Single crystal elucidation of Compound I (free form) Form A

| Crystal System | Monoclinic |
|---|---|
| Space Group | P2$_1$ |
| a (Å) | 15.477(3) |
| b (Å) | 12.741(2) |
| c (Å) | 16.369(3) |
| α (°) | 90 |
| β (°) | 99.350(5) |
| γ (°) | 90 |
| V (Å$^3$) | 3185.1(9) |
| Z/Z' | 2/2 |
| Temperature | 298K |

C. Solid State NMR

1. Solid State NMR Experimental (Applies to all Crystalline Forms of Compound I):

Bruker-Biospin 400 MHz wide-bore spectrometer equipped with Bruker-Biospin 4 mm HFX probe was used. Samples were packed into 4 mm ZrO2 rotors and spun under Magic Angle Spinning (MAS) condition with spinning speed typically set to 12.5 kHz. The proton relaxation time was measured using $^1$H MAS T$_1$ saturation recovery relaxation experiment in order to set up proper recycle delay of the $^{13}$C cross-polarization (CP) MAS experiment. The CP contact time of carbon CPMAS experiment was set to 2 ms. A CP proton pulse with linear ramp (from 50% to 100%) was employed. The carbon Hartmann-Hahn match was optimized on external reference sample (glycine). Carbon spectra were recorded with proton decoupling using TPPM15 decoupling sequence with the field strength of approximately 100 kHz.

2. Solid State NMR for Compound I (Free Form) Form A

Solid state $^{13}$C NMR data for Compound I (free form) Form A is provided in FIG. 2 and summarized in Table 4 below.

TABLE 4

Solid State NMR of Compound I (free form) Form A

| Peak # | Chem Shift [ppm] ± 0.2 ppm | Intensity [rel] |
|---|---|---|
| 1 | 165.9 | 42.7 |
| 2 | 164.6 | 16.9 |
| 3 | 163.2 | 16.6 |
| 4 | 159.8 | 29.3 |
| 5 | 158.5 | 14.9 |
| 6 | 157.6 | 11.6 |
| 7 | 154.1 | 17.7 |
| 8 | 153.2 | 22.5 |
| 9 | 151.3 | 30.6 |
| 10 | 143.8 | 51.7 |
| 11 | 136.9 | 53.8 |
| 12 | 130.2 | 48.5 |
| 13 | 116.4 | 52.2 |
| 14 | 115.1 | 20.7 |
| 15 | 113.7 | 37.4 |
| 16 | 112.9 | 26.1 |
| 17 | 104.6 | 27.2 |
| 18 | 103.9 | 29.5 |
| 19 | 95.7 | 49.9 |
| 20 | 69.1 | 67.4 |
| 21 | 63.6 | 31.9 |
| 22 | 61.8 | 47.4 |
| 23 | 58.3 | 25.8 |
| 24 | 49.7 | 30.8 |
| 25 | 47.2 | 26.4 |
| 26 | 43.3 | 28.8 |
| 27 | 39.6 | 22.8 |
| 28 | 37.0 | 32.0 |
| 29 | 33.9 | 38.8 |

TABLE 4-continued

Solid State NMR of Compound I (free form) Form A

| Peak # | Chem Shift [ppm] ± 0.2 ppm | Intensity [rel] |
|---|---|---|
| 30 | 31.9 | 53.4 |
| 31 | 30.5 | 94.5 |
| 32 | 29.5 | 35.6 |
| 33 | 26.9 | 41.6 |
| 34 | 25.6 | 100.0 |
| 35 | 19.9 | 72.7 |
| 36 | 19.0 | 67.8 |
| 37 | 6.6 | 82.8 |
| 38 | 3.7 | 78.1 |

D. Differential Scanning Calorimetry Analysis

DSC was performed using TA Discovery differential scanning calorimeter (TA Instruments, New Castle, DE). The instrument was calibrated with indium. Samples of approximately 1-10 mg were weighed into hermetic pans that were crimped using lids with one hole. The DSC samples were scanned from 25° C. to 300° C. at a heating rate of 10° C./min. Data was collected and analyzed by Trios Analysis software (TA Instruments, New Castle, DE). The thermogram showed a single melting endothermic peak at ~227° C.

Example 3: Compound I (Free Form) Form B 100 mg of Compound I calcium salt hydrate Form D was stirred in 5 mL of FESSIF V2 (Fed state simulated intestinal fluid, purchased from Biorelevant) at ambient temperature for 24 h. The slurry was centrifuged and the liquid was removed. The solid was washed with water twice and air-dried. The resulting solid was Compound I (free form) Form B.

A. X-Ray Powder Diffraction:

The XRPD pattern was acquired at room temperature in reflection mode using a Bruker Advance equipped with Vantec-1 detector. The sample was analyzed on a silicon sample holder from 3-40° 2-theta on continuous mode with step size of 0.0144531° and time per step of 0.25 s. Sample was spinning at 15 rpm. The XRPD diffractogram for Compound I (free form) Form B is provided at FIG. 3 and summarized at Table 5.

TABLE 5

XRPD signals for crystalline Form B of Compound I (free form)

| XRPD Peaks | Angle (degrees 2-Theta ± 0.2) | Intensity % |
|---|---|---|
| 1 | 16.3 | 100.0 |
| 2 | 5.5 | 84.6 |
| 3 | 17.7 | 67.6 |
| 4 | 15.2 | 46.1 |
| 5 | 21.7 | 44.0 |
| 6 | 27.2 | 41.6 |
| 7 | 5.7 | 35.9 |
| 8 | 10.8 | 20.5 |
| 9 | 23.6 | 18.8 |
| 10 | 28.3 | 13.6 |
| 11 | 25.5 | 12.1 |
| 12 | 25.9 | 11.2 |
| 13 | 24.4 | 10.3 |

B. Solid State NMR

Solid state $^{13}C$ NMR data for Compound I, Form B (free form) is provided in FIG. 4 and summarized in Table 6.

TABLE 6

Solid state NMR of Compound I (free form) Form B

| Peak # | Chem Shift [ppm] ± 0.2 ppm | Intensity [rel] |
|---|---|---|
| 1 | 168.8 | 16.4 |
| 2 | 168.3 | 33.8 |
| 3 | 166.3 | 36.4 |
| 4 | 158.5 | 27.0 |
| 5 | 155.5 | 37.3 |
| 6 | 152.5 | 16.3 |
| 7 | 150.6 | 25.4 |
| 8 | 142.8 | 58.5 |
| 9 | 137.2 | 66.9 |
| 10 | 129.1 | 41.6 |
| 11 | 116.8 | 47.7 |
| 12 | 112.6 | 42.7 |
| 13 | 108.1 | 61.0 |
| 14 | 97.8 | 66.2 |
| 15 | 96.7 | 55.7 |
| 16 | 69.3 | 67.4 |
| 17 | 64.4 | 27.7 |
| 18 | 64 | 56.8 |
| 19 | 56.7 | 45.0 |
| 20 | 50.9 | 65.2 |
| 21 | 41.4 | 42.9 |
| 22 | 37.6 | 84 |
| 23 | 31.3 | 7.6 |
| 24 | 30.6 | 65.4 |
| 25 | 28.9 | 91.1 |
| 26 | 27.9 | 77.5 |
| 27 | 27.3 | 67.2 |
| 28 | 25.3 | 89.2 |
| 29 | 22.5 | 64.1 |
| 30 | 20.1 | 100.0 |
| 31 | 18.1 | 97.2 |
| 32 | 6.5 | 47.4 |
| 33 | 6.0 | 56.0 |
| 34 | 4.9 | 55.6 |
| 35 | 2.3 | 39.8 |

Example 4: Compound I (Free Form) Form C

Compound I (free form) Form C was obtained by stirring Compound I (free form) Form A in IPA/H$_2$O (v/v, 75/25) at 25° C. for 24 h.

A. X-Ray Powder Diffraction:

XRPD was performed with a Panalytical X'Pert$^3$ Powder XRPD on a Si zero-background holder. The 2-theta position was calibrated against a Panalytical Si reference standard disc. The XRPD diffractogram for Compound I (free form) Form C is shown in FIG. 5 and summarized in Table 7.

TABLE 7

XRPD signals for crystalline Form C of Compound I (free form)

| XRPD Peaks | Angle (degrees 2-Theta ± 0.2) | Intensity % |
|---|---|---|
| 1 | 6.3 | 100.0 |
| 2 | 20.4 | 55.0 |
| 3 | 14.8 | 43.7 |
| 4 | 20.1 | 32.0 |
| 5 | 19.2 | 18.8 |
| 6 | 18.5 | 18.6 |
| 7 | 15.5 | 13.1 |
| 8 | 23.8 | 11.6 |
| 9 | 26.4 | 11.2 |

Example 5: Compound I Calcium Salt Hydrate Form A

Compound I calcium salt hydrate Form A is the most kinetically favored calcium salt hydrate form, providing higher dissolution, solubility, and exposure than the other calcium salt hydrate forms.

Compound I calcium salt hyrate Form A is prepared by charging 0.2 mmol of Compound I (free form) Form A and 0.1 mmol of Ca(OMe)$_2$ dry powder with IPA at ~45 mg/mL and spiked with ~10% of water and heated to 70° C. Initially, all solids dissolved. After 5 min, white solid precipitated out. The resulting slurry was stirred for 4 d at room temperature. The solid was isolated as Compound I calcium salt hydrate Form A by vacuum filtration and dried under vacuum at 40° C. for overnight (~78% isolated yield).

An alternative method of preparing Compound I calcium salt hydrate Form A utilized 10 g of Compound I (free form Form A) charged with 63 mL IPA and 7 mL water. The slurry was heated to 55-65° C. The mixture was charged with 1.1 equiv of NaOH. The mixture was stirred until the solution turned homogeneous. The solution was then cooled to 25° C. and seeded with 0.1 g of Compound I sodium salt hydrate Form A. The slurry was stirred for 18 h. The solution was then heated to 45° C. The slurry was seeded with 0.1 g of Compound I calcium salt hydrate Form A. A solution of 0.55 equiv CaCl$_2$), 9 mL IPA, and 1 mL water were added over a 5 h period of time. The resulting slurry was stirred for 2 h. The slurry was cooled to 20° C. over a 5 h period of time. The resulting solids were collected by vacuum filtration and the resulting wet cake was washed with 50 mL of water. The washed wet cake was allowed to air-dry for 1 h. The air-dried wet cake was transferred to a vacuum oven at 45° C. with a slight nitrogen bleed for 20 h to yield crystalline Compound I calcium salt hydrate Form A (8.5 g, 82% isolated yield).

A. X-Ray Powder Diffraction:

The XRPD patterns were acquired at room temperature in reflection mode using a Bruker Advance equipped with Vantec-1 detector. A sample was analyzed on a silicon sample holder from 3-40° 2-theta on continuous mode with step size of 0.0144531° and time per step of 0.25 s. The sample was spinning at 15 rpm. The XRPD diffractogram for Compound I calcium salt hydrate Form A is shown in FIG. 6 and summarized in Table 8.

TABLE 8

XRPD signals for crystalline Compound I calcium salt hydrate Form A

| XRPD Peaks | Angle (degrees 2-Theta ± 0.2) | Intensity % |
|---|---|---|
| 1 | 18.0 | 100.0 |
| 2 | 4.2 | 81.7 |
| 3 | 19.7 | 71.2 |
| 4 | 22.3 | 59.5 |
| 5 | 17.8 | 57.1 |
| 6 | 24.4 | 54.9 |
| 7 | 10.5 | 52.5 |
| 8 | 10.6 | 51.9 |
| 9 | 14.2 | 50.9 |
| 10 | 20.7 | 48.8 |
| 11 | 25.1 | 48.1 |
| 12 | 19.6 | 42.1 |
| 13 | 14.8 | 36.8 |
| 14 | 17.3 | 35.8 |
| 15 | 25.3 | 31.2 |
| 16 | 15.3 | 29.2 |
| 17 | 21.1 | 28.9 |

TABLE 8-continued

XRPD signals for crystalline Compound I calcium salt hydrate Form A

| XRPD Peaks | Angle (degrees 2-Theta ± 0.2) | Intensity % |
|---|---|---|
| 18 | 12.2 | 26.6 |
| 19 | 21.9 | 26.5 |
| 20 | 22.0 | 24.5 |
| 21 | 13.6 | 19.1 |
| 22 | 11.8 | 16.6 |
| 23 | 28.7 | 15.9 |
| 24 | 25.8 | 14.6 |
| 25 | 8.3 | 10.3 |

B. Single Crystal Elucidation

Crystals having the Compound I calcium salt hydrate Form A structure were grown by dissolving 1 mg of Compound I calcium salt hydrate Form A in 350 µL of a 90/10 mixture of dichloroethane/ethanol and then was vapor diffused with pentane over several days. X-ray diffraction data were acquired at both 100K and 298K on a Bruker diffractometer equipped with Cu Kα radiation (λ=1.5478 Å) and a CCD detector. The structure was solved and refined using SHELX programs (Sheldrick, G. M., Acta Cryst., (2008) A64, 112-122) and results are summarized in Table 9 below.

TABLE 9

Single crystal elucidation of Compound I calcium salt hydrate Form A

| Crystal System: | Monoclinic | Monoclinic |
|---|---|---|
| Space Group: | C2 | C2 |
| a (Å) | 11.1298(4) | 11.1871(10) |
| b (Å) | 13.7688(5) | 13.8793(12) |
| c (Å) | 22.2139(8) | 22.4114(18) |
| α (°) | 90 | 90 |
| β (°) | 101.9330(10) | 101.477(4) |
| γ (°) | 90 | 90 |
| V (Å$^3$) | 3330.6(2) | 3410.2(5) |
| Z/Z' | 2/0.5 | 2/0.5 |
| Temperature | 100K | 298K |

C. Solid State NMR

Solid state $^{13}$C NMR spectrum for Compound I calcium salt hydrate Form A is provided in FIG. 7 and summarized in Table 10.

TABLE 10

Solid state NMR of Compound I calcium salt hydrate Form A

| Peak # | Chem Shift ppm ± 0.2 | Intensity [rel] |
|---|---|---|
| 1 | 178.3 | 27.0 |
| 2 | 165.2 | 38.8 |
| 3 | 158.2 | 27.6 |
| 4 | 155.8 | 32.7 |
| 5 | 153.1 | 20.5 |
| 6 | 150.9 | 29.9 |
| 7 | 143.4 | 42.1 |
| 8 | 136.8 | 41.3 |
| 9 | 127.9 | 31.5 |
| 10 | 116.3 | 27.4 |
| 11 | 114.6 | 48.2 |
| 12 | 112.1 | 47.4 |
| 13 | 98.6 | 27.4 |
| 14 | 93.6 | 41.2 |
| 15 | 69.5 | 33.0 |
| 16 | 68.6 | 17.0 |
| 17 | 63.8 | 55.6 |
| 18 | 57.7 | 43.1 |

TABLE 10-continued

Solid state NMR of
Compound I calcium salt hydrate Form A

| Peak # | Chem Shift ppm ± 0.2 | Intensity [rel] |
|---|---|---|
| 19 | 51.8 | 50.2 |
| 20 | 42.9 | 34.2 |
| 21 | 37.2 | 49.9 |
| 22 | 31.2 | 16.9 |
| 23 | 29.6 | 48.1 |
| 24 | 26.4 | 100.0 |
| 25 | 20.8 | 77.4 |
| 26 | 17.0 | 65.8 |
| 27 | 7.8 | 44.7 |
| 28 | 5.3 | 48.8 |
| 29 | 2.6 | 18.7 |

D. Differential Scanning Calorimetry Analysis:

A DSC thermogram was obtained using TA Instruments DSC Q2000. Sample was heated at 10° C./min from 30° C. to 350° C. The thermogram showed an endothermic peak at ~223° C.

Example 6: Compound I Calcium Salt Hydrate Form B 25 g of Compound I (free form) Form A was charged with 50 mL ethanol and 100 mL water. The slurry was heated to 55-65° C. The mixture was charged with 1.1 equiv of NaOH. The mixture was stirred until the solution turned homogeneous. The solution was then cooled to 25° C. and seeded with 0.25 g of Compound I sodium salt hydrate Form A. The slurry was stirred for 20 h. The solution was then heated to 45° C. The slurry was seeded with 0.1 g of Compound I calcium salt (form not important). A solution of 0.55 equiv $CaCl_2$), 8 mL ethanol and 16 mL water was added over a 5 h period of time. The resulting slurry was stirred for 2 h. The slurry was cooled to 20° C. over a 5 h period of time. The resulting solids were collected by vacuum filtration and allowed to air-dry for 1 hour. The air-dried wet cake was transferred to an unheated vacuum oven with a slight nitrogen bleed for 20 h to yield 21 g crystalline Compound I calcium salt hydrate Form B (81% isolated yield).

Compound I calcium salt hydrate Form B is the most stable polymorphic form in water at ambient temperature. Compound I calcium salt Form B isomorphic solvates, solvate/hydrates, and hydrates share the same XRPD pattern as Compound I calcium salt hydrate Form B. The solvents can be small alcohols, such as MeOH, EtOH, IPA and/or water.

A. X-Ray Powder Diffraction:

The XRPD patterns are acquired at room temperature in reflection mode using a Bruker Advance equipped with Vantec-1 detector. A sample was analyzed on a silicon sample holder from 3-40° 2-theta on continuous mode with step size of 0.0144531° and time per step of 0.25 s. The sample was spinning at 15 rpm. The XRPD diffractogram for Compound I calcium salt hydrate Form B is provide in FIG. 8 and summarized in Table 11.

TABLE 11

XRPD signals for crystalline
Compound I calcium salt hydrate Form B

| XRPD Peaks | Angle (degrees 2-Theta ± 0.2) | Intensity % |
|---|---|---|
| 1 | 14.6 | 100.0 |
| 2 | 17.7 | 98.2 |
| 3 | 13.1 | 94.6 |
| 4 | 20.4 | 86.5 |
| 5 | 21.3 | 71.8 |
| 6 | 16.2 | 71.7 |
| 7 | 19.9 | 65.8 |
| 8 | 22.3 | 65.0 |
| 9 | 20.3 | 62.7 |
| 10 | 21.4 | 61.9 |
| 11 | 14.8 | 60.9 |
| 12 | 8.5 | 59.6 |
| 13 | 18.9 | 59.5 |
| 14 | 20.6 | 59.4 |
| 15 | 14.5 | 53.7 |
| 16 | 21.1 | 50.6 |
| 17 | 22.4 | 49.9 |
| 18 | 17.4 | 47.8 |
| 19 | 12.2 | 47.4 |
| 20 | 25.2 | 44.4 |
| 21 | 19.6 | 43.4 |
| 22 | 19.6 | 42.6 |
| 23 | 5.9 | 42.4 |
| 24 | 23.8 | 41.4 |
| 25 | 16.7 | 33.3 |
| 26 | 24.2 | 32.4 |
| 27 | 24.4 | 30.8 |
| 28 | 15.1 | 27.4 |
| 29 | 22.8 | 27.3 |
| 30 | 25.5 | 26.3 |
| 31 | 23.5 | 25.8 |
| 32 | 13.6 | 24.7 |
| 33 | 18.1 | 23.5 |
| 34 | 9.5 | 23.1 |
| 35 | 11.7 | 22.5 |
| 36 | 11.2 | 22.1 |
| 37 | 8.8 | 20.4 |
| 38 | 16.9 | 18.1 |
| 39 | 11.4 | 16.5 |
| 40 | 28.5 | 14.9 |
| 41 | 6.6 | 12.4 |
| 42 | 26.4 | 11.6 |
| 43 | 24.8 | 11.2 |
| 44 | 5.5 | 10.7 |
| 45 | 29.2 | 10.3 |

B. Single Crystal Elucidation

Crystals having the Compound I calcium salt hydrate Form B structure were grown by dissolving 1 mg of Compound I calcium salt hydrate Form A in 350 μL of boiling 80/20 mixture of methanol/dichloromethane, which was then allowed to cool over several days. X-ray diffraction data were acquired at 100K on a Bruker diffractometer equipped with Cu Kα radiation (λ=1.5478 Å) and a CCD detector. The structure was solved and refined using SHELX programs (Sheldrick, G. M., Acta Cryst., (2008) A64, 112-122) and results are summarized in Table 12 below.

TABLE 12

Single crystal elucidation of Compound I
calcium salt hydrate/solvate Form B

| Crystal System: | Monoclinic |
|---|---|
| Space Group: | $P2_1$ |
| a (Å) | 18.5188(5) |
| b (Å) | 13.0054(4) |
| c (Å) | 31.2178(9) |
| α (°) | 90 |
| β (°) | 106.8650(10) |

TABLE 12-continued

Single crystal elucidation of Compound I
calcium salt hydrate/solvate Form B

| | |
|---|---|
| γ (°) | 90 |
| V (Å³) | 7195.3(4) |
| Z/Z' | 2/2 |
| Temperature | 100K |

Figure 9:
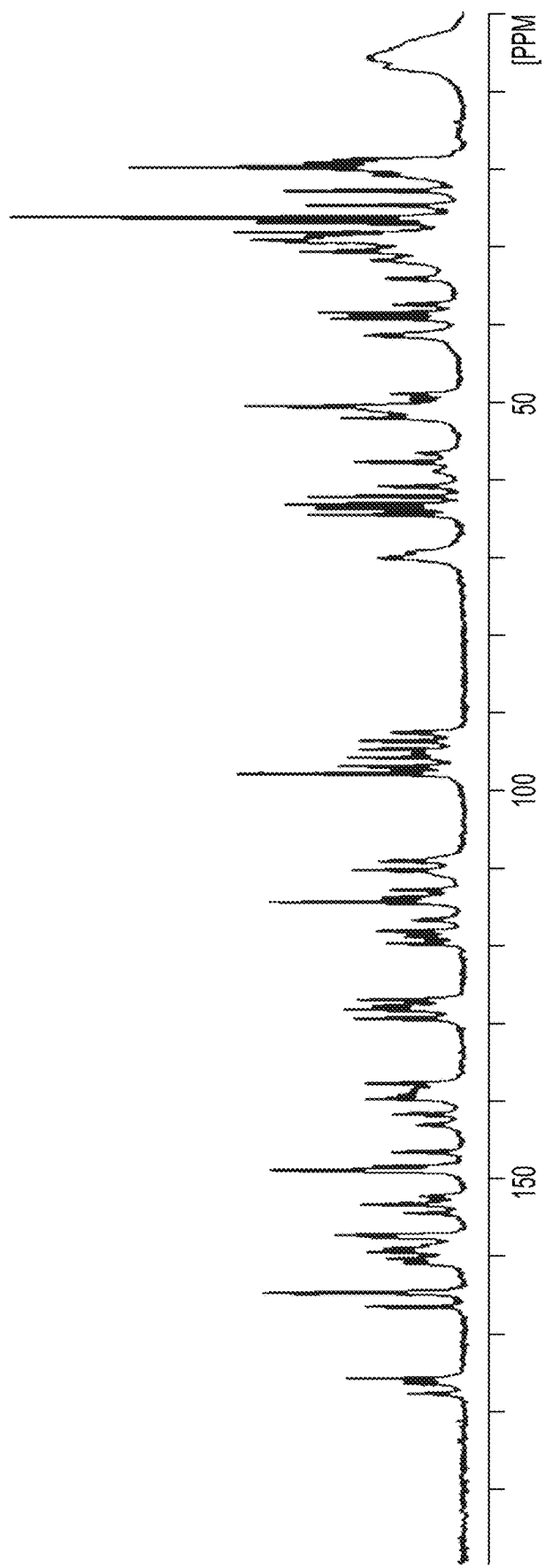
FIG. 9 shows a $^{13}$C solid state NMR spectrum of Compound I calcium salt hydrate Form B.

C. Solid State NMR:

Solid state $^{13}$C NMR spectrum for Compound I calcium salt hydrate Form B is provided in FIG. 9 and summarized in Table 13.

TABLE 13

Solid state NMR of
Compound I calcium salt hydrate Form B

| Peak # | Chem Shift [ppm] ± 0.2 | Intensity [rel] |
|---|---|---|
| 1 | 177.8 | 12.1 |
| 2 | 176.4 | 12.9 |
| 3 | 175.8 | 25.8 |
| 4 | 166.5 | 20.9 |
| 5 | 164.7 | 42.9 |
| 6 | 160.9 | 13.0 |
| 7 | 160.3 | 16.6 |
| 8 | 159.5 | 20.6 |
| 9 | 159.0 | 17.4 |
| 10 | 158.6 | 9.1 |
| 11 | 157.3 | 28.3 |
| 12 | 154.5 | 12.7 |
| 13 | 153.4 | 22.0 |
| 14 | 152.3 | 9.5 |
| 15 | 148.9 | 41.8 |
| 16 | 148.3 | 19.8 |
| 17 | 146.6 | 15.7 |
| 18 | 143.0 | 10.1 |
| 19 | 141.7 | 15.7 |
| 20 | 139.7 | 21.1 |
| 21 | 139.1 | 14.0 |
| 22 | 138.5 | 11.5 |
| 23 | 137.7 | 21.0 |
| 24 | 129.3 | 23.8 |
| 25 | 128.2 | 25.6 |
| 26 | 127.7 | 19.8 |
| 27 | 126.9 | 23.2 |
| 28 | 119.6 | 16.8 |
| 29 | 118.8 | 12.8 |
| 30 | 118.0 | 18.6 |
| 31 | 116.6 | 11.2 |
| 32 | 114.2 | 41.3 |
| 33 | 113.7 | 17.6 |
| 34 | 112.7 | 15.9 |
| 35 | 110.1 | 24.0 |
| 36 | 109.0 | 18.4 |
| 37 | 97.7 | 48.3 |
| 38 | 96.8 | 27.4 |
| 39 | 95.7 | 25.4 |
| 40 | 95.1 | 11.0 |
| 41 | 94.6 | 22.6 |
| 42 | 93.6 | 23.1 |
| 43 | 92.4 | 15.7 |
| 44 | 69.8 | 18.7 |
| 45 | 69.1 | 12.4 |
| 46 | 64.3 | 33.3 |
| 47 | 63.5 | 31.9 |
| 48 | 63.0 | 38.9 |
| 49 | 62.0 | 34.4 |
| 50 | 60.6 | 18.7 |
| 51 | 58.7 | 6.6 |
| 52 | 57.5 | 23.4 |
| 53 | 56.4 | 10.3 |
| 54 | 51.8 | 26.4 |
| 55 | 50.3 | 46.9 |
| 56 | 49.3 | 11.9 |
| 57 | 48.7 | 15.9 |
| 58 | 41.2 | 21.5 |
| 59 | 39.0 | 28.8 |
| 60 | 38.2 | 31.6 |
| 61 | 37.1 | 15.2 |
| 62 | 33.8 | 16.9 |
| 63 | 31.5 | 20.2 |
| 64 | 30.3 | 35.1 |
| 65 | 29.2 | 38.4 |
| 66 | 28.9 | 45.6 |
| 67 | 28.4 | 34.4 |
| 68 | 27.8 | 49.0 |
| 69 | 26.7 | 44.5 |
| 70 | 25.9 | 100.0 |
| 71 | 24.4 | 34.0 |
| 72 | 22.5 | 39.8 |
| 73 | 20.5 | 19.6 |
| 74 | 19.5 | 71.4 |
| 75 | 18.9 | 34.2 |
| 76 | 18.4 | 28.0 |
| 77 | 6.5 | 17.2 |
| 78 | 5.4 | 20.5 |
| 79 | 5.0 | 20.8 |
| 80 | 4.0 | 15.8 |

D. Differential Scanning Calorimetry Analysis of Compound I Calcium Salt Hydrate Form B DSC was performed using TA Discovery differential scanning calorimeter (TA Instruments, New Castle, DE). The instrument was calibrated with indium. Samples of approximately 1-10 mg were weighed into hermetic pans that were crimped using lids with one hole. The DSC samples were scanned from 25° C. to 300° C. at a heating rate of 10° C./min. Data was collected and analyzed by Trios Analysis software (TA Instruments, New Castle, DE). The thermogram shows multiple endothermic peaks at ~61° C. and ~110° C.

E. Compound I Calcium Salt Hydrate/Solvate Form B with MeOH

Compound I calcium salt hydrate/solvate Form B with MeOH was made by adding one drop of MeOH to air-dried Compound I calcium salt hydrate Form B. Solid state $^{13}$C NMR spectrum for Compound I calcium salt hydrate/solvate Form B with MeOH is provided in FIG. 10 and summarized in Table 14.

TABLE 14

Solid state NMR of Compound I
calcium salt hydrate/solvate Form B with MeOH

| Peak # | Chem Shift [ppm] ± 0.2 | Intensity [rel] |
|---|---|---|
| 1 | 177.6 | 15.9 |
| 2 | 176.1 | 35.0 |
| 3 | 166.5 | 19.2 |
| 4 | 164.7 | 49.6 |
| 5 | 162.1 | 7.4 |
| 6 | 161.2 | 9.8 |
| 7 | 159.4 | 32.7 |
| 8 | 157.7 | 29.5 |
| 9 | 154.4 | 15.2 |
| 10 | 153.3 | 25.8 |
| 11 | 152.5 | 18.2 |
| 12 | 148.9 | 53.9 |
| 13 | 146.7 | 8.3 |
| 14 | 143.5 | 8.7 |

TABLE 14-continued

Solid state NMR of Compound I
calcium salt hydrate/solvate Form B with MeOH

| Peak # | Chem Shift [ppm] ± 0.2 | Intensity [rel] |
|---|---|---|
| 15 | 142.1 | 10.5 |
| 16 | 140.5 | 10.1 |
| 17 | 138.7 | 15.1 |
| 18 | 137.7 | 12.6 |
| 19 | 129.5 | 16.6 |
| 20 | 128.4 | 18.6 |
| 21 | 127.7 | 23.4 |
| 22 | 127.2 | 16.2 |
| 23 | 118.9 | 25.9 |
| 24 | 118.5 | 28.9 |
| 25 | 116.8 | 11.3 |
| 26 | 114.4 | 22.8 |
| 27 | 113.2 | 13.8 |
| 28 | 112.6 | 21.5 |
| 29 | 110.2 | 18.2 |
| 30 | 109.0 | 7.9 |
| 31 | 108.1 | 11.6 |
| 32 | 107.5 | 6.8 |
| 33 | 97.8 | 29.8 |
| 34 | 96.9 | 24.2 |
| 35 | 96.2 | 18.0 |
| 36 | 95.7 | 26.4 |
| 37 | 94.9 | 22.0 |
| 38 | 93.8 | 20.1 |
| 39 | 93.0 | 12.5 |
| 40 | 69.4 | 15.1 |
| 41 | 64.4 | 40.2 |
| 42 | 63.6 | 36.9 |
| 43 | 63.0 | 37.8 |
| 44 | 62.0 | 33.0 |
| 45 | 61.4 | 12.5 |
| 46 | 60.6 | 16.6 |
| 47 | 60.2 | 10.3 |
| 48 | 58.6 | 7.5 |
| 49 | 57.3 | 19.2 |
| 50 | 56.5 | 14.9 |
| 51 | 55.7 | 9.1 |
| 52 | 52.1 | 20.6 |
| 53 | 50.5 | 50.3 |
| 54 | 49.3 | 75.6 |
| 55 | 41.8 | 9.2 |
| 56 | 40.7 | 24.2 |
| 57 | 38.8 | 23.7 |
| 58 | 38.3 | 32.0 |
| 59 | 37.3 | 14.2 |
| 60 | 33.9 | 27.2 |
| 61 | 32.9 | 16.8 |
| 62 | 31.3 | 16.6 |
| 63 | 30.6 | 24.1 |
| 64 | 30.1 | 36.7 |
| 65 | 28.9 | 55.1 |
| 66 | 28.3 | 34.0 |
| 67 | 28.0 | 46.7 |
| 68 | 26.8 | 31.0 |
| 69 | 26.5 | 46.2 |
| 70 | 25.9 | 100.0 |
| 71 | 25.1 | 22.9 |
| 72 | 24.6 | 40.1 |
| 73 | 23.3 | 18.7 |
| 74 | 22.7 | 35.6 |
| 75 | 20.4 | 24.6 |
| 76 | 19.5 | 63.4 |
| 77 | 18.7 | 31.6 |
| 78 | 5.9 | 20.4 |
| 79 | 4.1 | 16.3 |

F. Differential Scanning Calorimetry Analysis of Compound I Calcium Salt Hydrate/Solvate Form B with MeOH DSC was performed using TA Discovery differential scanning calorimeter (TA Instruments, New Castle, DE). The instrument was calibrated with indium. Samples of approximately 1-10 mg were weighed into hermetic pans that were crimped using lids with one hole. The DSC samples were scanned from 25° C. to 300° C. at a heating rate of 10° C./min. Data was collected and analyzed by Trios Analysis software (TA Instruments, New Castle, DE). The thermogram shows multiple endothermic peaks at ~64° C. and ~113° C.

Example 7: Compound I Calcium Salt Hydrate Form C

Direct crystallization—1 g Compound I (free form) Form A was reacted with calcium methoxide ($Ca(OMe)_2$) solid in 2/1 molar ratio in DCM at 40 mg/mL. The mixture was stirred at room temperature overnight. ~10% of water was spiked in the next day. The mixture was then stirred at room temperature for 1 week. The isolated solid was Compound I calcium salt hydrate Form C.

Conversion from amorphous calcium salt—1 g of Compound I (free form) Form A was charged into a round flask. $Ca(OMe)_2$ was added at 1:1 molar ratio. Then methanol was added into the flask to make ~15 mg/mL of Compound I. The mixture was stirred at room temperature for 30 min to 1 h. Majority solid was dissolved. The solution was then heated to 60° C. for 30 min to dissolve the remaining solid. The solution was vacuum filtered while hot and rotary evaporated to obtain white to off-white amorphous Compound I calcium salt. The material was further vacuum dried at 30° C. for 2-3 d. The resulting solid was Compound I Ca amorphous form. 45 mg Compound I amorphous calcium salt was stirred in DCM at 30 mg/mL for at least 2.5 week at room temperature. The solid isolated via filtration of this suspension was Compound I calcium salt hydrate Form C.

A. X-Ray Powder Diffraction

The powder x-ray diffraction measurement was performed using PANalytical's X-pert Pro diffractometer at room temperature with copper radiation (1.54060 Å). The incident beam optic was comprised of a variable divergence slit to ensure a constant illuminated length on the sample and on the diffracted beam sides. A fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 s. The XRPD diffractogram for Compound I calcium salt hydrate Form C is shown in FIG. 11 and summarized in Table 15.

TABLE 15

XRPD signals for crystalline Compound I calcium salt hydrate Form C

| XRPD Peaks | Angle (degrees 2-Theta ± 0.2) | Intensity % |
|---|---|---|
| 1 | 15.8 | 100.0 |
| 2 | 20.8 | 55.4 |
| 3 | 10.3 | 46.0 |
| 4 | 22.6 | 31.6 |
| 5 | 17.4 | 31.5 |
| 6 | 21.6 | 31.0 |
| 7 | 15.0 | 29.4 |
| 8 | 24.2 | 29.4 |
| 9 | 4.0 | 23.5 |
| 10 | 14.3 | 21.6 |
| 11 | 21.3 | 20.9 |
| 12 | 20.0 | 17.7 |
| 13 | 24.4 | 15.6 |
| 14 | 19.0 | 13.9 |

TABLE 15-continued

XRPD signals for crystalline
Compound I calcium salt hydrate Form C

| XRPD Peaks | Angle (degrees 2-Theta ± 0.2) | Intensity % |
|---|---|---|
| 15 | 25.1 | 13.8 |
| 16 | 26.3 | 13.4 |
| 17 | 13.3 | 13.0 |
| 18 | 28.3 | 11.8 |
| 19 | 11.8 | 11.6 |
| 20 | 23.1 | 11.5 |

B. Solid State NMR:

Solid state $^{13}$C NMR spectrum for Compound I calcium salt hydrate Form C is provided in FIG. 12 and summarized in Table 16.

TABLE 16

Solid state NMR of
Compound I calcium salt hydrate Form C

| Peak # | Chem Shift [ppm] ± 0.2 | Intensity [rel] |
|---|---|---|
| 1 | 178.3 | 21.8 |
| 2 | 165.9 | 19.9 |
| 3 | 165.2 | 19.8 |
| 4 | 158.5 | 25.6 |
| 5 | 155.9 | 34.0 |
| 6 | 154.0 | 11.2 |
| 7 | 152.9 | 9.8 |
| 8 | 151.5 | 16.3 |
| 9 | 150.6 | 15.6 |
| 10 | 143.5 | 25.3 |
| 11 | 142.7 | 27.1 |
| 12 | 137.7 | 49.3 |
| 13 | 129.6 | 22.5 |
| 14 | 128.0 | 26.1 |
| 15 | 117.4 | 18.3 |
| 16 | 115.7 | 19.2 |
| 17 | 114.6 | 40.2 |
| 18 | 114.3 | 38.1 |
| 19 | 112.9 | 34.1 |
| 20 | 112.0 | 35.3 |
| 21 | 100.0 | 22.9 |
| 22 | 96.0 | 37.4 |
| 23 | 95.6 | 30.7 |
| 24 | 93.7 | 25.4 |
| 25 | 68.5 | 9.8 |
| 26 | 65.9 | 17.2 |
| 27 | 64.1 | 47.5 |
| 28 | 57.6 | 42 |
| 29 | 52.7 | 34.2 |
| 30 | 51.2 | 34.0 |
| 31 | 43.6 | 22.3 |
| 32 | 42.7 | 24.7 |
| 33 | 37.8 | 70.6 |
| 34 | 30.0 | 32.6 |
| 35 | 29.5 | 32.2 |
| 36 | 27.9 | 45.3 |
| 37 | 27.1 | 55.3 |
| 38 | 26.4 | 100.0 |
| 39 | 21.4 | 10.2 |
| 40 | 19.9 | 44.2 |
| 41 | 19.2 | 28.6 |
| 42 | 18.9 | 30.4 |
| 43 | 6.7 | 7.8 |
| 44 | 4.7 | 10.0 |

C. Differential Scanning Calorimetry Analysis

DSC was performed using TA Discovery differential scanning calorimeter (TA Instruments, New Castle, DE). The instrument was calibrated with indium. Samples of approximately 1-10 mg were weighed into hermetic pans that were crimped using lids with one hole. The DSC samples were scanned from 25° C. to 300° C. at a heating rate of 10° C./min. Data was collected and analyzed by Trios Analysis software (TA Instruments, New Castle, DE). The thermogram showed multiple endothermic peaks at ~137° C. and ~203° C.

Example 8: Compound I Calcium Salt Hydrate Form D

Compound I calcium salt hydrate Form D is the most stable form of calcium salt hydrate under certain conditions, such as in mixtures of ethanol and water.

Approximately 25 mg of Compound I calcium salt hydrate Form A was charged with 0.5 mL of EtOH:water 67:33 w/w. The slurry was heated to 65° C. for 8 d. The resulting solid collected by vacuum filtration was Compound I calcium salt hydrate Form D.

Alternatively, Compound I calcium salt hydrate Form D was prepared from 89 g of Compound I sodium hydrate Form A charged with 1080 mL IPA and 120 mL water. The slurry was heated to 55-65° C. The slurry was charged with 18 g of Compound I calcium salt hydrate Form D seed. The slurry was wet-milled as a solution of 0.55 equiv CaCl$_2$), 81 mL IPA and 9 mL water was added over a 5 h period of time. The wet mill was allowed to run until the X-ray powder diffraction confirmed that the slurry was all Compound I calcium salt hydrate Form D. The resulting solids were collected by vacuum filtration and wet cake was washed with 350 mL of water. The washed wet cake was allowed to air-dry for 1 h. The air-dried wet cake was transferred to a vacuum oven at 45° C. with a slight nitrogen bleed for 20 h to yield crystalline Compound I calcium salt hydrate Form D (83.15 g, 90.6% isolated yield).

Compound I calcium salt hydrate Form D is the most stable polymorphic form in IPA/water at water activity 0.1-0.95 from ambient temperature to 60° C.

A. X-Ray Powder Diffraction:

X-ray powder diffraction (XRPD) spectra were recorded at room temperature in reflection mode using a PANalytical Empyrean system equipped with a sealed tube source and a PIXcel 1D Medipix-2 detector (Malvern PANalytical Inc, Westborough, Massachusetts). The X-Ray generator operated at a voltage of 45 kV and a current of 40 mA with copper radiation (1.54060 Å). The powder sample was placed in a back filled sample holder and loaded into the instrument. The sample was scanned over the range of about 3° to about 40° 2θ with a step size of 0.0131303° and 49.725 s per step. The XRPD diffractogram for Compound I calcium salt hydrate Form D is shown in FIG. 13 and summarized in Table 17.

TABLE 17

XRPD signals for crystalline
Compound I calcium salt hydrate Form D

| XRPD Peaks | Angle (degrees 2-Theta ± 0.2) | Intensity % |
|---|---|---|
| 1 | 16.2 | 100.0 |
| 2 | 22.8 | 79.8 |
| 3 | 6.1 | 79.3 |
| 4 | 19.7 | 61.5 |
| 5 | 15.5 | 53.6 |
| 6 | 15.4 | 53.0 |
| 7 | 22.1 | 52.9 |
| 8 | 21.5 | 49.1 |
| 9 | 5.5 | 47.0 |
| 10 | 23.0 | 43.3 |
| 11 | 18.1 | 41.5 |

TABLE 17-continued

XRPD signals for crystalline
Compound I calcium salt hydrate Form D

| XRPD Peaks | Angle (degrees 2-Theta ± 0.2) | Intensity % |
|---|---|---|
| 12 | 18.2 | 38.9 |
| 13 | 15.8 | 36.7 |
| 14 | 17.5 | 34.6 |
| 15 | 25.9 | 34.1 |
| 16 | 25.4 | 16 |
| 17 | 12.9 | 17 |
| 18 | 20.2 | 18 |
| 19 | 19.4 | 19 |
| 20 | 23.7 | 20 |
| 21 | 20.7 | 21 |
| 22 | 16.4 | 22 |
| 23 | 20.6 | 23 |
| 24 | 13.8 | 30.5 |
| 25 | 7.5 | 28.4 |
| 26 | 19.03 | 28.2 |
| 27 | 19.0 | 27.7 |
| 28 | 29.1 | 27.5 |
| 29 | 24.6 | 26.3 |
| 30 | 27.6 | 25.1 |
| 31 | 29.8 | 33.6 |
| 32 | 8.8 | 33.5 |
| 33 | 26.5 | 33.2 |
| 34 | 14.4 | 32.4 |
| 35 | 11.3 | 32.1 |
| 36 | 24.1 | 31.3 |
| 37 | 28.7 | 31.2 |
| 38 | 27.3 | 30.6 |
| 39 | 18.6 | 17.4 |
| 40 | 23.3 | 16.3 |
| 41 | 15.0 | 15.7 |
| 42 | 11.0 | 15.3 |
| 43 | 9.5 | 13.4 |
| 44 | 6.5 | 12.6 |
| 45 | 10.3 | 12.2 |

B. Single Crystal Elucidation

Crystals were selected from Compound I calcium salt hydrate Form D seeded process in ethanol/water. X-ray diffraction data were acquired at 100K on a Bruker diffractometer equipped with Cu $K_a$ radiation (l=1.5478), provided by a Rigaku MM007HF rotating anode, and an CMOS detector. The structure was solved and refined using SHELX program (Sheldrick, G. M., Acta Cryst., (2008) A64, 112-122) and results are summarized in Table 18.

TABLE 18

Single crystal elucidation of
Compound I calcium salt hydrate Form D

| Crystal System | Triclinic |
|---|---|
| Space Group | P1 |
| a (Å) | 12.783(3) |
| b (Å) | 16.639(3) |
| c (Å) | 18.190(4) |
| α (°) | 64.932(12) |
| β (°) | 75.095(14) |
| γ (°) | 68.220(13) |
| V (Å³) | 3231.3(13) |
| Z/Z' | 1/1 |
| Temperature | 100K |

C. Solid State NMR:

Solid state $^{13}$C NMR spectrum for Compound I calcium salt hydrate Form C is provided in FIG. 14 and summarized in Table 19.

TABLE 19

Solid state NMR of
Compound I calcium salt hydrate Form D

| Peak # | Chem Shift [ppm] ± 0.2 | Intensity [rel] |
|---|---|---|
| 1 | 179.8 | 22.0 |
| 2 | 176.9 | 14.0 |
| 3 | 176.3 | 13.7 |
| 4 | 165.8 | 34.1 |
| 5 | 164.4 | 33.6 |
| 6 | 160.9 | 33.0 |
| 7 | 159.9 | 32.8 |
| 8 | 158.5 | 23.1 |
| 9 | 154.8 | 22.2 |
| 10 | 154.3 | 24.4 |
| 11 | 153.3 | 16.2 |
| 12 | 149.5 | 33.1 |
| 13 | 147.9 | 20.4 |
| 14 | 143.8 | 28.0 |
| 15 | 142.5 | 27.7 |
| 16 | 142.0 | 29.6 |
| 17 | 140.4 | 25.0 |
| 18 | 139.5 | 19.3 |
| 19 | 137.3 | 20.4 |
| 20 | 136.7 | 29.3 |
| 21 | 130.2 | 29.6 |
| 22 | 127 | 16.4 |
| 23 | 125.6 | 28.3 |
| 24 | 120.9 | 11.5 |
| 25 | 118.5 | 47.2 |
| 26 | 117.5 | 27.1 |
| 27 | 115.0 | 7.6 |
| 28 | 113.8 | 15.0 |
| 29 | 112.0 | 10.9 |
| 30 | 110.7 | 42.5 |
| 31 | 108.8 | 10.6 |
| 32 | 100.1 | 13.7 |
| 33 | 98.6 | 36.6 |
| 34 | 95.2 | 23.9 |
| 35 | 94.7 | 41.8 |
| 36 | 93.2 | 26.1 |
| 37 | 92.6 | 22.0 |
| 38 | 70.1 | 27.2 |
| 39 | 68.3 | 42.8 |
| 40 | 63.5 | 46.0 |
| 41 | 62.3 | 30.6 |
| 42 | 61.4 | 24.0 |
| 43 | 58.4 | 4.2 |
| 44 | 56.7 | 20.9 |
| 45 | 55.2 | 28.2 |
| 46 | 52.1 | 22.1 |
| 47 | 51.8 | 23.1 |
| 48 | 50.3 | 16.2 |
| 49 | 49.4 | 30.2 |
| 50 | 44.3 | 11.2 |
| 51 | 40.4 | 9.3 |
| 52 | 39.3 | 38.6 |
| 53 | 35.0 | 41.6 |
| 54 | 33.4 | 35.8 |
| 55 | 32.0 | 41.7 |
| 56 | 29.8 | 45.0 |
| 57 | 28.4 | 45.8 |
| 58 | 26.9 | 43.7 |
| 59 | 24.7 | 31.2 |
| 60 | 20.1 | 100.0 |
| 61 | 18.8 | 62.3 |
| 62 | 18.5 | 64.2 |
| 63 | 18.2 | 58.0 |
| 64 | 6.5 | 60.3 |
| 65 | 5.1 | 47.4 |
| 66 | 4.7 | 47.8 |
| 67 | 3.8 | 54.4 |
| 68 | 3.3 | 52.2 |
| 69 | 1.6 | 22.5 |

D. Differential Scanning Calorimetry Analysis

DSC was performed using TA Discovery differential scanning calorimeter (TA Instruments, New Castle, DE). The instrument was calibrated with indium. Samples of approximately 1-10 mg were weighed into hermetic pans that were crimped using lids with one hole. The DSC samples were scanned from 25° C. to 300° C. at a heating rate of 10° C./min. Data was collected and analyzed by Trios Analysis software (TA Instruments, New Castle, DE). The thermogram showed multiple endothermic peaks at ~182° C., and ~208° C.

Example 9: Compound I Calcium Salt Hydrate Form E

Compound I calcium Form E was obtained via solid vapor diffusion of Compound I calcium salt hydrate Form A in EtOAc.

A. X-Ray Powder Diffraction:

XRPD was performed with a Panalytical X'Pert3 Powder XRPD on a Si zero-background holder. The 2 theta position was calibrated against a Panalytical Si reference standard disc. The XRPD diffractogram for Compound I calcium salt hydrate Form E is shown in FIG. 15 and summarized in Table 20.

TABLE 20

XRPD signals for crystalline Compound I calcium salt hydrate Form E

| XRPD Peaks | Angle (degrees 2-Theta ± 0.2) | Intensity % |
|---|---|---|
| 1 | 4.0 | 100.0 |
| 2 | 8.0 | 5.9 |
| 3 | 12.0 | 3.9 |
| 4 | 24.2 | 1.5 |
| 5 | 28.3 | 1.5 |

Example 10: Compound I Form F

Compound I Form F was obtained via slurry of Compound I calcium salt hydrate Form A in MEK at room temperature.

A. X-Ray Powder Diffraction

XRPD was performed with a Panalytical X'Pert3 Powder XRPD on a Si zero-background holder. The 2θ position was calibrated against a Panalytical Si reference standard disc. The XRPD diffractogram for Compound I Form F is shown in FIG. 16 and summarized in Table 21.

TABLE 21

XRPD signals for crystalline Compound I Form F

| XRPD Peaks | Angle (degrees 2-Theta ± 0.2) | Intensity % |
|---|---|---|
| 1 | 9.14 | 100.0 |
| 2 | 9.06 | 89.3 |
| 3 | 5.3 | 48.5 |
| 4 | 7.5 | 48.2 |
| 5 | 10.6 | 23.7 |
| 6 | 11.9 | 18.5 |

Compound I Form F is characterized by the following elemental analysis Table:

| Batch # | Ca | Compound I: Ca ratio | Na | Compound I: Na ratio |
|---|---|---|---|---|
| 1 | 14% | 1:2 | 5% | 1:1 |
| 2 | 7% | 1:1 | 3% | 1:0.8 |

Example 11: Compound I Calcium Salt Hydrate Form G

Compound I calcium salt hydrate Form G was obtained via fast cooling of Compound I calcium salt hydrate Form A solution in EtOH:$H_2O$ (v:v, 90:10).

A. X-Ray Powder Diffraction:

XRPD was performed with a Panalytical X'Pert3 Powder XRPD on a Si zero-background holder. The 2 theta position was calibrated against a Panalytical Si reference standard disc. The XRPD diffractogram for Compound I calcium salt hydrate Form G is shown in FIG. 17 and summarized in Table 22.

TABLE 22

XRPD signals for crystalline Compound I calcium salt hydrate Form G

| XRPD Peaks | Angle (degrees 2-Theta ± 0.2) | Intensity % |
|---|---|---|
| 1 | 5.9 | 100.0 |
| 2 | 14.8 | 67.3 |
| 3 | 14.7 | 63.9 |
| 4 | 6.0 | 58.4 |
| 5 | 8.8 | 17.4 |
| 6 | 11.8 | 14.6 |
| 7 | 11.9 | 8.8 |
| 8 | 26.6 | 6.5 |

Example 12: Compound I Calcium Salt EtOH Solvate Form A

Compound I calcium salt EtOH solvate Form A was obtained via fast cooling of Compound I calcium salt hydrate Form A solution in EtOH:$H_2O$ (85:15, v:v) from 50° C. to −20° C. immediately.

A. X-Ray Powder Diffraction:

XRPD was performed with a Panalytical X'Pert3 Powder XRPD on a Si zero-background holder. The 2θ position was calibrated against a Panalytical Si reference standard disc. The XRPD diffractogram for Compound I calcium salt EtOH solvate Form A is shown in FIG. 18 and summarized in Table 23.

TABLE 23

XRPD signals for Compound I calcium salt EtOH solvate Form A

| XRPD Peaks | Angle (degrees 2-Theta ± 0.2) | Intensity % |
|---|---|---|
| 1 | 4.1 | 100.0 |
| 2 | 17.1 | 26.9 |
| 3 | 4.8 | 23.9 |
| 4 | 8.2 | 19.7 |
| 5 | 8.5 | 19.2 |
| 6 | 5.6 | 16.6 |
| 7 | 16.5 | 14.2 |
| 8 | 20.3 | 11.1 |
| 9 | 11.1 | 10.8 |

TABLE 23-continued

XRPD signals for Compound I
calcium salt EtOH solvate Form A

| XRPD Peaks | Angle (degrees 2-Theta ± 0.2) | Intensity % |
|---|---|---|
| 10 | 14.2 | 10.7 |
| 11 | 9.5 | 10.4 |
| 12 | 7.0 | 10.4 |
| 13 | 16.1 | 10.2 |

Example 13: Compound I Calcium Salt EtOH Solvate Form B

Compound I calcium salt EtOH solvate Form B was obtained via temperature cycling between 60° C. and 5° C. with cooling rate of 0.2° C./min of Compound I calcium salt hydrate Form A in EtOH:n-heptane (1:1, v:v).

A. X-Ray Powder Diffraction

Compound I calcium salt EtOH solvate Form B XRPD was performed with a Panalytical X'Pert³ Powder XRPD on a Si zero-background holder. The 2 theta position was calibrated against a Panalytical Si reference standard disc. The XRPD diffractogram for Compound I calcium salt EtOH solvate Form A is shown in FIG. 19 and summarized in Table 24.

TABLE 24

XRPD signals for Compound I calcium salt
EtOH solvate Form B

| XRPD Peaks | Angle (degrees 2-Theta ± 0.2) | Intensity % |
|---|---|---|
| 1 | 4.5 | 100.0 |
| 2 | 5.0 | 32.1 |
| 3 | 15.4 | 12.0 |
| 4 | 20.3 | 11.2 |

Example 14: Compound I Calcium Salt EtOH Solvate Form C

Compound I calcium salt EtOH solvate Form C was obtained via slurry of Compound I calcium salt amorphous form in EtOH/H₂O (9:1, v:v) at room temperature.

A. X-Ray Powder Diffraction

XRPD on Compound I calcium salt EtOH solvate Form C was performed with a Panalytical X'Pert³ Powder XRPD on a Si zero-background holder. The 2 theta position was calibrated against a Panalytical Si reference standard disc. The XRPD diffractogram for Compound I calcium salt EtOH solvate Form C is shown in FIG. 20 and summarized in Table 25.

TABLE 25

XRPD signals for Compound I calcium
salt EtOH solvate Form C

| XRPD Peaks | Angle (degrees 2-Theta ± 0.2) | Intensity % |
|---|---|---|
| 1 | 4.2 | 100.0 |
| 2 | 5.0 | 43.2 |
| 3 | 5.7 | 13.5 |

Example 15: Compound I Calcium Salt IPA Solvate

~150 mg of Compound I calcium salt hydrate Form A was weighed into a 4 mL vial. 3 mL of IPA (~50 mg/mL Compound I Ca) was added. The mixture was stirred at room for 4 d. Solid Compound I calcium salt IPA solvate was isolated via centrifuge filtration.

A. X-Ray Powder Diffraction

The XRPD patterns were acquired at room temperature in reflection mode using a Bruker Advance equipped with Vantec-1 detector. A sample was analyzed on a silicon sample holder from 3-40° 2-theta on continuous mode with step size of 0.0144531° and time per step of 0.25 s. The sample was spinning at 15 rpm.

Figure 21:
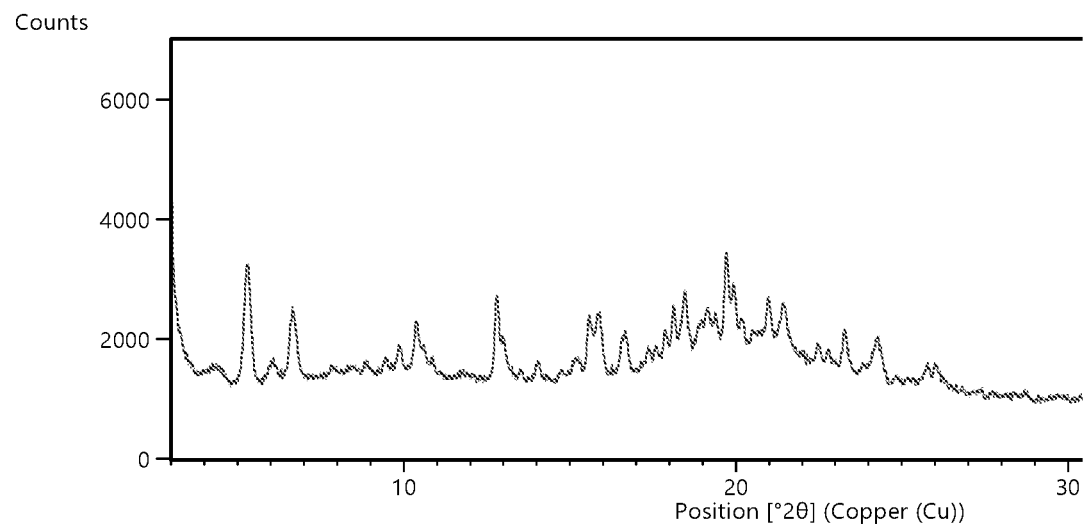
FIG. 21A and FIG. 21B provide XRPD patterns of crystalline Compound I calcium salt IPA solvate.
Figure 21:
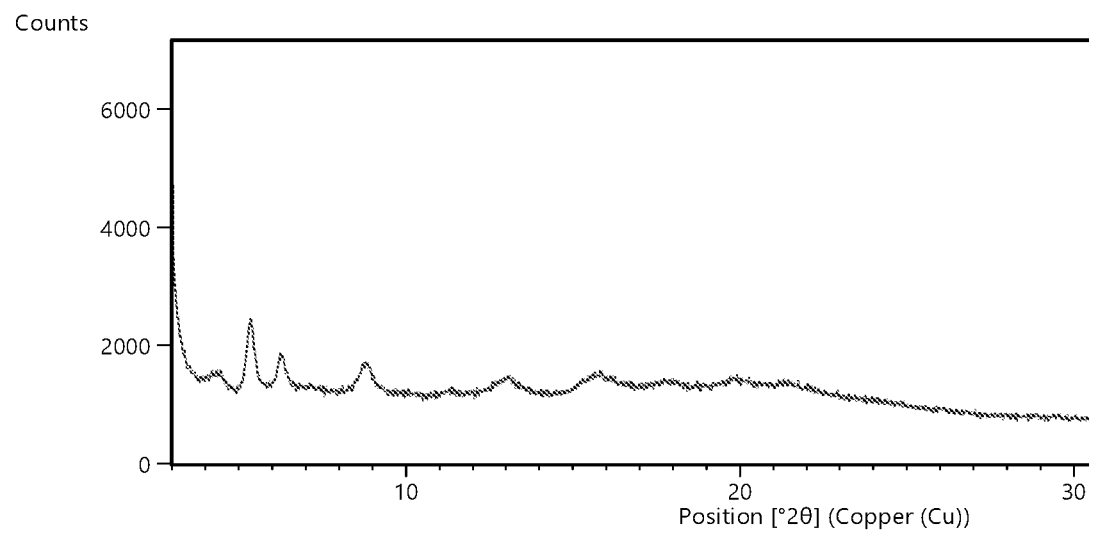

This material is labile. The X-Ray Powder Diffraction pattern varied depending on how the samples were dried. The XRPD diffractogram for wet Compound I calcium salt IPA solvate Form A is shown in FIG. 21A and summarized in Table 26. The XRPD diffractogram for air-dried Compound I calcium salt IPA solvate Form B is shown in FIG. 21B and summarized in Table 27.

TABLE 26

Compound I calcium salt IPA solvate
(wet sample) Form A

| XRPD Peaks | Angle (degrees 2-Theta ± 0.2) | Intensity % |
|---|---|---|
| 1 | 19.7 | 100.0 |
| 2 | 19.9 | 78.9 |
| 3 | 18.5 | 71.5 |
| 4 | 21.0 | 68.4 |
| 5 | 21.4 | 64.2 |
| 6 | 12.8 | 63.0 |
| 7 | 18.1 | 60.6 |
| 8 | 19.1 | 58.5 |
| 9 | 5.3 | 57.9 |
| 10 | 19.4 | 55.2 |
| 11 | 15.9 | 52.9 |
| 12 | 15.6 | 51.7 |
| 13 | 20.2 | 51.7 |
| 14 | 6.7 | 49.5 |
| 15 | 23.3 | 47.6 |
| 16 | 10.4 | 42.9 |
| 17 | 17.9 | 41.6 |
| 18 | 24.3 | 40.5 |
| 19 | 16.7 | 39.1 |
| 20 | 22.5 | 35.2 |
| 21 | 22.8 | 31.6 |
| 22 | 17.6 | 30.3 |
| 23 | 17.4 | 29.0 |
| 24 | 9.9 | 25.1 |
| 25 | 25.8 | 23.3 |
| 26 | 26.0 | 23.3 |
| 27 | 15.2 | 19.3 |
| 28 | 14.0 | 15.3 |
| 29 | 9.5 | 14.2 |
| 30 | 8.9 | 10.9 |
| 31 | 6.1 | 10.0 |

TABLE 27

Compound I calcium salt IPA solvate
(air-dried sample) Form B

| XRPD Peaks | Angle (degrees 2-Theta ± 0.2) | Intensity % |
|---|---|---|
| 1 | 5.3 | 100.0 |
| 2 | 6.3 | 48.6 |
| 3 | 8.8 | 43.9 |

TABLE 27-continued

Compound I calcium salt IPA solvate
(air-dried sample) Form B

| XRPD Peaks | Angle (degrees) 2-Theta ± 0.2) | Intensity % |
|---|---|---|
| 4 | 15.7 | 29.8 |
| 5 | 13.1 | 24.4 |
| 6 | 19.9 | 23.6 |
| 7 | 17.9 | 19.6 |
| 8 | 21.6 | 17.2 |
| 9 | 4.4 | 10.0 |

Example 16: Compound I Calcium Salt NPA Solvate

~45 mg of Compound I calcium salt hydrate Form A was stirred in ~0.5 mL of NPA at room temperature. ~5 mg of each of Compound I calcium salt hydrate Form B and D were added to the mixture. The mixture was stirred at room for 13 d. A solid was isolated via centrifuge filtration.

A. X-Ray Powder Diffraction

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96-well sample holder with mylar film and loaded into the instrument. The sample was scanned over the range of about 3° to about 40° 2θ with a step size of 0.0131303° and 49 s per step.

Figure 22A:
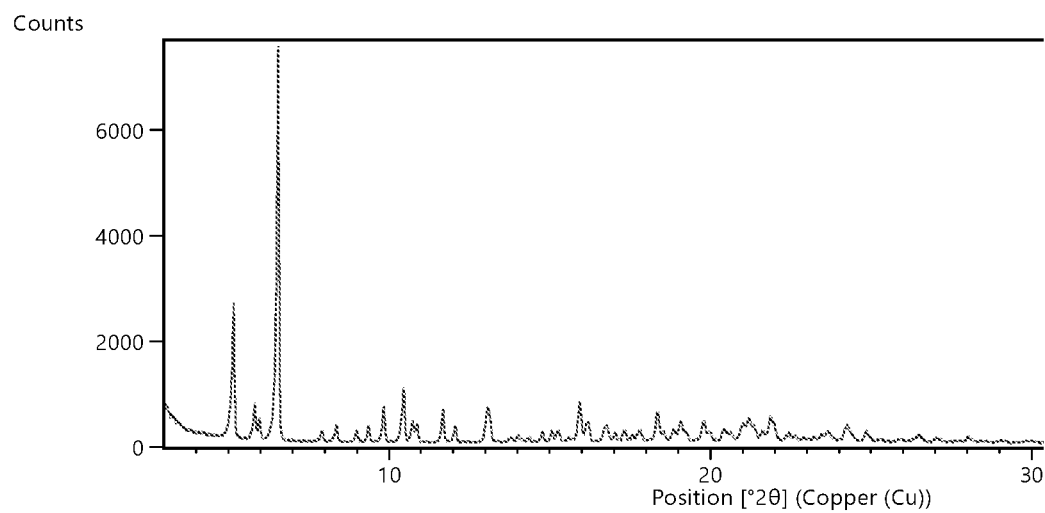
FIG. 22A and FIG. 22B provide XRPD patterns of crystalline Compound I calcium salt NPA solvate.
Figure 22B:
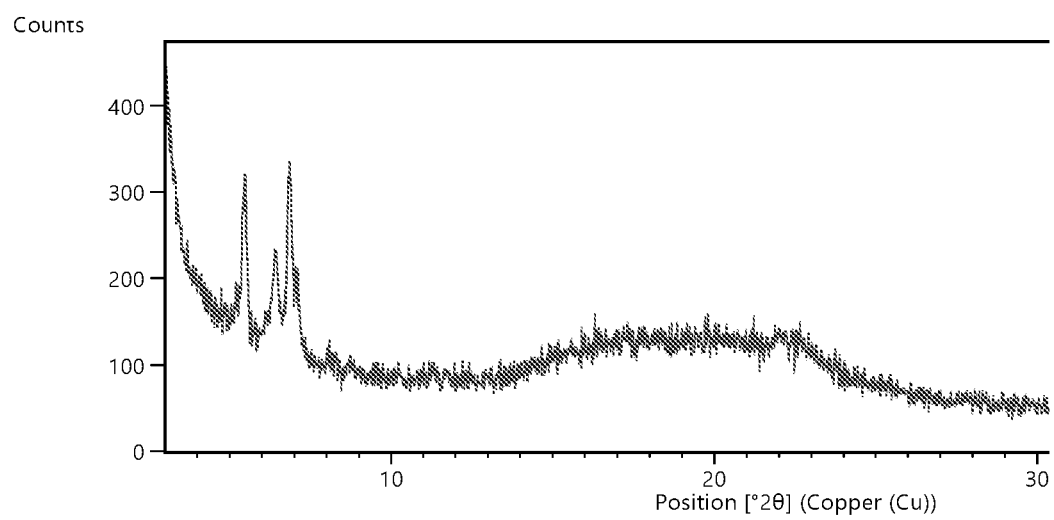

This material is labile. X-Ray Powder Diffraction pattern varied depending on how the samples were dried. The XRPD diffractogram for wet Compound I calcium salt NPA solvate Form A is shown in FIG. 22A and summarized in Table 28. The XRPD diffractogram for air-dried Compound I calcium salt NPA solvate Form B is shown in FIG. 22B and summarized in Table 29.

TABLE 28

Compound I calcium salt NPA solvate
(wet sample) Form A

| XRPD Peaks | Angle (degrees) 2-Theta ± 0.2) | Intensity % |
|---|---|---|
| 1 | 6.5 | 100.0 |
| 2 | 5.2 | 33.7 |
| 3 | 10.5 | 13.5 |
| 4 | 15.9 | 10.1 |

TABLE 29

Compound I calcium salt NPA solvate
(air-dried sample) Form B

| XRPD Peaks | Angle (degrees) 2-Theta ± 0.2) | Intensity % |
|---|---|---|
| 1 | 6.9 | 100.0 |
| 2 | 5.5 | 65.5 |
| 3 | 6.4 | 47.4 |
| 4 | 7.1 | 31.5 |

Example 17: Compound I Calcium Salt 2-BuOH Solvate 50 mg of Compound I calcium salt hydrate Form A was stirred in 1 mL of 2-butanol at room temperature for 4 d to provide Compound I calcium salt 2-BuOH solvate.

A. X-Ray Powder Diffraction

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96-well sample holder with mylar film and loaded into the instrument. The sample was scanned over the range of about 3° to about 40°2θ with a step size of 0.0131303° and 49 s per step.

Figure 23A:
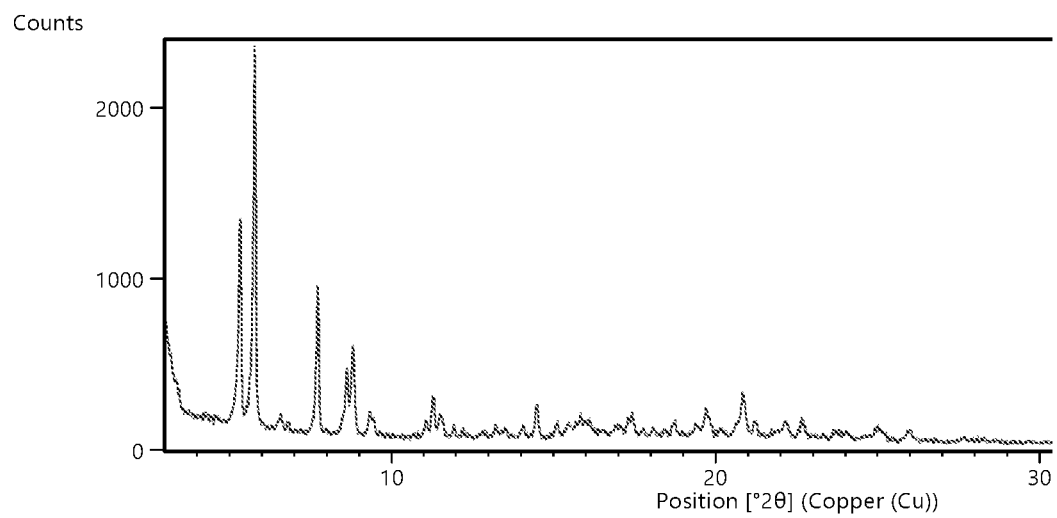
FIG. 23A and FIG. 23B provide XRPD patterns of crystalline Compound I calcium salt 2-BuOH solvate.
Figure 23B:
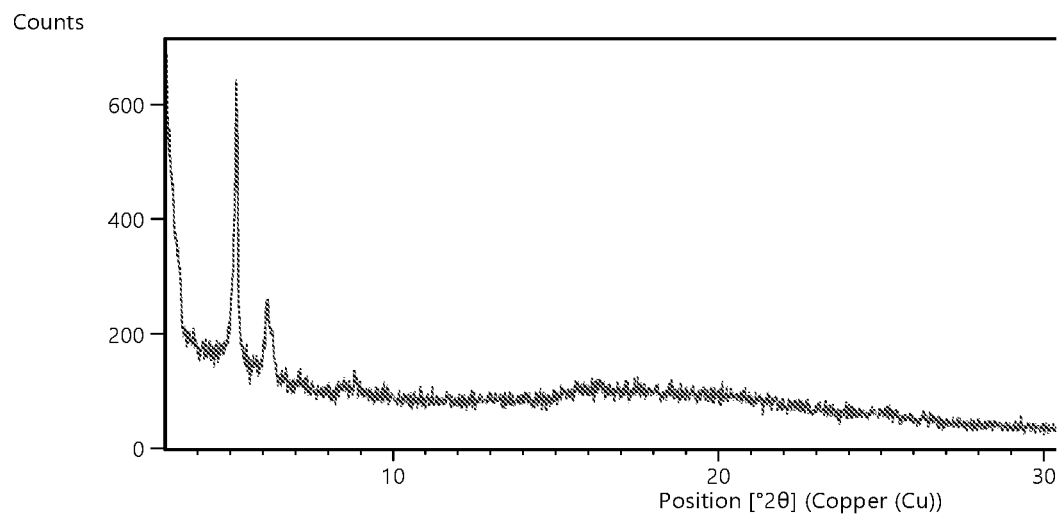

This material is labile. X-Ray Powder Diffraction pattern varied depending on how the samples were dried. The XRPD diffractogram for wet Compound I calcium salt 2-BuOH solvate Form A is shown in FIG. 23A and summarized in Table 30 The XRPD diffractogram for air-dried Compound I calcium salt 2-BuOH solvate Form B is shown in FIG. 23B and summarized in Table 31.

TABLE 30

Compound I calcium salt 2-BuOH
solvate (wet sample) Form A

| XRPD Peaks | Angle (degrees) 2-Theta ± 0.2) | Intensity % |
|---|---|---|
| 1 | 5.8 | 100.0 |
| 2 | 5.3 | 56.0 |
| 3 | 7.7 | 39.0 |
| 4 | 8.8 | 24.1 |
| 5 | 8.6 | 18.2 |
| 6 | 20.9 | 12.1 |
| 7 | 11.3 | 11.5 |

TABLE 31

Compound I calcium salt 2-BuOH solvate
(air-dried sample) Form B

| XRPD Peaks | Angle (degrees) 2-Theta ± 0.2) | Intensity % |
|---|---|---|
| 1 | 5.2 | 100.0 |
| 2 | 6.1 | 22.6 |
| 3 | 8.7 | 2.9 |

Example 18: Compound I Calcium Salt Acetone Solvate Form A

Compound I calcium salt acetone solvate Form A was made by slurrying Compound I calcium salt amorphous form in acetone at 4° C. This material was very labile. It quickly dried to Compound I calcium salt hydrate Form C when air-dried.

A. X-Ray Powder Diffraction

Figure 24:
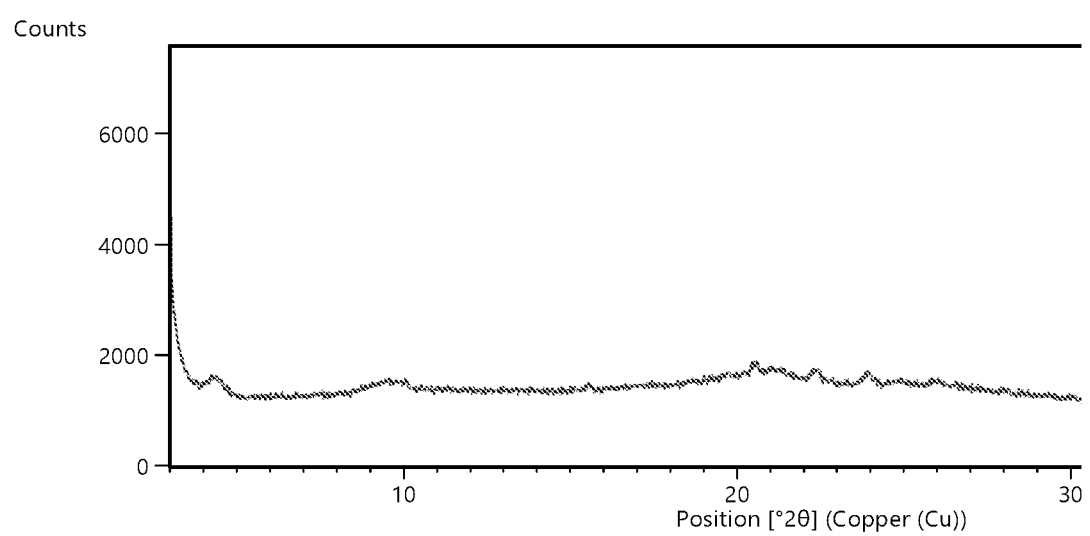
FIG. 24 provides an XRPD pattern of crystalline Compound I calcium salt acetone solvate Form A.

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96-well sample holder with mylar film and loaded into the instrument. The sample was scanned over the range of about 3° to about 40°2θ with a step size of 0.0131303° and 49 s per step. The XRPD diffractogram for Compound I calcium salt acetone solvate Form A is shown in FIG. 24 and summarized in Table 32.

TABLE 32

Compound I calcium salt acetone solvate Form A

| XRPD Peaks | Angle (degrees 2-Theta ± 0.2) | Intensity % |
|---|---|---|
| 1 | 20.5 | 100.0 |
| 2 | 22.4 | 80.8 |
| 3 | 23.9 | 75.6 |
| 4 | 4.3 | 59.5 |
| 5 | 9.6 | 57.9 |
| 6 | 26.0 | 41.6 |

Example 19: Compound I Calcium Salt DCM Solvate Form A

Compound I calcium salt DCM solvate Form A was made by adding DCM to Compound I calcium salt hydrate Form C. This material was very labile. It quickly dried to Compound I calcium salt hydrate Form C when filtered.

A. X-Ray Powder Diffraction

Figure 25:
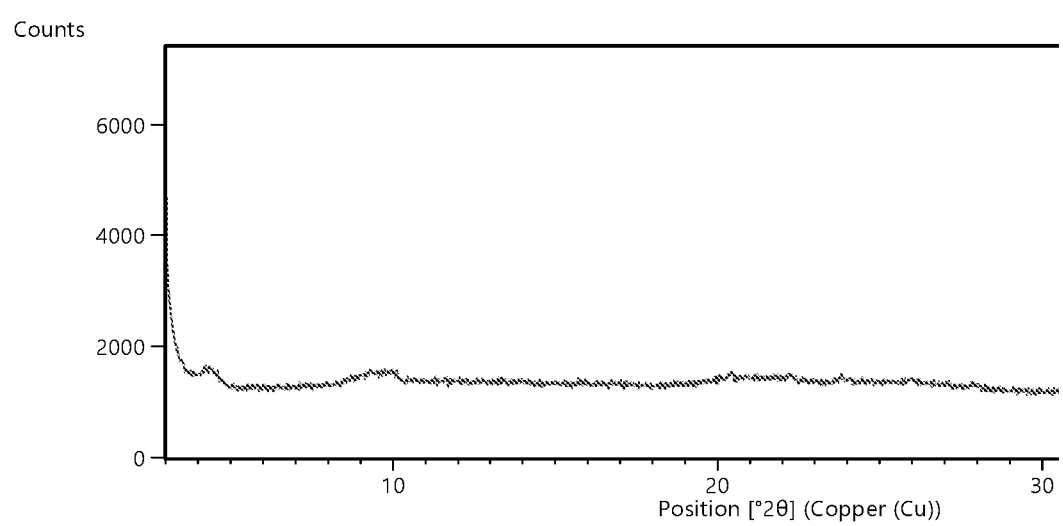
FIG. 25 provides an XRPD pattern of crystalline Compound I calcium salt DCM solvate Form A.

The XRPD patterns were acquired at room temperature in reflection mode using a Bruker Advance equipped with Vantec-1 detector. A sample was analyzed on a silicon sample holder from 3-40° 2-theta on continuous mode with step size of 0.0144531° and time per step of 0.25 s. The sample was spinning at 15 rpm. The XRPD diffractogram for Compound I calcium salt DCM solvate Form A is shown in FIG. 25 and summarized in Table 33.

TABLE 33

Compound I calcium salt DCM solvate (air-dried sample) Form A

| XRPD Peaks | Angle (degrees 2-Theta ± 0.2) | Intensity % |
|---|---|---|
| 1 | 9.9 | 100.0 |
| 2 | 4.3 | 86.5 |
| 3 | 23.9 | 33.1 |
| 4 | 20.6 | 29.4 |

B. Solid State NMR

Figure 26:
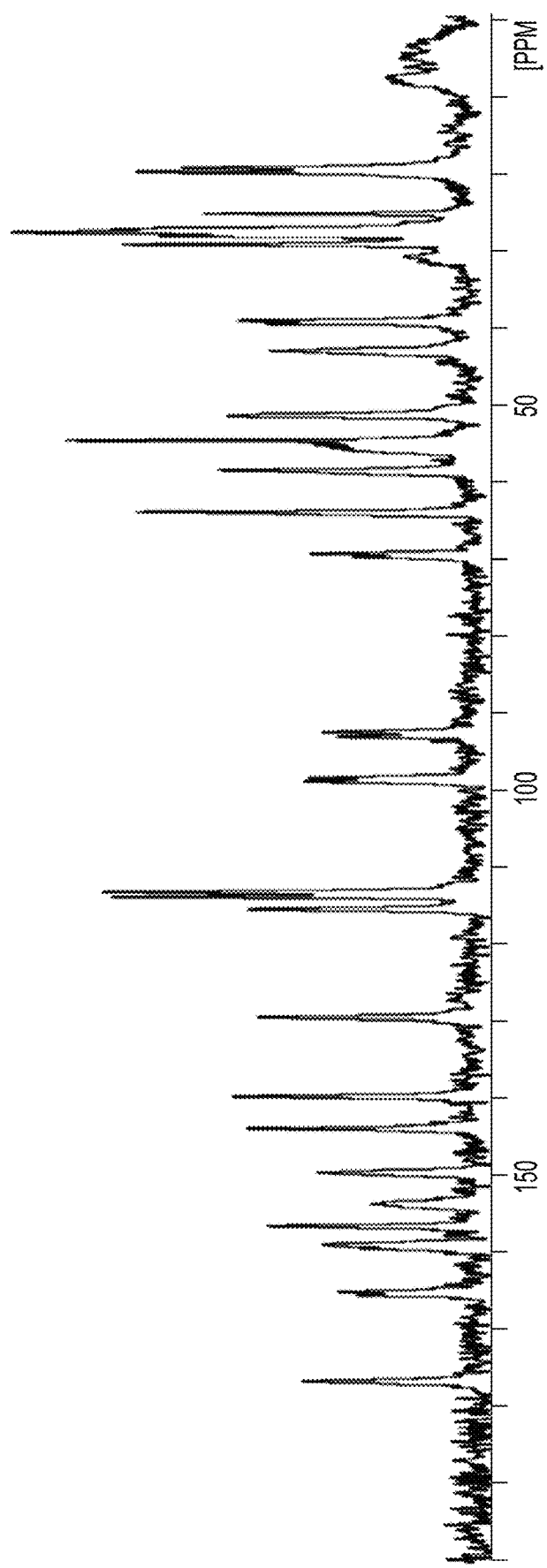
FIG. 26 shows a $^{13}$C solid state NMR spectrum of Compound I calcium salt DCM solvate Form A.

Solid state $^{13}$C NMR spectrum for Compound I calcium salt DCM solvate Form A is provided in FIG. 26 and summarized in Table 34.

TABLE 34

Solid state NMR of Compound I calcium salt DCM solvate Form A

| Peak # | Chem Shift [ppm] ± 0.2 | Intensity [rel] |
|---|---|---|
| 1 | 176.7 | 36.4 |
| 2 | 165.5 | 24.3 |
| 3 | 165.1 | 28.8 |
| 4 | 159.0 | 32.3 |
| 5 | 156.5 | 44.6 |
| 6 | 153.8 | 21.6 |

TABLE 34-continued

Solid state NMR of Compound I calcium salt DCM solvate Form A

| Peak # | Chem Shift [ppm] ± 0.2 | Intensity [rel] |
|---|---|---|
| 7 | 149.6 | 33.3 |
| 8 | 143.9 | 48.3 |
| 9 | 139.7 | 52.3 |
| 10 | 129.5 | 46.3 |
| 11 | 115.4 | 48.6 |
| 12 | 113.8 | 77.6 |
| 13 | 113.2 | 80.4 |
| 14 | 98.8 | 36.1 |
| 15 | 98.4 | 35.2 |
| 16 | 93.6 | 9 |
| 17 | 93.1 | 28.8 |
| 18 | 92.5 | 32.4 |
| 19 | 69.7 | 25.6 |
| 20 | 69.2 | 35.4 |
| 21 | 63.9 | 72.6 |
| 22 | 58.5 | 54.7 |
| 23 | 57.1 | 8.9 |
| 24 | 55.2 | 33.9 |
| 25 | 54.9 | 34.5 |
| 26 | 54.6 | 88.7 |
| 27 | 51.5 | 52.9 |
| 28 | 42.9 | 43.8 |
| 29 | 39.4 | 44.8 |
| 30 | 39.0 | 50.6 |
| 31 | 30.7 | 14.6 |
| 32 | 29.2 | 75.3 |
| 33 | 28.1 | 67.4 |
| 34 | 27.6 | 100.0 |
| 35 | 27.2 | 77.5 |
| 36 | 25.2 | 58.6 |
| 37 | 19.8 | 72.6 |
| 38 | 19.2 | 63.0 |
| 39 | 7.6 | 18.4 |
| 40 | 6.1 | 14.5 |
| 41 | 5.0 | 15.5 |
| 42 | 3.5 | 14.0 |

Example 20: Compound I Calcium Salt Ethylene Glycol Solvate Form A 75 mg of Compound I calcium salt hydrate Form A was stirred in 1 mL of ethylene glycol at room temperature for 4 d. Sample was isolated via centrifuge filtration, then dried at 60° C. over 3 d to provide Compound I calcium salt ethylene glycol solvate Form A.

A. X-Ray Powder Diffraction

Figure 27:
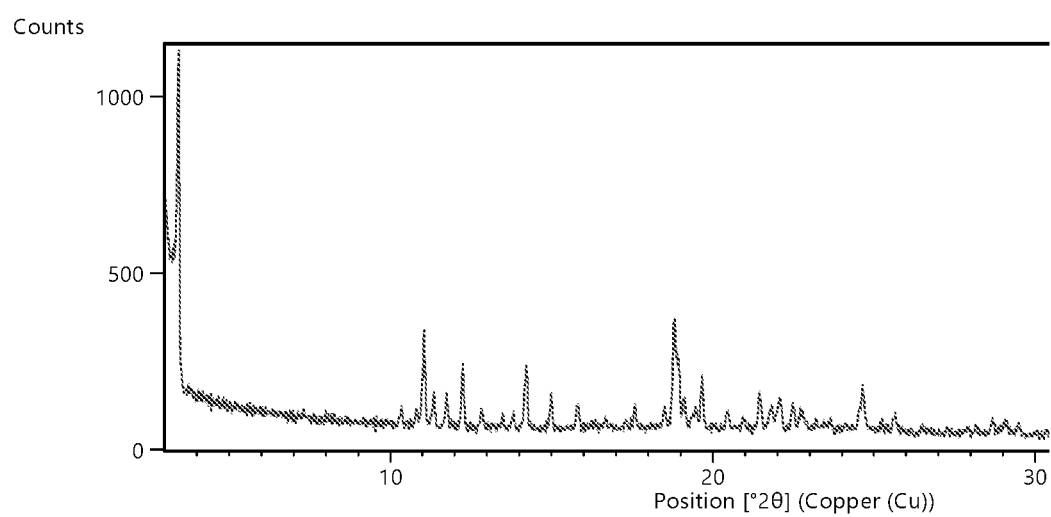
FIG. 27 provides an XRPD pattern of crystalline Compound I calcium salt ethylene glycol solvate Form A.

X-ray powder diffraction (XRPD) spectra were recorded at room temperature in transmission mode using a PANalytical Empyrean system equipped with a sealed tube source and a PIXcel ID Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96-well sample holder with mylar film and loaded into the instrument. The sample was scanned over the range of about 3° to about 40°2θ with a step size of 0.0131303° and 49 s per step. The XRPD diffractogram for Compound I calcium salt ethylene glycol solvate Form A is shown in FIG. 27 and summarized in Table 35.

TABLE 35

Compound I calcium salt ethylene glycol solvate Form A

| XRPD Peaks | Angle (degrees 2-Theta ± 0.2) | Intensity % |
|---|---|---|
| 1 | 3.4 | 100.0 |
| 2 | 18.8 | 31.8 |
| 3 | 11.0 | 27.0 |
| 4 | 14.2 | 17.4 |
| 5 | 12.2 | 15.8 |
| 6 | 19.7 | 15.4 |
| 7 | 24.7 | 12.4 |

B. Solid State NMR

Figure 28:
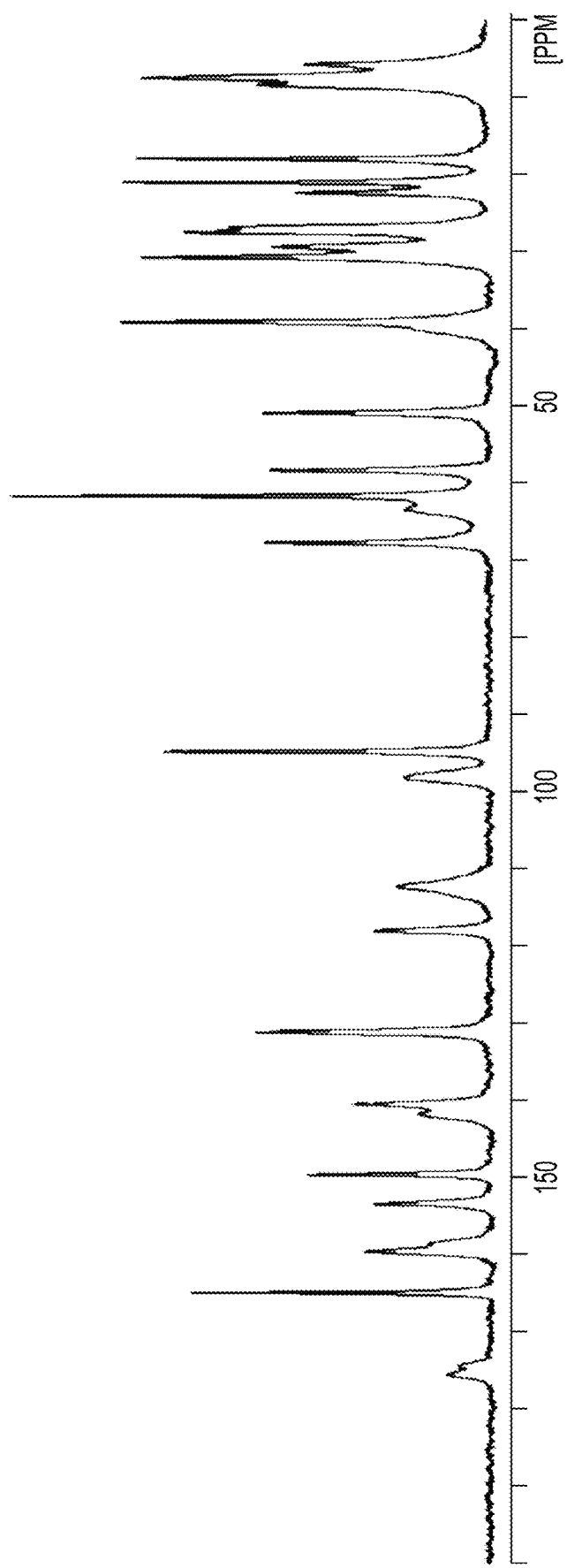
FIG. 28 shows a $^{13}$C solid state NMR spectrum of Compound I calcium salt ethylene glycol solvate Form A.

Solid state $^{13}$C NMR spectrum for Compound I calcium salt ethylene glycol solvate Form A is provided in FIG. 28 and summarized in Table 36.

TABLE 36

Solid state NMR Compound I calcium salt ethylene glycol solvate Form A

| Peak # | Chem Shift [ppm] ± 0.2 | Intensity [rel] |
|---|---|---|
| 1 | 175.7 | 8.9 |
| 2 | 174.5 | 6.7 |
| 3 | 165.0 | 61.5 |
| 4 | 159.7 | 26.1 |
| 5 | 158.7 | 12.9 |
| 6 | 153.5 | 24.2 |
| 7 | 149.7 | 37.9 |
| 8 | 141.8 | 14.7 |
| 9 | 140.5 | 28.1 |
| 10 | 131.2 | 48.7 |
| 11 | 118.0 | 24.1 |
| 12 | 112.2 | 19 |
| 13 | 98.1 | 17.7 |
| 14 | 94.7 | 67.2 |
| 15 | 67.5 | 46.6 |
| 16 | 63.4 | 17.7 |
| 17 | 61.5 | 100 |
| 18 | 58.1 | 45.6 |
| 19 | 50.7 | 47.1 |
| 20 | 38.9 | 76.1 |
| 21 | 30.5 | 72.0 |
| 22 | 29.1 | 45.0 |
| 23 | 27.2 | 63.5 |
| 24 | 26.6 | 53.8 |
| 25 | 22.1 | 40.2 |
| 26 | 20.7 | 75.8 |
| 27 | 17.6 | 73.1 |
| 28 | 8.0 | 48.3 |
| 29 | 7.1 | 72.2 |
| 30 | 5.4 | 38.4 |

Example 21: Compound I Calcium Salt Ethylene Glycol Solvate Form B

Compound I calcium salt ethylene glycol solvate Form B was obtained via slurry of Compound I calcium salt hydrate Form A in ethylene glycol at 80° C.

A. X-Ray Powder Diffraction

Figure 29:
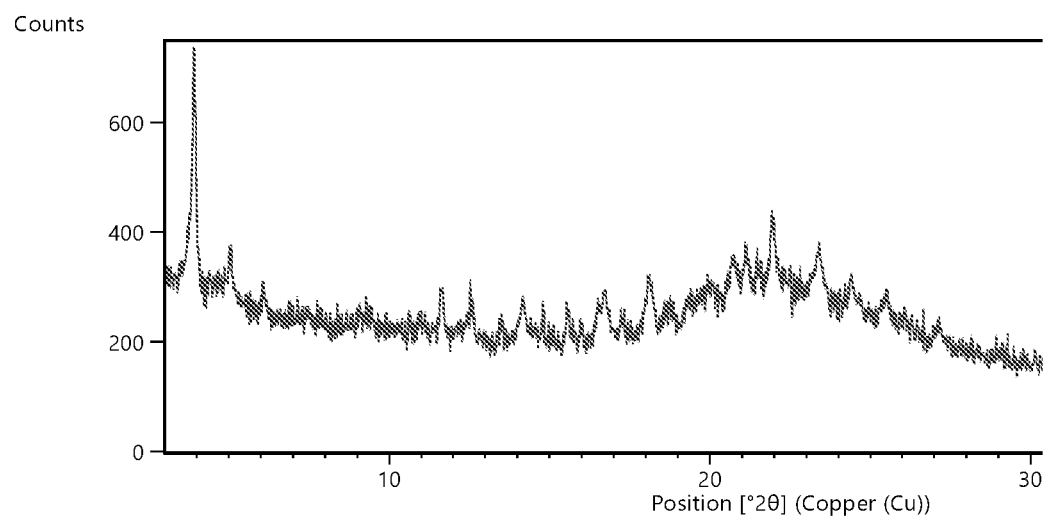
FIG. 29 provides an XRPD pattern of crystalline Compound I calcium salt ethylene glycol solvate Form B.

XRPD was performed with a Panalytical X'Pert³ Powder XRPD on a Si zero-background holder. The 2 theta position was calibrated against a Panalytical Si reference standard disc. The XRPD diffractogram for Compound I calcium salt ethylene glycol solvate Form B is shown in FIG. 29 and summarized in Table 37.

TABLE 37

Compound I calcium salt ethylene glycol solvate Form B

| XRPD Peaks | Angle (degrees 2-Theta ± 0.2) | Intensity % |
|---|---|---|
| 1 | 3.9 | 100.0 |
| 2 | 22.0 | 38.7 |
| 3 | 23.4 | 27.6 |
| 4 | 21.1 | 27.0 |
| 5 | 20.7 | 25.8 |
| 6 | 5.0 | 24.6 |
| 7 | 21.5 | 21.3 |
| 8 | 18.1 | 20.2 |
| 9 | 11.6 | 17.6 |
| 10 | 12.5 | 15.3 |
| 11 | 14.2 | 14.7 |
| 12 | 24.4 | 14.3 |
| 13 | 16.7 | 14.1 |

Example 22: Compound I Calcium Salt 1,2-Dimethoxyethane Solvate Form A 50 mg of Compound I calcium salt hydrate Form A was stirred in 1 mL of 1,2-dimethoxyethane at room temperature for 4 d to provide Compound I calcium salt 1,2-dimethoxyethane solvate Form A.

A. X-Ray Powder Diffraction

Figure 30:
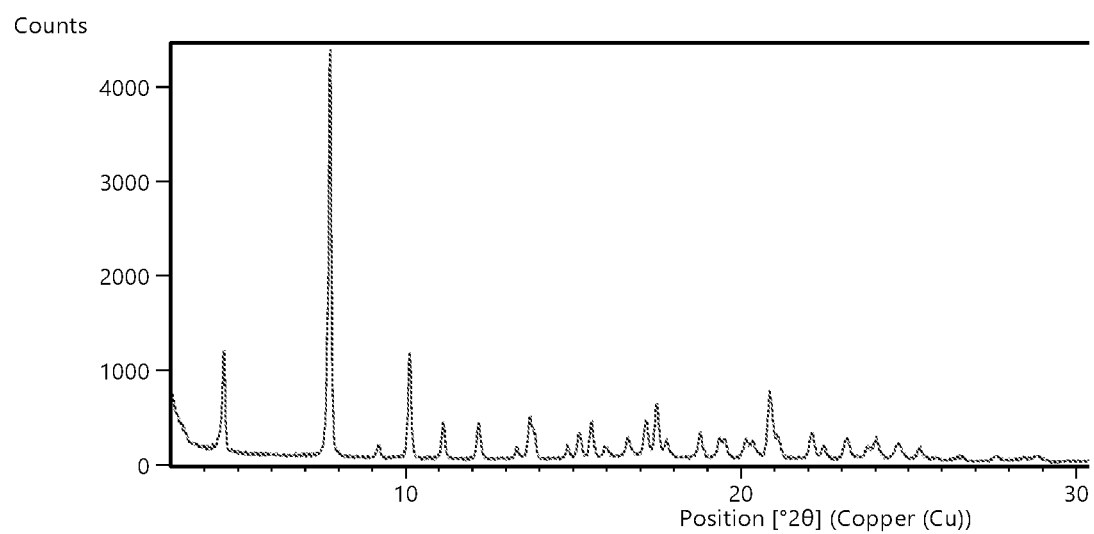
FIG. 30 provides an XRPD pattern of crystalline Compound I calcium salt 1,2-dimethoxyethane solvate Form A.

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96-well sample holder with mylar film and loaded into the instrument. The sample was scanned over the range of about 3° to about 400 2θ with a step size of 0.0131303° and 49 s per step. The XRPD diffractogram for Compound I calcium salt 1,2-dimethoxyethane solvate Form A is shown in FIG. 30 and summarized in Table 38.

TABLE 38

Compound I calcium salt 1,2-dimethoxyethane solvate Form A

| XRPD Peaks | Angle (degrees 2-Theta ± 0.2) | Intensity % |
|---|---|---|
| 1 | 7.7 | 100.0 |
| 2 | 10.1 | 25.7 |
| 3 | 4.6 | 24.5 |
| 4 | 20.9 | 17.2 |
| 5 | 17.5 | 13.4 |
| 6 | 13.7 | 10.6 |

B. Solid State NMR

Figure 31:
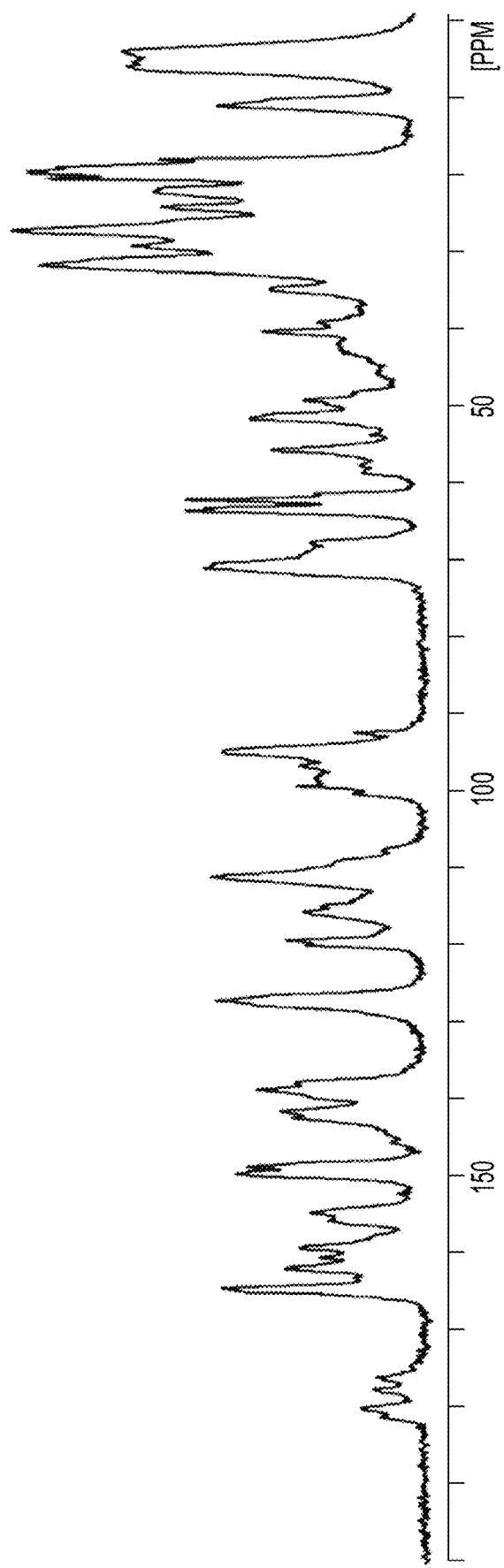
FIG. 31 shows a $^{13}$C solid state NMR spectrum of Compound I calcium salt 1,2-dimethoxyethane solvate Form A.

Solid state $^{13}$C NMR spectrum for Compound I calcium salt 1,2-dimethoxyentane solvate Form A is provided in FIG. 31 and summarized in Table 39.

TABLE 39

Solid state NMR Compound I calcium salt
1,2-dimethoxyethane solvate Form A

| Peak # | Chem Shift [ppm] ± 0.2 | Intensity [rel] |
|---|---|---|
| 1 | 181.5 | 9.9 |
| 2 | 180.1 | 15.1 |
| 3 | 177.7 | 12.6 |
| 4 | 176.2 | 11.9 |
| 5 | 164.6 | 49.3 |
| 6 | 162.0 | 34.1 |
| 7 | 160.7 | 25.4 |
| 8 | 159.5 | 30.5 |
| 9 | 154.9 | 27.8 |
| 10 | 149.8 | 45.8 |
| 11 | 148.9 | 43.2 |
| 12 | 142.5 | 32.3 |
| 13 | 141.6 | 35.4 |
| 14 | 138.8 | 40.7 |
| 15 | 127.3 | 50.9 |
| 16 | 120.1 | 28.9 |
| 17 | 119.4 | 33.5 |
| 18 | 115.8 | 29.6 |
| 19 | 115.0 | 25.3 |
| 20 | 111.2 | 52.0 |
| 21 | 107.9 | 10.7 |
| 22 | 100.3 | 17.7 |
| 23 | 99.4 | 31.4 |
| 24 | 98.3 | 27.0 |
| 25 | 96.8 | 30.4 |
| 26 | 95.0 | 49.3 |
| 27 | 92.5 | 17.4 |
| 28 | 71.1 | 53.6 |
| 29 | 67.7 | 27.8 |
| 30 | 63.7 | 58.3 |
| 31 | 63.3 | 53.6 |
| 32 | 62.3 | 58.1 |
| 33 | 61.5 | 27.1 |
| 34 | 58.7 | 15.3 |
| 35 | 57.7 | 15.9 |
| 36 | 55.8 | 37.3 |
| 37 | 53.8 | 13.4 |
| 38 | 51.8 | 42.3 |
| 39 | 49.3 | 29.4 |
| 40 | 46.0 | 11.7 |
| 41 | 42.0 | 21.3 |
| 42 | 40.4 | 39.6 |
| 43 | 39.2 | 26.1 |
| 44 | 34.9 | 37.6 |
| 45 | 31.8 | 93.6 |
| 46 | 29.3 | 71.3 |
| 47 | 27.3 | 100.0 |
| 48 | 24.2 | 64.2 |
| 49 | 22.2 | 66.0 |
| 50 | 20.5 | 92.0 |
| 51 | 19.7 | 96.4 |
| 52 | 19.1 | 89.6 |
| 53 | 18.1 | 64.4 |
| 54 | 11.1 | 50.6 |
| 55 | 5.9 | 72.1 |
| 56 | 4.0 | 73.7 |

Example 23: Compound I Calcium Salt
1,2-Dimethoxyethane Solvate Form B

Compound I calcium salt 1,2-dimethoxyethane solvate Form B was obtained via slurry of Compound I calcium salt hydrate Form A in 1,2-dimethoxyethane at room temperature.

A. X-Ray Powder Diffraction

Figure 32:
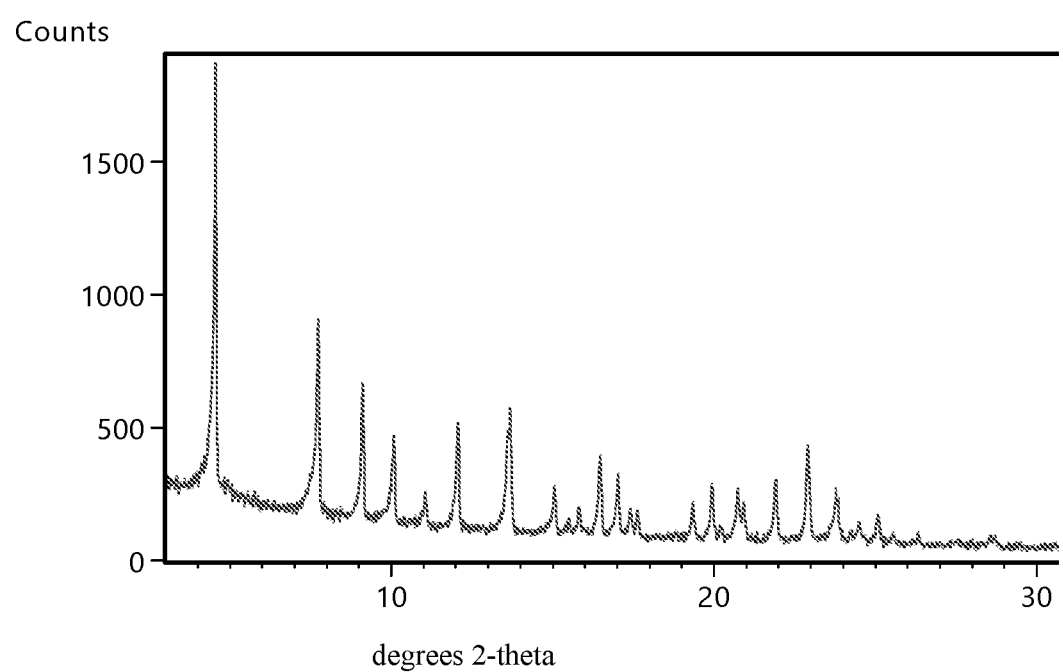
FIG. 32 provides an XRPD pattern of crystalline Compound I calcium salt 1,2-dimethoxyethane solvate Form B.

XRPD was performed with a Panalytical X'Pert³ Powder XRPD on a Si zero-background holder. The 2θ position was calibrated against a Panalytical Si reference standard disc. The XRPD diffractogram for Compound I calcium salt 1,2-dimethoxy ethane solvate Form B is shown in FIG. 32 and summarized in Table 40.

TABLE 40

Compound I calcium salt 1,2-dimethoxyethane solvate Form B

| XRPD Peaks | Angle (degrees 2-Theta ± 0.2) | Intensity % |
|---|---|---|
| 1 | 4.6 | 100.0 |
| 2 | 7.7 | 43.7 |
| 3 | 9.1 | 30.4 |
| 4 | 13.7 | 27.4 |
| 5 | 12.1 | 23.7 |
| 6 | 22.9 | 20.6 |
| 7 | 10.1 | 19.2 |
| 8 | 16.5 | 18.0 |
| 9 | 17.0 | 14.4 |
| 10 | 21.9 | 13.6 |
| 11 | 19.9 | 11.8 |
| 12 | 20.7 | 11.6 |
| 13 | 15.1 | 10.7 |
| 14 | 23.8 | 10.4 |

Example 24: Compound I Calcium Salt CPME Solvate Form A

Compound I calcium salt cyclopentyl methyl ether (CPME) solvate Form A was obtained via slurry of Compound I calcium salt Form A in IPA/CPME (1:1, v/v) at room temperature.

A. X-Ray Powder Diffraction

Figure 33:
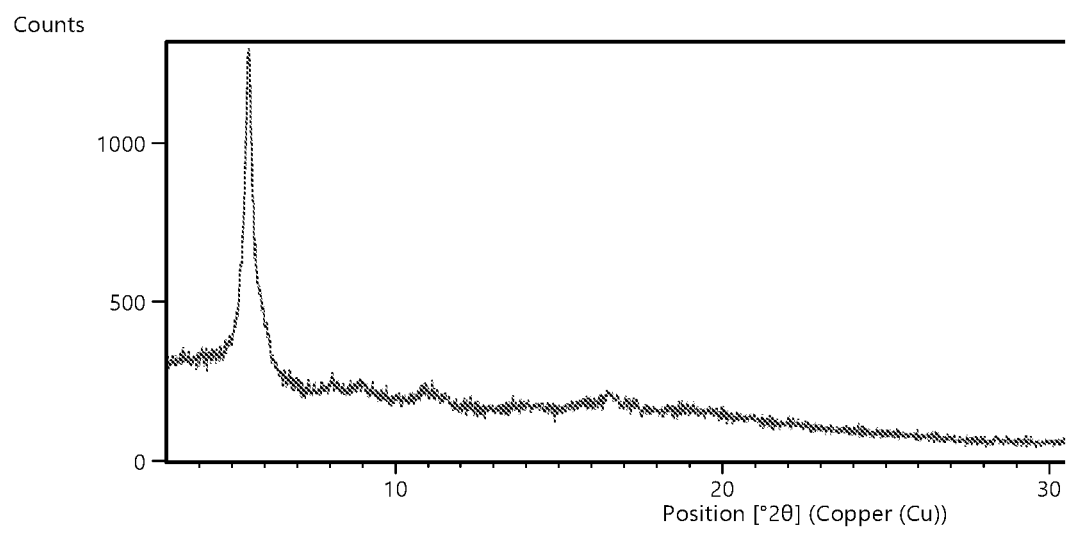
FIG. 33 provides an XRPD pattern of crystalline Compound I calcium salt CPME solvate Form A.

XRPD was performed with a Panalytical X'Pert³ Powder XRPD on a Si zero-background holder. The 2θ position was calibrated against a Panalytical Si reference standard disc. The XRPD diffractogram for Compound I calcium salt CPME solvate Form A is shown in FIG. 33 and summarized in Table 41.

TABLE 41

Compound I calcium salt CPME solvate Form A

| XRPD Peaks | Angle (degrees 2-Theta ± 0.2) | Intensity % |
|---|---|---|
| 1 | 5.5 | 100 |
| 2 | 16.6 | 4.38 |
| 3 | 11.0 | 3.86 |

Example 25: Compound I Sodium Salt Hydrate Form A

About 60 mg of Compound I sodium salt amorphous material was charged with either IPA/water (>4% of water by volume) or ACN/water (>1% of water by volume) mixture at 40 mg/mL and stirred at room temperature for 2 weeks. The solid was isolated as Compound I sodium salt hydrate Form A by vacuum filtration and dried under vacuum at 40° C. for over weekend.

Alternatively, 100 g of Compound I (free form) was charged with 400 mL IPA and 400 mL water. The slurry was heated to 55-65° C. The slurry was charged with 1.1 equiv of NaOH. The mixture was allowed to stir until the solution turned homogeneous. The solution was then cooled to 40° C. and seeded with 1 g of the Compound I Na hydrate Form A. Water (800 mL) was charged over a 5 h period. The resulting slurry was allowed to stir for 2 h. The slurry was cooled to 20° C. over a 5 h period of time. The resulting solids were collected by vacuum filtration and wet cake was washed with 500 mL of water. The washed wet cake was allowed to air-dry for 1 h. The air-dried wet cake was transferred to a vacuum oven at 45° C. with a slight nitrogen bleed for 20 h to yield 96.2 g crystalline Compound I sodium hydrate Form A (93% isolated yield).

A. X-Ray Powder Diffraction

The XRPD patterns are acquired at room temperature in reflection mode using a Bruker Advance equipped with Vantec-1 detector. Sample was analyzed on a silicon sample holder from 3-40° 2-theta on continuous mode with step size of 0.0144531° and time per step of 0.25 s. Sample was spinning at 15 rpm. The XRPD diffractogram for Compound I sodium salt hydrate Form A is shown in FIG. 34 and summarized in Table 42.

TABLE 42

Compound I sodium salt hydrate Form A

| XRPD Peaks | Angle (degrees 2-Theta ± 0.2) | Intensity % |
|---|---|---|
| 1 | 5.4 | 100.0 |
| 2 | 15.9 | 63.5 |
| 3 | 17.6 | 43.0 |
| 4 | 15.3 | 23.7 |
| 5 | 18.6 | 16.8 |
| 6 | 21.3 | 15.8 |
| 7 | 23.9 | 14.0 |
| 8 | 20.0 | 11.1 |
| 9 | 26.7 | 10.3 |

B. Single Crystal Elucidation

X-ray diffraction data were acquired at 100K on a Bruker diffractometer utilizing synchrotron radiation (0.7288 Å), provided by beamline 12.2.1 at the Advanced Light Source Lawrence Berkeley National Laboratory, and an CMOS detector. The structure was solved and refined using SHELX program (Sheldrick, G. M., Acta Cryst., (2008) A64, 112-122) and results are summarized in Table 43 below.

TABLE 43

Single crystal elucidation of Compound I sodium salt hydrate Form A

| | |
|---|---|
| Crystal System: | Orthorhombic |
| Space Group: | P212121 |
| a (Å) | 8.2320(3) |
| b (Å) | 11.8526(4) |
| c (Å) | 33.0905(12) |
| α (°) | 90 |
| β (°) | 90 |
| γ (°) | 90 |
| γ (Å$^3$) | 3228.7(2) |
| Z/Z' | 4/1 |
| Temperature | 100 K |

C. Solid State NMR

Solid state $^{13}$C NMR spectrum for Compound I sodium salt hydrate Form A (275K; CZ; $^1$H T$_1$=5.4 s; D$_1$=7 s) is provided in FIG. 35 and summarized in Table 44.

TABLE 44

Solid state NMR Compound I sodium salt hydrate Form A

| Peak # | Chem Shift [ppm] | Intensity [rel] |
|---|---|---|
| 1 | 177.0 | 18.0 |
| 2 | 166.3 | 27.2 |
| 3 | 159.6 | 51.8 |
| 4 | 153.1 | 13.8 |
| 5 | 148.6 | 17.7 |
| 6 | 140.6 | 32.6 |

TABLE 44-continued

Solid state NMR Compound I sodium salt hydrate Form A

| Peak # | Chem Shift [ppm] | Intensity [rel] |
|---|---|---|
| 7 | 138.5 | 40.8 |
| 8 | 129.2 | 30.2 |
| 9 | 118.3 | 22.4 |
| 10 | 114.7 | 35.3 |
| 11 | 107.0 | 42.3 |
| 12 | 97.1 | 37.7 |
| 13 | 96.4 | 50.4 |
| 14 | 70.6 | 51.9 |
| 15 | 63.4 | 46.9 |
| 16 | 56.6 | 36.9 |
| 17 | 51.9 | 58.4 |
| 18 | 40.0 | 32.1 |
| 19 | 38.3 | 50.3 |
| 20 | 31.5 | 29.5 |
| 21 | 28.9 | 100.0 |
| 22 | 28.5 | 56.3 |
| 23 | 28.1 | 51.5 |
| 24 | 26.2 | 72.6 |
| 25 | 21.9 | 46.7 |
| 26 | 19.7 | 77.5 |
| 27 | 18.4 | 76.5 |
| 28 | 6.5 | 80.3 |
| 29 | 1.2 | 22.5 |

D. Differential Scanning Calorimetry Analysis

A DSC thermogram was obtained using TA Instruments DSC Q2000. Sample was heated at 10° C./min from 30° C. to 350° C. The thermogram showed two endothermic peaks at ~108° C. and ~290° C.

Example 26: Compound I Sodium Salt Neat Form B

Compound I sodium salt neat Form B was obtained from desolvating/dehydrating ~10 mg of Compound I sodium salt hydrate Form C in a TGA pan at 10° C./min to 306° C.

A. X-Ray Powder Diffraction:

The powder x-ray diffraction measurement was performed using PANalytical's X-pert Pro diffractometer at room temperature with copper radiation (1.54060 Å). The incident beam optic was comprised of a variable divergence slit to ensure a constant illuminated length on the sample and on the diffracted beam sides. A fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 s. The XRPD diffractogram for Compound I sodium salt neat Form B is shown in FIG. 36 and summarized in Table 45.

TABLE 45

Compound I sodium salt neat Form B

| XRPD Peaks | Angle (degrees 2-Theta ± 0.2) | Intensity % |
|---|---|---|
| 1 | 20.5 | 100.0 |
| 2 | 18.1 | 75.5 |
| 3 | 11.0 | 65.9 |
| 4 | 22.2 | 54.1 |
| 5 | 14.3 | 50.0 |
| 6 | 17.4 | 42.8 |
| 7 | 21.5 | 38.2 |
| 8 | 15.3 | 38.0 |

TABLE 45-continued

Compound I sodium salt neat Form B

| XRPD Peaks | Angle (degrees 2-Theta ± 0.2) | Intensity % |
|---|---|---|
| 9 | 15.6 | 33.6 |
| 10 | 22.6 | 31.9 |
| 11 | 20.8 | 28.5 |
| 12 | 12.8 | 25.0 |
| 13 | 20.1 | 22.1 |
| 14 | 25.5 | 20.3 |
| 15 | 23.4 | 17.6 |
| 16 | 11.7 | 17.0 |
| 17 | 24.7 | 16.9 |
| 18 | 18.5 | 16.1 |
| 19 | 16.3 | 15.0 |
| 20 | 18.8 | 12.0 |
| 21 | 29.9 | 11.5 |
| 22 | 26.2 | 10.5 |

B. Differential Scanning Calorimetry Analysis

DSC was performed using TA Discovery differential scanning calorimeter (TA Instruments, New Castle, DE). The instrument was calibrated with indium. Samples of approximately 1-10 mg were weighed into hermetic pans that were crimped using lids with one hole. The DSC samples were scanned from 25° C. to 350° C. at a heating rate of 10° C./min. Data was collected and analyzed by Trios Analysis software (TA Instruments, New Castle, DE). The thermogram showed an endothermic peak at ~338° C.

Example 27: Compound I Sodium Salt Hydrate Form C

~66 mg of Compound I amorphous sodium salt was charged with ACN at 45 mg/mL and stirred at room temperature for 2 d. The solid was isolated by vacuum filtration and air-dried to provide Compound I sodium salt hydrate Form C A. X-Ray Powder Diffraction:

The powder x-ray diffraction measurement was performed using PANalytical's X-pert Pro diffractometer at room temperature with copper radiation (1.54060 Å). The incident beam optic was comprised of a variable divergence slit to ensure a constant illuminated length on the sample and on the diffracted beam sides. A fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 s. The XRPD diffractogram for Compound I sodium salt hydrate Form C is shown in FIG. 37 and summarized in Table 46.

TABLE 46

Compound I sodium salt hydrate Form C

| XRPD Peaks | Angle (degrees 2-Theta ± 0.2) | Intensity % |
|---|---|---|
| 1 | 6.1 | 100.0 |
| 2 | 13.4 | 95.8 |
| 3 | 19.2 | 84.8 |
| 4 | 21.7 | 64.6 |
| 5 | 20.0 | 57.1 |
| 6 | 19.5 | 56.9 |
| 7 | 20.7 | 48.4 |
| 8 | 10.3 | 46.8 |
| 9 | 7.9 | 45.2 |
| 10 | 18.8 | 43.9 |
| 11 | 15.9 | 43.2 |
| 12 | 4.5 | 38.6 |
| 13 | 23.6 | 32.5 |
| 14 | 17.0 | 30.9 |
| 15 | 22.5 | 29.8 |
| 16 | 11.3 | 26.4 |
| 17 | 25.2 | 26.1 |
| 18 | 18.4 | 25.8 |
| 19 | 22.0 | 24.8 |
| 20 | 23.4 | 23.2 |
| 21 | 14.2 | 22.3 |
| 22 | 24.4 | 21.8 |
| 23 | 26.1 | 21.1 |
| 25 | 24.2 | 21.0 |
| 26 | 25.5 | 20.1 |
| 27 | 26.8 | 17.4 |
| 28 | 23.0 | 16.9 |
| 32 | 16.7 | 11.5 |
| 36 | 9.0 | 10.8 |

B. Differential Scanning Calorimetry Analysis

DSC was performed using TA Discovery differential scanning calorimeter (TA Instruments, New Castle, DE). The instrument was calibrated with indium. Samples of approximately 1-10 mg were weighed into hermetic pans that were crimped using lids with one hole. The DSC samples were scanned from 25° C. to 350° C. at a heating rate of 10° C./min. Data was collected and analyzed by Trios Analysis software (TA Instruments, New Castle, DE). The thermogram showed endothermic peaks at ~51° C., ~339° C. and an exothermic peak at 301° C.

Example 28: Compound I Sodium Salt Hydrate Form D

Compound I sodium salt hydrate Form D was obtained by vacuum drying of Compound I sodium salt hydrate Form C under vacuum at 80° C. overnight.

A. X-Ray Powder Diffraction:

The powder x-ray diffraction measurement was performed using PANalytical's X-pert Pro diffractometer at room temperature with copper radiation (1.54060 Å). The incident beam optic was comprised of a variable divergence slit to ensure a constant illuminated length on the sample and on the diffracted beam sides. A fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 s. The XRPD diffractogram for Compound I sodium salt hydrate Form D is shown in FIG. 38 and summarized in Table 47.

TABLE 47

Compound I sodium salt hydrate Form D

| XRPD Peaks | Angle (degrees 2-Theta ± 0.2) | Intensity % |
|---|---|---|
| 1 | 5.3 | 100.0 |
| 2 | 18.5 | 90.5 |
| 3 | 19.9 | 78.7 |
| 4 | 17.5 | 59.7 |
| 5 | 15.9 | 44.5 |
| 6 | 15.1 | 43.6 |
| 7 | 6.3 | 35.0 |
| 8 | 14.8 | 32.8 |
| 9 | 19.0 | 32.5 |
| 10 | 22.4 | 32.2 |
| 11 | 10.9 | 31.7 |
| 12 | 21.1 | 31.7 |
| 13 | 23.8 | 31.7 |
| 14 | 22.8 | 30.0 |
| 15 | 7.8 | 26.8 |
| 16 | 24.0 | 26.6 |
| 17 | 25.3 | 23.1 |
| 18 | 24.3 | 20.1 |
| 19 | 27.3 | 18.8 |
| 20 | 22.2 | 18.5 |
| 21 | 4.9 | 17.0 |
| 22 | 26.0 | 16.2 |
| 23 | 29.1 | 15.2 |
| 24 | 26.3 | 15.1 |
| 25 | 13.5 | 14.1 |
| 26 | 9.3 | 13.7 |
| 27 | 11.9 | 13.7 |
| 28 | 16.8 | 13.3 |
| 30 | 9.8 | 10.0 |
| 31 | 20.8 | 10.0 |

B. Differential Scanning Calorimetry Analysis

DSC was performed using TA Discovery differential scanning calorimeter (TA Instruments, New Castle, DE). The instrument was calibrated with indium. Samples of approximately 1-10 mg were weighed into hermetic pans that were crimped using lids with one hole. The DSC samples were scanned from 25° C. to 300° C. at a heating rate of 10° C./min. Data was collected and analyzed by Trios Analysis software (TA Instruments, New Castle, DE). The thermogram showed multiple endothermic peaks at ~137° C. and ~203° C.

Example 29: Compound I Potassium Salt Hydrate Form A

Compound I potassium hydrate Form A was obtained by reacting Compound I (free form) Form A of with 0.1 N Potassium hydroxide in water at 1:1 molar ratio. The reaction mixture was subjected to heating and cooling cycles from 60° C. to room temperature for 2 cycles with air cooling and stirred at room temperature for about one week.

A. X-Ray Powder Diffraction

The powder x-ray diffraction measurement was performed using PANalytical's X-pert Pro diffractometer at room temperature with copper radiation (1.54060 Å). The incident beam optic was comprised of a variable divergence slit to ensure a constant illuminated length on the sample and on the diffracted beam sides. A fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 s. The XRPD diffractogram for Compound I potassium salt hydrate Form A is shown in FIG. 39 and summarized in Table 48.

TABLE 48

Compound I potassium salt hydrate Form A

| XRPD Peaks | Angle (degrees 2-Theta ± 0.2) | Intensity % |
|---|---|---|
| 1 | 20.4 | 100.0 |
| 2 | 25.8 | 47.9 |
| 3 | 15.3 | 47.4 |
| 4 | 26.4 | 44.5 |
| 5 | 29.9 | 42.8 |
| 6 | 29.1 | 33.9 |
| 7 | 20.1 | 33.8 |
| 8 | 10.7 | 32.5 |
| 9 | 24.4 | 32.4 |
| 10 | 27.0 | 32.1 |
| 11 | 24.0 | 30.8 |
| 12 | 23.5 | 30.2 |
| 13 | 27.3 | 28.6 |
| 14 | 16.8 | 28.2 |
| 15 | 11.4 | 25.6 |
| 16 | 19.6 | 23.8 |
| 17 | 27.9 | 22.9 |
| 18 | 21.4 | 21.1 |
| 19 | 25.4 | 20.8 |
| 20 | 13.5 | 20.4 |
| 21 | 18.2 | 18.5 |
| 22 | 21.9 | 16.0 |
| 23 | 13.0 | 15.0 |
| 24 | 22.5 | 14.1 |
| 25 | 18.6 | 12.7 |
| 26 | 12.4 | 12.0 |
| 27 | 13.9 | 11.4 |

B. Differential Scanning Calorimetry Analysis

DSC was performed using TA Discovery differential scanning calorimeter (TA Instruments, New Castle, DE). The instrument was calibrated with indium. Samples of approximately 1-10 mg were weighed into hermetic pans that were crimped using lids with one hole. The DSC samples were scanned from 25° C. to 300° C. at a heating rate of 10° C./min. Data was collected and analyzed by Trios Analysis software (TA Instruments, New Castle, DE). The thermogram showed multiple endothermic peaks at ~75° C. and ~98° C.

Example 30: Compound I Potassium Salt Hydrate Form B

Compound I potassium salt hydrate Form B was obtained by slurrying amorphous Compound I potassium salt in ACN at room temperature for 3 or 4 weeks and continued slurrying at 60° C. for 6 h.

A. X-Ray Powder Diffraction

The powder x-ray diffraction measurement was performed using PANalytical's X-pert Pro diffractometer at room temperature with copper radiation (1.54060 Å). The incident beam optic was comprised of a variable divergence slit to ensure a constant illuminated length on the sample and on the diffracted beam sides. A fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 s. The XRPD diffractogram for Compound I potassium salt hydrate Form B is shown in FIG. 40 and summarized in Table 49.

TABLE 49

Compound I potassium salt hydrate Form B

| XRPD Peaks | Angle (degrees 2-Theta ± 0.2) | Intensity % |
|---|---|---|
| 1 | 6.8 | 100.0 |
| 2 | 21.5 | 84.2 |
| 3 | 4.7 | 69.9 |
| 4 | 12.0 | 65.0 |
| 5 | 15.2 | 60.9 |
| 6 | 14.0 | 56.8 |
| 7 | 19.0 | 43.0 |
| 8 | 12.8 | 40.3 |
| 9 | 16.1 | 39.3 |
| 10 | 23.3 | 38.7 |
| 11 | 20.4 | 36.5 |
| 12 | 8.0 | 35.9 |
| 13 | 24.0 | 34.9 |
| 14 | 19.5 | 33.2 |
| 15 | 25.6 | 27.2 |
| 16 | 27.6 | 24.9 |
| 17 | 18.3 | 22.1 |
| 18 | 16.4 | 21.1 |
| 19 | 24.4 | 19.2 |
| 20 | 24.6 | 17.2 |
| 21 | 4.3 | 16.6 |
| 22 | 20.1 | 16.5 |
| 23 | 9.3 | 15.5 |
| 24 | 17.1 | 14.5 |
| 25 | 14.8 | 14.0 |
| 26 | 20.8 | 12.6 |
| 27 | 28.2 | 12.5 |
| 28 | 11.2 | 11.1 |
| 29 | 22.1 | 10.7 |
| 30 | 25.3 | 10.2 |
| 31 | 26.3 | 10.2 |

Example 31: Compound I Potassium Salt Hydrate Forms C and D

Approximately 1 g of amorphous Compound I potassium salt was stirred in ~8.5 mL of ACN at ambient temperature for 10 d. This mixture was filtered. The resulting solid was Compound I potassium salt hydrate Form C. Compound I potassium salt hydrate Form C was dried at ~29° C. under vacuum. The resulting solid was Compound I potassium salt hydrate Form D.

A. X-Ray Powder Diffraction:

The XRPD patterns are acquired at room temperature in reflection mode using a Bruker Advance equipped with Vantec-1 detector. Sample was analyzed on a silicon sample holder from 3-40° 2-theta on continuous mode with step size of 0.0144531° and time per step of 0.25 s. Sample was spinning at 15 rpm. The XRPD diffractogram for Compound I potassium salt hydrate Form C and Form D are shown in FIG. 41 and FIG. 42 and summarized in Table 50 and Table 51.

TABLE 50

Compound I potassium salt hydrate Form C

| XRPD Peaks | Angle (degrees 2-Theta ± 0.2) | Intensity % |
|---|---|---|
| 1 | 6.3 | 100.0 |
| 2 | 4.8 | 79.7 |
| 3 | 14.2 | 74.3 |
| 4 | 19.0 | 33.9 |
| 5 | 19.7 | 31.2 |
| 6 | 15.3 | 28.7 |
| 7 | 21.3 | 27.2 |
| 8 | 23.8 | 26.0 |
| 9 | 11.2 | 24.4 |
| 10 | 25.5 | 24.0 |
| 11 | 23.0 | 23.5 |
| 12 | 16.1 | 22.2 |
| 13 | 11.6 | 20.7 |
| 14 | 12.0 | 20.4 |
| 15 | 20.5 | 20.3 |
| 16 | 24.4 | 19.4 |
| 17 | 7.7 | 19.2 |
| 18 | 18.5 | 18.5 |
| 19 | 16.4 | 17.0 |
| 20 | 6.7 | 16.8 |
| 21 | 15.8 | 15.5 |
| 22 | 26.5 | 13.3 |
| 23 | 12.7 | 13.1 |
| 24 | 13.5 | 10.9 |
| 25 | 9.5 | 10.3 |
| 26 | 27.1 | 10.2 |

TABLE 51

Compound I potassium salt hydrate Form D

| XRPD Peaks | Angle (degrees 2-Theta ± 0.2) | Intensity % |
|---|---|---|
| 1 | 4.8 | 100.0 |
| 2 | 4.4 | 56.1 |
| 3 | 14.3 | 51.6 |
| 4 | 15.3 | 50.6 |
| 5 | 13.1 | 50.1 |
| 6 | 7.0 | 44.0 |
| 7 | 21.9 | 43.9 |
| 8 | 12.2 | 42.4 |
| 9 | 18.5 | 32.2 |
| 10 | 24.2 | 29.7 |
| 11 | 25.1 | 26.3 |
| 12 | 19.7 | 24.4 |
| 13 | 8.1 | 21.1 |
| 14 | 26.4 | 20.1 |
| 15 | 22.9 | 19.1 |
| 16 | 17.4 | 17.6 |
| 17 | 16.4 | 15.1 |
| 18 | 8.8 | 11.2 |

B. Solid State NMR

Figure 43:
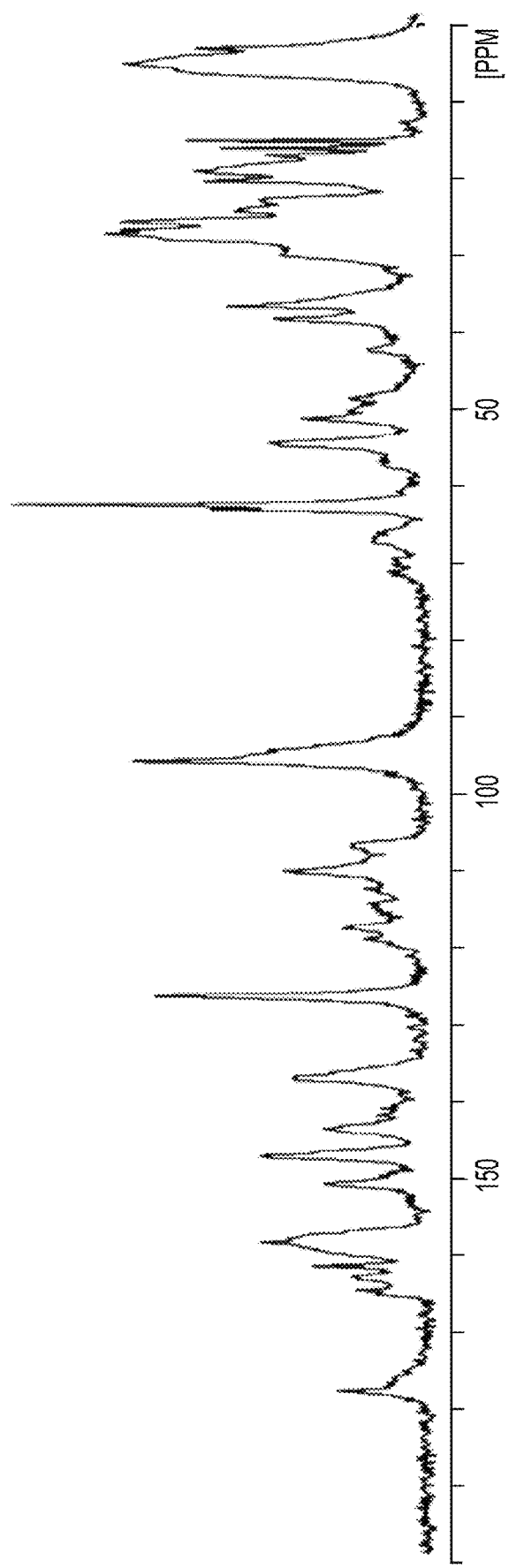
FIG. 43 shows a $^{13}$C solid state NMR spectrum of Compound I potassium salt hydrate Form D.

Solid state $^{13}$C NMR spectrum for Compound I potassium salt hydrate Form D is provided in FIG. 43 and summarized in Table 52.

TABLE 52

Solid state NMR Compound I potassium salt hydrate Form D

| Peak # | Chem Shift [ppm] ± 0.2 | Intensity [rel] |
|---|---|---|
| 1 | 178.9 | 21.6 |
| 2 | 165.8 | 16.8 |
| 3 | 164.1 | 18.0 |
| 4 | 162.6 | 27.6 |
| 5 | 159.6 | 39.7 |
| 6 | 151.9 | 24.6 |
| 7 | 148.3 | 40.0 |
| 8 | 144.7 | 24.9 |
| 9 | 143.0 | 11.8 |
| 10 | 142.1 | 10.8 |
| 11 | 138.2 | 32.1 |
| 12 | 127.5 | 65.6 |
| 13 | 120.1 | 14.9 |

TABLE 52-continued

Solid state NMR Compound I potassium salt hydrate Form D

| Peak # | Chem Shift [ppm] ± 0.2 | Intensity [rel] |
|---|---|---|
| 14 | 118.7 | 20.2 |
| 15 | 115.4 | 14.4 |
| 16 | 113.5 | 15.1 |
| 17 | 111.2 | 34.4 |
| 18 | 108.0 | 18.3 |
| 19 | 96.9 | 71.5 |
| 20 | 72.7 | 8.1 |
| 21 | 72.0 | 9.5 |
| 22 | 71.2 | 8.6 |
| 23 | 68.1 | 13.0 |
| 24 | 64.2 | 52.1 |
| 25 | 63.5 | 100.0 |
| 26 | 55.5 | 38.0 |
| 27 | 52.2 | 30.4 |
| 28 | 51.2 | 19.1 |
| 29 | 49.5 | 18.6 |
| 30 | 43.1 | 14.3 |
| 31 | 39.2 | 36.9 |
| 32 | 37.6 | 48.2 |
| 33 | 31.0 | 35.3 |
| 34 | 28.2 | 77.3 |
| 35 | 27.8 | 73.8 |
| 36 | 26.5 | 74.1 |
| 37 | 25.2 | 46.5 |
| 38 | 23.7 | 40.3 |
| 39 | 21.3 | 53.9 |
| 40 | 20.0 | 56.4 |
| 41 | 17.9 | 39.1 |
| 42 | 16.9 | 50.4 |
| 43 | 16.0 | 57.9 |
| 44 | 5.9 | 73.1 |
| 45 | 4.0 | 55.8 |

Example 32: Compound I Ammonia Salt Hydrate Form A

Stock suspension of Compound I (free form) Form A in acetone at 0.1 M concentration was prepared and reacted at 1:1 molar ratio with ammonium hydroxide in water. The clear solution was left stirred at room temperature for 2 weeks. This resulted in a light brown solid.

A. X-Ray Powder Diffraction

The powder x-ray diffraction measurement was performed using PANalytical's X-pert Pro diffractometer at room temperature with copper radiation (1.54060 Å). The incident beam optic was comprised of a variable divergence slit to ensure a constant illuminated length on the sample and on the diffracted beam sides. A fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 s. The XRPD diffractogram for Compound I ammonia salt hydrate Form A is shown in FIG. 44 and summarized in Table 53

TABLE 53

Compound I ammonia salt hydrate Form A

| XRPD Peaks | Angle (degrees 2-Theta ± 0.2) | Intensity % |
|---|---|---|
| 1 | 5.5 | 100.0 |
| 2 | 15.3 | 44.9 |
| 3 | 17.7 | 44.9 |
| 4 | 19.6 | 35.4 |
| 5 | 20.9 | 30.6 |
| 6 | 18.0 | 25.7 |
| 7 | 16.3 | 25.2 |
| 8 | 23.6 | 24.5 |
| 9 | 18.7 | 18.8 |
| 10 | 24.4 | 17.7 |
| 11 | 14.2 | 16.0 |
| 12 | 18.9 | 15.6 |
| 13 | 21.1 | 12.6 |
| 14 | 21.7 | 12.0 |
| 15 | 7.5 | 11.7 |
| 16 | 13.9 | 11.2 |
| 17 | 22.4 | 10.8 |

Example 33: Compound I Calcium Salt Form H 49.5 g of Compound I sodium salt was charged with 222.75 mL ethanol and 24.75 mL water. The slurry was heated to 45° C. and seeded with 0.495 g of Compound I calcium salt hydrate Form A. A solution of 4.723 g calcium chloride, 4.26 mL ethanol and 0.47 mL water was charged over 4 hour period of time. The slurry was stirred at 45° C. for 3 days. The resulting solids were collected by vacuum filtration. The wet cake was transferred to a vacuum oven with a slight nitrogen bleed. 5.12 g of the dry product obtained above was charge with 30 mL IPA and 20 mL water. The slurry was heated to 25° C. The slurry was stirred for 12 hours. 50 mL IPA was charged over 5 hour period of time. The slurry was allowed to stir for 6 days. 1 mL of the slurry was taken into a separate vial and shaken at 25° C. for 18 days. The 1 mL slurry was then stored at room temperature and the solids contains Compound I calcium salt Form H.

A. X-Ray Powder Diffraction:

The XRPD patterns were acquired at room temperature in reflection mode using a Bruker Advance equipped with Vantec-1 detector. A sample was analyzed on a silicon sample holder from 3-40° 2-theta on continuous mode with step size of 0.0144531° and time per step of 0.25 s. The sample was spinning at 15 rpm. The XRPD diffractogram for Compound I calcium salt hydrate Form A is shown in FIG. 45 and summarized in Table 54.

TABLE 54

XRPD signals for crystalline Compound I calcium salt Form H

| XRPD Peaks | Angle (degrees 2-Theta ± 0.2) | Intensity % |
|---|---|---|
| 1 | 14.5 | 100.0 |
| 2 | 5.8 | 76.2 |
| 3 | 13.0 | 72.6 |
| 4 | 17.5 | 62.5 |
| 5 | 20.2 | 57.7 |
| 6 | 17.3 | 51.0 |
| 7 | 16.0 | 50.6 |
| 8 | 19.5 | 48.5 |
| 9 | 18.7 | 43.9 |
| 10 | 19.8 | 40.7 |
| 11 | 21.1 | 40.0 |
| 12 | 22.0 | 38.9 |
| 13 | 22.2 | 34.0 |

TABLE 54-continued

XRPD signals for crystalline Compound I calcium salt Form H

| XRPD Peaks | Angle (degrees 2-Theta ± 0.2) | Intensity % |
|---|---|---|
| 14 | 12.0 | 31.1 |
| 15 | 21.3 | 30.4 |
| 16 | 23.6 | 29.5 |
| 17 | 8.3 | 29.0 |
| 18 | 25.0 | 28.6 |
| 19 | 11.6 | 28.1 |
| 20 | 23.3 | 27.8 |
| 21 | 16.6 | 22.5 |
| 22 | 8.7 | 22.3 |
| 23 | 24.0 | 21.7 |
| 24 | 25.2 | 20.6 |
| 25 | 24.3 | 19.2 |
| 26 | 11.0 | 19.1 |
| 27 | 26.3 | 18.6 |
| 28 | 17.9 | 18.3 |
| 29 | 22.6 | 18.3 |
| 30 | 11.2 | 16.3 |
| 31 | 29.0 | 15.1 |
| 32 | 14.9 | 15.0 |
| 33 | 28.3 | 14.7 |
| 34 | 13.4 | 13.5 |
| 35 | 26.1 | 13.3 |
| 36 | 9.3 | 12.8 |
| 37 | 16.8 | 11.6 |
| 38 | 24.6 | 11.5 |
| 39 | 27.9 | 10.6 |
| 40 | 13.8 | 10.1 |

B. Single Crystal Elucidation

X-ray diffraction data were acquired at 100K on a Bruker diffractometer utilizing synchrotron radiation (0.7288 Å), provided by beamline 12.2.1 at the Advanced Light Source Lawrence Berkeley National Laboratory, and an CMOS detector. The structure was solved and refined using SHELX program (Sheldrick, G. M., Acta Cryst., (2008) A64, 112-122) and results are summarized in Table 55 below.

TABLE 55

Single crystal elucidation of Compound I calcium salt Form H

| Crystal System: | Triclinic |
|---|---|
| Space Group: | P1 |
| a (Å) | 8.6511(4) |
| b (Å) | 17.7759(9) |
| c (Å) | 24.0661(12) |
| α (°) | 82.471(3) |
| β (°) | 86.951(2) |
| γ (°) | 86.564(2) |
| V (Å³) | 3658.6(3) |
| Z/Z' | 1/2 |
| Temperature | 100 K |

C. Solid State NMR

Solid state $^{13}C$ NMR spectrum for Compound I calcium salt Form H is provided in FIG. 46 and summarized in Table 56.

TABLE 56

Solid state NMR of Compound I calcium salt Form H

| Peak # | Chem Shift [ppm] ± 0.2 | Intensity [rel] |
|---|---|---|
| 1 | 177.4 | 7.3 |
| 2 | 176.8 | 8.6 |
| 3 | 175.5 | 14.5 |
| 4 | 166.8 | 16.4 |
| 5 | 164.7 | 39.3 |

TABLE 56-continued

Solid state NMR of Compound I calcium salt Form H

| Peak # | Chem Shift [ppm] ± 0.2 | Intensity [rel] |
|---|---|---|
| 6 | 160.7 | 23.5 |
| 7 | 159.6 | 17.2 |
| 8 | 158.7 | 14.6 |
| 9 | 157.8 | 14.4 |
| 10 | 157.3 | 16.4 |
| 11 | 157.0 | 11.1 |
| 12 | 155.0 | 9 |
| 13 | 153.4 | 16.7 |
| 14 | 152.7 | 8.9 |
| 15 | 148.9 | 35.9 |
| 16 | 147.0 | 11.8 |
| 17 | 143.0 | 13.3 |
| 18 | 141.4 | 20.8 |
| 19 | 140.3 | 15.1 |
| 20 | 139.0 | 17.8 |
| 21 | 138.7 | 18.8 |
| 22 | 138.0 | 19.5 |
| 23 | 129.4 | 18.8 |
| 24 | 128.3 | 34.7 |
| 25 | 126.7 | 26.0 |
| 26 | 118.9 | 18.3 |
| 27 | 117.0 | 24.7 |
| 28 | 115.1 | 22.7 |
| 29 | 113.7 | 22.3 |
| 30 | 113.3 | 23.0 |
| 31 | 111.4 | 12.0 |
| 32 | 110.4 | 26.2 |
| 33 | 110.1 | 13.6 |
| 34 | 98.0 | 21.6 |
| 35 | 97.5 | 29.1 |
| 36 | 97.1 | 28.0 |
| 37 | 96.4 | 17.9 |
| 38 | 95.9 | 22.2 |
| 39 | 94.6 | 20.3 |
| 40 | 93.7 | 25.8 |
| 41 | 92.5 | 22.6 |
| 42 | 69.7 | 34.0 |
| 43 | 68.9 | 11.9 |
| 44 | 64.6 | 24.0 |
| 45 | 63.3 | 51.5 |
| 46 | 61.7 | 28.3 |
| 47 | 60.9 | 21.2 |
| 48 | 57.7 | 23.0 |
| 49 | 56.6 | 16.2 |
| 50 | 51.6 | 27.8 |
| 51 | 49.5 | 31.5 |
| 52 | 49.0 | 28.4 |
| 53 | 42.8 | 11.1 |
| 54 | 41.5 | 19.5 |
| 55 | 38.9 | 33.8 |
| 56 | 38.6 | 42.0 |
| 57 | 37.9 | 25.4 |
| 58 | 33.6 | 14.0 |
| 59 | 31.8 | 20.3 |
| 60 | 31.2 | 36.8 |
| 61 | 30.2 | 26.2 |
| 62 | 29.2 | 27.5 |
| 63 | 28.7 | 38.1 |
| 64 | 27.2 | 100.0 |
| 65 | 26.9 | 58.4 |
| 66 | 25.7 | 30.9 |
| 67 | 23.9 | 25.2 |
| 68 | 22.1 | 32.1 |
| 69 | 20.5 | 20.5 |
| 70 | 19.7 | 31.9 |
| 71 | 19.4 | 75.5 |
| 72 | 18.9 | 33.5 |
| 73 | 18.2 | 44.4 |
| 74 | 6.3 | 29.0 |
| 75 | 4.8 | 45.1 |
| 76 | 3.3 | 36.3 |
| 77 | 2.8 | 30.5 |

D. Differential Scanning Calorimetry Analysis:

A DSC thermogram was obtained using TA Instruments DSC Q2000. Sample was heated at 10° C./min from 30° C. to 400° C. The thermogram showed endothermic peaks at ~69° C. and ~113° C.

Example 34: Compound I (Free Form) Form D

Carbonyl carbon $^{13}$C labeled Compound I (free form) Form D was obtained by filtration to remove suspended reaction solids. The removed solids were washed with isopropyl acetate (2×30 mL). The layers from the filtrate were separated to give a fine suspended solid at the rag layer. The aqueous layer was discarded. The organic layer was washed with 8% aq. w/v trisodium citrate (120 mL). Brine (2×10 mL) was added to aid in the phase separation. The aqueous layer was discarded. The organic layer was washed with 1:1 v:v water:brine (80 mL). The fine, suspended solid at the rag layer persisted. The aqueous layer was discarded. The organic layer was polish filtered through a pad of celite filtering agent. The filter pad was washed with isopropyl acetate (30 mL). The filtrate was concentrated under reduced pressure and propanol (180 mL) was added. The mixture was concentrated under reduced pressure. This step was repeated. To the mixture was added toluene (180 mL) and the mixture was concentrated under reduced pressure. This step was repeated to give a thick slurry which was further concentrated to 60 mL of toluene. After stirring the slurry overnight, the solid was collected by filtration and the filter cake was washed with toluene (2×20 mL). The solid was dried under vacuum with a nitrogen bleed at 50° C. until the loss on drying was not more than 1% to give 13.2 g (65% isolated yield) of the product as white to off-white solid.

A. X-Ray Powder Diffraction

XRPD spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40°2θ with a step size of 0.0131303° and 49 s per step. The XRPD diffractogram for Compound I (free form) Form D is provided in FIG. 47 and the XRPD data are summarized below in Table 57.

TABLE 57

XRPD signals for crystalline Form D of Compound I (free form)

| XRPD Peaks | Angle (degrees 2-Theta ± 0.2) | Intensity % |
|---|---|---|
| 1 | 3.7 | 100.0 |
| 2 | 7.4 | 82.3 |
| 3 | 7.3 | 62.6 |
| 4 | 17.3 | 45.8 |
| 5 | 10.4 | 40.0 |
| 6 | 12.2 | 36.0 |
| 7 | 16.1 | 31.7 |
| 8 | 17.0 | 29.4 |
| 9 | 20.8 | 28.4 |
| 10 | 18.4 | 27.2 |
| 11 | 8.2 | 25.9 |
| 12 | 22.4 | 24.7 |
| 13 | 19.7 | 23.4 |
| 14 | 13.0 | 20.1 |
| 15 | 23.4 | 16.9 |
| 16 | 21.6 | 11.5 |
| 17 | 8.4 | 10.7 |
| 18 | 25.4 | 10.7 |

B. Solid State NMR

Solid state $^{13}$C NMR data for Compound I (free form) Form D is provided in FIG. 48 and summarized in Table 58 below.

TABLE 58

Solid State NMR of Compound I (free form) Form D

| Peak # | Chem Shift [ppm] ± 0.2 | Intensity [rel] |
|---|---|---|
| 1 | 166.1 | 100.0 |
| 2 | 164.6 | 75.7 |
| 3 | 158.9 | 1.8 |
| 4 | 155.2 | 1.5 |
| 5 | 153.7 | 0.8 |
| 6 | 152.7 | 1.0 |
| 7 | 152.2 | 0.5 |
| 8 | 151.3 | 1.3 |
| 9 | 149.6 | 1.2 |
| 10 | 142.2 | 1.0 |
| 11 | 141.1 | 1.8 |
| 12 | 135.7 | 1.6 |
| 13 | 130.7 | 0.6 |
| 14 | 129.2 | 0.7 |
| 15 | 128.1 | 1.3 |
| 16 | 114.2 | 1.4 |
| 17 | 113.6 | 2.3 |
| 18 | 111.6 | 0.6 |
| 19 | 110.9 | 0.7 |
| 20 | 110.2 | 0.6 |
| 21 | 108.3 | 0.8 |
| 22 | 107.4 | 1.2 |
| 23 | 96.8 | 1.7 |
| 24 | 94.9 | 1.0 |
| 25 | 94.2 | 1.3 |
| 26 | 69.8 | 0.4 |
| 27 | 68.8 | 0.9 |
| 28 | 68.0 | 0.5 |
| 29 | 66.8 | 1.4 |
| 30 | 65.7 | 1.4 |
| 31 | 63.9 | 0.7 |
| 32 | 63.0 | 3.8 |
| 33 | 61.0 | 1.4 |
| 34 | 59.9 | 1.5 |
| 35 | 52.5 | 1.8 |
| 36 | 51.6 | 1.5 |
| 37 | 50.5 | 0.8 |
| 38 | 39.5 | 3.6 |
| 39 | 38.9 | 1.9 |
| 40 | 37.5 | 1.1 |
| 41 | 31.8 | 1.2 |
| 42 | 30.6 | 1.0 |
| 43 | 29.3 | 1.3 |
| 44 | 27.6 | 2.3 |
| 45 | 26.1 | 2.8 |
| 46 | 25.6 | 2.4 |
| 47 | 24.9 | 2.8 |
| 48 | 23.2 | 0.7 |
| 49 | 21.6 | 1.3 |
| 50 | 20.9 | 1.5 |
| 51 | 20.0 | 1.6 |
| 52 | 19.7 | 1.6 |
| 53 | 18.9 | 1.5 |
| 54 | 16.5 | 1.5 |
| 55 | 15.7 | 1.7 |
| 56 | 14.0 | 0.5 |
| 57 | 6.6 | 1.0 |
| 58 | 5.9 | 1.0 |

TABLE 58-continued

Solid State NMR of Compound I (free form) Form D

| Peak # | Chem Shift [ppm] ± 0.2 | Intensity [rel] |
|---|---|---|
| 59 | 5.1 | 1.0 |
| 60 | 4.0 | 1.0 |

Example 35: Compound I Sodium Salt Hydrate Form E

Compound I sodium salt hydrate Form E provides Compound I calcium salt in higher purity than obtained using Compound I amorphous sodium salt, which can be confirmed using analytical techniques such as HPLC or ssNMR.

1 g of Compound I sodium salt hydrate Form A, 5 mL of IPA, and 5 mL of water were charged to a 50 mL Easymax vessel and heated to 65° C. The resulted solution was cooled to 45° C. in 20 min. 0.01 g of Compound I sodium salt hydrate Form A seeds were added to the solution. The mixture was held at 45° C. for 1 hr. 10 mL of water was then charged to the vessel over 5 hours. The mixture was cooled to 20° C. over 4 hrs. The precipitated solids were filtered off, washed on filter with 10 mL IPA:water 1:3 v:v, and air dried. The final solid was a mixture of Compound I sodium salt hydrate Form A and Form E.

~522.3 g of Compound I sodium salt hydrate (mixture of Form A and Form E), 2.64 kg IPA, 43.5 g 2.0 M NaOH, and 3.54 kg of water were charged to a 10 L jacketed lab reactor and heated to 73° C. The resultant solution was polish filtered and cooled to 58° C. 6.18 kg of water was added to the solution. Then 4.9 g Compound I sodium salt hydrate Form E seeds were added to the solution at 40° C. The mixture was cooled to 5° C. over 12 hrs and then held at 5° C. overnight. The precipitated solids were filtered off and washed with a mixture of 1.745 kg water+0.58 kg IPA, and then dried under vacuum at 40° C. The final solid was Compound I sodium salt hydrate Form E.

Alternative Preparation

Compound I sodium salt hydrate Form A (20 g, 31.213 mmol, 1 equiv.) was dissolved in IPA/water 1:1 (200 mL, 10 volumes) at 65° C. The solution is cooled to 45° C. and seeded with a mixture of Compound I sodium salt hydrate Form A and Form E (200 mg, 1% w/w, mix of forms A and E). The seeded homogenous solution was then charged with water (200 mL) over 5 hours. The solution was then cooled to 20° C. over 5 hours. The solids were isolated by filtration, washed with a minimum amount of IPA/water (1:3), and dried in a vacuum oven until a constant weight was reached. The yield of Compound I sodium salt hydrate Form E was 97.49%.

A. X-Ray Powder Diffraction:

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40°2θ with a step size of 0.0131303° and 49 s per step.

The XRPD diffractogram for Compound I sodium salt hydrate Form E is provided in FIG. 49 and the XRPD data are summarized below in Table 59.

TABLE 59

XRPD signals for crystalline Compound I sodium salt hydrate Form E

| Peak # | Angle (Degrees 2-Theta ± 0.2) | Intensity % |
|---|---|---|
| 1 | 4.3 | 100.0 |
| 2 | 10.6 | 69.8 |
| 3 | 13.4 | 47.0 |
| 4 | 13.0 | 41.8 |
| 5 | 11.7 | 25.3 |
| 6 | 17.3 | 22.2 |
| 7 | 22.3 | 21.3 |
| 8 | 20.0 | 21.2 |
| 9 | 19.2 | 20.4 |
| 10 | 23.1 | 20.3 |
| 11 | 14.1 | 19.9 |
| 12 | 21.4 | 17.4 |
| 13 | 14.9 | 16.0 |
| 14 | 21.5 | 14.4 |
| 15 | 18.8 | 12.2 |
| 16 | 14.2 | 10.6 |
| 17 | 18.1 | 10.2 |

B. Single Crystal Elucidation

X-ray diffraction data were acquired at 100K on a Bruker diffractometer equipped with Cu $K_\alpha$ radiation ($\lambda$=1.54178 Å) and a CMOS detector. The structure was solved and refined using SHELX programs (Sheldrick, G. M., Acta Cryst., (2008) A64, 112-122) and results are summarized in Table 60 below.

TABLE 60

Single crystal elucidation of Compound I sodium salt hydrate Form E

| | |
|---|---|
| Crystal System | Orthorhombic |
| Space Group | C222$_1$ |
| a (Å) | 12.6556(9) |
| b (Å) | 13.1640(7) |
| c (Å) | 39.928(4) |
| α (°) | 90 |
| β (°) | 90 |
| γ (°) | 90 |
| V (Å$^3$) | 6651.9(9) |
| Z/Z' | 8/1 |
| Temperature | 100 K |

C. Solid State NMR

Solid state $^{13}$C NMR spectrum for Compound I sodium salt hydrate Form E is provided in FIG. 50 and summarized in Table 61.

TABLE 61

Solid state NMR of Compound I sodium salt hydrate Form E

| Peak # | Chem Shift [ppm] ± 0.2 | Intensity [rel] |
|---|---|---|
| 1 | 177.4 | 20.5 |
| 2 | 165.2 | 33.0 |
| 3 | 161.3 | 17.9 |
| 4 | 155.4 | 22.1 |
| 5 | 153.6 | 15.5 |
| 6 | 149.9 | 22.6 |
| 7 | 142.7 | 34.7 |
| 8 | 140.3 | 28.1 |
| 9 | 128.4 | 37.2 |
| 10 | 121.3 | 22.8 |
| 11 | 113.5 | 36.9 |
| 12 | 111.5 | 12.1 |
| 13 | 111.1 | 23.8 |
| 14 | 101.0 | 41.1 |
| 15 | 93.1 | 44.7 |
| 16 | 69.5 | 53.4 |
| 17 | 62.6 | 36.9 |

TABLE 61-continued

Solid state NMR of Compound I sodium salt hydrate Form E

| Peak # | Chem Shift [ppm] ± 0.2 | Intensity [rel] |
|---|---|---|
| 18 | 61.9 | 10.0 |
| 19 | 55.2 | 28.4 |
| 20 | 50.6 | 13.2 |
| 21 | 50.0 | 40.2 |
| 22 | 38.2 | 25.7 |
| 23 | 30.9 | 51.6 |
| 24 | 30.2 | 51.3 |
| 25 | 29.0 | 51.2 |
| 26 | 27.8 | 58.0 |
| 27 | 26.8 | 59.4 |
| 28 | 25.8 | 53.9 |
| 29 | 21.1 | 100.0 |
| 30 | 17.2 | 75.9 |
| 31 | 7.2 | 41.3 |
| 32 | 6.5 | 46.0 |
| 33 | 5.9 | 41.9 |
| 34 | 2.1 | 35.8 |

Example 36: Compound I Sodium Salt IPA Solvate

~200 mg of amorphous Compound I sodium salt hydrate Form A was charged with 2 mL of IPA. The slurry stirred at ambient temperature for 5 days. The resulting solid is Compound I sodium IPA solvate. The solvate is labile, and changes form upon vacuum drying at 40° C. overnight.

A. X-Ray Powder Diffraction

X-ray powder diffraction (XRPD) spectra were recorded at room temperature in transmission mode using a PANalytical Empyrean system equipped with a sealed tube source and a PIXcel 1D Medipix-3 detector (Malvern PANalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40°2θ with a step size of 0.0131303° and 49 s per step.

The XRPD diffractogram for Compound I sodium salt IPA (wet) solvate Form A and Compound I sodium salt IPA (dry) solvate Form B are provided in FIG. 51 and FIG. 52, respectively and the XRPD data are summarized below in Table 62 and Table 63, respectively.

TABLE 62

XRPD signals for crystalline Compound I sodium salt IPA (wet) solvate Form A

| Peak # | Angle (Degrees 2-Theta ± 0.2) | Intensity % |
|---|---|---|
| 1 | 3.6 | 100.0 |
| 2 | 3.5 | 94.3 |
| 3 | 9.5 | 12.4 |

TABLE 63

XRPD signals for crystalline Compound I sodium salt IPA (dry) solvate Form B

| Peak # | Angle (Degrees 2-Theta ± 0.2) | Intensity % |
|---|---|---|
| 1 | 4.0 | 100.0 |
| 2 | 18.5 | 19.3 |
| 3 | 5.3 | 19.3 |
| 4 | 9.7 | 17.7 |
| 5 | 20.0 | 15.6 |
| 6 | 7.9 | 11.4 |
| 7 | 11.0 | 10.3 |
| 8 | 13.9 | 10.2 |

C. Solid State NMR

Solid state $^{13}$C NMR spectrum for Compound I sodium salt IPA (dry) solvate Form B is provided in FIG. 53 and summarized in Table 64.

TABLE 64

Solid state NMR of Compound I sodium salt IPA (dry) solvate Form B

| Peak # | Chem Shift [ppm] ± 0.2 | Intensity [rel] |
|---|---|---|
| 1 | 180.3 | 10.9 |
| 2 | 178.7 | 16.6 |
| 3 | 166.2 | 11.4 |
| 4 | 164.7 | 31.4 |
| 5 | 161.6 | 39.1 |
| 6 | 159.5 | 45.4 |
| 7 | 153.0 | 20.1 |
| 8 | 149.6 | 37.9 |
| 9 | 142.0 | 23.1 |
| 10 | 140.3 | 34.5 |
| 11 | 138.4 | 18.1 |
| 12 | 135.9 | 76.1 |
| 13 | 129.2 | 18.4 |
| 14 | 127.7 | 33.6 |
| 15 | 127.0 | 31.0 |
| 16 | 118.1 | 24.0 |
| 17 | 117.0 | 24.8 |
| 18 | 114.1 | 48.1 |
| 19 | 106.8 | 18.3 |
| 20 | 105.4 | 34.6 |
| 21 | 97.1 | 30.2 |
| 22 | 96.1 | 48.3 |
| 23 | 95.5 | 50.2 |
| 24 | 94.4 | 30.8 |
| 25 | 70.5 | 14.0 |
| 26 | 68.9 | 21.7 |
| 27 | 67.6 | 27.8 |
| 28 | 64.1 | 37.5 |
| 29 | 63.5 | 26.2 |
| 30 | 61.8 | 80.9 |
| 31 | 59.5 | 51.8 |
| 32 | 56.4 | 13.8 |
| 33 | 54.5 | 27.0 |
| 34 | 53.6 | 38.7 |
| 35 | 51.7 | 20.6 |
| 36 | 39.7 | 82.8 |
| 37 | 32.7 | 58.2 |
| 38 | 31.5 | 39.3 |
| 39 | 30.5 | 37.6 |
| 40 | 28.7 | 55.5 |
| 41 | 27.2 | 100.0 |
| 42 | 26.1 | 97.5 |
| 43 | 24.6 | 61.5 |
| 44 | 20.2 | 53.5 |
| 45 | 19.5 | 80.2 |
| 46 | 18.4 | 58.0 |
| 47 | 6.4 | 44.8 |
| 48 | 5.1 | 57.1 |
| 49 | 3.6 | 47.6 |

Example 37: Preparation of a Tablet Containing 5 mg of Compound I

Microcrystalline cellulose was passed through a stainless steel screen (30 mesh) and 210.1 g was charged into a 10 L Bohle Bin. Compound I was passed through a stainless steel screen (30 mesh) and 210.0 g was charged into the 10 L Bohle Bin. The bin was sealed and the components are blended for 2 min at a speed of 32 RPM to yield a microcrystalline cellulose/Compound I blend. The microcrystalline cellulose/Compound I blend was discharged into a stainless steel container. The following materials are sieved through a stainless steel 30 mesh screen and added to the 10 L Bohle bin in this order: lactose (approximately half of 1022.2 g), microcrystalline cellulose (approximately half of 812 g), microcrystalline cellulose/Compound I blend, polyvinylpyrrolidone/vinyl acetate (210.1 g), croscarmellose sodium (133 g), microcrystalline cellulose (the remaining half portion from the 812 g amount), and lactose (the remaining half portion from the 1022.2 g amount). The bin was sealed and the components were blended for 18.5 min at a speed of 32 rpm. Sodium stearyl fumarate Pruv® was passed through a 60 mesh stainless steel and 53.1 g was charged into the Bohle bin. The bin was sealed and the components were blended for 4 min at a speed of 32 rpm. The bin was tested for homogeneity. The blend was added to a Piccola Tablet press and compressed into tablets weighing 67.0 mg.

TABLE 65

Compound I tablet composition

| Component | % w/w tablet (approx.) | Tablet quantity (approx.) |
|---|---|---|
| Compound I (Ca salt hydrate Form A) | 8 | 5 mg |
| Microcrystalline cellulose (pre-blend) | 8 | 5 mg |
| Polyvinylpyrrolidone/vinyl acetate | 8 | 5 mg |
| Microcrystalline cellulose (tablet-blend) | 31 | 21 mg |
| Lactose monohydrate | 38 | 26 mg |
| Croscarmellose sodium | 5 | 3 mg |
| Sodium stearyl fumarate pruv ® | 2 | 1 mg |

Example 38: Bioactivity Assay

Solutions

Base medium (ADF+++) consisted of Advanced DMEM/Ham's F12, 2 mM Glutamax, 10 mM HEPES, 1µ/ml penicillin/streptomycin.

Intestinal enteroid maintenance medium (IEMM) consisted of ADF+++, 1×B27 supplement, 1×$N_2$ supplement, 1.25 mM N-acetyl cysteine, 10 mM Nicotinamide, 50 ng/mL hEGF, 10 nM Gastrin, 1 µg/mL hR-spondin-1, 100 ng/mL hNoggin, TGF-b type 1 inhibitor A-83-01, 100 µg/mL Primocin, 10 µM P38 MAPK inhibitor SB202190.

Bath 1 Buffer consisted of 1 mM $MgCl_2$, 160 mM NaCl, 4.5 mM KCl, 10 mM HEPES, 10 mM Glucose, 2 mM $CaCl_2$).

Chloride Free Buffer consisted of 1 mM Magnesium Gluconate, 2 mM Calcium Gluconate, 4.5 mM Potassium Gluconate, 160 mM Sodium Gluconate, 10 mM HEPES, 10 mM Glucose.

Bath1 Dye Solution consisted of Bath 1 Buffer, 0.04% Pluronic F127, 20 µM Methyl Oxonol, 30 µM CaCCinh-A01, 30 µM Chicago Sky Blue.

Chloride Free Dye Solution consisted of Chloride Free Buffer, 0.04% Pluronic F127, 20 µM Methyl Oxonol, 30 µM CaCCinh-A01, 30 µM Chicago Sky Blue.

Chloride Free Dye Stimulation Solution consisted of Chloride Free Dye Solution, 10 µM forskolin, 100 µM IBMX, and 300 nM Compound III.

Cell Culture

Human intestinal epithelial enteroid cells were obtained from the Hubrecht Institute for Developmental Biology and Stem Cell Research, Utrecht, The Netherlands and expanded in T-Flasks as previously described (Dekkers J F, Wiegerinck C L, de Jonge H R, Bronsveld I, Janssens H M, de Winter-de Groot K M, Brandsma A M, de Jong N W M, Bijvelds M J C, Scholte B J, Nieuwenhuis E E S, van den Brink S, Clevers H, van der Ent C K, Middendorp S and M Beekman J M. A functional CFTR assay using primary cystic fibrosis intestinal organoids is described in Nat Med. 2013 July; 19(7):939-45.

Enteroid Cell Harvesting and Seeding

Cells were recovered in cell recovery solution, collected by centrifugation at 650 rpm for 5 min at 4° C., resuspended in TryPLE and incubated for 5 min at 37° C. Cells were then collected by centrifugation at 650 rpm for 5 min at 4° C. and resuspended in IEMM containing 10 µM ROCK inhibitor (RI). The cell suspension was passed through a 40 µm cell strainer and resuspended at 1×106 cells/mL in IEMM containing 10 µM RI. Cells were seeded at 5000 cells/well into multi-well plates and incubated for overnight at 37° C., 95% humidity and 5% $CO_2$ prior to assay.

Membrane Potential Dye Assay

Enteroid cells were incubated with test compound in IEMM for 18-24 h at 37° C., 95% humidity and 5% $CO_2$. Following compound incubations, a membrane potential dye assay was employed using a FLIPR Tetra to directly measure the potency and efficacy of the test compound on CFTR-mediated chloride transport following acute addition of 10 µM forskolin and 300 nM Compound III. Briefly, cells were washed 5 times in Bath 1 Buffer. Bath 1 Dye Solution was added and the cells were incubated for 25 min at room temperature. Following dye incubation, cells were washed 3 times in Chloride Free Dye Solution. Chloride transport was initiated by addition of Chloride Free Dye Stimulation Solution and the fluorescence signal was read for 15 min. The CFTR-mediated chloride transport for each condition was determined from the AUC of the fluorescence response to acute forskolin and 300 nM Compound III stimulation. Chloride transport was then expressed as a percentage of the chloride transport following treatment with 3 µM Compound I, 3 µM Compound II, and 300 nM acute Compound III triple combination control (% Activity).

The following represents the data in Table 66:

Max Activity: +++ is >60%; ++ is 30-60%; + is <30%. $EC_{50}$: +++ is <1 µM; ++ is 1-3 µM; + is >3 µM; and ND is "not determined."

TABLE 66

Assay Data for Compound I

| Molecule | Max. Activity | $EC_{50}$ |
|---|---|---|
| Compound I | +++ | +++ |

Example 39: Compound I Increases Chloride Transport Alone and in Combination with Compound II and/or Compound III in F508del/F508del HBE and F508del/MF HBE Ussing chamber studies were conducted to measure F508del CFTR-mediated chloride transport in HBE cells derived from 3 F508del homozygous donors and 5 F508del/MF donors (G542X, 3 donors; E585X, 1 donor; 3905InsT, 1 donor). As a positive control, maximally effective concentrations of N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (see WO 2018/064632) and N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (see WO 2016/057572) in combination with Compound II/Compound III were included in each experiment.

In these CF cell lines, CFTR-mediated chloride transport was low in the absence of CFTR modulators, which is consistent with little-to-no CFTR at the cell surface. Treatment with Compound I alone for 16 to 24 h caused a modest increase in chloride transport in both F508del/F508del HBE and F508del/MF HBE cells. The combination of Compound I and Compound II further increased chloride transport when compared to Compound I alone and was similar to Compound II/Compound III. Addition of Compound III strongly potentiated chloride transport in the presence of Compound I or in combination with Compound I/Compound II. Synergy analyses showed that the effect of Compound I was highly synergistic with a fixed concentration of Compound III or Compound II/Compound III and was modestly synergistic with a fixed combination of Compound II. At most Compound I concentrations, Compound I/Compound II/Compound III increased chloride transport more than Compound I/Compound II or Compound I/Compound III. However, the efficacy of Compound I/Compound III and Compound I/Compound II/Compound III was similar at their respective $EC_{90}$ values. The respective $EC_{90}$ values under conditions that maximally activate CFTR for Compound I/Compound III and Compound I/Compound II/Compound III were 0.848 µM and 0.152 µM in F508del/F508del HBE and 1.15 µM and 0.122 µM in F508del/MF HBE.

Following a single oral administration of Compound I in male animals, Compound I mean $t_{max}$ values were 9 h in rats, 4 h in dogs, and 3 h in monkeys. Mean oral bioavailability (F) was low to moderate in rats (76.9%), dogs (49.7%), and monkeys (12.9%).

| | | Compound I Pharmacokinetic Parameters Following a Single Oral Administration of Compound I in Male Rats, Dogs, and Monkeys | | | | |
|---|---|---|---|---|---|---|
| Species | Nominal Dose (mg/kg) | $AUC0_{\infty}$ (µg·h/mL) | $C_{max}$ (µg/mL) | $t_{max}$ (h) | $t_{1/2}$ (h) | F (%) |
| Rat | 3 | 31.9 ± 11.1 | 1.10 ± 0.337 | 9.33 ± 2.31 | 22.6 ± 2.83 | 76.9 |
| Dog | 1 | 38.5 ± 4.70 | 2.44 ± 0.178 | 4.00 ± 0.00 | 11.1 ± 1.09 | 49.7 |
| Monkey | 1 | 0.795 ± 0.233 | 0.102 ± 0.0132 | 3.33 ± 1.15 | 3.07 ± 1.16 | 12.9 |

Note:

Data are presented as mean ± SD (n = 3).

As the dose increased, systemic exposure of Compound I increased in a more than doseproportional manner in rats and dogs. Dosenormalized exposure was higher in female rats than male rats. In dogs, systemic exposures to Compound I were similar in both sexes. Following repeated oral administration of Compound I for 28 d in rats and dogs, accumulation of Compound I exposure was observed. Systemic exposure to Compound I on Day 28 was higher than on Day 1 (Day 28/Day 1 $AUC_{024h}$ ratio ranged from 1.63 to 2.70 in male rats, 5.01 to 8.26 in female rats, 1.73 to 2.64 in male dogs, and 1.82 to 2.23 in female dogs).

Example 40: Safety and Efficacy Study of Compound I

A safety analysis of an ongoing clinical study was performed for 37 subjects in Cohorts A1 to A5, 33 subjects in Cohort B, and 17 subjects in Cohort C, who were exposed to at least 1 dose of study drug (Compound I or placebo) as a monotherapy and as part of a triple combination with Compound II or Compound III. Compound I was generally safe and well-tolerated up to a dose of 60 mg qd in monotherapy and 20 mg qd in triple combination with Compound II and Compound III.

The invention claimed is:
1. Compound I calcium salt hydrate Form A

(Compound I)

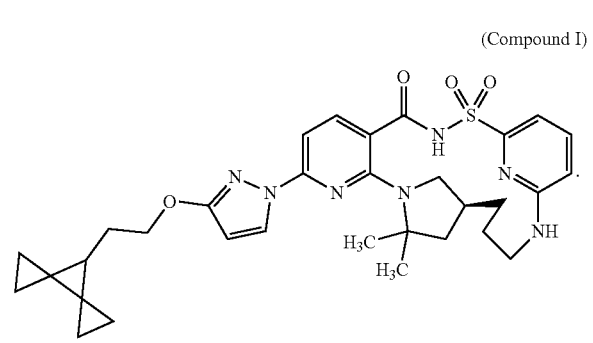 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]

2. A pharmaceutical composition comprising the Compound I calcium salt hydrate Form A according to claim 1.
3. The pharmaceutical composition according to claim 2, further comprising one or more additional CFTR modulating compounds.
4. The pharmaceutical composition according to claim 3, wherein the one or more additional CFTR modulating compounds are selected from
(a) Compound II (Compound II)

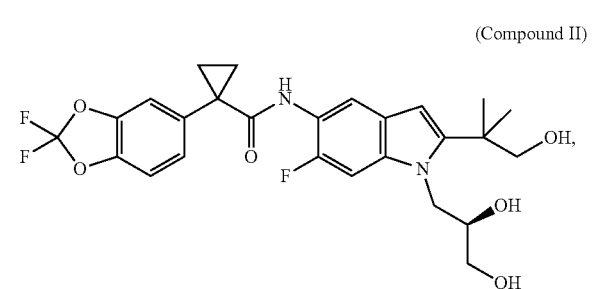 [SMILES: CC(C)(CO)c1cc2cc(NC(=O)C3(c4ccc5c(c4)OC(F)(F)O5)CC3)c(F)cc2n1C[C@@H](O)CO]

(b) Compound III (Compound III)

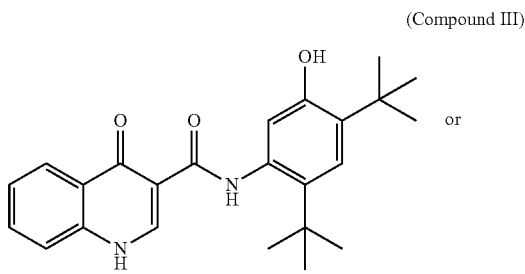 [SMILES: CC(C)(C)c1cc(C(C)(C)C)c(NC(=O)c2c[nH]c3ccccc3c2=O)cc1O]

or

Compound III-d (Compound III-d)

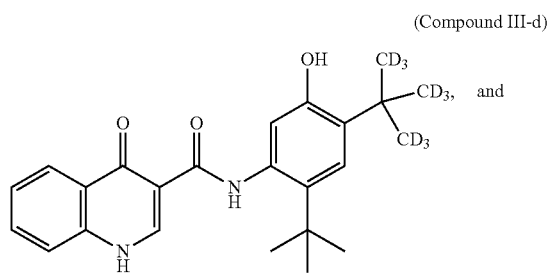 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

and (c) Compound IV (Compound IV)

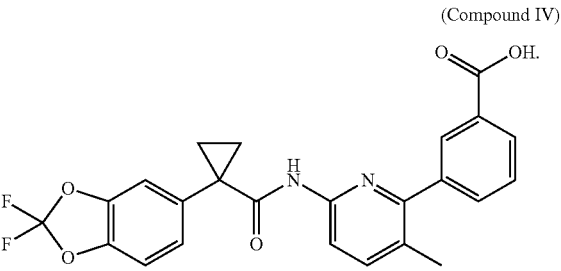 [SMILES: Cc1ccc(NC(=O)C2(c3ccc4c(c3)OC(F)(F)O4)CC2)nc1-c1cccc(C(=O)O)c1]

5. A method of treating cystic fibrosis comprising administering the Compound I calcium salt hydrate Form A according to claim 1 to a subject in need thereof.
6. The method of treating cystic fibrosis according to claim 5, wherein the Compound I calcium salt hydrate Form A is administered with one or more additional CFTR modulating compounds.
7. The method of treating cystic fibrosis according to claim 6, wherein the one or more additional CFTR modulating compound are selected from
(a) Compound II (Compound II)

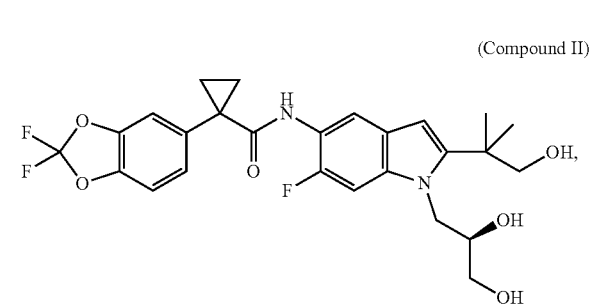 [SMILES: CC(C)(CO)c1cc2cc(NC(=O)C3(c4ccc5c(c4)OC(F)(F)O5)CC3)c(F)cc2n1C[C@@H](O)CO]

(b) Compound III (Compound III)

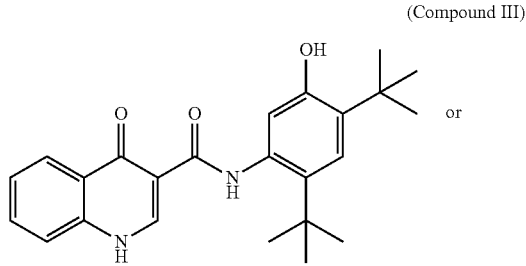 [SMILES: CC(C)(C)c1cc(C(C)(C)C)c(NC(=O)c2c[nH]c3ccccc3c2=O)cc1O]

Compound III-d

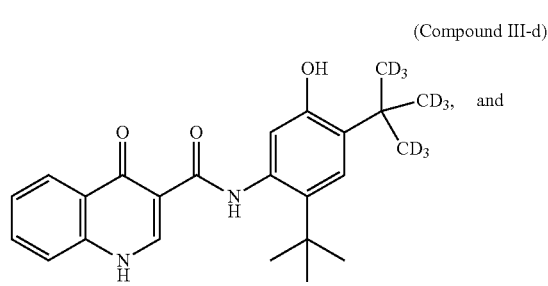 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

(Compound III-d)

and (c) Compound IV

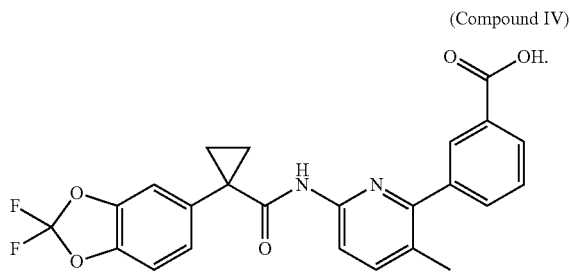 [SMILES: Cc1ccc(NC(=O)C2(c3ccc4c(c3)OC(F)(F)O4)CC2)nc1-c1cccc(C(=O)O)c1]

(Compound IV)

8. A method of preparing the Compound I calcium salt hydrate Form A according to claim 1, comprising:
  (a) charging Compound I Form A and calcium methoxide (Ca(OMe)$_2$) with IPA/H$_2$O
  (b) heating to 70° C., and
  (c) isolating the resulting solids,
to provide substantially crystalline Compound I calcium salt hydrate Form A.

9. Compound I calcium salt hydrate Form A (Compound I)

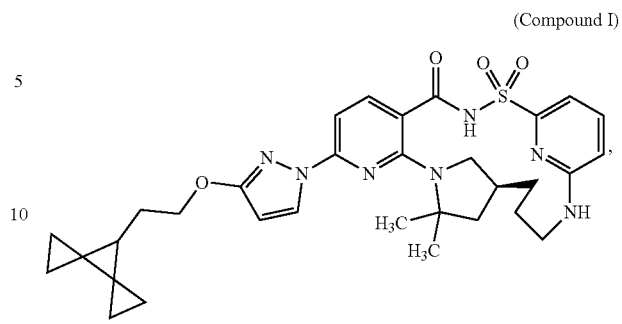

characterized by an X-ray powder diffractogram (XRPD) having signals at 4.2±0.2 degrees two-theta, 18.0±0.2 degrees two-theta, and 19.7±0.2 degrees two-theta.

10. The Compound I calcium salt hydrate Form A according to claim 9, characterized by an X-ray powder diffractogram (XRPD) having (a) signals at 4.2±0.2 degrees two-theta, 18.0±0.2 degrees two-theta, and 19.7±0.2 degrees two-theta; and (b) signals at one or more of 10.5±0.2 degrees two-theta, 10.6±0.2 degrees two-theta, and 17.8±0.2 degrees two-theta.

11. The Compound I calcium salt hydrate Form A according to claim 9, characterized by an X-ray powder diffractogram (XRPD) having (a) signals at 4.2±0.2 degrees two-theta, 18.0±0.2 degrees two-theta, and 19.7±0.2 degrees two-theta; and (b) signals at two or more of 10.5±0.2 degrees two-theta, 10.6±0.2 degrees two-theta, and 17.8±0.2 degrees two-theta.

12. The Compound I calcium salt hydrate Form A according to claim 9, characterized by an X-ray powder diffractogram (XRPD) having (a) signals at 4.2±0.2 degrees two-theta, 18.0±0.2 degrees two-theta, and 19.7±0.2 degrees two-theta; and (b) signals at 10.5±0.2 degrees two-theta, 10.6±0.2 degrees two-theta, and 17.8±0.2 degrees two-theta.

13. The Compound I calcium salt hydrate Form A according to claim 1, characterized by an X-ray powder diffractogram substantially similar to FIG. 6.

14. The Compound I calcium salt hydrate Form A according to claim 1, characterized by a monoclinic crystal system, a C$_2$ space group, and unit cell dimensions measured at 100 K on a Bruker diffractometer equipped with Cu K$_\alpha$ radiation ($\lambda$=1.5478 Å) of

| a | 11.13 ± .01 Å | α | 90° |
|---|---|---|---|
| b | 13.77 ± .01 Å | β | 101.93 ± .01° |
| c | 22.21 ± .01 Å | γ | 90°. |

15. Compound I calcium salt hydrate Form A (Compound I)

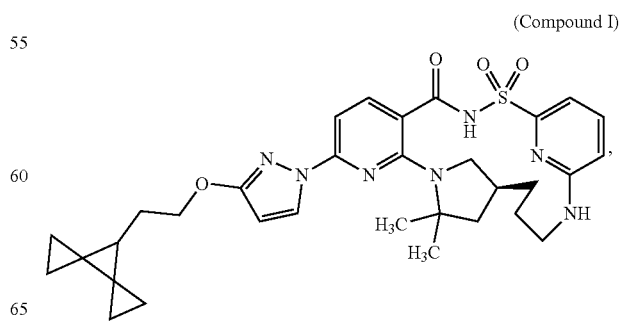

characterized by a $^{13}$C solid state nuclear magnetic resonance ($^{13}$C ssNMR) spectrum with a peak at 17.0±0.2 ppm.

16. The Compound I calcium salt hydrate Form A according to claim 15, characterized by a $^{13}$C ssNMR spectrum with a peak at 7.8±0.2 ppm.

17. The Compound I calcium salt hydrate Form A according to claim 15, characterized by a $^{13}$C ssNMR spectrum with peaks at 17.0±0.2 ppm and 7.8±0.2 ppm.

18. The Compound I calcium salt hydrate Form A according to claim 15, characterized by a $^{13}$C ssNMR spectrum substantially similar to FIG. 7.

19. The pharmaceutical composition according to claim 2, wherein at least 85% of the Compound I is Compound I calcium salt hydrate Form A.

20. The pharmaceutical composition according to claim 2, wherein at least 95% of the Compound I is Compound I calcium salt hydrate Form A.

* * * * *